United States Patent
Wu et al.

(10) Patent No.: US 11,390,625 B2
(45) Date of Patent: Jul. 19, 2022

(54) ARYL-PHOSPHORUS-OXYGEN COMPOUND AS EGFR KINASE INHIBITOR

(71) Applicant: Chia Tai Tianqing Pharmaceutical Group Co., Ltd., Lianyungang (CN)

(72) Inventors: Lingyun Wu, Shanghai (CN); Xile Liu, Shanghai (CN); Charles Z. Ding, Shanghai (CN); Shuhui Chen, Shanghai (CN); Lihong Hu, Shanghai (CN); Lele Zhao, Shanghai (CN); Wei Pan, Shanghai (CN); Guoping Hu, Shanghai (CN); Jian Li, Shanghai (CN); Ning Zhao, Shanghai (CN); Jun Zhao, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 9 days.

(21) Appl. No.: 16/631,416

(22) PCT Filed: Jul. 19, 2018

(86) PCT No.: PCT/CN2018/096344
§ 371 (c)(1),
(2) Date: Jan. 15, 2020

(87) PCT Pub. No.: WO2019/015655
PCT Pub. Date: Jan. 24, 2019

(65) Prior Publication Data
US 2020/0207768 A1 Jul. 2, 2020

(30) Foreign Application Priority Data

Jul. 19, 2017 (CN) .................. 201710592778.X
Dec. 6, 2017 (CN) .................. 201711277584.7
Feb. 8, 2018 (CN) .................. 201810130633.2
Apr. 19, 2018 (CN) .................. 201810355614.X

(51) Int. Cl.
| C07D 401/12 | (2006.01) |
| C07D 401/14 | (2006.01) |
| C07D 409/14 | (2006.01) |
| C07D 471/10 | (2006.01) |
| A61P 35/04 | (2006.01) |
| C07D 519/00 | (2006.01) |
| C07K 16/28 | (2006.01) |

(52) U.S. Cl.
CPC ............ *C07D 471/10* (2013.01); *A61P 35/04* (2018.01); *C07D 401/12* (2013.01); *C07D 401/14* (2013.01); *C07D 409/14* (2013.01); *C07D 519/00* (2013.01); *C07K 16/2863* (2013.01)

(58) Field of Classification Search
CPC ... C07D 401/12; C07D 401/14; C07D 409/14
See application file for complete search history.

(56) References Cited

U.S. PATENT DOCUMENTS 10,059,694 B2    8/2018    Ding

FOREIGN PATENT DOCUMENTS

| CN | 103153064 A | 6/2013 |
| CN | 103501612 A | 1/2014 |
| CN | 105017160 A | 11/2015 |
| CN | 106699810 A | 5/2017 |
| KR | 2016-0147170 A | 12/2016 |
| WO | WO 2013/169401 A1 | 11/2013 |
| WO | WO 2016/082713 A1 | 6/2016 |
| WO | WO 2017/086829 A1 | 5/2017 |
| WO | WO 2017/086832 A1 | 5/2017 |

OTHER PUBLICATIONS

International Search Report for International Patent Application No. PCT/CN2018/096344, dated Sep. 27, 2018, with English translation (8 pages).
Written Opinion of International Searching Authority for International Patent Application No. PCT/CN2018/096344, dated Sep. 27, 2018, with English translation (11 pages).

*Primary Examiner* — Brian E McDowell
(74) *Attorney, Agent, or Firm* — Nixon Peabody LLP

(57) ABSTRACT

Disclosed is a class of new aryl-phosphorus-oxygen compounds as shown in formula (I) as EGFR kinase inhibitors, and pharmaceutically acceptable salts thereof.

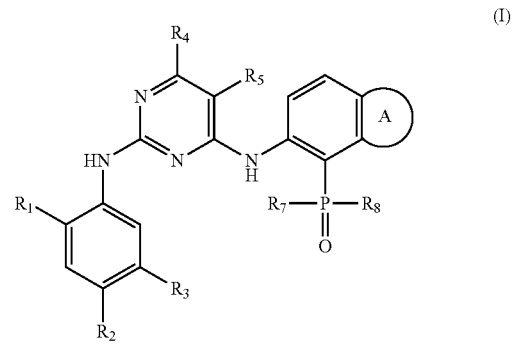

16 Claims, No Drawings

ARYL-PHOSPHORUS-OXYGEN COMPOUND AS EGFR KINASE INHIBITOR

This application is a nationalization application of PCT/CN2018/096344 filed on Jul. 19, 2018, and claims the following priority to:
CN201710592778.X, filed on Jul. 19, 2017;
CN201711277584.7, filed on Dec. 6, 2017;
CN201810130633.2, filed on Feb. 8, 2018;
CN201810355614.X, filed on Apr. 19, 2018; which are incorporated by reference in their entireties.

FIELD OF THE INVENTION

The present application relates to an aryl-phosphine-oxygen compound as an EGFR kinase inhibitor, and specifically discloses a compound represented by formula (I) and a pharmaceutically acceptable salt thereof.

BACKGROUND OF THE INVENTION

Lung cancer is one of the most common malignant tumors. There will be about 1.6 million new cases of lung cancer cases each year worldwide, and there will be 1.4 million deaths from lung cancer each year. Among them, non-small cell lung cancer (NSCLC) accounts for about 80%-85% of all lung cancers (the 10th Lung Cancer Summit Forum).

EGFR (epidermal growth factor receptor)-TKI (tyrosine kinase inhibitor), as a small molecule inhibitor, competitively binds to EGFR with endogenous ligands and inhibits activation of tyrosine kinase, resulting in blocking the EGFR signaling pathway, and ultimately producing a series of biological effects such as inhibiting tumor cell proliferation and metastasis, and promoting tumor cell apoptosis, and it is one of the main targets for lung cancer treatment.

Osimertinib (AZD9291) is a third-generation EGFR-TKI-targeted drug. Although it has higher responsivity to drug resistance caused by T790M mutation, patients also develop drug resistance (Clin Cancer Res; 21 (17), 2015). In 2015, the drug resistance analysis on 15 patients with AZD9291 was first reported in Nature Medicine, 21, 560-562, 2015, wherein the third mutation obtained, i.e. EGFR C797S mutation, was one of the main mechanisms leading to drug resistance of Osimertinib, accounting for about 40%. At the same time, the drug resistance of AZD9291 was also reported in several conferences, and among them, 2015 WCLC, Oxnard GR reported drug resistance analysis of 67 patients, of which C797S accounted for about 22%; 2017 ASCO, Piotrowska also reported 23 cases, and C797S also accounted for about 22%; and 2017 ASCO, Zhou Caicun et al reported the analysis of drug resistance mechanisms in 99 patients, of which C797S accounted for about 22%. Therefore, it is of great study significance to overcome the resistance of AZD9291 to C797S mutation and provide patients a safer and more effective fourth-generation EGFR C797S/T790M inhibitor.

In 2016, "Nature, 534, 129-132, 2016" reported compound EAI045 capable of overcoming the drug resistance of Osimertinib to C797S. EAI045 belongs to an allosteric inhibitor that shows better tumor inhibition effect in the mouse in vivo pharmacodynamic model with L858R/T790M/C797S mutations when combined with EGFR monoclonal antibody such as cetuximab; but this compound failed to enter clinical studies. In 2017, Nature Communications, 8:14768, 2017 reported that Brigatinib (AP26113) in combination with EGFR monoclonal antibody (such as cetuximab) can overcome the drug resistance of the third-generation targeting drug Osimertinib caused by C797S mutation. It was shown that both the combination of Brigatinib with panitumumab or cetuximab exhibits good anti-tumor efficacy from the results in the PC9 (EGFR-C797S/T790M/del19) mouse pharmacodynamic model.

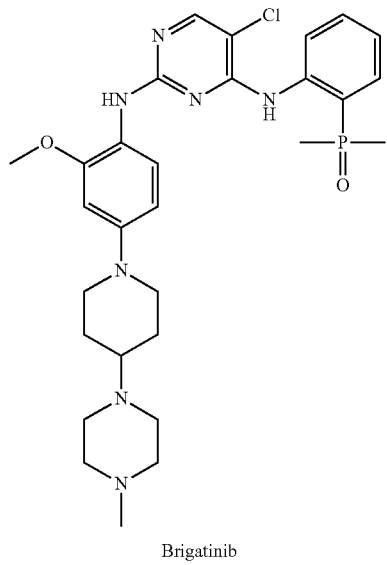

Brigatinib

WO2012051587A1 discloses Comparative Example 1, but fails to provide any data on its effect.

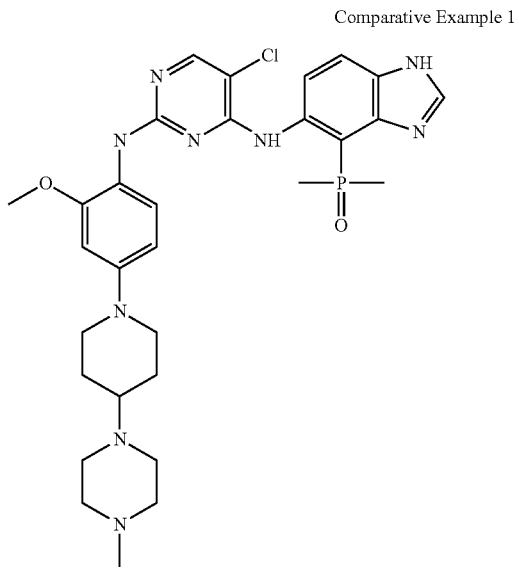 [SMILES: COc1cc(N2CCC(N3CCN(C)CC3)CC2)ccc1Nc1ncc(Cl)c(Nc2ccc3[nH]cnc3c2P(C)(C)=O)n1]

Comparative Example 1

SUMMARY OF THE INVENTION

The present application provides a compound represented by formula (I) or a pharmaceutically acceptable salt thereof,

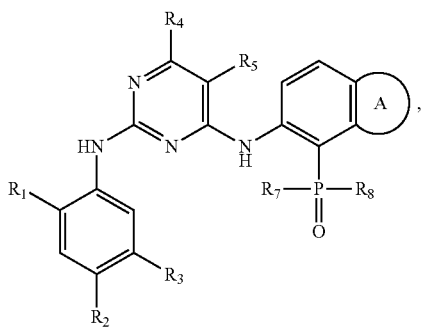

wherein, ring A is selected from phenyl, 5- to 6-membered heteroaryl, 5- to 7-membered heterocycloalkyl, $C_{5-7}$ cycloalkenyl, and $C_{5-7}$ cycloalkyl, wherein said phenyl, 5- to 6-membered heteroaryl, 5- to 7-membered heterocycloalkyl, $C_{5-7}$ cycloalkenyl and $C_{5-7}$ cycloalkyl are optionally substituted with $R_6$;

and the structural unit

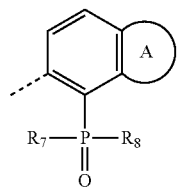

is not selected from

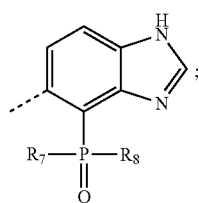

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, $-OC(=O)NH_2$, $-OC(=O)NHR$, $-OC(=O)NRR$, $-NRC(=O)OR$, $-NHC(=O)OR$, $-NHC(=O)OH$, $-O(CH_2)_nNR_aR_b$, $C_{1-6}$ alkyl, $C_{3-6}$ cycloalkyl and 5- or 6-membered heterocyclic group containing 1, 2 or 3 N or O atoms, wherein said $C_{1-6}$ alkyl, $C_{3-6}$ cycloalkyl, and 5- or 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring is optionally substituted with 1, 2 or 3 R groups;

each $R_6$ is independently selected from H, halogen, CN, OH, $NH_2$, $C_{1-6}$ alkyl, $C_{1-6}$ heteroalkyl, $=O$ and $=S$;

$R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$ and $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from $-C(=O)N(R)-$, $-N(R)-$, $-C(=NR)-$, $-(R)C=N-$, $-S(=O)_2N(R)-$, $-S(=O)N(R)-$, N, $-NH-$, $-O-$, $-S-$, $-C(=O)O-$, $-C(=O)-$, $-C(=S)-$, $-S(=O)-$, $-S(=O)_2-$ and $-N(R)C(=O)N(R)-$;

in any one of the cases as described above, the number of the heteroatom or heteroatom group is each independently selected from 1, 2 or 3.

In some embodiments of the present application, the above R is selected from F, Cl, Br, I, CN, OH, $NH_2$, $CH_3$, $CH_3CH_2$, $CH_3CH_2CH_2$, $(CH_3)_2CH$, $CH_3O$, $(CH_3)_2N$,

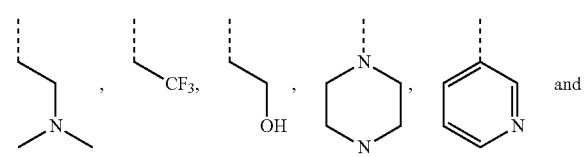

In some embodiments of the present application, the above $R_1$ is selected from H, halogen, $C_{1-3}$ alkyl and $C_{1-3}$ heteroalkyl, $C_{2-5}$ alkenyloxy, and $C_{4-6}$ cycloalkyloxy, wherein said $C_{1-3}$ alkyl, $C_{1-3}$ heteroalkyl, $C_{2-5}$ alkenyloxy and $C_{4-6}$ cycloalkyloxy are optionally substituted with 1, 2 or 3 R groups, and R is as defined in the present application.

In some embodiments of the present application, the above $R_1$ is selected from H, F, Cl, Br, I, $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

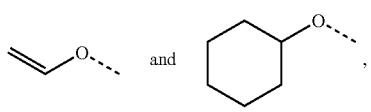

wherein said $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

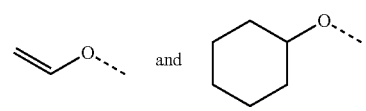

are optionally substituted with 1, 2 or 3 R groups, and R is as defined in the present application.

In some embodiments of the present application, the above $R_2$ is selected from H, halogen, CN, OH, $NO_2$, $NH_2$, $C_{3-12}$ cycloalkyl, and 3- to 12-membered heterocycloalkyl, wherein said $NH_2$, $C_{3-12}$ cycloalkyl and 3- to 12-membered heterocycloalkyl are optionally substituted with 1, 2 or 3 R groups, and R is as defined in the present application.

In some embodiments of the present application, the above $R_2$ is selected from H, halogen, CN, OH, $NH_2$, $NO_2$, —NHR, —N(R)$_2$,

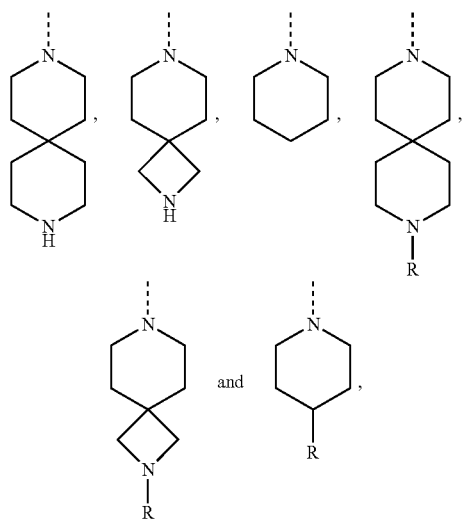

and R is as defined in the present application.

In some embodiments of the present application, the above $R_2$ is selected from H, F, Cl, Br, CN, OH, $NH_2$,

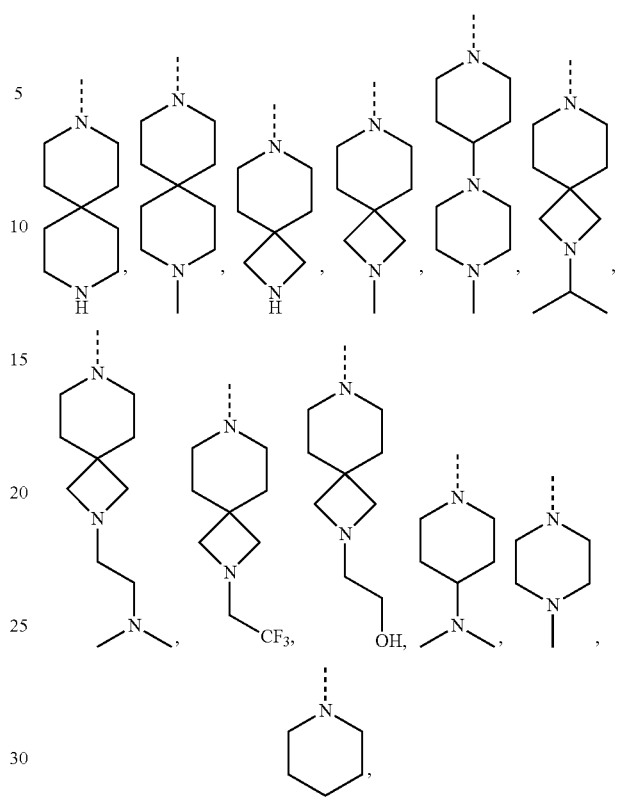

—NHCH$_2$CH$_3$, —NHCH$_3$, —N(CH$_3$)$_2$ and

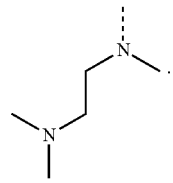

In some embodiments of the present application, the above $R_6$ is selected from H, F, Cl, Br, CN, OH, $NH_2$, $CH_3$, $CH_3CH_2$, $CH_3CH_2CH_2$, $(CH_3)_2CH$, $CH_3O$, =S and =O.

In some embodiments of the present application, ring A is selected from phenyl, thienyl, pyridyl, pyrazinyl, pyrazolyl, cyclopentanonyl, cyclopentenyl, thiazolyl, isothiazolyl, and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$, and $R_6$ is as defined in the present application.

In some embodiments of the present application, the structural unit

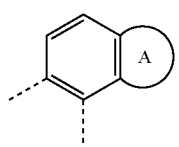

is selected from

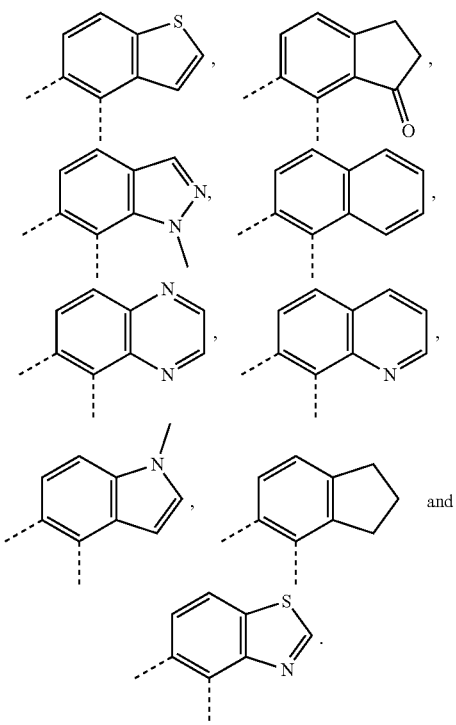

In some embodiments of the present application, the above $R_a$ and $R_b$ are each independently selected from H, $CH_3$, $CH_3CH_2$, and $—S(=O)_2CH_3$, wherein said $CH_3$, $CH_3CH_2$, and $—S(=O)_2CH_3$ are optionally substituted with 1, 2 or 3 R groups, and R is as defined in the present application.

In some embodiments of the present application, the above $R_a$ and $R_b$ are each independently selected from H,

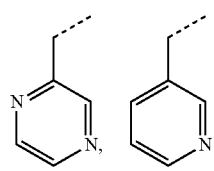

and $—S(=O)_2CH_3$.

In some embodiments of the present application, the above $R_3$ is selected from

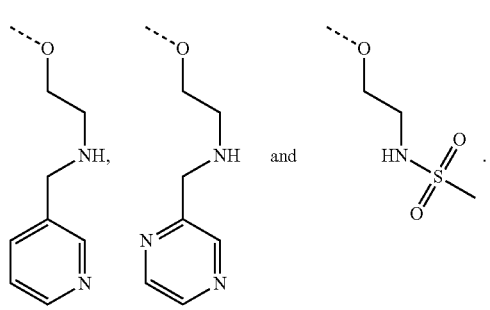

In some embodiments of the present application, the above $R_3$ is selected from H, F, Cl, Br, $CH_3$, $CH_3CH_2$, $(CH_3)_2CH$,

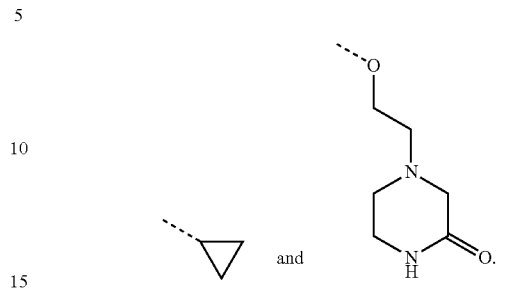

In some embodiments of the present application, the above $R_5$ is selected from H, F, Cl, Br, I, CN, $CH_3$, $CH_3CH_2$, $CH_3CH_2CH_2$, $(CH_3)_2CH$,

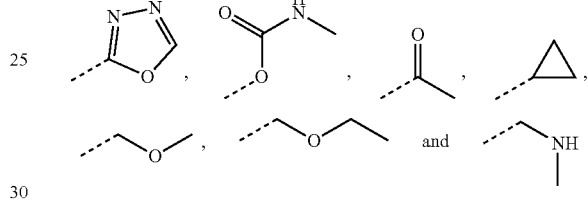

wherein said $CH_3$, $CH_3CH_2$, $CH_3CH_2CH_2$, $(CH_3)_2CH$,

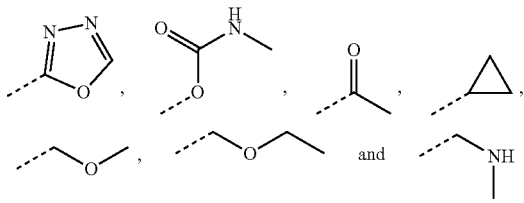

are optionally substituted with 1, 2 or 3 R groups, and R is as defined in the present application.

In some embodiments of the present application, the above $R_5$ is selected from H, Cl, Br, CN, $CH_3$, $CH_3CH_2$, $CH_3CH_2CH_2$, $(CH_3)_2CH$,

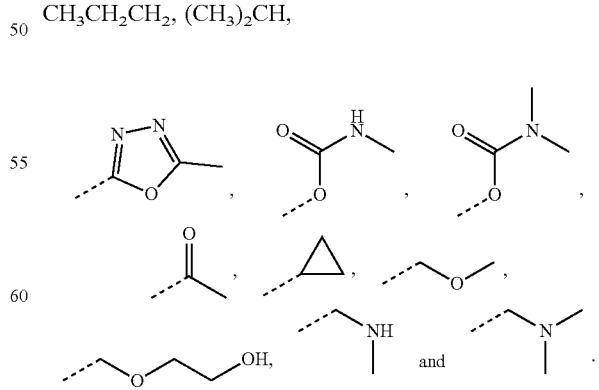

In some embodiments of the present application, the structural unit

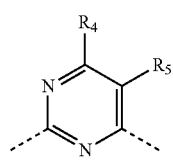

is selected from

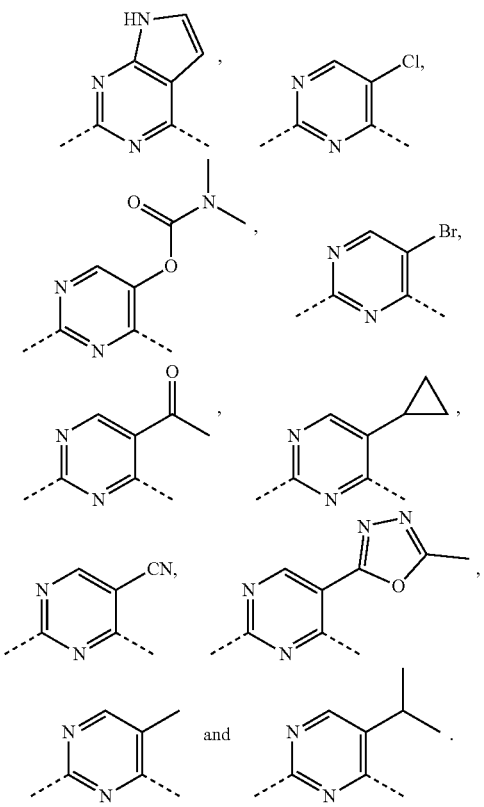

In some embodiments of the present application, the above $R_7$ and $R_8$ are each independently selected from H or $CH_3$.

In some embodiments of the present application, the above R is selected from F, Cl, Br, I CN, OH, $NH_2$, $CH_3$, $CH_3CH_2$, $CH_3CH_2CH_2$, $(CH_3)_2CH$, $CH_3O$, $(CH_3)_2N$,

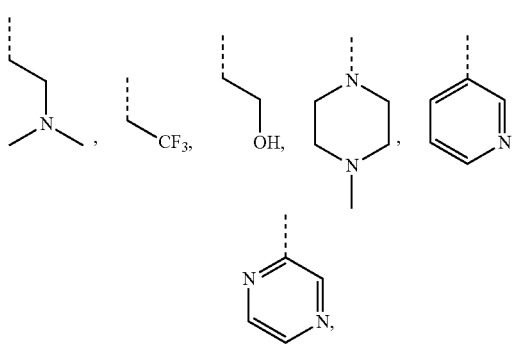

and other variables are as defined above.

In some embodiments of the present application, the above $R_1$ is selected from H, halogen, $C_{1-3}$ alkyl and $C_{1-3}$ heteroalkyl, $C_{2-5}$ alkenyloxy, and $C_{4-6}$ cycloalkyloxy, wherein said $C_{1-3}$ alkyl, $C_{1-3}$ heteroalkyl, $C_{2-5}$ alkenyloxy and $C_{4-6}$ cycloalkyloxy are optionally substituted with 1, 2 or 3 R groups, and R and other variables are as defined above.

In some embodiments of the present application, the above $R_1$ is selected from H, F, Cl, Br, I, $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

wherein said $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

are optionally substituted with 1, 2 or 3 R groups, and R and other variables are as defined above.

In some embodiments of the present application, the above $R_2$ is selected from H, halogen, CN, OH, $NO_2$, $NH_2$, $C_{3-12}$ cycloalkyl, and 3- to 12-membered heterocycloalkyl, wherein said $NH_2$, $C_{3-12}$ cycloalkyl and 3- to 12-membered heterocycloalkyl are optionally substituted with 1, 2 or 3 R groups, and R and other variables are as defined above.

In some embodiments of the present application, the above $R_2$ is selected from H, halogen, CN, OH, $NH_2$, $NO_2$, —NHR, —N(R)$_2$,

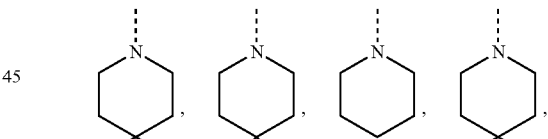

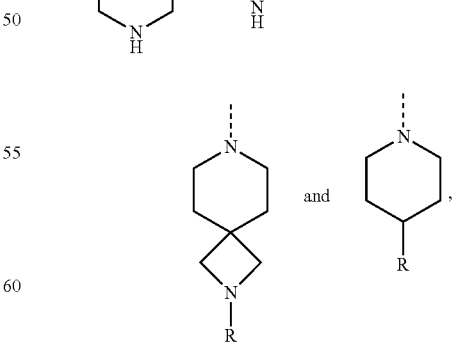

and R and other variables are as defined above.

In some embodiments of the present application, the above $R_2$ is selected from H, F, Cl, Br, CN, OH, $NH_2$, $NO_2$,

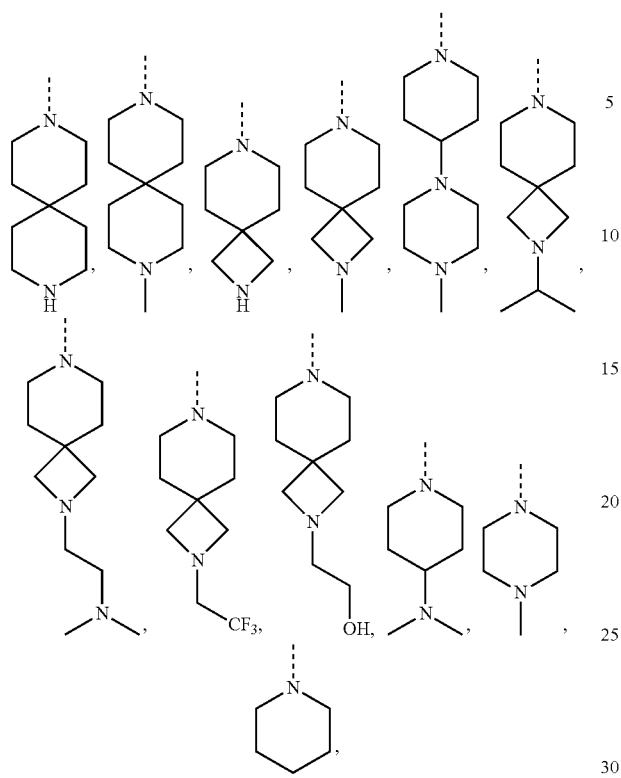

—NHCH$_2$CH$_3$, —NHCH$_3$, —N(CH$_3$)$_2$ and

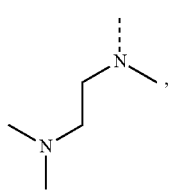

and other variables are as defined above.

In some embodiments of the present application, the above R$_6$ is selected from H, F, Cl, Br, CN, OH, NH$_2$, CH$_3$, CH$_3$CH$_2$, CH$_3$CH$_2$CH$_2$, (CH$_3$)$_2$CH, CH$_3$O, =S and =O, and other variables are as defined above.

In some embodiments of the present application, ring A is selected from phenyl, thienyl, pyridyl, pyrazinyl, pyrazolyl, cyclopentanonyl, cyclopentenyl, thiazolyl, isothiazolyl, and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with R$_6$, and R$_6$ and other variables are as defined above.

In some embodiments of the present application, the above structural unit

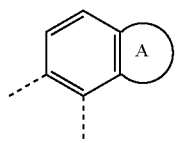

is selected from

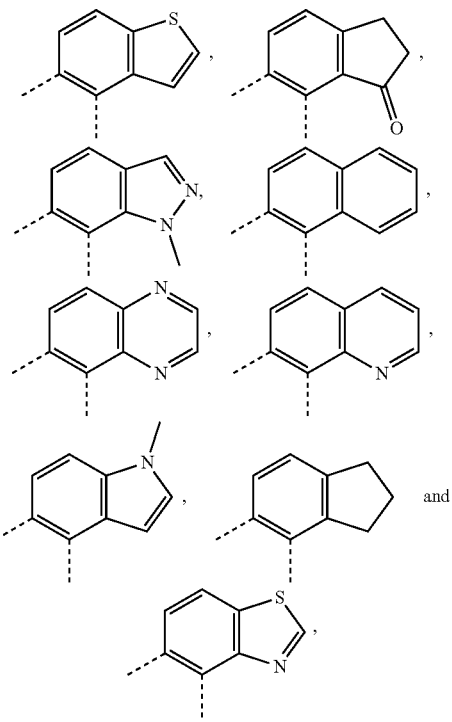

and other variables are as defined above.

In some embodiments of the present application, the above R$_a$ and R$_b$ are each independently selected from H, CH$_3$, CH$_3$CH$_2$, and —S(=O)$_2$CH$_3$, wherein said CH$_3$, CH$_3$CH$_2$, and —S(=O)$_2$CH$_3$ are optionally substituted with 1, 2 or 3 R groups, and R and other variables are as defined above.

In some embodiments of the present application, the above R$_a$ and R$_b$ are each independently selected from H,

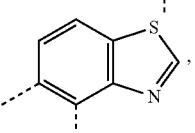

and —S(=O)$_2$CH$_3$, and other variables are as defined above.

In some embodiments of the present application, the above R$_3$ is selected from

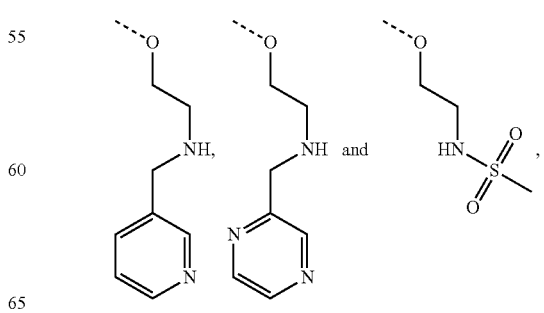

and other variables are as defined above.

In some embodiments of the present application, the above $R_3$ is selected from H, F, Cl, Br, $CH_3$, $CH_3CH_2$, $(CH_3)_2CH$,

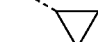 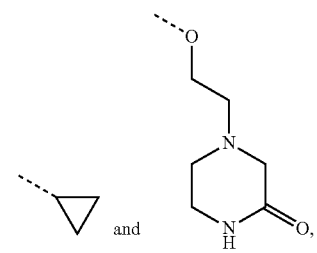

and other variables are as defined above.

In some embodiments of the present application, the above $R_5$ is selected from H, F, Cl, Br, I, CN, $CH_3$, $CH_3CH_2$, $CH_3CH_2CH_2$, $(CH_3)_2CH$,

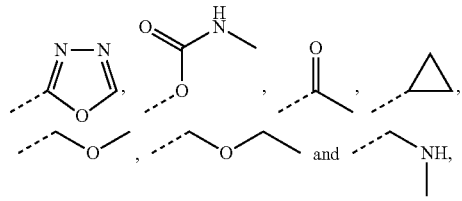

wherein said $CH_3$, $CH_3CH_2$, $CH_3CH_2CH_2$ $(CH_3)_2CH$,

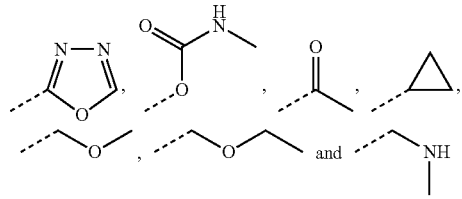

are optionally substituted with 1, 2 or 3 R groups, and R and other variables are as defined above.

In some embodiments of the present application, the above $R_5$ is selected from H, Cl, Br, CN, $CH_3$, $CH_3CH_2$, $CH_3CH_2CH_2$, $(CH_3)_2CH$,

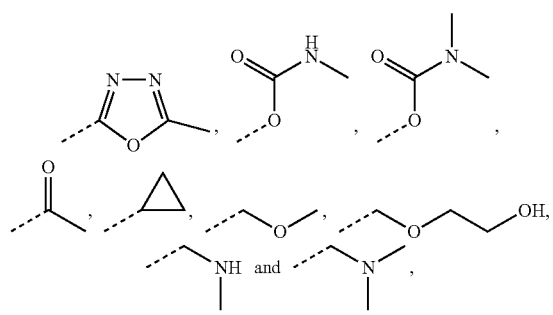

and other variables are as defined above.

In some embodiments of the present application, the above structural unit

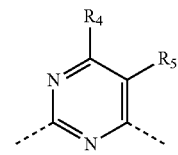

is selected from

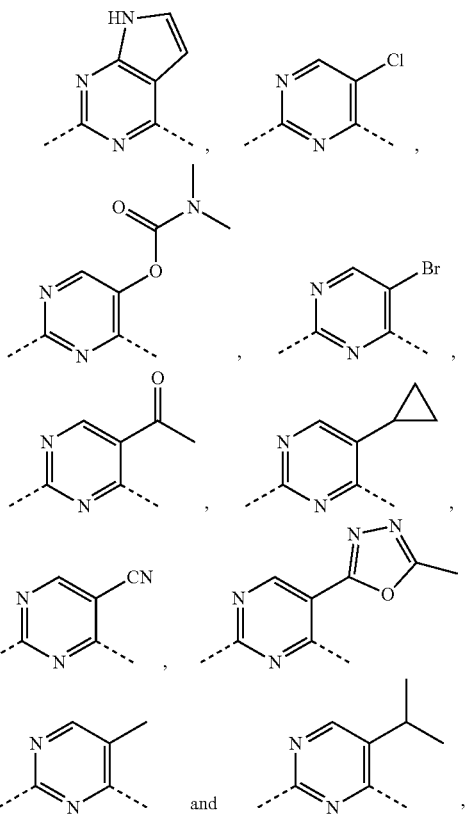

and other variables are as defined above.

In some embodiments of the present application, the above $R_7$ and $R_8$ are each independently selected from H or $CH_3$, and other variables are as defined above.

In some embodiments of the present application, the above compound or the pharmaceutically acceptable salt thereof is selected from (II)

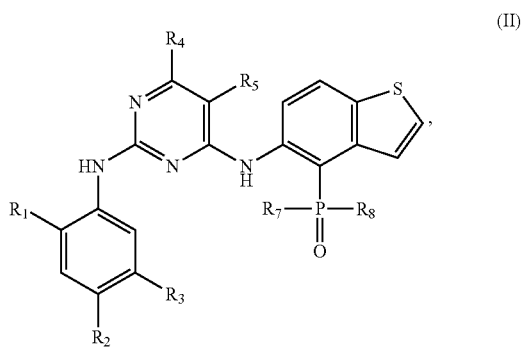

-continued
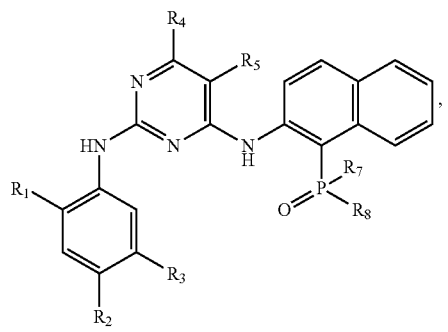
(III)
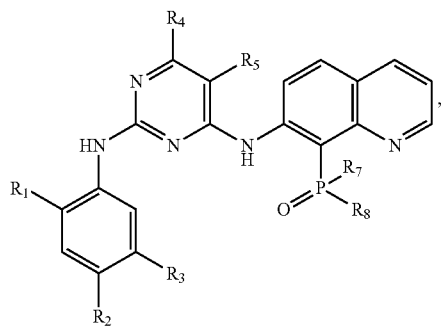
(IV)
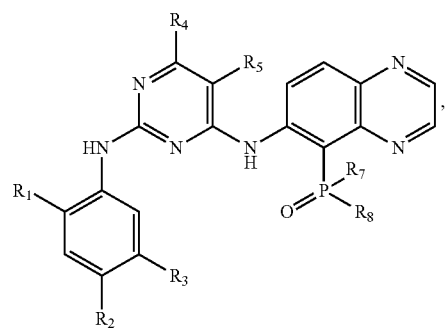
(V)
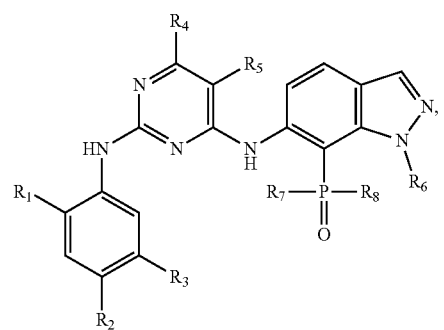
(VI)
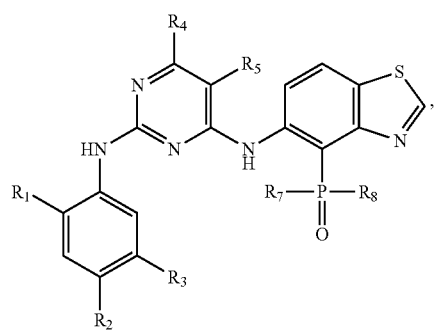
(VII)
-continued
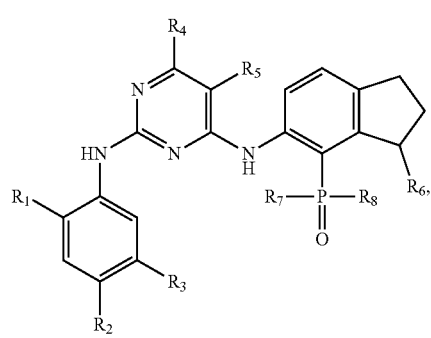
(VIII)
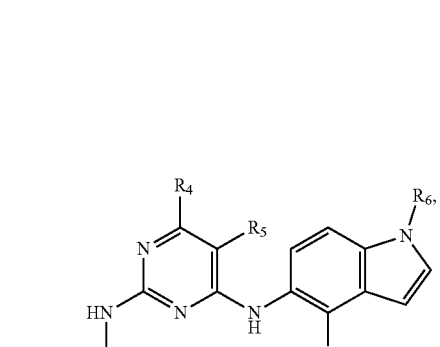
(IX)
wherein, $R_1$, $R_2$, $R_3$, $R_4$, $R_5$, $R_6$, $R_7$ and $R_8$ are as defined above.
In some embodiments of the present application, the above compound or the pharmaceutically acceptable salt thereof is selected from
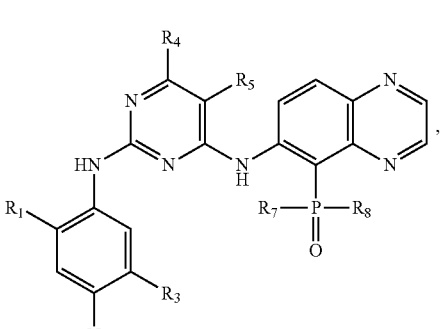
(V-1)
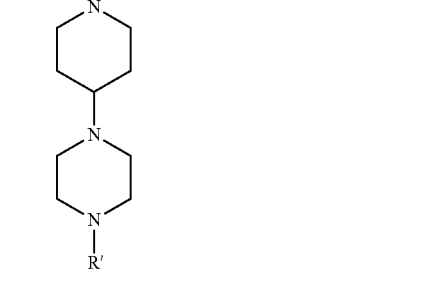

-continued

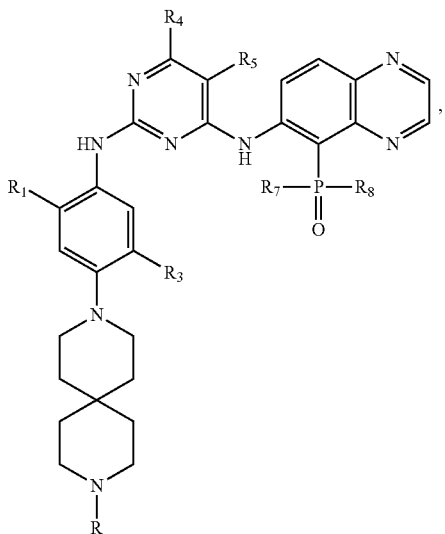
(V-2)

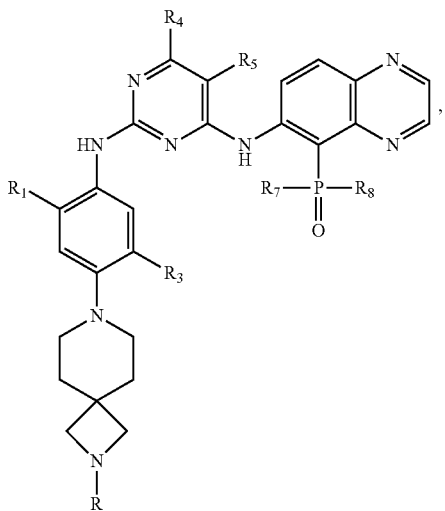
(V-3)

wherein $R_1$, $R_3$, $R_4$, $R_5$, $R_7$, $R_8$, R and R' are as defined above.

The present application provides a compound represented by formula (I') or a pharmaceutically acceptable salt thereof,

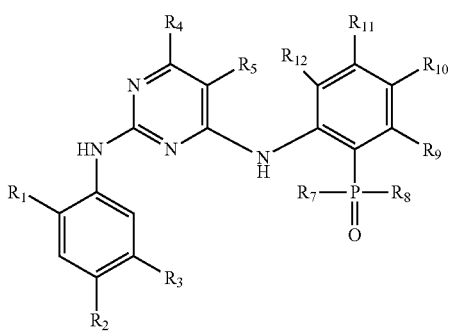
(I')

wherein, $R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy group are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)N(R)$_2$, —NRC(=O)OR, —NHC(=O)OR, —NHC(=O)OH, —O(CH$_2$)$_n$NR$_a$R$_b$, $C_{1-6}$ alkyl, $C_{3-6}$ cycloalkyl and 5- to 6-membered heterocyclic group containing 1, 2 or 3 N or O atoms, wherein said $C_{1-6}$ alkyl, $C_{3-6}$ cycloalkyl and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively, $R_4$ and $R_5$ are bonded together to form a 5- to 6-membered ring containing 1, 2 or 3 atoms independently selected from N, S and O, wherein the 5- to 6-membered ring containing 1, 2 or 3 atoms independently selected from N, S or O is optionally substituted with 1, 2 or 3 R groups;

$R_9$ and $R_{10}$ are bonded together to form ring A, and the structural unit

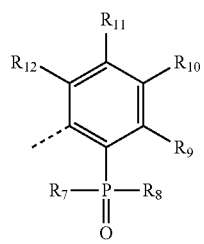

is not selected from:

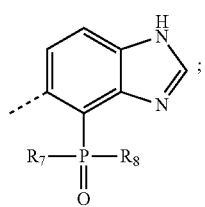

or alternatively $R_{10}$ and $R_{11}$ are bonded together to form ring A;

or alternatively $R_{11}$ and $R_{12}$ are bonded together to form ring A;

ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_6$ is selected from H, halogen, CN, OH, $NH_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, wherein said 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$, or $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, and 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— or —N(R)C(=O)N(R)—;

in any one of the cases as described above, the number of the heteroatom or heteroatom group is independently selected from 1, 2 or 3.

In some embodiments of the present application, the above compound represented by formula (I') or the pharmaceutically acceptable salt thereof is selected from formula (I),

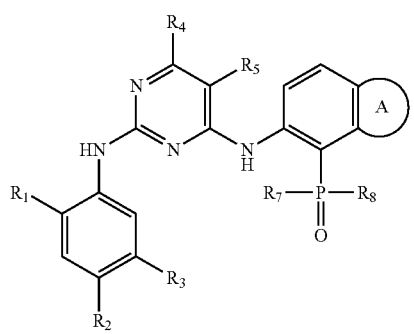

wherein,
ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

and the structural unit

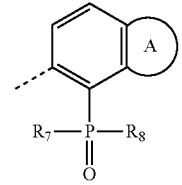

is not selected from:

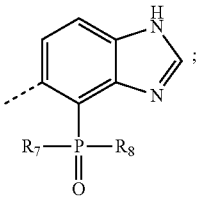

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy or $C_{3-6}$ cycloalkyloxy, —OC(=O)$NH_2$, —OC(=O)NHR, —OC(=O)NRR, —NRC(=O)OR, —NHC(=O)OR, —NHC(=O)OH, —O(CH$_2$)$_n$NR$_a$R$_b$, $C_{1-6}$ alkyl, $C_{3-6}$ cycloalkyl and 5- to 6-membered heterocyclic group containing 1, 2 or 3 N or O atoms, wherein said $C_{1-6}$ alkyl, $C_{3-6}$ cycloalkyl and 5- to 6-membered heterocyclic group containing 1, 2 or 3 N or O atoms are optionally substituted with 1, 2 or 3 R groups;

n is selected from 0, 1, 2 and 3;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring is optionally substituted with 1, 2 or 3 R groups;

each $R_6$ is independently selected from H, halogen, CN, OH, $NH_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, $C_{3-6}$ heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CF_2H$ and $CFH_2$;

"hetero" represents a heteroatom or a hetero atom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— or —N(R)C(=O)N(R)—;

in any one of the cases as described above, the number of the heteroatom or heteroatom group is each independently selected from 1, 2 or 3.

In some embodiments of the present application, the compound represented by the above formula (I') or the pharmaceutically acceptable salt thereof is selected from formula ($I_a$),

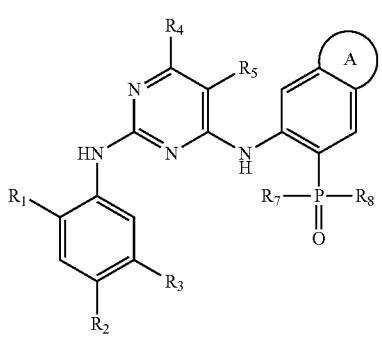

($I_a$)

wherein, ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)N(R)$_2$, —NRC(=O)OR, —NHC(=O)OR, —NHC(=O)OH, —O($CH_2$)$_n$$NR_aR_b$, $C_{1-6}$ alkyl, $C_{3-6}$ cycloalkyl and 5- to 6-membered heterocyclic group containing 1, 2 or 3 N or O atoms, wherein said $C_{1-6}$ alkyl, $C_{3-6}$ cycloalkyl, and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring containing 1, 2 or 3 atoms independently selected from N, S or O is optionally substituted with 1, 2 or 3 R groups;

$R_6$ is selected from H, halogen, CN, OH, $NH_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$, or $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is each independently selected from 1, 2 or 3.

In some embodiments of the present application, the compound represented by the above formula (I') or the pharmaceutically acceptable salt thereof is selected from formula ($I_b$),

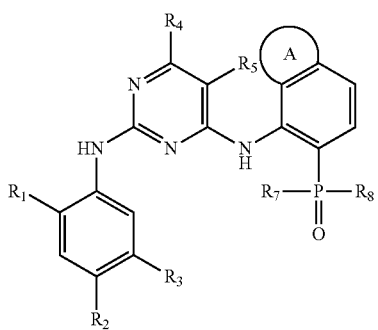

(I$_b$)

wherein, ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)N(R)$_2$, —NRC(=O)OR, —NHC(=O)OR, —NHC(=O)OH, —O($CH_2$)$_n$N$R_aR_b$, $C_{1-6}$ alkyl, $C_{3-6}$ cycloalkyl and 5- to 6-membered heterocyclic group containing 1, 2 or 3 N or O atoms, wherein said $C_{1-6}$ alkyl, $C_{3-6}$ cycloalkyl, and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring containing 1, 2 or 3 atoms independently selected from N, S or O is optionally substituted with 1, 2 or 3 R groups;

$R_6$ is selected from H, halogen, CN, OH, $NH_2$, $C_{1-6}$ alkyl, $C_{1-6}$ heteroalkyl, =O and =S; $R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$, or $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is each independently selected from 1, 2 or 3.

In some embodiments of the present application, in formula (I'), the above R is selected from F, Cl, Br, I, CN, OH, $NH_2$, $CH_3$, $CH_3CH_2$, $CH_3CH_2CH_2$, $(CH_3)_2CH$, $CH_3O$, $(CH_3)_2N$,

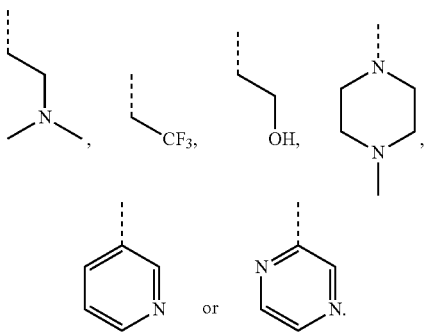

or

In some embodiments of the present application, in the formula (I'), the above $R_1$ is selected from H, halogen, $C_{1-3}$ alkyl and $C_{1-3}$ heteroalkyl, $C_{2-5}$ alkenyloxy or $C_{4-6}$ cycloalkyloxy, wherein said $C_{1-3}$ alkyl, $C_{1-3}$ heteroalkyl, $C_{2-5}$ alkenyloxy and $C_{4-6}$ cycloalkyloxy are optionally substituted with 1, 2 or 3 R groups.

In some embodiments of the present application, in the formula (I'), the above $R_1$ is selected from H, F, Cl, Br, I, $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

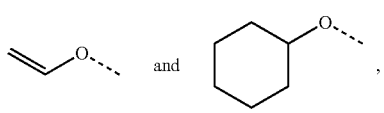

wherein said CH$_3$, CH$_3$CH$_2$, CH$_3$CH$_2$CH$_2$, (CH$_3$)$_2$CH, CH$_3$O, CH$_3$CH$_2$O, CH$_3$CH$_2$CH$_2$O, (CH$_3$)$_2$CHO,

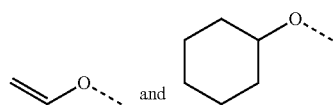

are optionally substituted with 1, 2 or 3 R groups.

In some embodiments of the present application, in formula (I'), the above R$_2$ is selected from H, halogen, CN, OH, NO$_2$, NH$_2$, C$_{3-12}$ cycloalkyl and 3- to 12-membered heterocycloalkyl, wherein said NH$_2$, C$_{3-12}$ cycloalkyl and 3- to 12-membered heterocycloalkyl are optionally substituted with 1, 2 or 3 R groups.

In some embodiments of the present application, in formula (I'), R$_2$ is selected from H, halogen, CN, OH, NH$_2$, NO$_2$, —NHR, —N(R)$_2$,

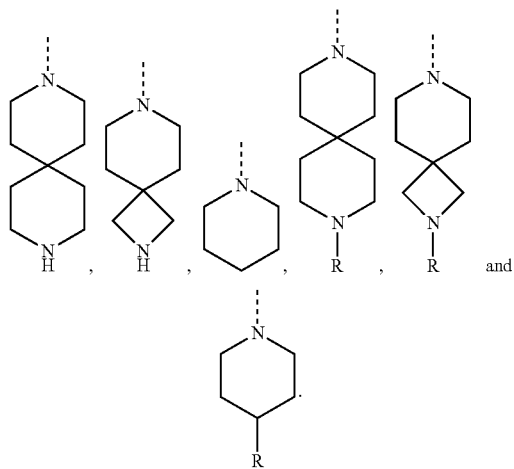

In some embodiments of the present application, in formula (I'), the above R$_2$ is selected from H, F, Cl, Br, CN, OH, NH$_2$, NO$_2$,

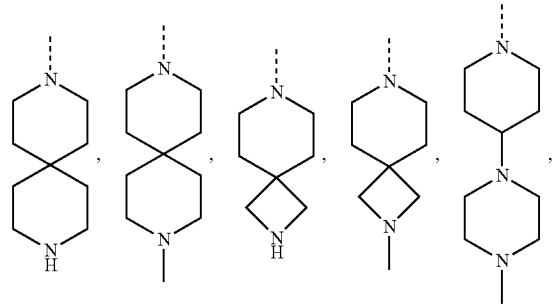

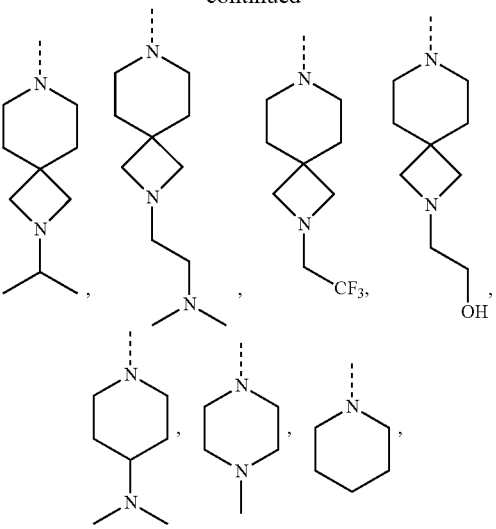

—NHCH$_2$CH$_3$, —NHCH$_3$, —N(CH$_3$)$_2$ and

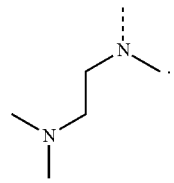

In some embodiments of the present application, in formula (I'), the above R$_6$ is selected from H, F, Cl, Br, CN, OH, NH$_2$, CH$_3$, CH$_3$CH$_2$, CH$_3$CH$_2$CH$_2$, (CH$_3$)$_2$CH, CH$_3$O, =S and =O.

In some embodiments of the present application, in formula (I'), when R$_9$ and R$_{10}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with R$_6$.

In some embodiments of the present application, in formula (I'), when R$_9$ and R$_{10}$ are bonded together to form ring A, the structural unit

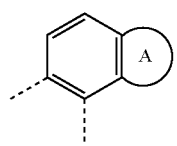

is selected from

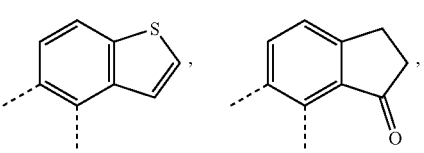

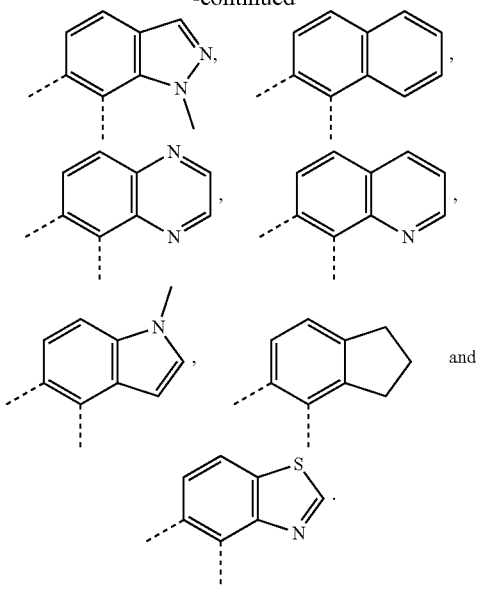

In some embodiments of the present application, in formula (I'), when $R_{10}$ and $R_{11}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$.

In some embodiments of the present application, in formula (I'), when $R_{10}$ and $R_{11}$ are bonded together to form ring A, the structural unit

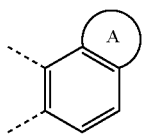

is selected from

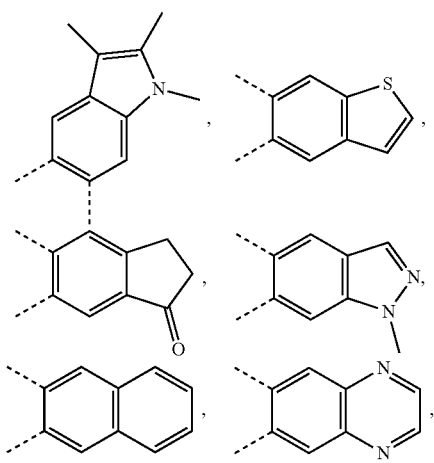

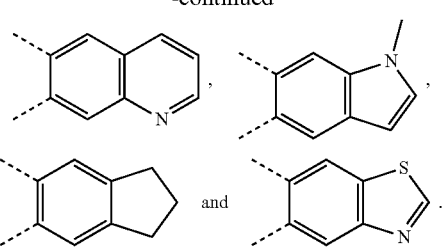

In some embodiments of the present application, in formula (I'), when $R_{11}$ and $R_{12}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$.

In some embodiments of the present application, in formula (I'), when $R_{11}$ and $R_{12}$ are bonded together to form ring A, the structural unit is selected from

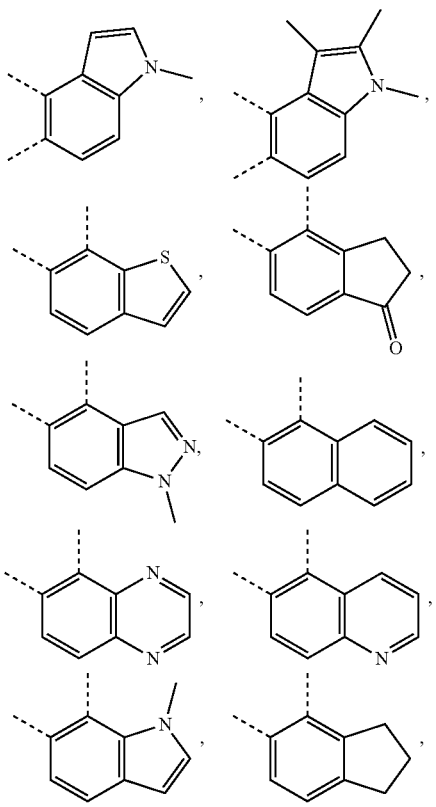

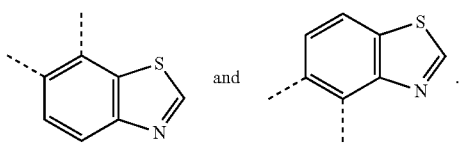 and

In some embodiments of the present application, in formula (I'), the above $R_a$ and $R_b$ are each independently selected from H, $CH_3$, $CH_3CH_2$ and $—S(=O)_2CH_3$, wherein said $CH_3$, $CH_3CH_2$, and $—S(=O)_2CH_3$ are optionally substituted with 1, 2 or 3 R groups.

In some embodiments of the present application, in formula (I'), the above $R_a$ and $R_b$ are each independently selected from H,

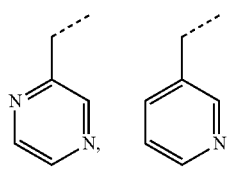

and $—S(=O)_2CH_3$.

In some embodiments of the present application, in formula (I'), the above $R_3$ is selected from

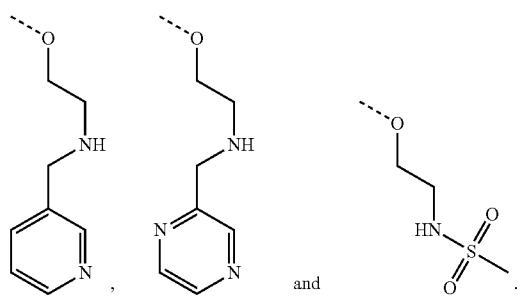

In some embodiments of the present application in formula (I'), the above $R_3$ is selected from H, F, Cl, Br, $CH_3$, $CH_3CH_2$ and

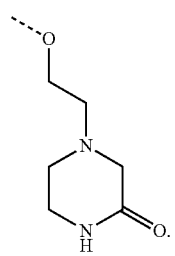

In some embodiments of the present application, in formula (I'), the above $R_5$ is selected from H, F, Cl, Br, I, CN, $CH_3$, $CH_3CH_2$, $CH_3CH_2CH_2$, $(CH_3)_2CH$,

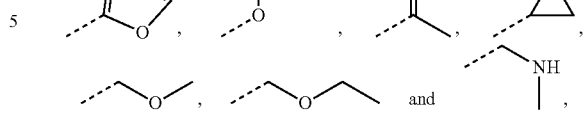

wherein said $CH_3$, $CH_3CH_2$, $CH_3CH_2CH_2$, $(CH_3)_2CH$,

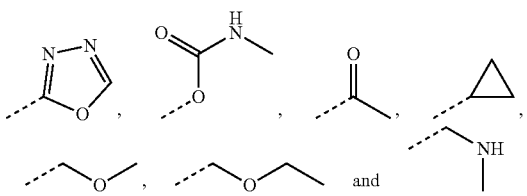

are optionally substituted with 1, 2 or 3 R groups.

In some embodiments of the present application, in formula (I'), the above $R_5$ is selected from H, Cl, Br, CN, $CH_3$, $CH_3CH_2$, $CH_3CH_2CH_2$, $(CH_3)_2CH$,

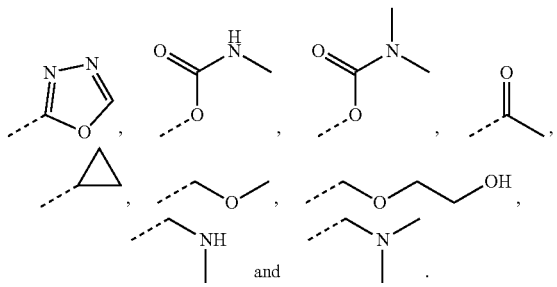

In some embodiments of the present application, in formula (I'), the above structural unit

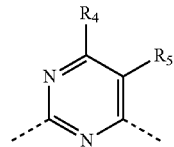

is selected from

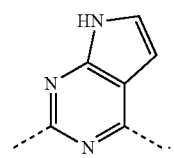

In some embodiments of the present application, in formula (I'), the above $R_7$ and $R_8$ are each independently selected from H or $CH_3$.

In some embodiments of the present application, in formula (I'), the above R is selected from F, Cl, Br, I, CN, OH, $NH_2$, $CH_3$, $CH_3CH_2$, $CH_3CH_2CH_2$, $(CH_3)_2CH$, $CH_3O$, $(CH_3)_2N$,

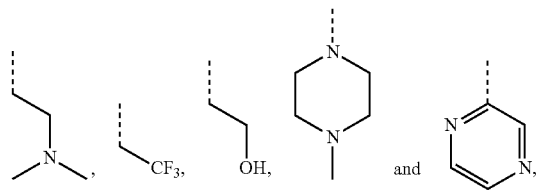

and other variables are as defined above.

In some embodiments of the present application, in formula (I'), the above $R_1$ is selected from H, halogen, $C_{1-3}$ alkyl and $C_{1-3}$ heteroalkyl, $C_{2-5}$ alkenyloxy and $C_{4-6}$ cycloalkyloxy, wherein said $C_{1-3}$ alkyl, $C_{1-3}$ heteroalkyl, $C_{2-5}$ alkenyloxy, and $C_{4-6}$ cycloalkyloxy are optionally substituted with 1, 2 or 3 R groups, and other variables are as defined above.

In some embodiments of the present application, in formula (I'), the above $R_1$ is selected from H, F, Cl, Br, I, $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

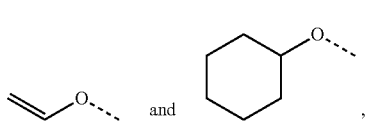

wherein said $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

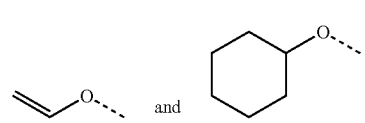

are optionally substituted with 1, 2 or 3 R groups, and other variables are as defined above.

In some embodiments of the present application, in formula (I'), the above $R_2$ is selected from H, halogen, CN, OH, $NO_2$, $NH_2$, $C_{3-12}$ cycloalkyl and 3- to 12-membered heterocycloalkyl, wherein said $NH_2$, $C_{3-12}$ cycloalkyl and 3- to 12-membered heterocycloalkyl are optionally substituted with 1, 2 or 3 R groups, and other variables are as defined above.

In some embodiments of the present application, in formula (I'), the above $R_2$ is selected from H, halogen, CN, OH, $NH_2$, $NO_2$, —NHR, —N(R)$_2$,

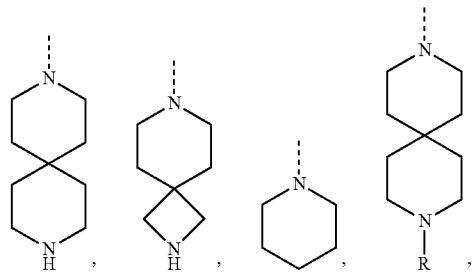

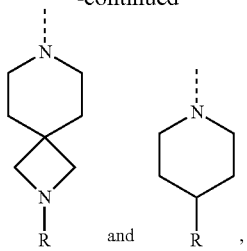

and other variables are as defined above.

In some embodiments of the present application, in formula (I'), the above $R_2$ is selected from H, F, Cl, Br, CN, OH, $NH_2$, $NO_2$,

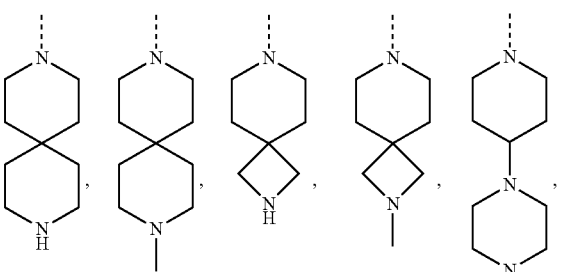

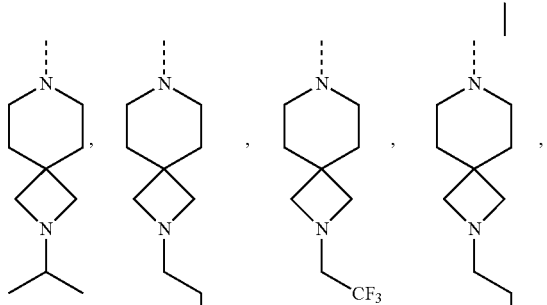

—NHCH$_2$CH$_3$, —NHCH$_3$, —N(CH$_3$)$_2$ and

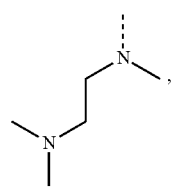

and other variables are as defined above.

In some embodiments of the present application, in formula (I'), the above $R_6$ is selected from H, F, Cl, Br, CN, OH, $NH_2$, $CH_3$, $CH_3CH_2$, $CH_3CH_2CH_2$, $(CH_3)_2CH$, $CH_3O$, =S and =O, and other variables are as defined above.

In some embodiments of the present application, in formula (I'), when $R_9$ and $R_{10}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl areis optionally substituted with $R_6$, and other variables are as defined above.

In some embodiments of the present application, in formula (I'), when $R_9$ and $R_{10}$ are bonded together to form ring A, the structural unit

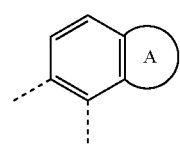

is selected from

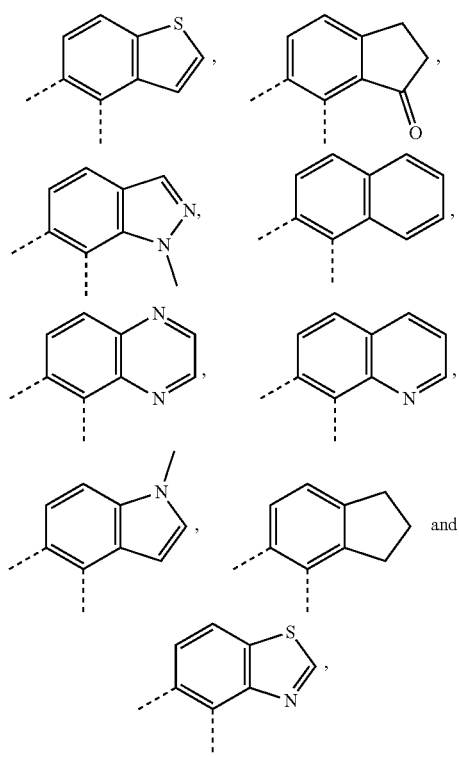

and other variables are as defined above.

In some embodiments of the present application, in formula (I'), when $R_{10}$ and $R_{11}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$, and other variables are as defined above.

In some embodiments of the present application, in formula (I'), when $R_{10}$ and $R_{11}$ are bonded together to form ring A, the structural unit

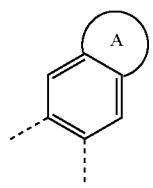

is selected from

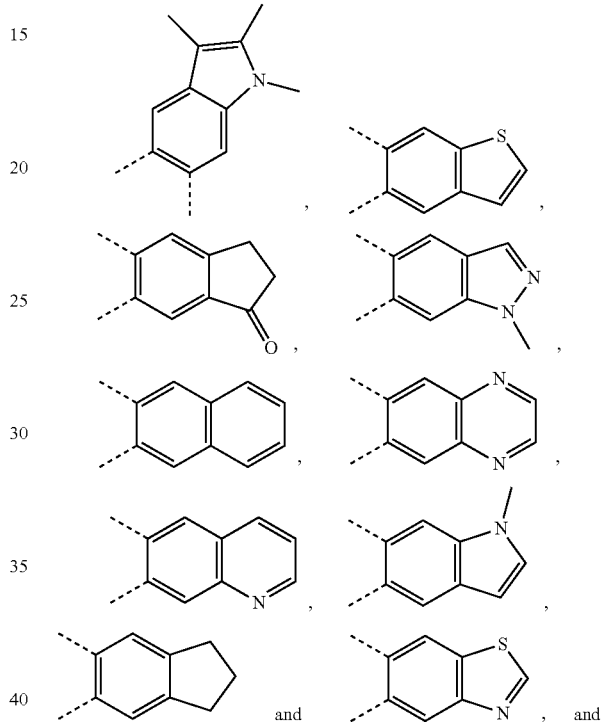

and other variables are as defined above.

In some embodiments of the present application, in formula (I'), when $R_{11}$ and $R_{12}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, imidazolyl, isothiazolyl and pyrrolyl are optionally substituted with $R_6$, and other variables are as defined above.

In some embodiments of the present application, in formula (I'): when $R_{11}$ and $R_{12}$ are bonded together to form ring A, the structural unit

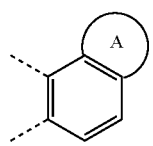

is selected from

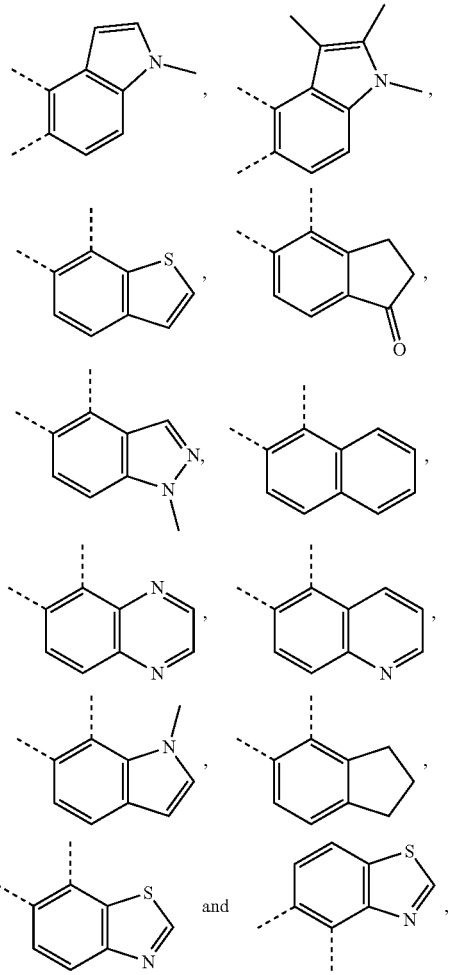

and other variables are as defined above.

In some embodiments of the present application, in formula (I'), the above $R_a$ and $R_b$ are each independently selected from H, $CH_3$, $CH_3CH_2$, and —S(=O)$_2$CH$_3$, wherein said $CH_3$, $CH_3CH_2$, and —S(=O)$_2$CH$_3$ are optionally substituted with 1, 2 or 3 R groups, and other variables are as defined above.

In some embodiments of the present application in formula (I'), the above $R_a$ and $R_b$ are each independently selected from H,

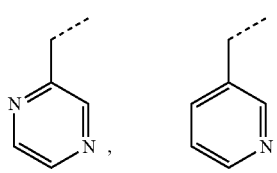

and —S(=O)$_2$CH$_3$, and other variables are as defined above.

In some embodiments of the present application, in formula (I'), the above $R_3$ is selected from

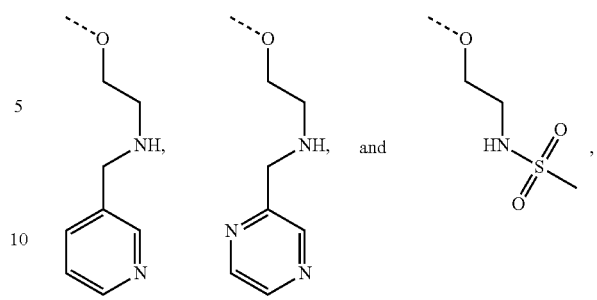

and other variables are as defined above.

In some embodiments of the present application, in formula (I'), the above $R_3$ is selected from H, F, Cl, Br, $CH_3$, $CH_3CH_2$, $(CH_3)_2CH$,

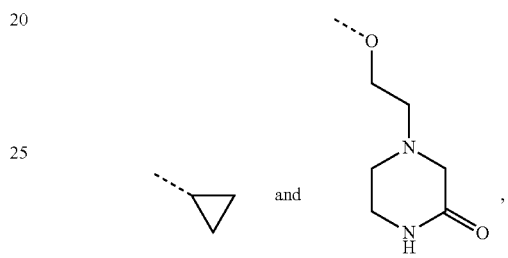

and other variables are as defined above.

In some embodiments of the present application, in formula (I'), the above $R_5$ is selected from H, F, Cl, Br, I, CN, $CH_3$, $CH_3CH_2$, $CH_3CH_2CH_2$, $(CH_3)_2CH$,

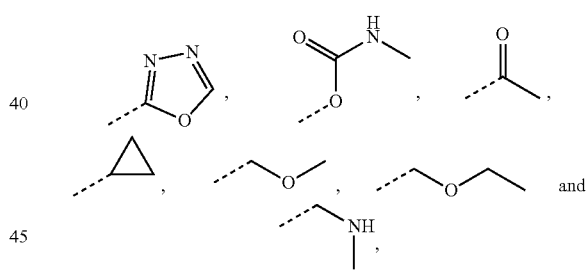

wherein said $CH_3$, $CH_3CH_2$, $CH_3CH_2CH_2$, $(CH_3)_2CH$,

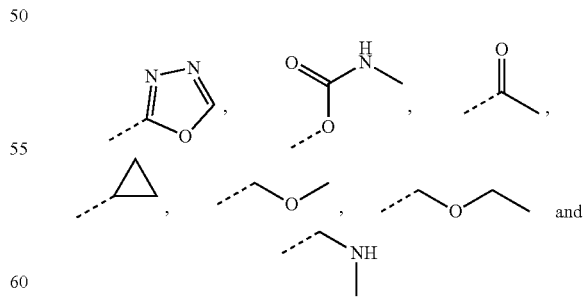

are optionally substituted with 1, 2 or 3 R groups, and other variables are as defined above.

In some embodiments of the present application, in formula (I'), the above $R_5$ is selected from H, Cl, Br, CN, $CH_3$, $CH_3CH_2$, $CH_3CH_2CH_2$, $(CH_3)_2CH$,

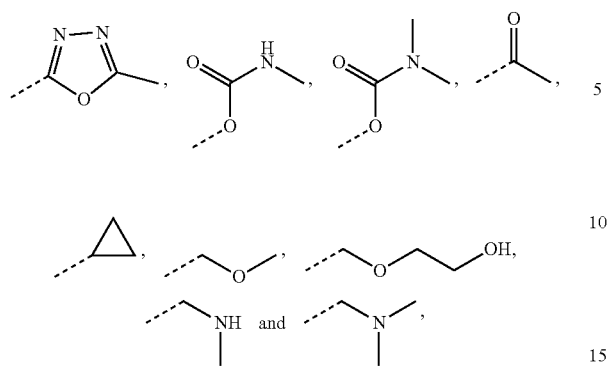

and others variables are as defined above.

In some embodiments of the present application, in formula (I'), the above structural unit

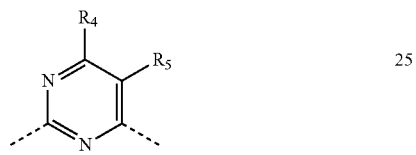

is selected from

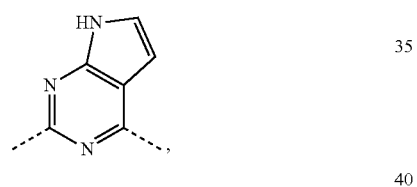

and other variables are as defined above.

In some embodiments of the present application, in formula (I'), the above $R_7$ and $R_8$ are each independently selected from H or $CH_3$, and other variables are as defined above.

In some embodiments of the present application, in formula (I'), the above compound or the pharmaceutically acceptable salt thereof is selected from

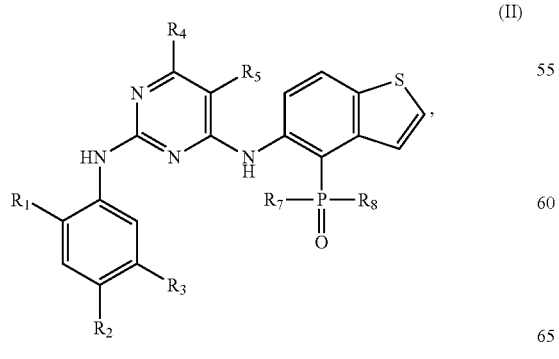

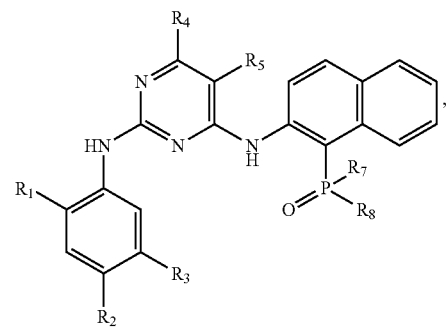

(III)

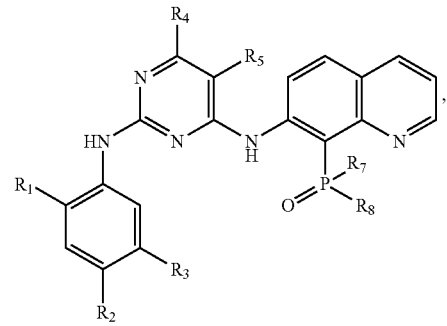

(IV)

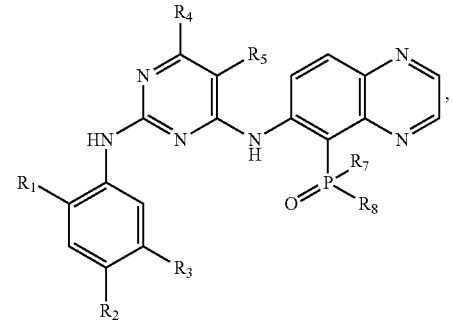

(V)

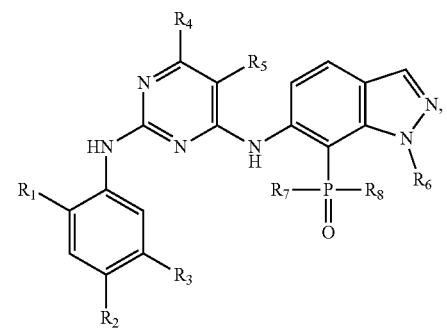

(VI)

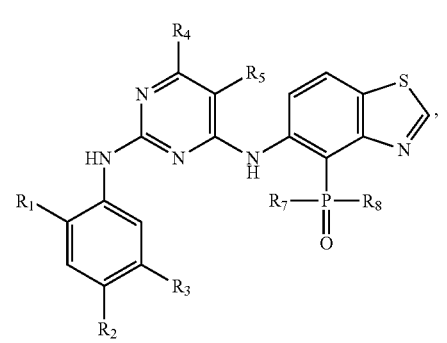

(VII)

-continued

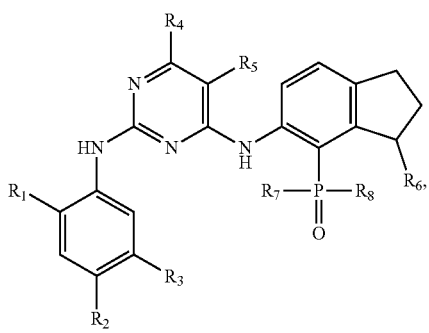
(VIII)

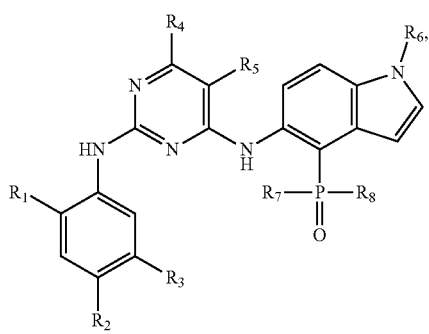
(IX)

wherein $R_1$, $R_2$, $R_3$, $R_4$, $R_5$, $R_6$, $R_7$ and $R_8$ are as defined above.

The present application provides a compound represented by formula (I") or a pharmaceutically acceptable salt thereof,

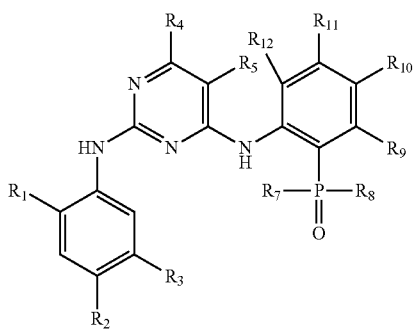
(I")

wherein, $R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)N(R)$_2$, —NRC(=O)OR, —NHC(=O)OR, —NHC(=O)OH, —O(CH$_2$)$_n$$R_a$$R_b$, $C_{1-6}$ alkyl and 5- to 6-membered heterocyclic group containing 1, 2 or 3 N or O atoms, wherein said $C_{1-6}$ alkyl and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring containing 1, 2 or 3 atoms independently selected from N, S or O is optionally substituted with 1, 2 or 3 R groups;

$R_9$ and $R_{10}$ are bonded together to form ring A;

or alternatively $R_{10}$ and $R_{11}$ are bonded together to form ring A;

or alternatively $R_{11}$ and $R_{12}$ are bonded together to form ring A;

ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_6$ is selected from H, halogen, CN, OH, $NH_2$, $C_{1-6}$ alkyl, $C_{1-6}$ heteroalkyl, =O and =S; $R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$, or $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is each independently selected from 1, 2 or 3.

In some embodiments of the present application, the compound represented by the above formula (I″) or the pharmaceutically acceptable salt thereof is selected from formula (I),

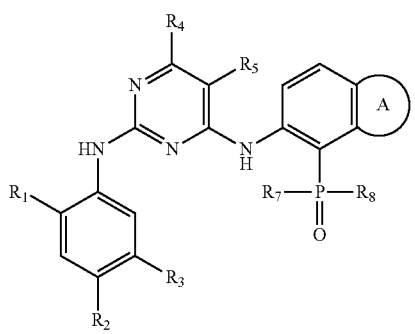

wherein, ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$; and the structural unit

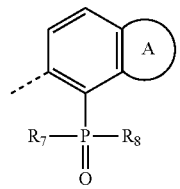

is not selected from:

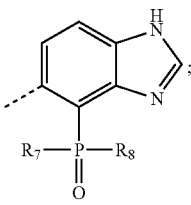

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)NRR, —NRC(=O)OR, —NHC(=O)OR, —NHC(=O)OH, —O(CH$_2$)$_n$NR$_a$R$_b$, $C_{1-6}$ alkyl and 5- to 6-membered heterocyclic group containing 1, 2 or 3 N or O atoms, wherein said $C_{1-6}$ alkyl and 5- to 6-membered heterocyclic group containing 1, 2 or 3 N or O atoms are optionally substituted with 1, 2 or 3 R groups;

n is selected from 0, 1, 2 or 3;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring is optionally substituted with 1, 2 or 3 R groups;

each $R_6$ is independently selected from H, halogen, CN, OH, $NH_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl, wherein the $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CF_2H$ and $CFH_2$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is independently selected from 1, 2 or 3.

In some embodiments of the present application, the compound represented by the above formula (I″) or the pharmaceutically acceptable salt thereof is selected from formula ($I_a$),

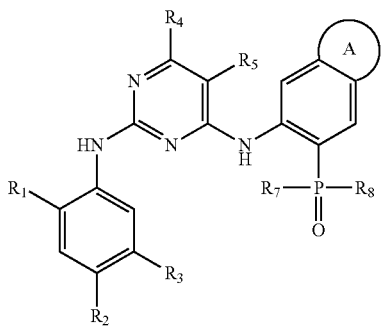

(I_a)

wherein, ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, pheny and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)N(R)$_2$, —NRC(=O)OR, —NHC(=O)OR, —NHC(=O)OH, —O(CH$_2$)$_n$NR$_a$R$_b$, $C_{1-6}$ alkyl and 5- to 6-membered heterocyclic group containing 1, 2 or 3 N or O atoms, wherein said $C_{1-6}$ alkyl and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, and said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively, $R_4$ and $R_5$ are bonded together to form a 5- to 6-membered ring containing 1, 2 or 3 atoms independently selected from N, S or O, wherein the 5- to 6-membered ring containing 1, 2 or 3 atoms independently selected from N, S or O is optionally substituted with 1, 2 or 3 R groups;

$R_6$ is selected from H, halogen, CN, OH, $NH_2$, $C_{1-6}$ alkyl, $C_{1-6}$ heteroalkyl, =O and =S; $R_7$ and $R_8$ are each independently selected from H or $C_{1-6}$ alkyl;

or alternatively $R_7$ and $R_8$ are bonded together to form a 5- to 6-membered heterocyclic ring, wherein said 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CF_2H$ and $CFH_2$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is each independently selected from 1, 2 or 3.

In some embodiments of the present application, the compound represented by the above formula (I") or the pharmaceutically acceptable salt thereof is selected from formula ($I_b$),

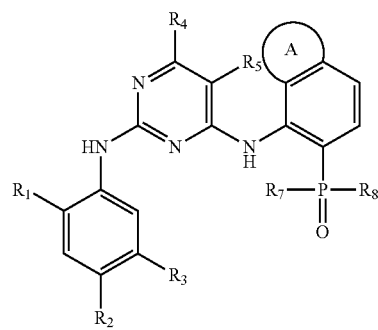

($I_b$)

wherein, ring A is selected from phenyl, 5- to 6-membered heteroaryl, 5- to 7-membered heterocycloalkyl, and $C_{5-7}$ cycloalkyl, wherein said phenyl, 5- to 6-membered heteroaryl, 5- to 7-membered heterocycloalkyl and $C_{5-7}$ cycloalkyl are optionally substituted with $R_6$;

$R_1$ is selected from H, halogen, $C_{1-6}$ alkyl, $C_{1-6}$ heteroalkyl, $C_{2-6}$ alkenyloxy and $C_{3-6}$ cycloalkyloxy, wherein said $C_{1-6}$ alkyl, $C_{1-6}$ heteroalkyl, $C_{2-6}$ alkenyloxy, and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)NH$_2$, —OC(=O)NHR, —OC(=O)N(R)$_2$, —NRC(=O)OR, —NHC(=O)OR, —NHC(=O)OH, —O(CH$_2$)$_n$NR$_a$R$_b$, $C_{1-6}$ alkyl and 5- to 6-membered heterocyclic group containing 1, 2 or 3 N or O atoms, wherein said $C_{1-6}$ alkyl and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, wherein said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, NH$_2$, $C_{1-4}$ alkyl, $C_{1-4}$ heteroalkyl, $C_{3-6}$ cycloalkyl, phenyl and 5- to 6-membered heterocyclic group, wherein said NH$_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

or alternatively $R_4$ and $R_5$ are bonded together to form a 5- to 6-membered ring containing 1, 2 or 3 atoms independently selected from N, S or O, wherein the 5- to 6-membered ring containing 1, 2 or 3 atoms independently selected from N, S or O is optionally substituted with 1, 2 or 3 R groups;

$R_6$ is selected from H, halogen, CN, OH, NH$_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, wherein the 5- to 6-membered heterocyclic ring is optionally substituted with 1, 2 or 3 R groups;

R is selected from halogen, CN, OH, NH$_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl and 5- to 6-membered heteroaryl are optionally substituted with 1, 2 or 3 R' groups;

R' is selected from H, F, Cl, Br, I, CN, OH, NH$_2$, CH$_3$, CH$_3$CH$_2$, CH$_3$CH$_2$CH$_2$, (CH$_3$)$_2$CH, CH$_3$O, CF$_3$, CF$_2$H and CFH$_2$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, or 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatom group is each independently selected from 1, 2 or 3.

In some embodiments of the present application, in formula (I"), the above R is selected from F, Cl, Br, I, CN, OH, NH$_2$, CH$_3$, CH$_3$CH$_2$, CH$_3$CH$_2$CH$_2$, (CH$_3$)$_2$CH, CH$_3$O, (CH$_3$)$_2$N,

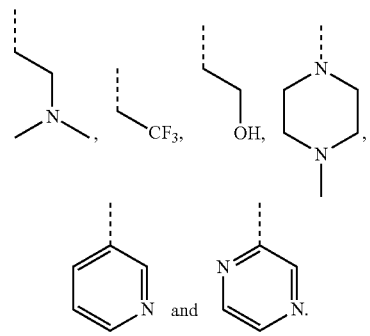

In some embodiments of the present application, in formula (I"), the above $R_1$ is selected from H, halogen, $C_{1-3}$ alkyl, $C_{1-3}$ heteroalkyl, $C_{2-5}$ alkenyloxy, and $C_{4-6}$ cycloalkyloxy, wherein said $C_{1-3}$ alkyl, $C_{1-3}$ heteroalkyl, $C_{2-5}$ alkenyloxy and $C_{4-6}$ cycloalkyloxy are optionally substituted with 1, 2 or 3 R groups.

In some embodiments of the present application, in formula (I"), the above $R_1$ is selected from H, F, Cl, Br, I, CH$_3$, CH$_3$CH$_2$, CH$_3$CH$_2$(CH$_3$)$_2$CH, CH$_3$O, CH$_3$CH$_2$O, CH$_3$CH$_2$CH$_2$O, (CH$_3$)$_2$CHO,

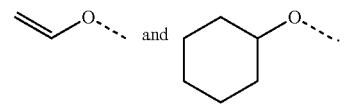

In some embodiments of the present application, in formula (I"), the above $R_2$ is selected from H, halogen, CN, OH, NO$_2$, NH$_2$, $C_{3-12}$ cycloalkyl and 3- to 12-membered heterocycloalkyl, wherein said NH$_2$, $C_{3-12}$ cycloalkyl and 3- to 12-membered heterocycloalkyl are optionally substituted with 1, 2 or 3 R groups.

In some embodiments of the present application, in formula (I"), the above $R_2$ is selected from H, halogen, CN, OH, NH$_2$, NO$_2$, —NHR, —N(R)$_2$,

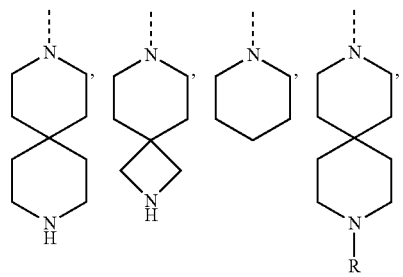

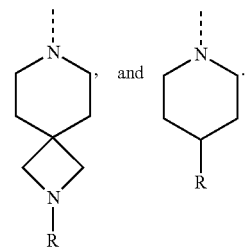

In some embodiments of the present application, in formula (I"), the above $R_2$ is selected from H, F, Cl, Br, CN, OH, $NH_2$, $NO_2$,

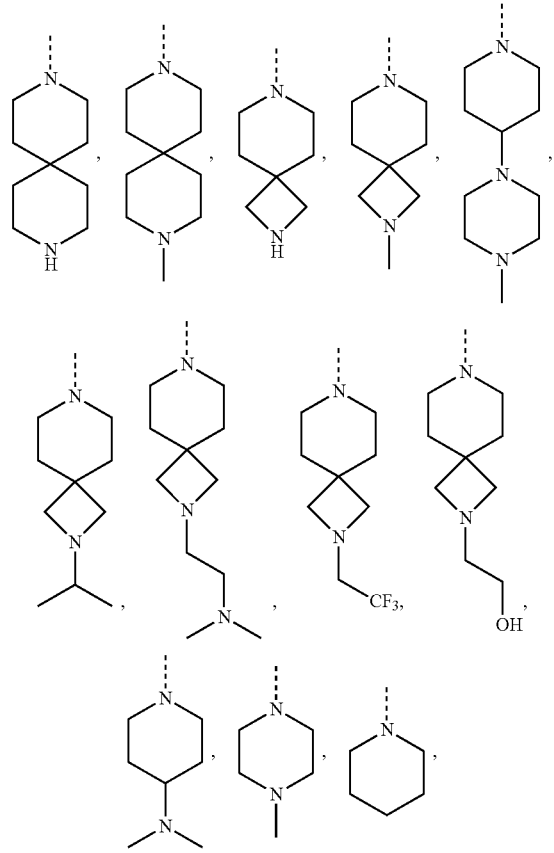

—$NHCH_2CH_3$, —$NHCH_3$, —$N(CH_3)_2$ and

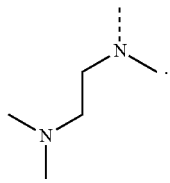

In some embodiments of the present application, in formula (I"), the above $R_6$ is selected from H, F, Cl, Br, CN, OH, $NH_2$, $CH_3$, $CH_3CH_2$, $CH_3CH_2CH_2$, $(CH_3)_2CH$, $CH_3O$, =S and =O.

In some embodiments of the present application, in formula (I"), when $R_9$ and $R_{10}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$.

In some embodiments of the present application, in formula (I"), when $R_9$ and $R_{10}$ are bonded together to form ring A, the structural unit

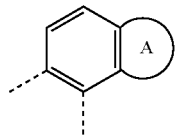

is selected from

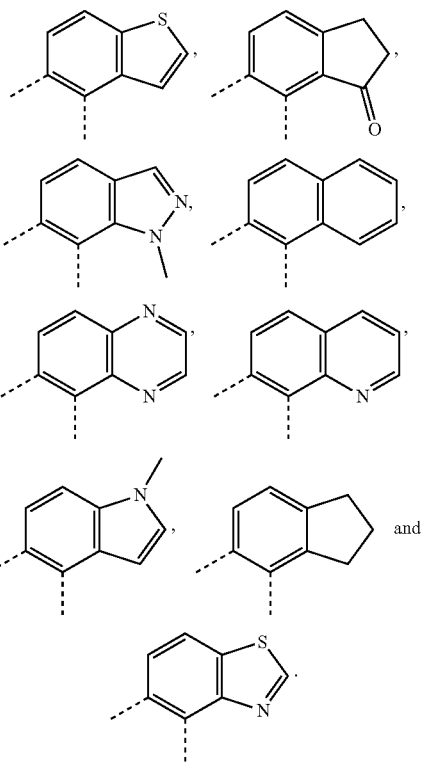

In some embodiments of the present application, in formula (I"), when $R_{10}$ and $R_{11}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$.

In some embodiments of the present application, in formula (I"), when $R_{10}$ and $R_{11}$ are bonded together to form ring A, the above structural unit

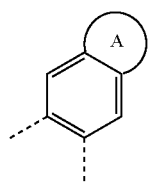

is selected from

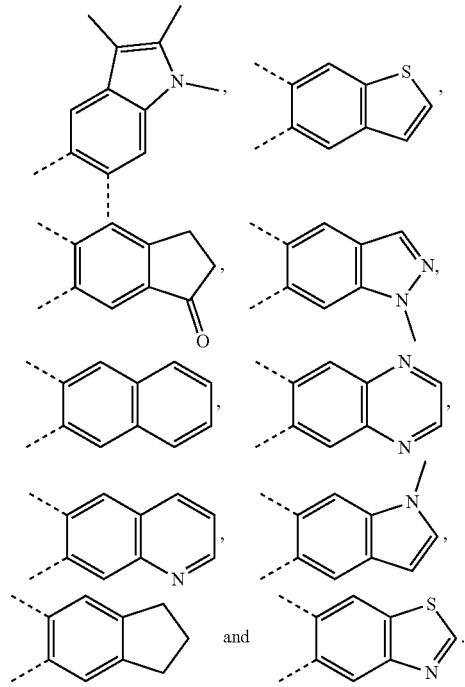

In some embodiments of the present application, in formula (I"), when $R_{11}$ and $R_{12}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$.

In some embodiments of the present application, in formula (I"), when $R_{11}$ and $R_{12}$ are bonded together to form ring A, the structural unit

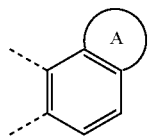

is selected from

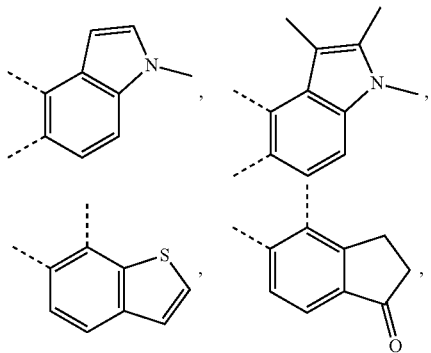

-continued

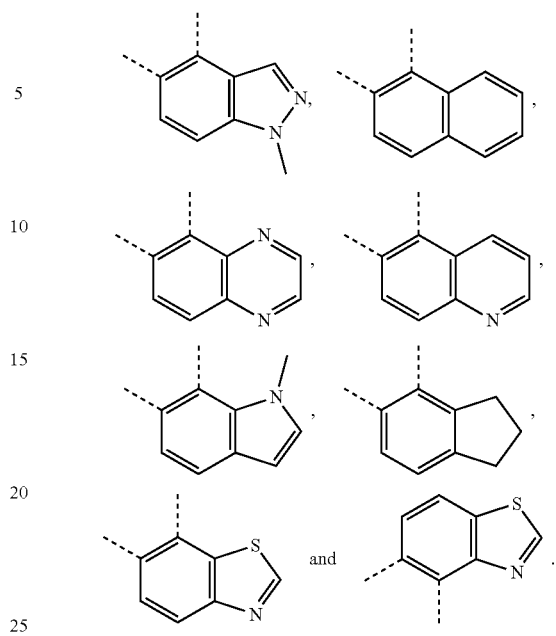

In some embodiments of the present application, in formula (I"), the above $R_a$ and $R_b$ are each independently selected from H, $CH_3$, $CH_3CH_2$, and $-S(=O)_2CH_3$, wherein said $CH_3$, $CH_3CH_2$, and $-S(=O)_2CH_3$ are optionally substituted with 1, 2 or 3 R groups.

In some embodiments of the present application, in formula (I"), the above $R_a$ and $R_b$ are each independently selected from H,

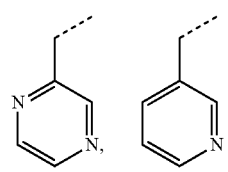

and $-S(=O)_2CH_3$.

In some embodiments of the present application, in formula (I"), the above $R_3$ is selected from

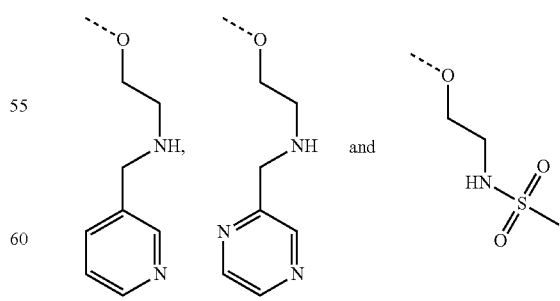

In some embodiments of the present application, in formula (I"), the above $R_3$ is selected from H, F, Cl, Br, $CH_3$, $CH_3CH_2$ and

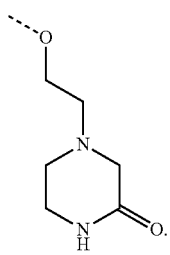

In some embodiments of the present application, in formula (I"), the above $R_5$ is selected from H, F, Cl, Br, I, CN, $CH_3$, $CH_3CH_2$, $CH_3CH_2CH_2$, $(CH_3)_2CH$,

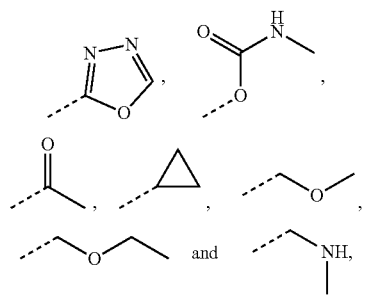

wherein said $CH_3$, $CH_3CH_2$, $CH_3CH_2CH_2$, $(CH_3)_2CH$,

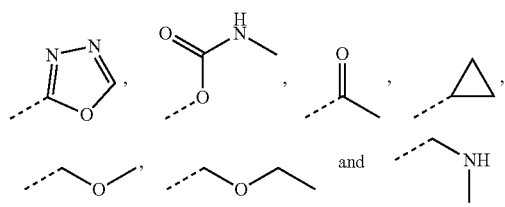

are optionally substituted with 1, 2 or 3 R groups.

In some embodiments of the present application, in formula (I"), the above $R_5$ is selected from H, Cl, Br, CN, $CH_3$, $CH_3CH_2$, $CH_3CH_2CH_2$, $(CH_3)_2CH$

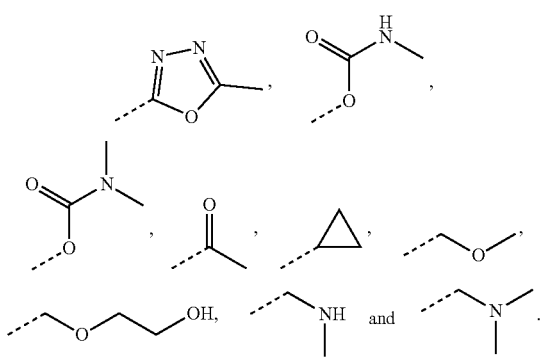

In some embodiments of the present application, in formula (I"), the above structural unit

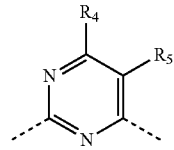

is selected from

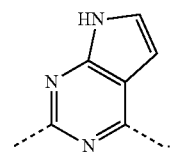

In some embodiments of the present application, in formula (I"), the above $R_7$ and $R_8$ are each independently selected from H or $CH_3$.

In some embodiments of the present application, in formula (I"), the above R is selected from F, Cl, Br, I, CN, OH, $NH_2$, $CH_3$, $CH_3CH_2$, $CH_3CH_2CH_2$, $(CH_3)_2CH$, $CH_3O$, $(CH_3)_2N$,

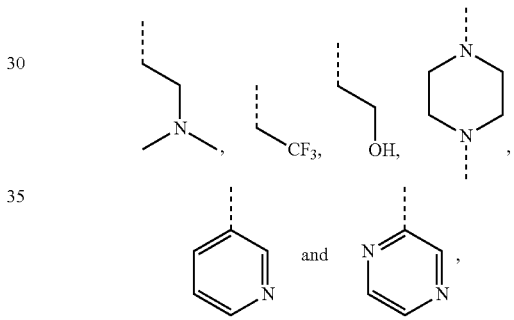

and other variables are as defined above.

In some embodiments of the present application, in formula (I"), the above $R_1$ is selected from H, halogen, $C_{1-3}$ alkyl, $C_{1-3}$ heteroalkyl, $C_{2-5}$ alkenyloxy, and $C_{4-6}$ cycloalkyloxy, wherein said $C_{1-3}$ alkyl, $C_{1-3}$ heteroalkyl, $C_{2-5}$ alkenyloxy, and $C_{4-6}$ cycloalkyloxy are optionally substituted with 1, 2 or 3 R groups, ad other variables are as defined above.

In some embodiments of the present application, in formula (I"), the above $R_1$ is selected from H, F, Cl, Br, I, $CH_3$, $CH_3CH_2$, $CH_3CH_2CH_2$, $(CH_3)_2CH$, $CH_3O$, $CH_3CH_2O$, $CH_3CH_2CH_2O$, $(CH_3)_2CHO$,

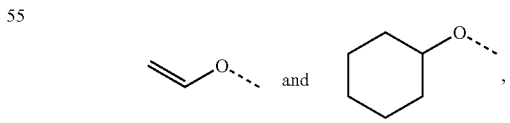

and other variables are as defined above.

In some of the present application, in formula (I"), the above $R_2$ is selected from H, halogen, CN, OH, $NO_2$, $NH_2$, $C_{3-12}$ cycloalkyl and 3- to 12-membered heterocycloalkyl, wherein said $NH_2$, $C_{3-12}$ cycloalkyl and 3- to 12-membered heterocycloalkyl are optionally substituted with 1, 2 or 3 R groups, and other variables are as defined above.

In some embodiments of the present application, in formula (I"), the above R₂ is selected from H, halogen, CN, OH, NH₂, NO₂, —NHR, —N(R)₂,

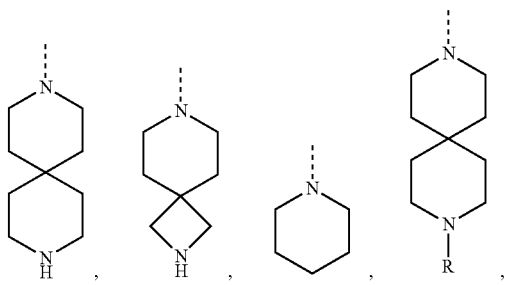

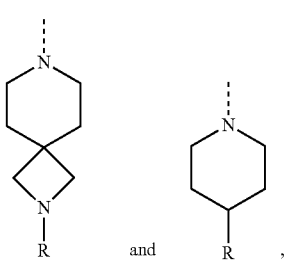

and other variables are as defined above.

In some embodiments of the present application, in formula (I"), the above R₂ is selected from H, F, Cl, Br, CN, OH, NH₂, NO₂,

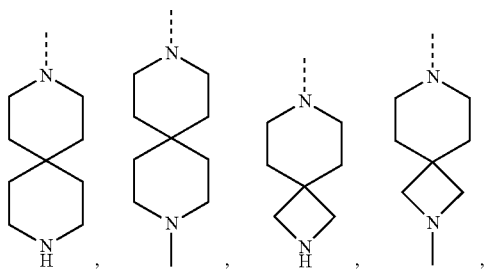

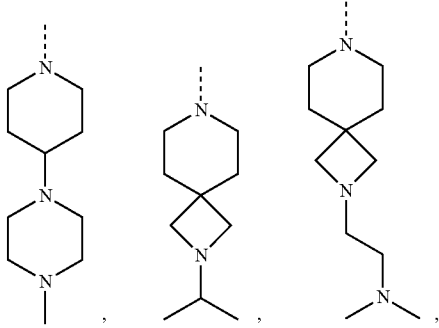

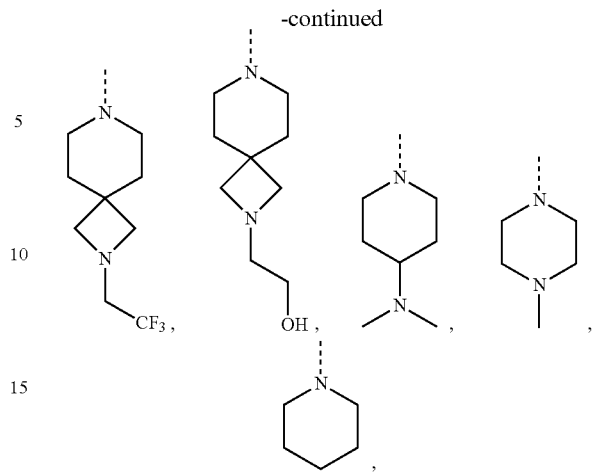

—NHCH₂CH₃, —NHCH₃, —N(CH₃)₂ and

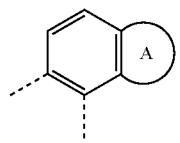

and other variables are as defined above.

In some embodiments of the present application, in formula (I"), the above R₆ is selected from H, F, Cl, Br, CN, OH, NH₂, CH₃, CH₃CH₂, CH₃CH₂CH₂, (CH₃)₂CH, CH₃O, =S and =O, and other variables are as defined above.

In some embodiments of the present application, in formula (I"), when R₉ and R₁₀ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with R₆, and other variables are as defined above.

In some embodiments of the present application, in formula (I"), when R₉ and R₁₀ are bonded together to form ring A, the structural unit

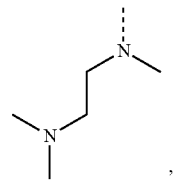

is selected from

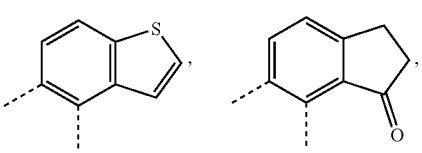

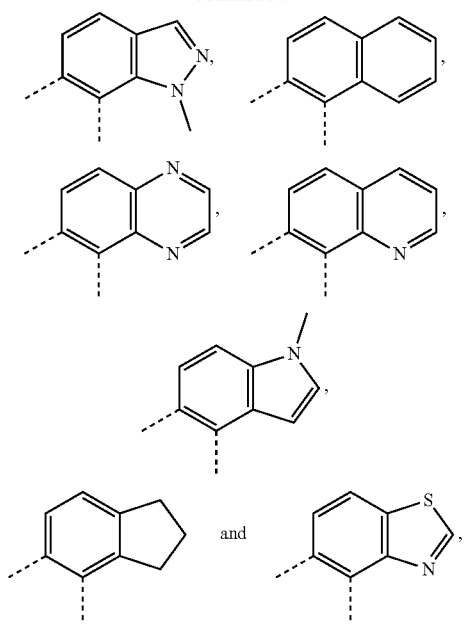

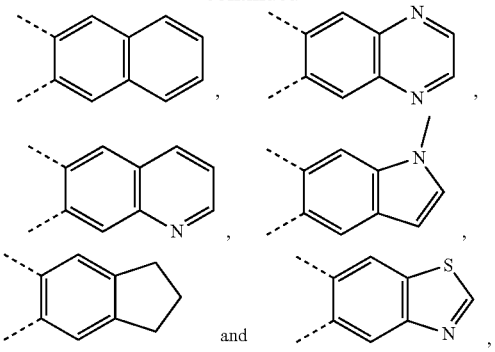

and other variables are as defined above.

In some embodiments of the present application, in formula (I''), when $R_{10}$ and $R_{11}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$, and other variables are as defined above.

In some embodiments of the present application, in formula (I''), when $R_{10}$ and $R_{11}$ are bonded together to form ring A, the structural unit

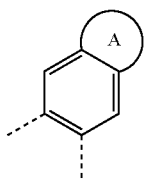

is selected from

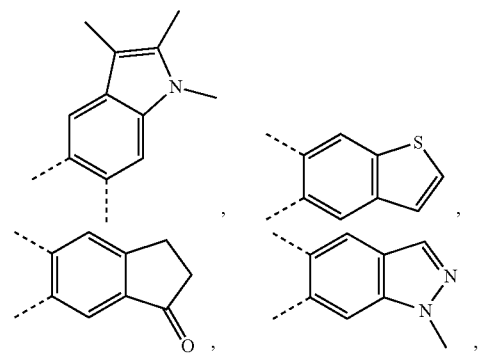

and other variables are as defined above.

In some embodiments of the present application, in formula (I''), when $R_{11}$ and $R_{12}$ are bonded together to form ring A, ring A is selected from phenyl, thienyl, pyridyl, pyrazinyl, pyrazolyl, cyclopentanonyl, cyclopentenyl, thiazolyl, isothiazolyl and pyrrolyl, wherein said phenyl, thienyl, pyridyl, pyrazinyl, pyrazolyl, cyclopentanonyl, cyclopentenyl, thiazolyl, isothiazolyl and pyrrolyl are optionally substituted with $R_6$, and other variables are as defined above.

In some embodiments of the present application, in formula (I''), when $R_{11}$ and $R_{12}$ are bonded together to form a ring A, the above structural unit

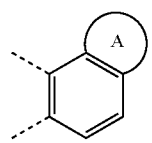

is selected from

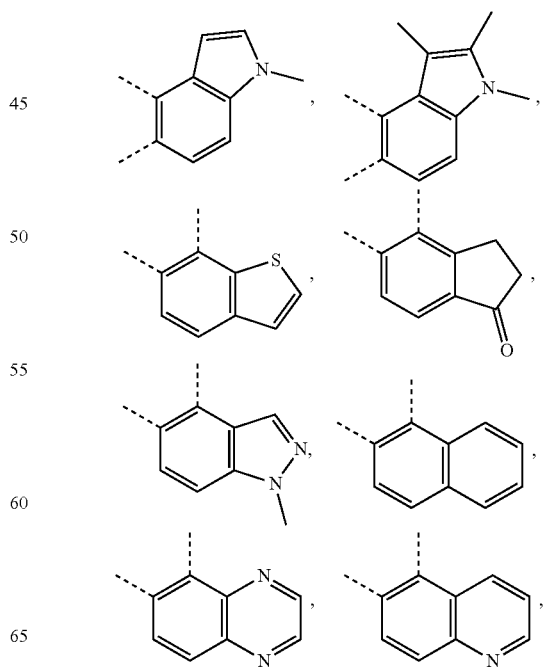

-continued

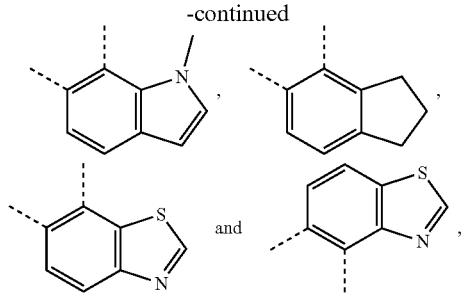

and other variables are as defined above.

In some embodiments of the present application, in formula (I"), the above $R_a$ and $R_b$ are each independently selected from H, $CH_3$, $CH_3CH_2$, and $—S(=O)_2CH_3$, wherein said $CH_3$, $CH_3CH_2$, and $—S(=O)_2CH_3$ are optionally substituted with 1, 2 or 3 R groups, and other variables are as defined above.

In some embodiments of the present application, in formula (I"), the above $R_a$ and $R_b$ are each independently selected from H,

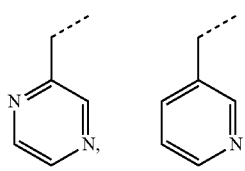

and $—S(=O)_2CH_3$, and other variables are as defined above.

In some embodiments of the present application, in formula (I"), the above $R_3$ is selected from

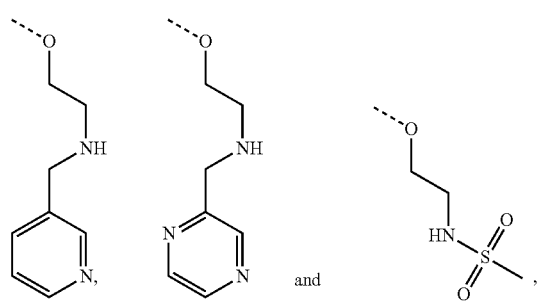

and other variables are as defined above.

In some embodiments of the present application, in formula (I"), the above $R_3$ is selected from H, F, Cl, Br, $CH_3$, $CH_3CH_2$ and

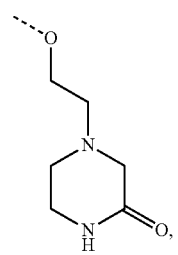

and other variables are as defined above.

In some embodiments of the present application, in formula (I"), the above $R_5$ is selected from H, F, Cl, Br, I, CN, $CH_3$, $CH_3CH_2$, $CH_3CH_2CH_2$, $(CH_3)_2CH$,

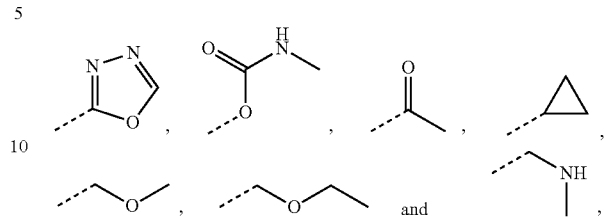

wherein said $CH_3$, $CH_3CH_2$, $CH_3CH_2CH_2$, $(CH_3)_2CH$,

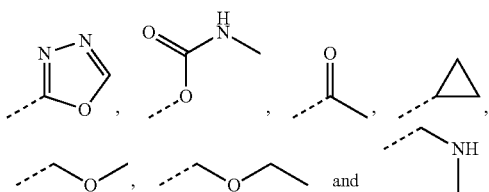

are optionally substituted with 1, 2 or 3 R groups, and other variables are as defined above.

In some embodiments of the present application, in formula (I"), the above $R_5$ is selected from H, Cl, Br, CN, $CH_3$, $CH_3CH_2$, $CH_3CH_2CH_2$, $(CH_3)_2CH$,

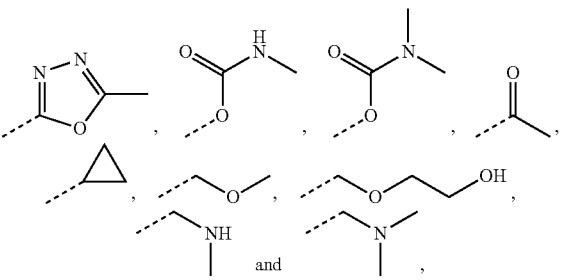

and other variables are as defined above.

In some embodiments of the present application, in formula (I"), the above structural unit

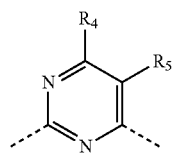

is selected from

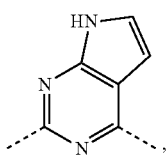

and other variables are as defined above.

In some embodiments of the present application, in formula (I"), the above $R_7$ and $R_8$ are each independently selected from H or $CH_3$, and other variables are as defined above.

In some embodiments of the present application, in formula (I"), the above compound or the pharmaceutically acceptable salt thereof is selected from

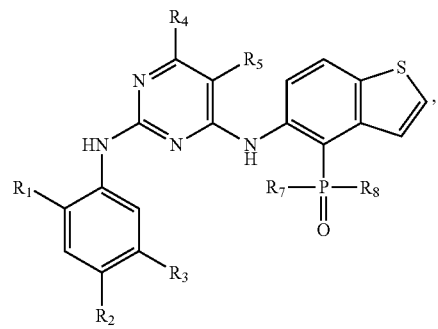
(II)

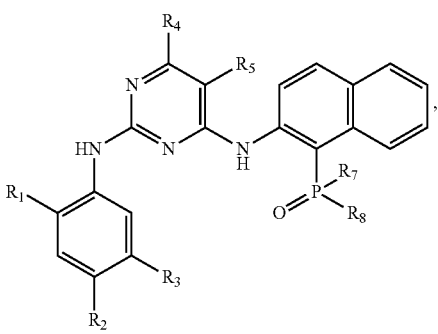
(III)

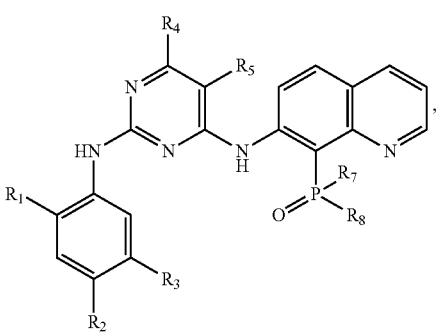
(IV)

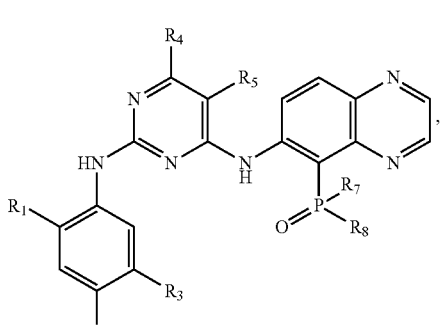
(V)

-continued

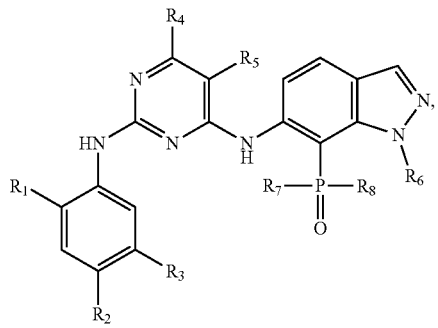
(VI)

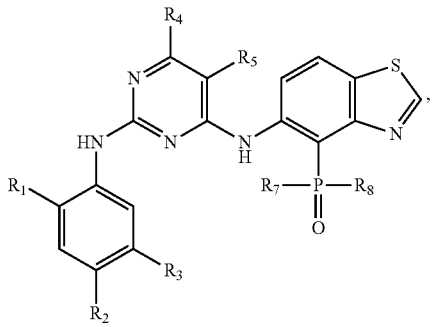
(VII)

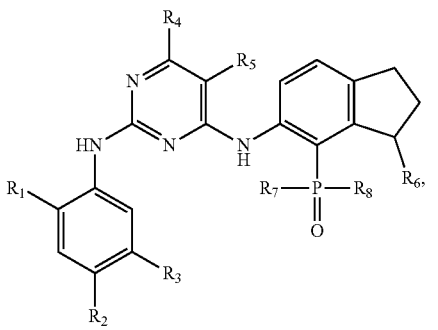
(VIII)

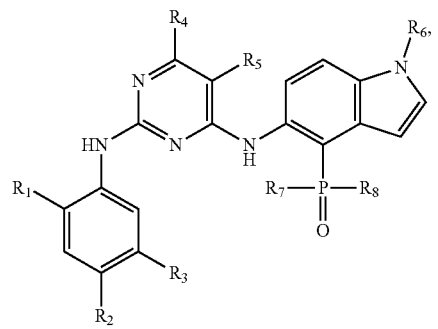
(IX)

wherein $R_1$, $R_2$, $R_3$, $R_4$, $R_5$, $R_6$, $R_7$ and $R_8$ are as defined above.

The present application provides a compound represented by formula (I''') or a pharmaceutically acceptable salt thereof,

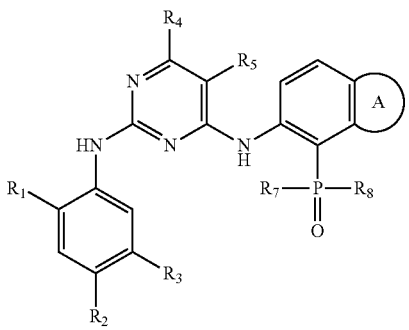

wherein, ring A is selected from phenyl, 5- to 6-membered heteroaryl, 5- to 7-membered heterocycloalkyl, or $C_{5-7}$ cycloalkyl, which is optionally substituted with $R_6$; and the structural unit

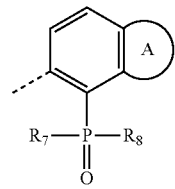

is not selected from

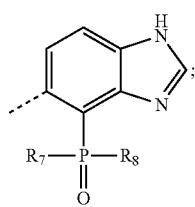

$R_1$ is selected from H or halogen, or selected from $C_{1-6}$ alkyl, $C_{1-6}$ heteroalkyl, $C_{3-6}$ alkenyloxy or $C_{3-6}$ cycloalkoxy group, which is optionally substituted with 1, 2 or 3 R groups;

$R_2$ is selected from: H, halogen, CN, OH, or $NO_2$, or selected from $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl, or 3- to 14-membered heterocyclic group, which is optionally substituted with 1, 2 or 3 R groups;

$R_3$ is selected from H, halogen, $C_{1-6}$ alkoxy, $C_{3-6}$ alkenyloxy or $C_{3-6}$ cycloalkyloxy, —OC(=O)$NH_2$, —OC(=O)NHR, —OC(=O)NRR, —NRC(=O)OR, —NHC(=O)OR, or —NHC(=O)OH, or selected from $C_{1-6}$ alkyl, or 5- to 6-membered heterocyclic group containing 1, 2 or 3 N or O atoms, which is optionally substituted with 1, 2 or 3 R groups;

$R_4$ is selected from: H or $NH_2$;

$R_5$ is selected from H or halogen, or selected from $NH_2$, $C_{1-4}$ alkyl, $C_{1-4}$ heteroalkyl, phenyl or 5- to 6-membered heterocyclic group, which is optionally substituted with 1, 2 or 3 R groups;

or alternatively $R_4$ and $R_5$ are bonded together to form a 5- to 6-membered ring containing 1, 2 or 3 heteroatoms independently selected from N, S or O, which is optionally substituted with 1, 2 or 3 R groups;

$R_6$ is independently selected from: H, halogen, CN, OH, $NH_2$, $C_{1-6}$ alkyl, $C_{1-6}$ heteroalkyl, =O, or =S;

$R_7$ and $R_8$ are each independently selected from H, $C_{1-6}$ alkyl;

R is selected from halogen, CN, OH, or $NH_2$, or selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, $C_{3-6}$ heterocycloalkyl, phenyl or 5- to 6-membered heteroaryl, which is optionally substituted with 1, 2 or 3 R' groups;

R' is selected from: H, F, Cl, Br, I, CN, OH, $NH_2$, $CH_3$, $CH_3CH_2$, $CH_3CH_2CH_2$, $(CH_3)_2CH$, or $CH_3O$;

"hetero" represents a heteroatom or a heteroatom group, and each "hetero" group in said 5- to 6-membered heterocyclic group, $C_{1-6}$ heteroalkyl, 3- to 14-membered heterocyclic group, $C_{1-4}$ heteroalkyl, $C_{1-6}$ heteroalkyl, $C_{3-6}$ heterocycloalkyl, or 5- to 6-membered heteroaryl is independently selected from: —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$—, or —N(R)C(=O)N(R)—;

in any one of the cases as described above, the number of the heteroatom or heteroatom group is each independently selected from 1, 2 or 3.

In some embodiments of the present application, in formula (I'''), the above R is selected from: F, Cl, Br, I, CN, OH, $NH_2$, $CH_3$, $CH_3CH_2$, $CH_3CH_2CH_2$, $(CH_3)_2CH$, or $CH_3O$.

In some embodiments of the present application, in formula (I'''), the above $R_1$ is selected from: H, F, Cl, Br, I, $C_{1-6}$ alkyl, or $C_{1-6}$ heteroalkyl.

In some embodiments of the present application, in formula (I'''), the above $R_1$ is selected from:

In some embodiments of the present application, in formula (I'''), the above $R_2$ is selected from: H, halogen, CN, OH, or $NO_2$, or selected from $C_{3-14}$ cycloalkyl, or 3- to 14-membered heterocyclic group, which is optionally substituted with 1, 2 or 3 R groups.

In some embodiments of the present application, in formula (I'''), the above $R_2$ is selected from: H, halogen, CN, OH, $NH_2$, $NO_2$, —NHR, —NRR,

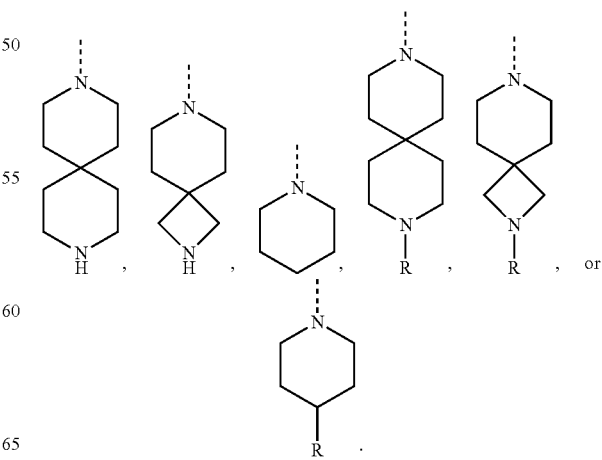

In some embodiments of the present application, in formula (I'''), the above $R_2$ is selected from:

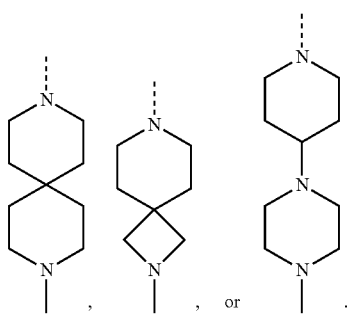

In some embodiments of the present application, in formula (I'''), the above ring A is selected from phenyl, thienyl, pyridyl, pyrazinyl, pyrazolyl, or cyclopentanonyl, which is optionally substituted with $R_6$.

In some embodiments of the present application, in formula (I'''), the above structural unit

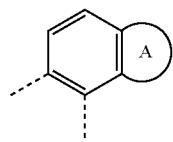

is selected from

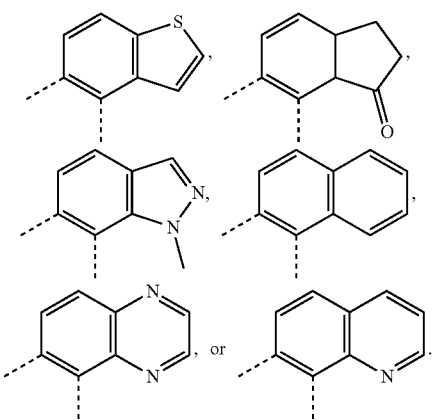

In some embodiments of the present application, in formula (I'''), the above $R_3$ is selected from: H, Cl, and $CH_3$.

In some embodiments of the present application, in formula (I'''), the above $R_4$ is selected from: H.

In some embodiments of the present application, in formula (I'''), the above $R_5$ is selected from: H, or Cl.

In some embodiments of the present application, in formula (I'''), the above $R_6$ is selected from: H, or $CH_3$.

In some embodiments of the present application, in formula (I'''), the above R is selected from F, Cl, Br, I, CN, OH, $NH_2$, $CH_3$, $CH_3CH_2$, $CH_3CH_2CH_2$, $(CH_3)_2CH$, or $CH_3O$, and other variables are as defined above.

In some embodiments of the present application, in formula (I'''), the above R is selected from F, Cl, Br, I, CN, OH, $NH_2$, $CH_3$, $CH_3CH_2$, $CH_3CH_2CH_2$, $(CH_3)_2CH$, or $CH_3O$, and other variables are as defined above.

In some embodiments of the present application, in formula (I'''), the above $R_1$ is selected from: H, F, Cl, Br, I, $C_{1-6}$ alkyl, or $C_{1-6}$ heteroalkyl, and other variables are as defined above.

In some embodiments of the present application, in formula (I'''), the above $R_1$ is selected from:

and the other variables are as defined above.

In some embodiments of the present application, in formula (I'''), the above $R_2$ is selected from: H, halogen, CN, OH, or $NO_2$, or selected from $C_{3-14}$ cycloalkyl or 3- to 14-membered heterocyclic group optionally substituted with 1, 2 or 3 R groups, and other variables are as defined above.

In some embodiments of the present application, in formula (I'''), the above $R_2$ is selected from: H, halogen, CN, OH, $NH_2$, $NO_2$, —NHR, —NRR,

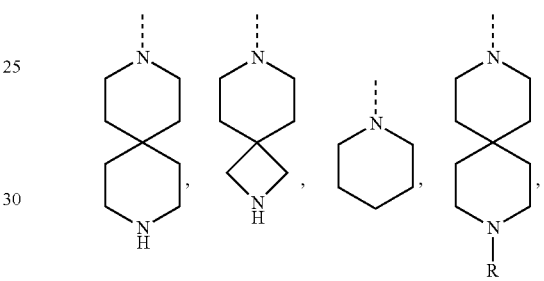

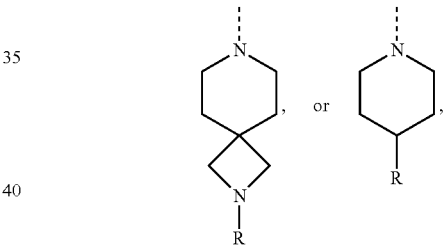

and other variables are as defined above.

In some embodiments of the present application, in formula (I'''), the above $R_2$ is selected from:

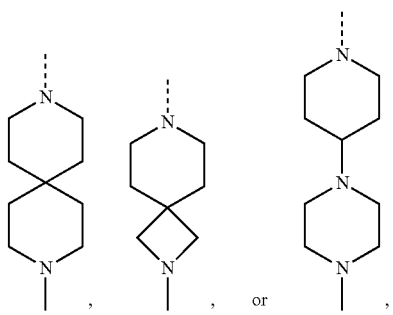

and other variables are as defined above.

In some embodiments of the present application, in formula (I'''), the above ring A is selected from phenyl, thienyl, pyridyl, pyrazinyl, pyrazolyl, or cyclopentanonyl, which is optionally substituted with $R_6$, and other variables are as defined above.

In some embodiments of the present application, in formula (I'''), the above structural unit

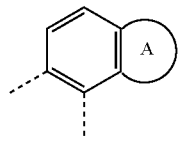

is selected from:

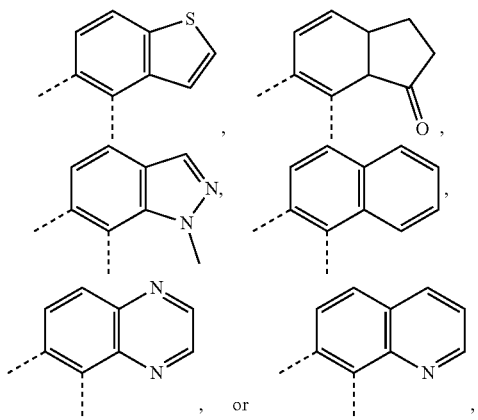

and other variables as defined above.

In some embodiments of the present application, in formula (I'''), the above $R_3$ is selected from H, Cl, or $CH_3$, and other variables are as defined above.

In some embodiments of the present application, in formula (I'''), the above $R_4$ is selected from H, and other variables are as defined above.

In some embodiments of the present application, in formula (I'''), the above $R_5$ is selected from H, or Cl, and other variables are as defined above.

In some embodiments of the present application, in Formula (I'''), the above $R_6$ is selected from H, or $CH_3$, and other variables are as defined above.

In some embodiments of the present application, in formula (I'''), the above $R_7$ and $R_8$ above are each independently selected from $CH_3$, and other variables are as defined above.

In some embodiments of the present application, in formula (I'''), the above compound or the pharmaceutically acceptable salt thereof is selected from

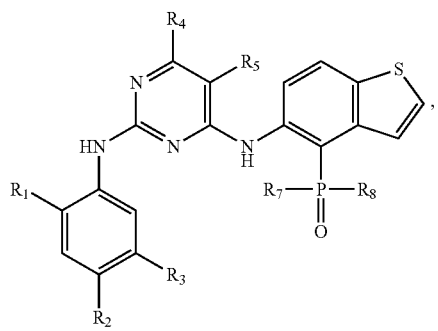
(II)

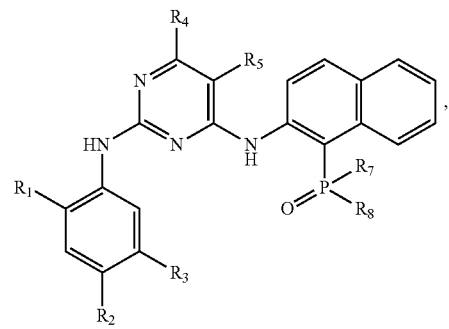
(III)

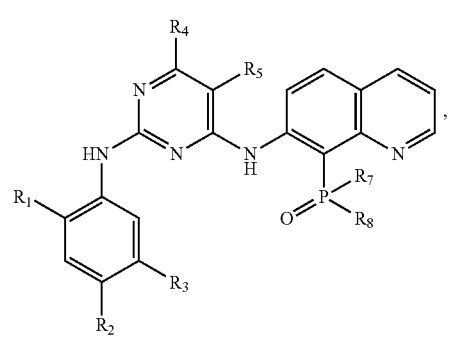
(IV)

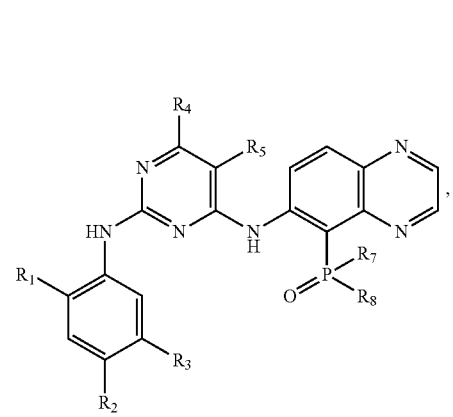
(V)

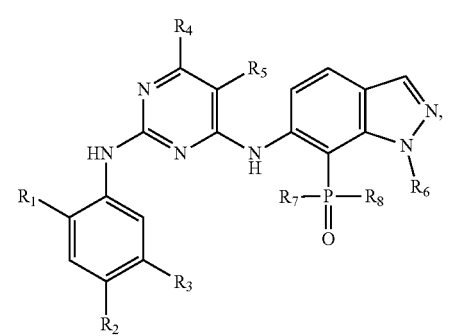
(VI)

wherein $R_1$, $R_2$, $R_3$, $R_4$, $R_5$, $R_6$, $R_7$ and $R_8$ are as defined above.

The present application also provides the following compounds or the pharmaceutically acceptable salts thereof.

67
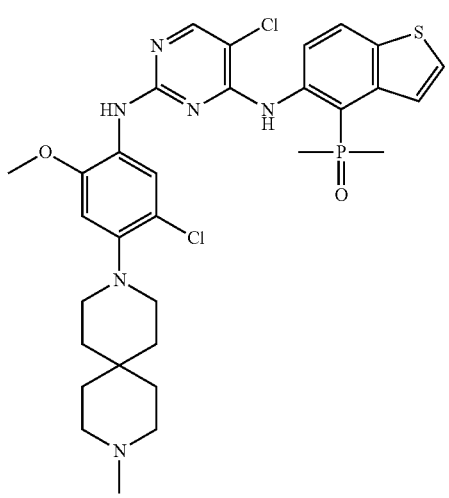
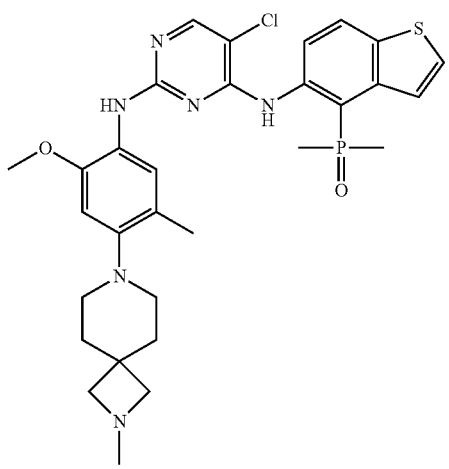
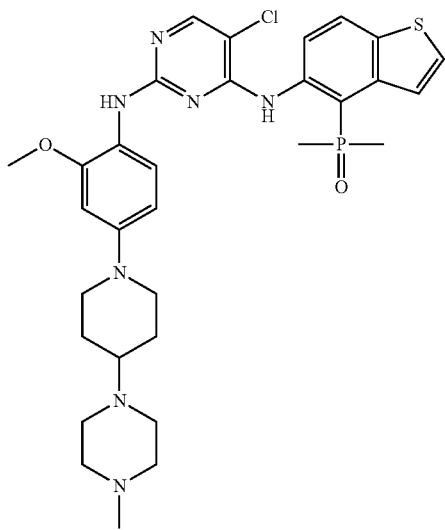
68
-continued
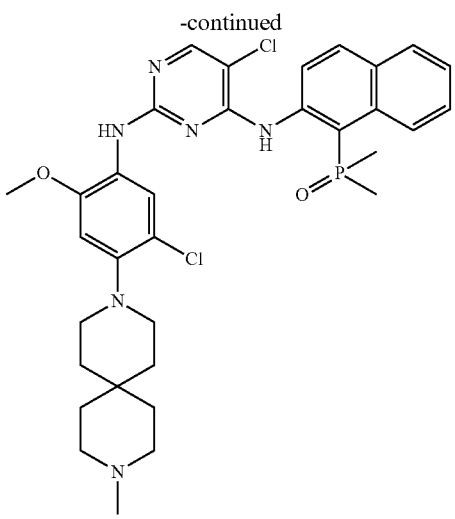
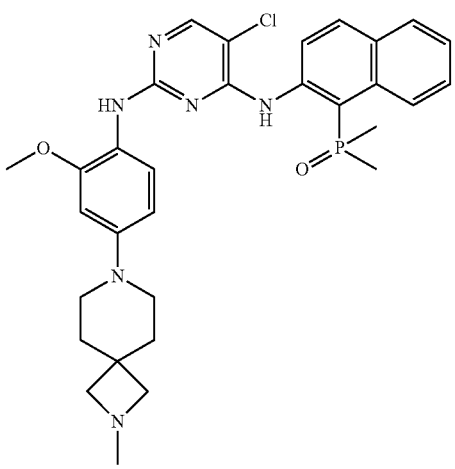
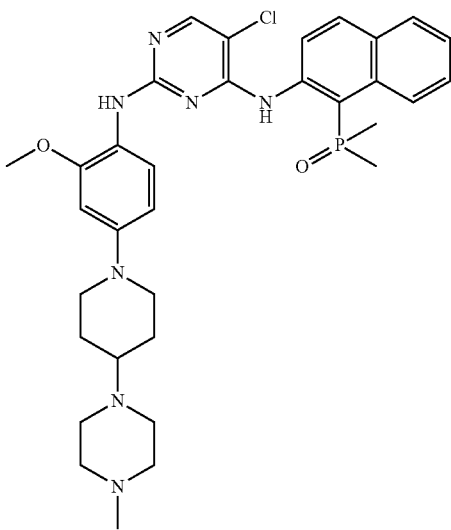

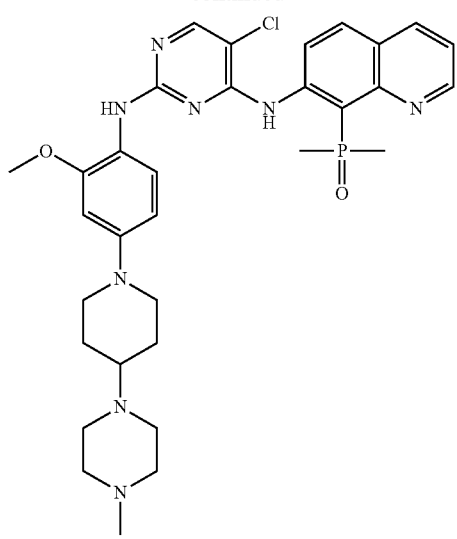
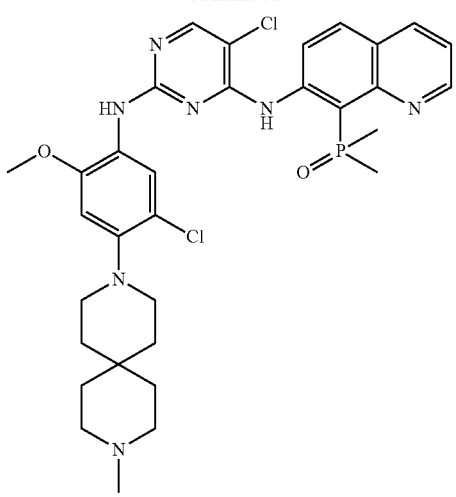
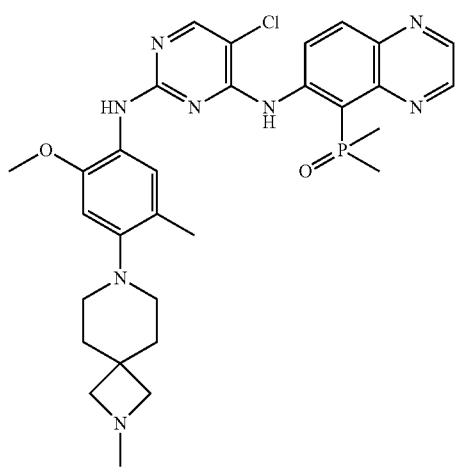
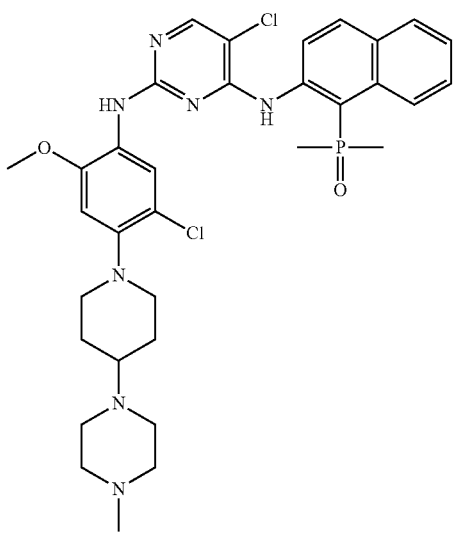
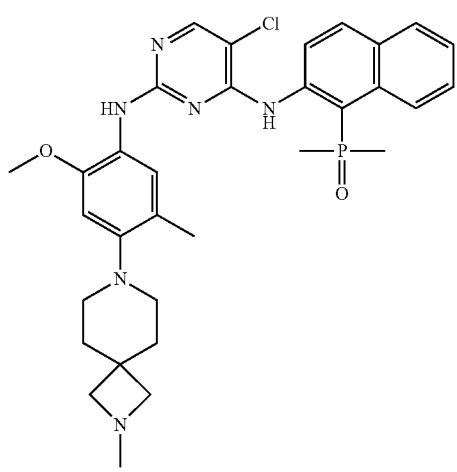
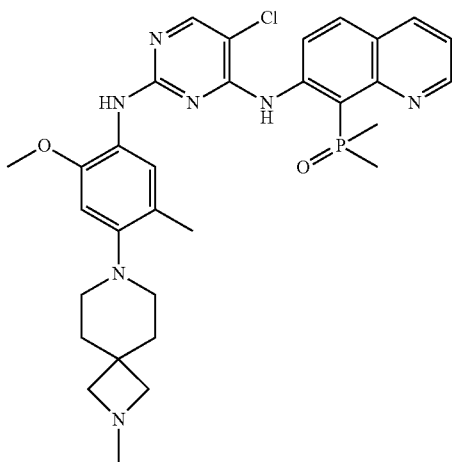

71
-continued
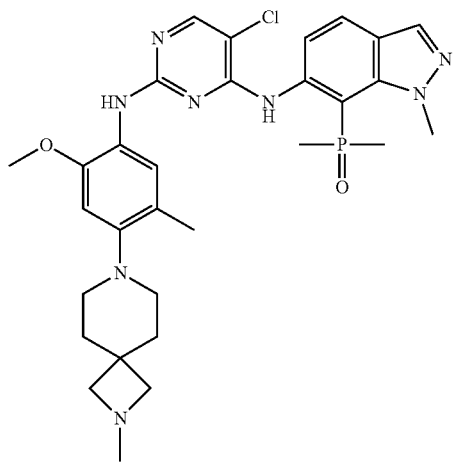
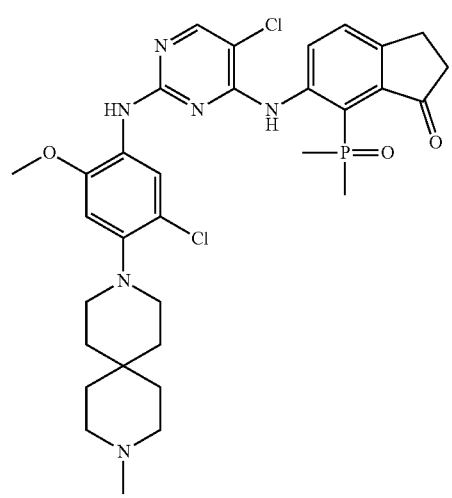
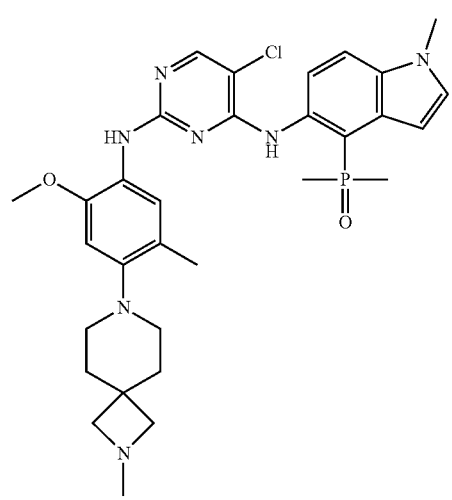
72
-continued
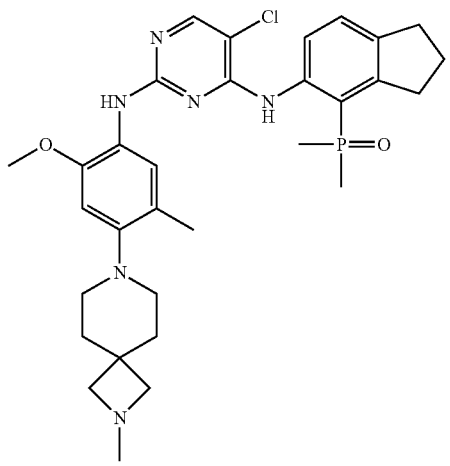
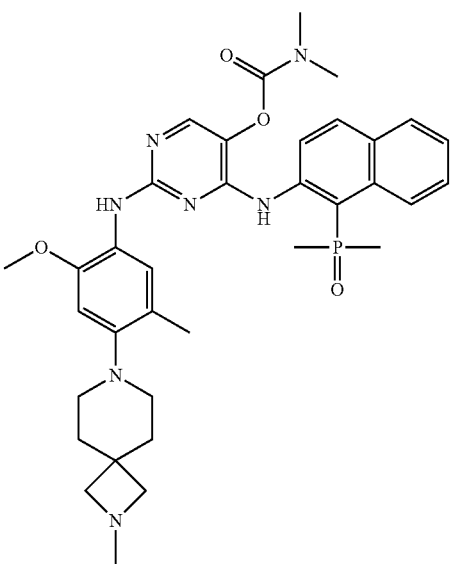
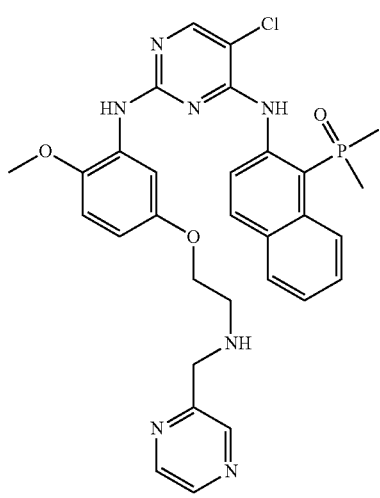

| 73 | 74 |
|---|---|
| -continued | -continued |
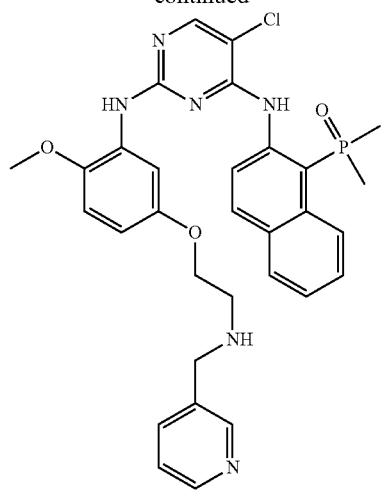
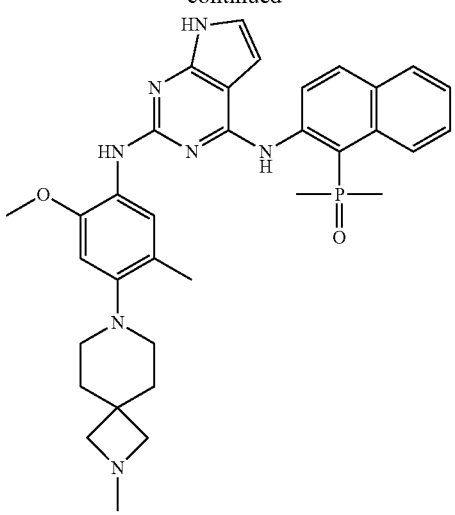
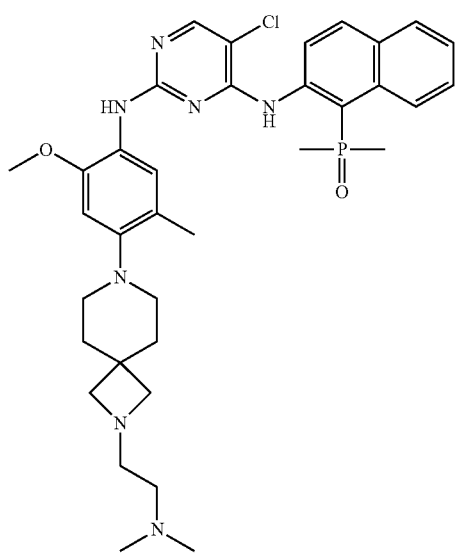
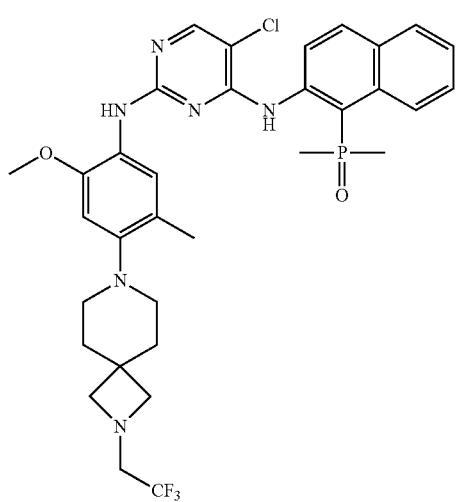
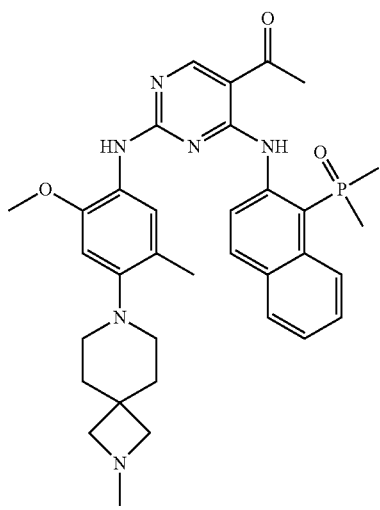

75
-continued
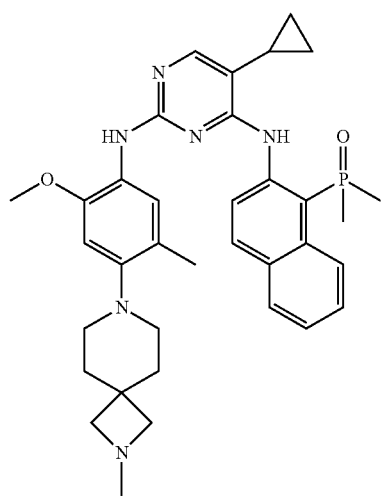
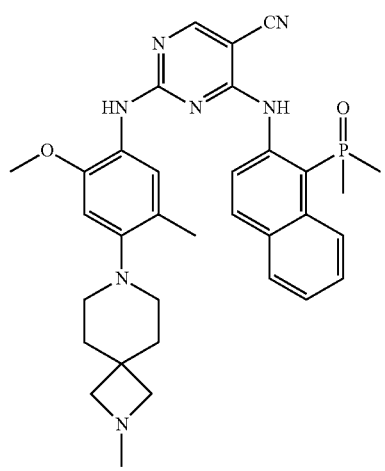
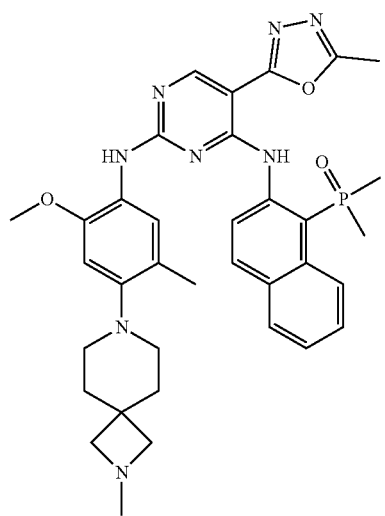
76
-continued
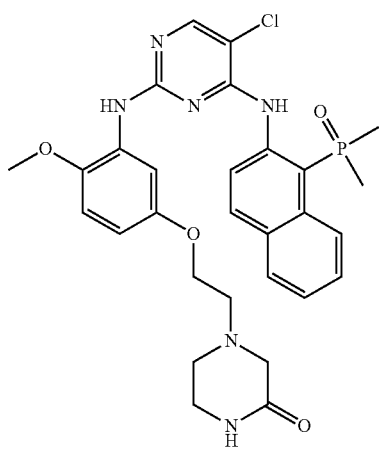
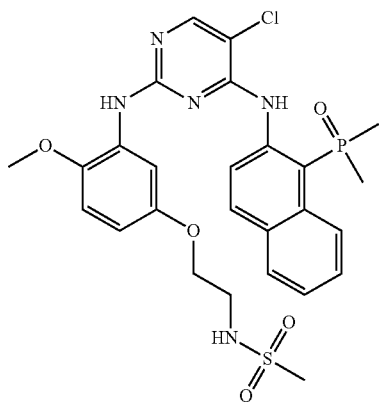
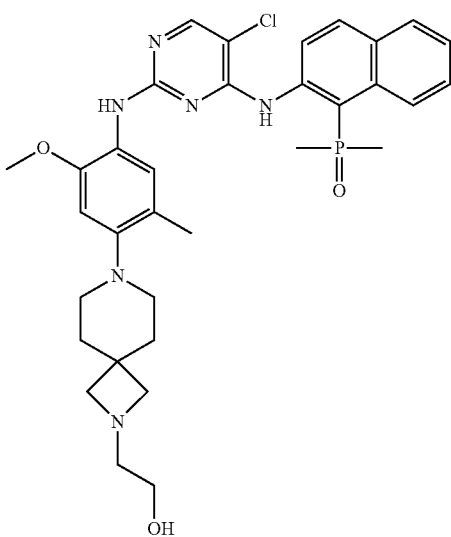

77
-continued
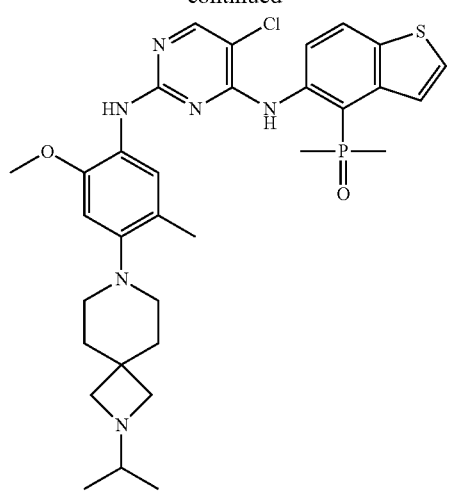
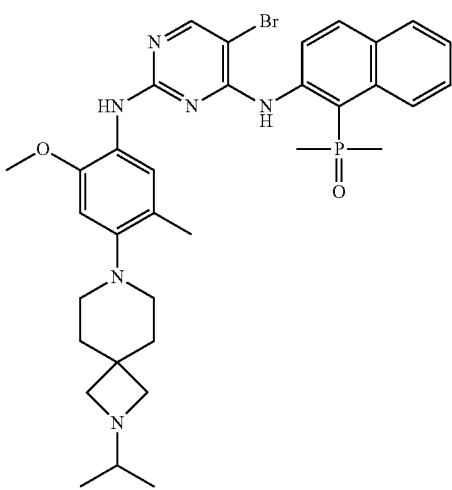
78
-continued
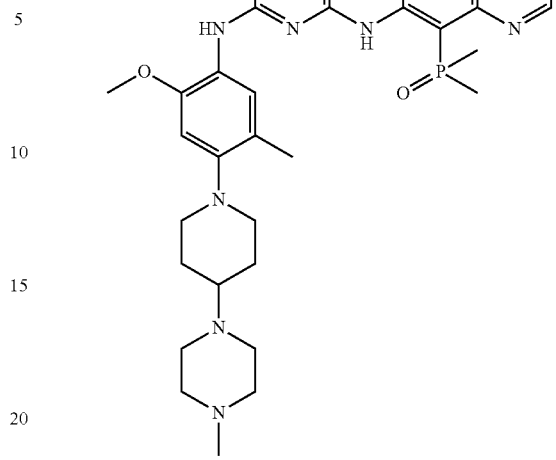
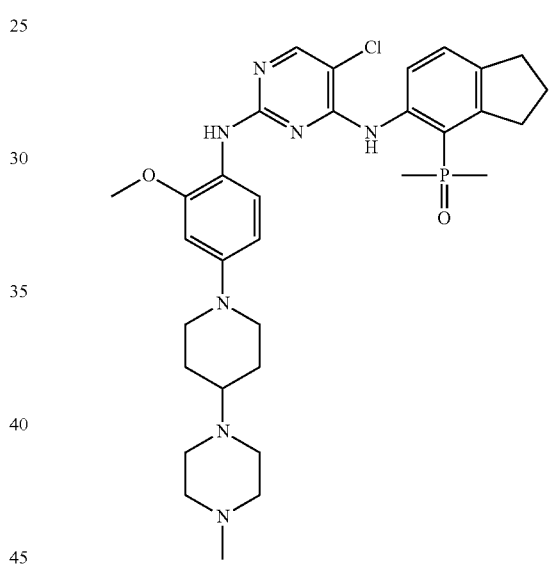
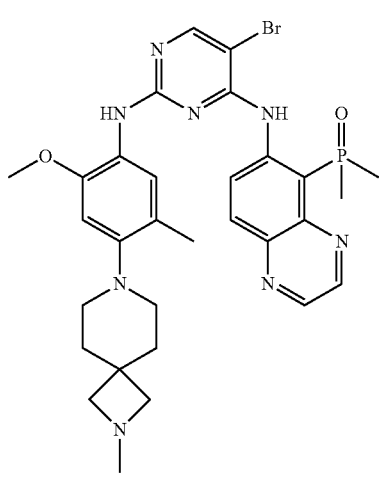

79
-continued
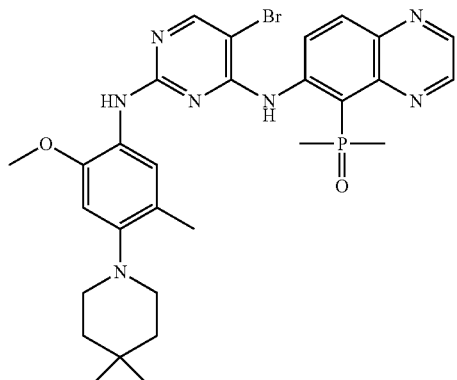
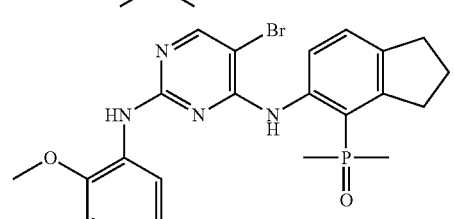
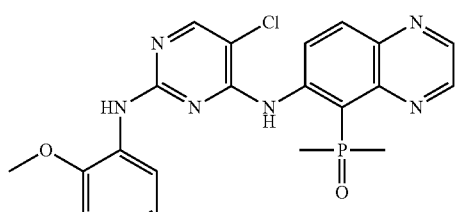
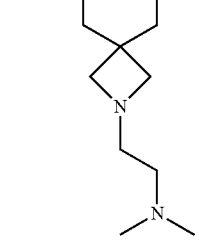
80
-continued
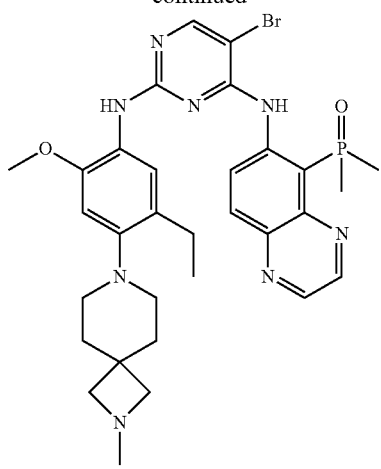
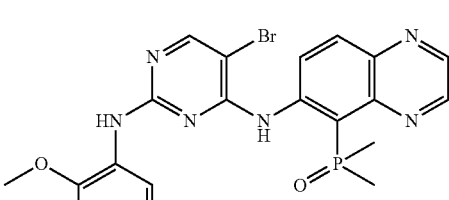
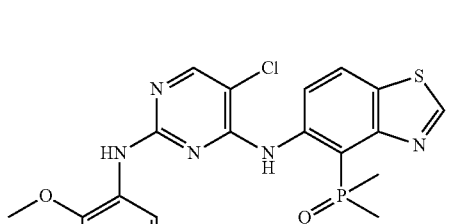
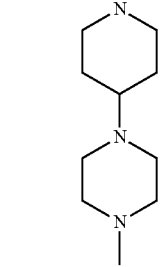

81
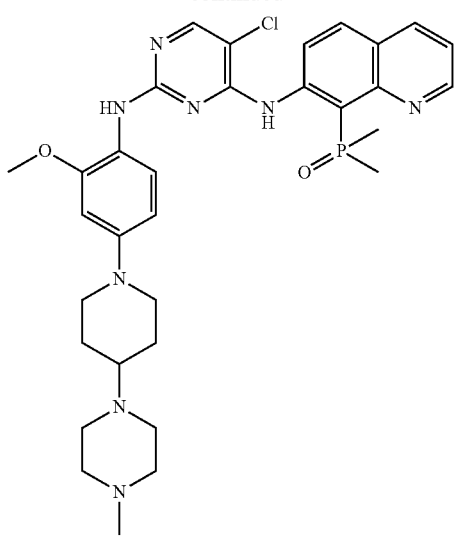
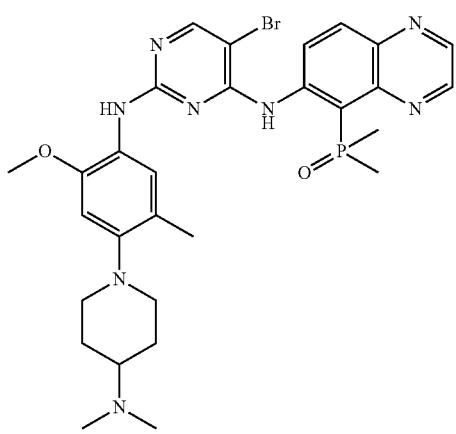
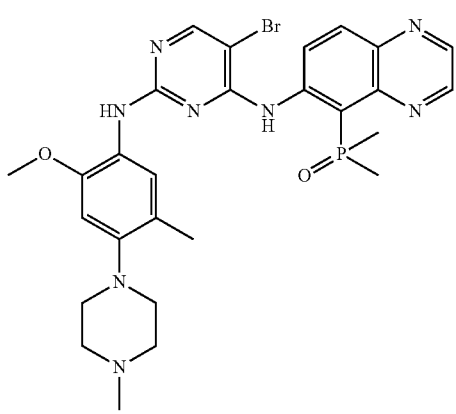
82
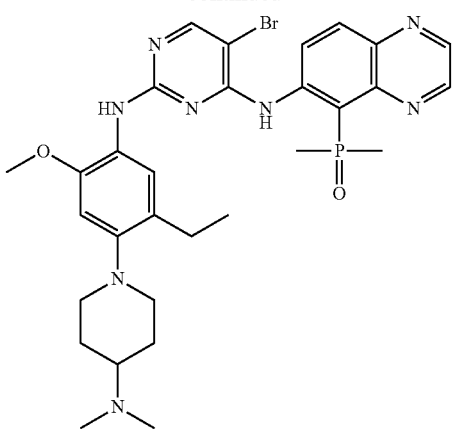
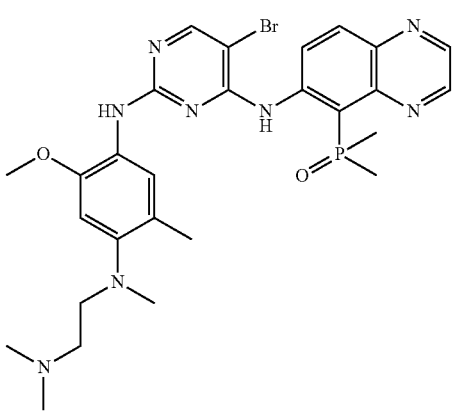
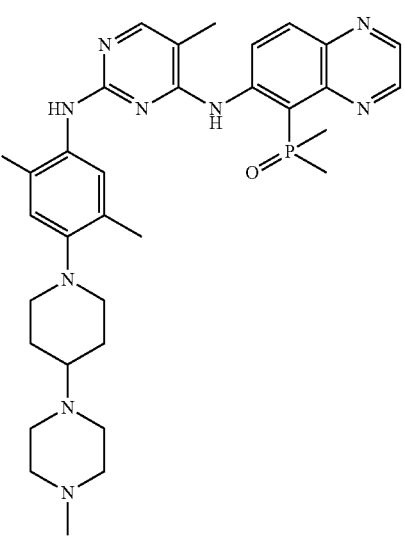

83
-continued
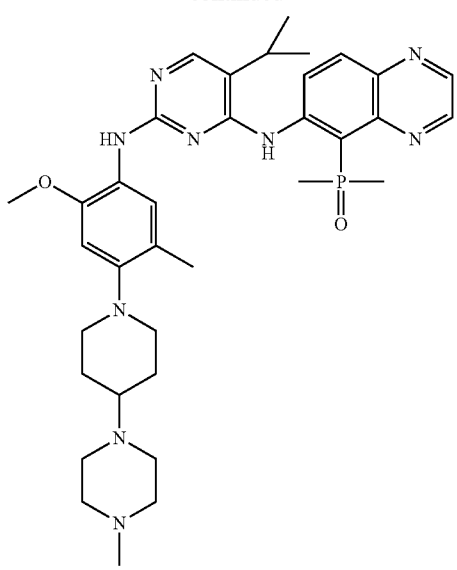
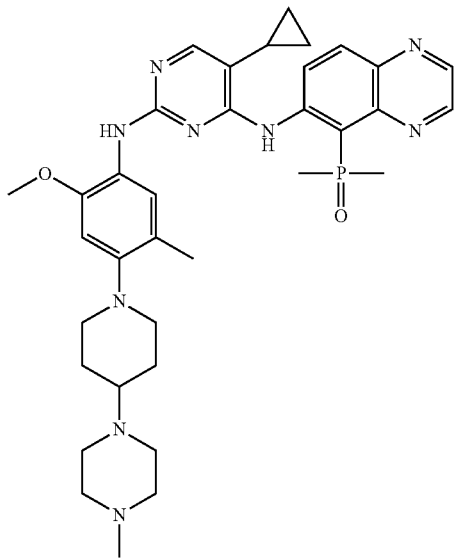
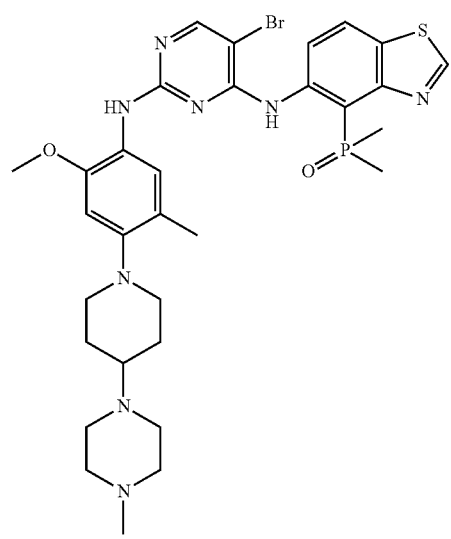
84
-continued
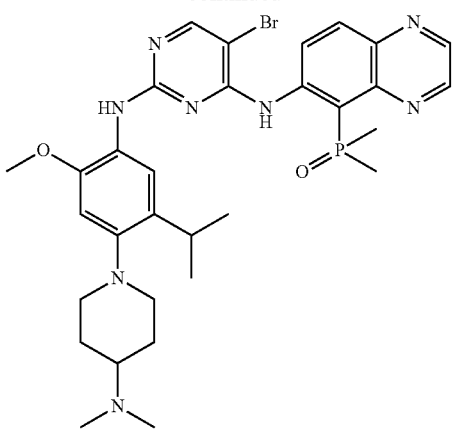
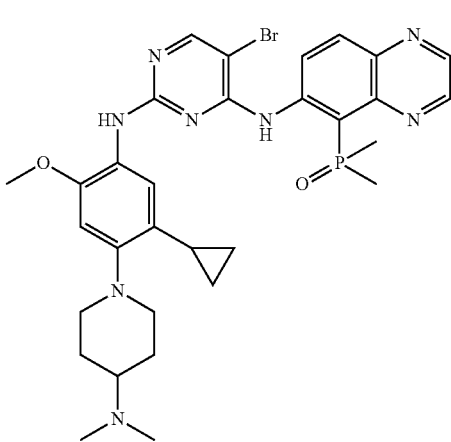
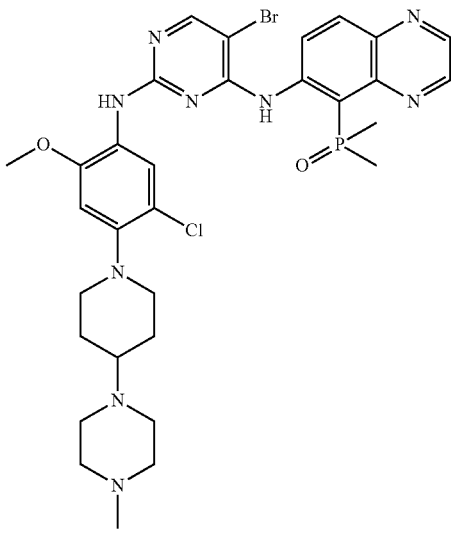

85
-continued
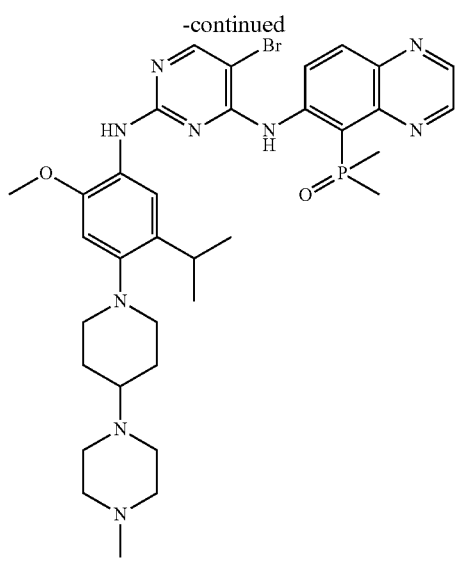
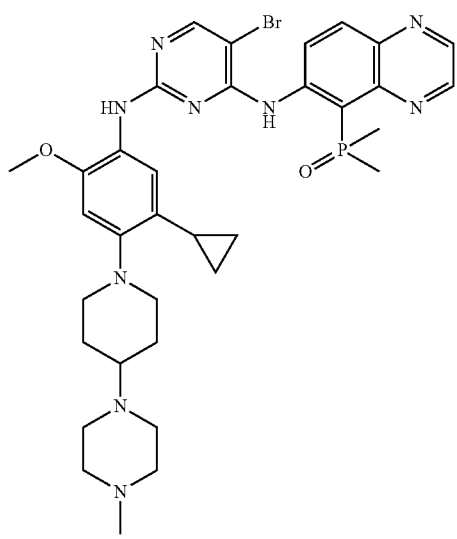
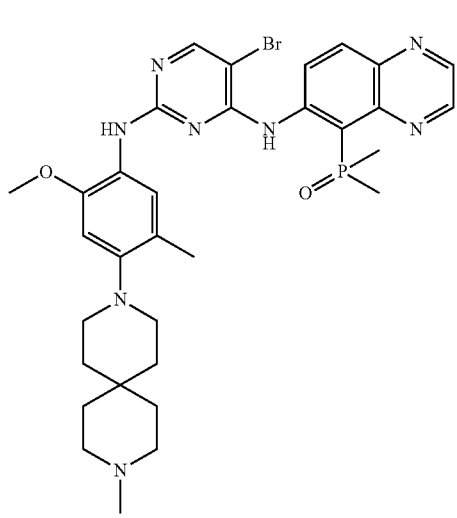
86
-continued
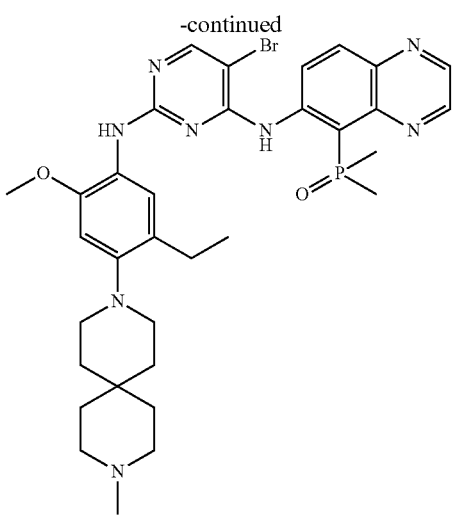
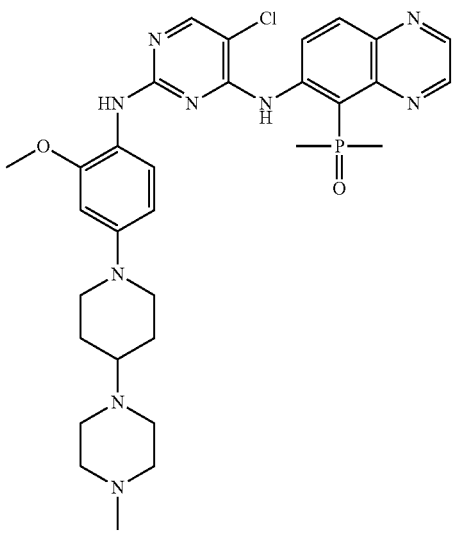
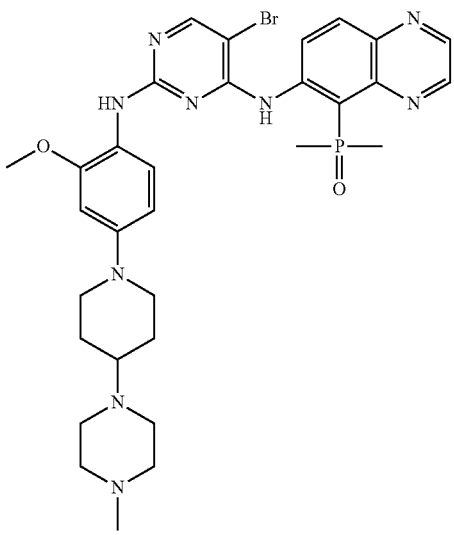

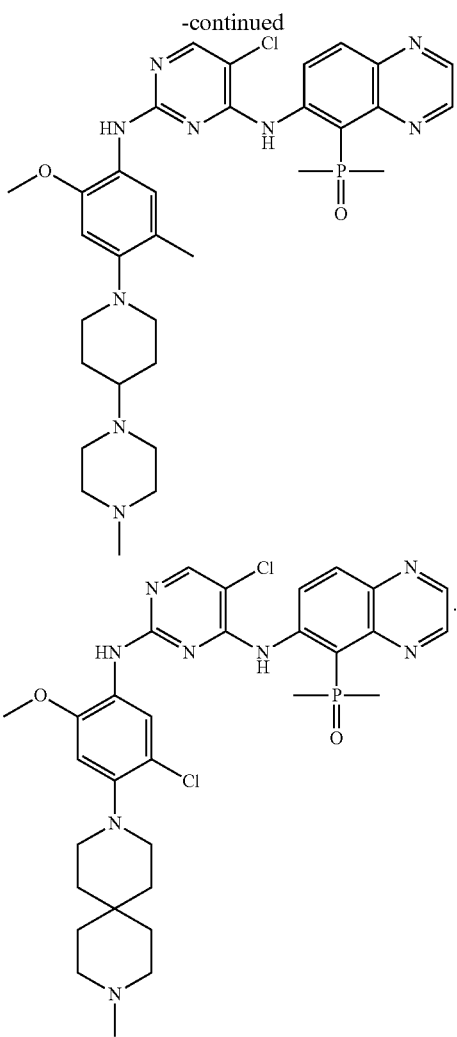

The present application also provides a pharmaceutical composition comprising a therapeutically effective amount of the above compound or the pharmaceutically acceptable salt thereof, and a pharmaceutically acceptable carrier.

The present application also provides use of the above compound or the pharmaceutically acceptable salt thereof, or the above pharmaceutical composition in the manufacture of a medicament for treating cancer.

The present application also provides use of the above compound or the pharmaceutically acceptable salt thereof, or the above pharmaceutical composition for treating cancer.

The application also provides a method for treating cancer, comprising administering to a subject a therapeutically effective amount of the above compound, or the pharmaceutically acceptable salt thereof, or the pharmaceutical composition thereof.

The present application also provides use of the above compound or the pharmaceutically acceptable salt thereof in combination with EGFR monoclonal antibody in the manufacture of a medicament for treating cancer.

The application also provides a method for treating cancer, comprising administering to a subject a therapeutically effective amount of the above compound or the pharmaceutically acceptable salt thereof or the pharmaceutical composition thereof, and an EGFR monoclonal antibody.

In some embodiments of the present application, the above EGFR monoclonal antibody is cetuximab.

The application also provides a method for treating cancer, comprising administering to a subject a therapeutically effective amount of the above compound or the pharmaceutically acceptable salt thereof or the pharmaceutical composition thereof, and a MEK inhibitor.

In some embodiments of the present application, the cancer is lung cancer.

In the present application, still other embodiments are derived from any combination of the above variables.

Technical Effect

The compounds of the present application show excellent antiproliferative activity on EGFR Ba/F3 cell with three mutations (Δ19del/T790M/C797S) and phosphorylation activity in the model of EGFR Ba/F3 cell with three mutations (Δ19del/T790M/C797S).

The compound of the present application exhibits unexpected inhibitory activity compared to Comparative Example 1.

Definitions and Introductions

Unless otherwise stated, the following terms and phrases as used herein are intended to have the following meanings. A particular term or phrase should not be considered to be indefinite or unclear in absence of a specific definition, but should be interpreted as its ordinary meanings. When a trade name appears herein, it is intended to refer to the corresponding commodity or active ingredient thereof. The term "pharmaceutically acceptable" as used herein refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to a salt of the compound of the present application, which is prepared from a compound having a specific substituent found in the present application and a relatively non-toxic acid or base. When the compound of the present application contains a relatively acidic functional group, the base addition salt thereof can be obtained by contacting such compound in neutral form with a sufficient amount of base in a pure solution or a suitable inert solvent. When the compound of the present application contains a relatively basic functional group, the acid addition salt thereof can be obtained by contacting such compound in neutral form with a sufficient amount of acid in a pure solution or a suitable inert solvent. Examples of the pharmaceutically acceptable acid addition salt include inorganic acid salts, organic acid salts, ammonium salts, and salts of organic acids such as glucuronic acid. Certain specific compounds of the application contain basic and acidic functional groups, which can be converted to either base or acid addition salt.

The pharmaceutically acceptable salts of the present application can be synthesized from the parent compound containing an acidic moiety or a basic moiety by conventional chemical methods. Generally, such salt is prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided herein also exists in prodrug form. The prodrug of the compound described herein is the compound that readily undergoes chemical change under physiological condition, to be converted into the compound of the application. Furthermore, the prodrug can be converted to the compounds of the application by a chemical or biochemical method in an in vivo environment.

Certain compounds of the application can exist in an unsolvated from or a solvated form, including a hydrated form. Generally, the solvated form is equivalent to the unsolvated form, and both are encompassed within the scope of the application.

The compounds of the present application may exist in specific geometric or stereoisomeric forms. All such compounds envisaged by the present invention include cis and trans isomers, (−)- and (+)-enantiomer pairs, (R)- and (S)-enantiomers, diastereoisomers, (D)-isomers, (L)-isomers, and racemic mixtures thereof, and other mixtures thereof, such as enantiomers or diastereomers enriched mixtures, all of which fall within the scope of the present application. Other asymmetric carbon atoms may be present in the substituents such as alkyl. All these isomers and their mixtures are included within the scope of the present application.

Unless otherwise indicated, the term "enantiomer" or "optical isomer" refers to stereoisomers that are mirror images of each other.

Unless otherwise indicated, the term "cis-trans isomer" or "geometric isomer" is caused by the inability of a double bond or a single bond of carbon atoms on the ring to freely rotate.

Unless otherwise indicated, the term "diastereomer" refers to stereoisomers in which the molecules have two or more chiral centers and are not mirror images of each other.

Unless otherwise indicated, "(D)" or "(+)" stands for dextrorotation, "(L)" or "(−)" stands for levorotation, "(DL)" or "(±)" stands for racemization.

Unless otherwise indicated, the absolute configuration of a stereogenic center is represented by a wedge solid bond (⏋) and a wedge dashed bond (⏌), and the relative configuration of a stereogenic center is represented by a straight solid bond (⏋) and a straight dashed bond (⏌). A wave line (⏋) represents a wedge solid bond (⏋) or a wedge dashed bond (⏌), or represents a straight solid bond (⏋) and a straight dashed bond (⏌).

The compounds of the present application may be present in particular. Unless otherwise indicated, the terms "tautomer" or "tautomeric form" refer to the fact that the different functional isomers are in dynamic equilibrium at room temperature and can be rapidly converted into each other. If tautomers are possible (such as in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise indicated, the term "enriched in one isomer", "isomer enriched", "enriched in one enantiomer" or "enantiomer enriched" refers to that the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomeric (ee value) is 80%.

The optically active (R)- and (S)-isomers as well as the D and L isomers can be prepared by chiral synthesis or chiral reagents or other conventional techniques. If an enantiomer of a certain compound of the present application is desired, it may be prepared by asymmetric synthesis or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by a conventional method well known in the art, followed by recovering to give the pure enantiomer. In addition, the separation of the enantiomers and diastereomers is generally accomplished by the use of chromatography adopting a chiral stationary phase, and optionally in combination with chemical derivatization method (e.g., formation of carbamates from amines). The compounds of the present application may contain non-natural proportions of atomic isotopes on one or more atoms which constitute the compound. For example, the compound may be labeled with a radioisotope, such as tritium ($^3H$), iodine-125 ($^{125}I$) or C-14 ($^{14}C$). Any isotopic composition transformations of the compound of the application, whether are radioactive or not, are included within the scope of the present application.

The term "pharmaceutically acceptable carrier" refers to any formulation or carrier medium capable of delivering an effective amount of an active substance of the present application, without interfering with the biological activity of the active substance and having no toxic side effects on the host or patient. Representative carriers include water, oils, vegetables and minerals, cream bases, lotion bases, ointment bases, etc. These bases include suspensions, tackifiers, transdermal enhancers etc. Their formulations are well known to those skilled in the cosmetic field or topical drug arts.

The term "excipient" generally refers to the carrier, diluent and/or medium which is required to formulate an effective pharmaceutical composition.

The term "effective amount" or "therapeutically effective amount" with respect to drugs or pharmacologically active agents refers to a sufficient amount of a drug or agent that is non-toxic but can achieve the desired effect. For the oral dosage form in the present application, the "effective amount" of one active substance in a composition means the amount required to achieve the desired effect when used in combination with another active substance in the composition. The determination of the effective amount will vary with each individual, depending on the age and general condition of the subject, as well as the specific active substance. The appropriate effective amount in each case can be determined by the skilled in the art according to a routine experiment.

The term "active ingredient", "therapeutic agent", "active substance" or "active agent" refers to a chemical entity that can effectively treat a target disorder, disease or condition.

"Optional" or "optionally" means that the subsequently described event or situation may, but is not necessarily to, occur, and the description includes instances in which the event or situation occurs and instances in which the event or situation does not occur.

The term "substituted" means that any one or more of the hydrogen atoms on a specific atom are substituted by a substituent (which may include heavy hydrogen and variants of hydrogen), as long as the valence state of the specific atom is normal and the substituted compound is stable. When the substituent is oxygen (i.e., =O), it means that two hydrogen atoms are substituted. Oxygen substitution does not occur on an aromatic group. The term "optionally substituted" means that it may or may not be substituted, unless otherwise specified; the type and number of the substituent may be arbitrary as long as being chemically achievable.

When any variable (e.g., R) appears more than once in composition or structure of a compound, its definition in each case is independent. Thus, for example, if a group is substituted by 0-2 R, this group may be optionally substituted by at most two R, and R in each case has an independent option. Furthermore, the combination of substituents and/or variants thereof is permissible only if such combination results in stable compounds.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure is actually A. When a substituent can be bond to more than one atom on a ring, the substituent may be bonded to any atom on the ring.

For example, the structural unit

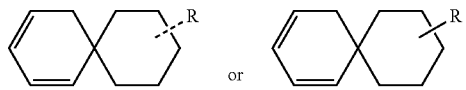

means that the substituent R may occur at any position on cyclohexyl or cyclohexadiene. When the listed substituents are not indicated by which atom is attached to the substituted group, such a substituent may be bonded through any of its atoms, for example, pyridyl as a substituent may be bonded to the substituted group through any one of carbon atoms on the pyridine ring. When the enumerative linking group does not indicate the direction for linking, the direction for linking is arbitrary. For example, the linking group L in

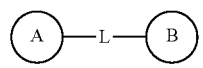

is -M-W—, then the -M-W— can link ring A and ring B to form

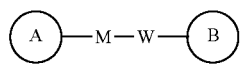

in the direction same as left-to-right reading order, and form

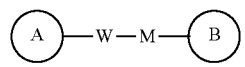

in the direction contrary to left-to-right reading order. Combinations of the linking groups, substituents and/or variants thereof are permissible only if such combinations result in stable compounds.

Unless otherwise specified, the term "hetero" refers to a heteroatom or a heteroatomic group (i.e., an atomic group containing a heteroatom), including the atom other than carbon (C) and hydrogen (H), and the atomic group containing these heteroatoms, including, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and —C(=O)N(H)—, —N(H)—, —C(=NH)—, —S(=O)$_2$N(H)— or —S(=O)N(H)—, each of which is optionally substituted.

Unless otherwise specified, "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a bicyclic ring, a spiral ring, a fused ring or a bridged ring. The number of the atom on the ring is usually defined as the membernumber of the ring. For example, "5- to 7-membered ring" means that 5 to 7 atoms are arranged on a ring. Unless otherwise specified, the ring optionally contains 1 to 3 heteroatoms. Thus, a "5- to 7-membered ring" includes, for example, phenyl, pyridine, and piperidinyl; on the other hand, the term "5- to 7-membered heterocycloalkyl ring" includes pyridyl and piperidinyl, but excluding phenyl. The term "ring" also includes a ring system containing at least one ring, wherein each "ring" independently meets the above definition.

Unless otherwise specified, the term "heterocycle" or "heterocyclyl" refers to a stable monocyclic, bicyclic or tricyclic ring containing a heteroatom or heteroatom group, which can be saturated, partially unsaturated or unsaturated (aromatic), and can contain carbon atoms and 1, 2, 3 or 4 ring heteroatoms independently selected from N, O and S, wherein any of the above heterocycles can be fused to a benzene ring to form a bicyclic ring. Nitrogen and sulfur heteroatoms can be optionally oxidized (i.e., NO and S(O)$_p$, p is 1 or 2). Nitrogen atom can be substituted or unsubstituted (i.e., N or NR, wherein R is H or other substituents as already defined herein). The heterocycle can be attached to the pendant groups of any heteroatom or carbon atom to form a stable structure. If the resulting compound is stable, the heterocycles described herein can undergo substitution at a carbon or nitrogen position. Nitrogen atom on the heterocycle is optionally quaternized. In a preferred embodiment, when the total number of S and O atom in the heterocycle is more than 1, the heteroatom is not adjacent to each other. In another preferred embodiment, the total number of S and O atom of the heterocycle is not more than 1. The term "aromatic heterocyclic group" or "heteroaryl" as used herein refers to a stable 5-, 6-, or 7-membered monocyclic or bicyclic, or 7-, 8-, 9- or 10-membered bicyclic heterocyclic aromatic ring, which contains carbon atoms and 1, 2, 3 or 4 ring heteroatoms independently selected from N, O and S. Nitrogen atom can be substituted or unsubstituted (i.e., N or NR, wherein R is H or other substituents as already defined herein). Nitrogen and sulfur heteroatoms can be optionally oxidized (i.e., NO and S(O), p is 1 or 2). It is worth noting that the total number of S and O atom of an aromatic heterocycle is not more than 1. The bridged ring is also included in the definition of the heterocycle. A bridged ring is formed when one or more atoms (i.e., C, O, N, or S) link two non-adjacent carbon or nitrogen atoms. A preferred bridged ring includes, but not limited to, one carbon atom, two carbon atoms, one nitrogen atom, two nitrogen atoms, and one carbon-nitrogen group. It is worth noting that a bridge always converts a monocyclic ring to a tricyclic ring. In the bridged ring, the substituent on the ring may also be present on the bridge. Examples of the heterocyclic compound include, but are not limited to, acridinyl, azocinyl, benzimidazolyl, benzofuranyl, benzothiolfuranyl, benzothiolphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbazolinyl, chromanyl, chromene, cinnolinyl decahydroquinolinyl, 2H,6H-1,5,2-dithiazinyl, dihydrofuro[2,3-b]tetrahydrofuranyl, furyl, furazanyl, imidazolidinyl, imidazolinyl, imidazolyl, 1H-indazolyl, indolenyl, indolinyl, indolizinly, indolyl, 3H-indolyl, isobenzofuranyl, isoindolyl, isoindolinyll, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzoxanthinyl, phenoloxazinyl, phthalazinyl, piperazinyl, piperidinyl, piperidinonyl, 4-piperidinonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthiophenyl, thienooxazolyl, thienothiazolyl, thienoimidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused ring and spiro ring compounds.

Unless otherwise specified, the term "hydrocarbyl" or its hyponyms (e.g., alkyl, alkenyl, alkynyl, aryl, etc.), by itself or as part of another substituent, refers to a straight, branched chain or cyclic hydrocarbon radical or a combination thereof, that can be fully saturated (such as alkyl), mono- or polyunsaturated (e.g., alkenyl, alkynyl, and aryl), can be mono- or polysubstituted, and can be monovalent (e.g., methyl), divalent (e.g., methylene) or multivalent (e.g., methenyl), can include a divalent or multivalent group, have a specified number of carbon atom (e.g., $C_1$-$C_{12}$ represents 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic hydrocarbyl and aromatic hydrocarbyl, the aliphatic hydrocarbyl includes linear and cyclic hydrocarbyl, specifically includes but not limited to alkyl, alkenyl, and alkynyl, and the aromatic hydrocarbyl includes, but is not limited to, 6- to 12-membered aromatic hydrocarbyl, such as phenyl, naphthyl and the like. In some embodiments, the term "hydrocarbyl" means a straight or branched group or a combination thereof, which can be fully saturated, mono- or polyunsaturated, and can include a divalent or multivalent radical. Examples of the saturated hydrocarbyl radical include, but are not limited to, methyl, ethyl, n-propyl, isopropyl, n-butyl, t-butyl, isobutyl, sec-butyl, isobutyl, cyclohexyl, (cyclohexyl)methyl, cyclopropylmethyl, and the homolog or isomer of n-pentyl, n-hexyl, n-heptyl, n-octyl and the like. The unsaturated hydrocarbyl group has one or more double or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, heteroaryl, etc.), by itself or in combination with another term, denotes a stable straight, branched or cyclic hydrocarbon radical or any combination thereof, which have a specified number of carbon atoms and at least one heteroatom.

Unless otherwise specified, the term "heteroalkyl" by itself or in combination with another term denotes a stable straight chain, branched hydrocarbon radical or a combination thereof, having a specified number of carbon atoms and at least one heteroatom. In a specific embodiment, a heteroatom is selected from B, O, N, and S, wherein nitrogen and sulfur atoms are optionally oxidized, and the nitrogen heteroatom is optionally quaternized. The heteroatom or heteroatom group can be located at any internal position of a heterohydrocarbyl, including the position where the hydrocarbyl is attached to the rest part of the molecule. But the terms "alkoxy", "alkylamino" and "alkylthio" (or thioalkoxy) belong to customary expression, which denotes an alkyl which are attached to the rest part of the molecule via an oxygen atom, an amino or a sulfur atom respectively. Examples of "heteroalkyl" include, but are not limited to, —OCH$_3$, —OCH$_2$CH$_3$, —OCH$_2$CH$_2$CH$_3$, —OCH(CH$_3$)$_2$, —N(CH$_3$)$_2$, —CH$_2$—CH$_2$—O—CH$_3$, —CH$_2$_CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —S(O)$_2$—CH$_3$, —CH$_2$—CH$_2$—S(O)$_2$—CH$_3$, —CH═CH—O—CH$_3$, —CH$_2$—CH═N—OCH$_3$ and —CH═CH—N(CH$_3$)—CH$_3$. Up to two heteroatoms can be continuous, such as —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.), by itself or in combination with other terms, represents a cyclized "hydrocarbyl" or "heterohydrocarbyl", respectively. Furthermore, for heterohydrocarbyl or heterocyclohydrocarbyl (e.g., heteroalkyl or heterocycloalkyl), a heteroatom can occupy the position where the heterocyclic ring is attached to the rest part of the molecule. Examples of cyclohydrocarbyl include, but are not limited to, cyclopentyl, cyclohexyl, 1-cyclohexenyl, 3-cyclohexenyl, cycloheptyl, and the like. Non-limiting examples of heterocyclic groups include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothiophen-2-yl, tetrahydrothiophen-3-yl, 1-piperazinyl and 2-piperazinyl.

Unless otherwise specified, the term "alkyl" refers to a straight or branched saturated hydrocarbon group, which can be mono- (e.g., —CH$_2$F) or poly-substituted (e.g., —CF$_3$), and can be monovalent (e.g., methyl), divalent (e.g., methylene) or multivalent (e.g., methenyl). Examples of alkyl include methyl (Me), ethyl (Et), propyl (such as, n-propyl and isopropyl), butyl (such as n-butyl, isobutyl, s-butyl, t-butyl), pentyl (such as n-pentyl, isopentyl, neopentyl) and the like.

Unless otherwise specified, "alkenyl" refers to an alkyl group having one or more carbon-carbon double bonds at any position of the chain, which can be mono-substituted or poly-substituted, and can be monovalent, divalent or multivalent. Examples of alkenyl include vinyl, propenyl, butenyl, pentenyl, hexenyl, butadienyl, pentadienyl, hexadienyl and the like. The term "alkenyloxy" refers to an alkenyl group which are each attached to the rest part of the molecule through an oxygen atom, examples including, but not limited to, $CH_2=CH-O-$, $CH_3CH=CH-O-$.

Unless otherwise specified, "alkynyl" refers to an alkyl group having one or more carbon-carbon triple bonds at any position of the chain, which can be mono-substituted or poly-substituted, and can be monovalent, divalent or multivalent. Examples of alkynyl include ethynyl, propynyl, butynyl, pentynyl and the like.

Unless otherwise specified, "cycloalkyl" includes any stable cyclic or polycyclic hydrocarbyl, and any carbon atom is saturated, which can be mono-substituted or poly-substituted, and can be monovalent, divalent or multivalent. Examples of such cycloalkyl include, but are not limited to, cyclopropyl, norbornanyl, [2.2.2]bicyclooctane, [4.4.0]bicyclodecanyl, and the like. However, the term "cycloalkyloxy" refers to the cycloalkyl group which are each attached to the rest part of the molecule through an oxygen atom, examples including, but not limited to,

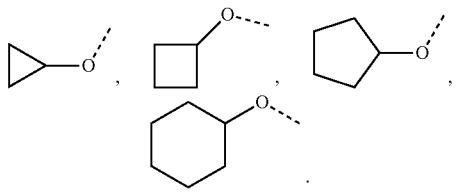

Unless otherwise specified, "cycloalkenyl" includes any stable cyclic or polycyclic hydrocarbyl containing one or more unsaturated carbon-carbon double bonds at any position of the ring, which can be mono-substituted or poly-substituted, and an be monovalent, divalent or multivalent. Examples of such cycloalkenyl include, but are not limited to, cyclopentenyl, cyclohexenyl, and the like.

Unless otherwise specified, "cycloalkynyl" includes any stable cyclic or polycyclic hydrocarbyl containing one or more carbon-carbon triple bonds at any position of the ring, which can be mono-substituted or poly-substituted, and can be monovalent, divalent or multivalent.

Unless otherwise specified, the term "halo" or "halogen", by itself or as part of another substituent, refers to fluorine, chlorine, bromine or iodine atom. Furthermore, the term "haloalkyl" is intended to include both monohaloalkyl and polyhaloalkyl. For example, the term "halo($C_1$-$C_4$)alkyl" is intended to include, but not limited to, trifluoromethyl, 2,2,2-trifluoroethyl, 4-chlorobutyl, 3-bromopropyl, and the like. Unless otherwise specified, examples of haloalkyl include, but not limited to, trifluoromethyl, trichloromethyl, pentafluoroethyl, and pentachloroethyl.

"Alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to, methoxy, ethoxy, n-propoxy, isopropoxy, n-butoxy, sec-butoxy, tert-butoxy, n-pentyloxy and S-pentyloxy.

Unless otherwise specified, the term "aryl" refers to a polyunsaturated aromatic substituent, can be mono- or poly-substituted, can be monovalent, divalent or polyvalent, can be a single ring or multiple rings (for example, 1 to 3 rings; wherein at least one ring is aromatic), which are fused together or covalently connected.

Unless otherwise specified, the term "heteroaryl" refers to an aryl (or ring) containing one to four heteroatoms. In an illustrative example, the heteroatom is selected from B, N, O, and S, wherein nitrogen and sulfur atoms are optionally oxidized, and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolyl and 6-quinolinyl. The substituent of any of the above aryl and heteroaryl ring system is selected from the acceptable substituents described below.

Unless otherwise specified, when combined with other terms (such as aryloxy, arylthio, aralkyl), the aryl includes the aryl and heteroaryl rings as defined above. Thus, the term "aralkyl" is intended to include the groups (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxymethyl 3-(1-naphthyloxy)propyl, and the like.

The term "leaving group" refers to a functional group or atom which can be replaced by another functional group or atom through a substitution reaction (for example an affinity substitution reaction). For example, representative leaving groups include triflate; chlorine, bromine and iodine; sulfonate, such as mesylate, tosylate, p-bromobenzenesulfonate, p-toluenesulfonate and the like; acyloxy, such as acetoxy, trifluoroacetoxy and the like.

The term "protecting group" includes, but is not limited to, "amino protecting group", "hydroxy protecting group" or "thiol protecting group". The term "amino protecting group" refers to a protecting group suitable for preventing side reactions at the nitrogen position on the amino. Representative amino protecting groups include, but are not limited to, formyl; acyl, such as alkanoyl (e.g., acetyl, trichloroacetyl or trifluoroacetyl); alkoxycarbonyl, such as, tert-butoxycarbonyl (Boc); arylmethoxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; silyl, such as trimethylsilyl (TMS) and tert-butyldimethylsilyl (TBS), etc. The term "hydroxy protecting group" refers to a protecting group suitable for use in preventing side reactions of hydroxyl. Representative hydroxy protecting groups include, but are not limited to, alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (benzhydryl, DPM); silyl, such as trimethylsilyl (TMS), tert-butyl dimethylsilyl (TBS), etc.

The compounds of the present application can be prepared by a variety of synthetic methods well known by those skilled in the art, including the following exemplified embodiments, the embodiments formed by combining them with other chemical synthesis methods, and equivalent alternatives known to those skilled in the art. Preferred embodiments include, but are not limited to the examples of the present invention.

The solvents used in the present application are commercially available. The present application employs the following abbreviations: aq represents aqua; eq represents equivalent; CDI represents carbonyldiimidazole; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; BOC represents t-butyl carbonyl, which is an amine protecting group; HOAc represents acetic acid; Na(OAc)$_3$BH represents sodium borohydride acetate; THF represents tetrahydrofuran; Boc$_2$O represents di-tert-butyl dicarbonate; TFA represents trifluoroacetic acid; Cu(acac)$_2$ represents copper acetylacetonate; DIEA represents diisopropylethylamine; Xantphos represents 9,9-dimethyl-4,5-bisdiphenylphospheno xanthene; Pd(OAc)$_2$ represents palladium acetate; Pd(dppf)Cl$_2$ represents [1,1'-bis(diphenylphosphino)ferrocene]palladium dichloride; K$_3$PO$_4$ represents potassium phosphate; K$_2$CO$_3$ represents potassium carbonate; NaHCO$_3$ represents sodium hydrogencarbonate; Na$_2$CO$_3$ represents sodium carbonate; HCl represents hydrogen chloride; Pd/C represents palladium carbon; ICl represents iodine chloride; NaH represents sodium hydride; DMAP represents 4-dimethyl aminopyridine; DIPEA/DIEA represents N,N'-diisopropylethylamine; DPPF represents 1,1'-bis (diphenylphosphino)ferrocene; DCE represents 1,2-dichloroethane; DME represents dimethoxyethane.

Compounds are named manually or by ChemDraw® software, and the commercially available compounds use their vendor directory names.

DETAILED DESCRIPTION

The application is described in detail below with the following examples, but does not mean any adverse limitation to the application. The present application has been specified herein, wherein the particular embodiments of the present application are disclosed. Various variation and modifications will be made to the embodiments of the present application without departing from the spirit and scope of the present application, which would be apparent for the skilled in the art.

Example 1

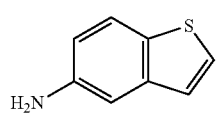

Compound 1A

Under protection of nitrogen gas, 5-bromobenzothiophene (10 g, 46.93 mmol), K$_3$PO$_4$ (9.96 g, 46.93 mmol) and Cu(acac)$_2$ (644 mg, 1.16 mmol, 0.05 eq.) were dissolved in DMF solution in liquid ammonia (2M, 50 mL). The reaction solution was reacted in a high-pressure reactor at 100° C. for 12 hours. The reaction solution was filtered and the filtrate was concentrated to give a crude product. The crude product was purified by column chromatography to obtain compound 1A. $^1$H NMR (400 MHz, CDCl$_3$) δ=7.65 (d, J=8.5 Hz, 1H), 7.39 (d, J=5.3 Hz, 1H), 7.16 (d, J=5.3 Hz, 1H), 7.11 (s, 1H), 6.79 (dd, J=1.8, 8.5 Hz, 1H), 3.67 (br s, 2H).

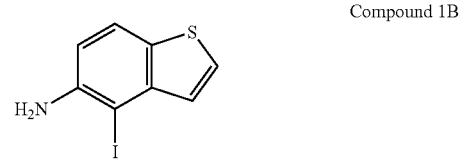 [SMILES: Nc1ccc2sccc2c1I]

Compound 1B

Compound 1A (3.8 g, 25.47 mmol) and NaHCO$_3$ (4.28 g, 50.93 mmol) were dissolved in 50 mL of DCM and then added dropwise with iodine chloride (4.96 g, 30.56 mmol, 1.56 mL), and the reaction solution was reacted at 20° C. for 1 hour. After the reaction was completed, the reaction solution was added with 100 mL of DCM and washed respectively with water and saturated brine. The organic phases were combined, dried and concentrated to give compound 1B.

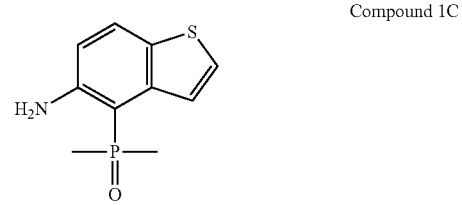

Compound 1C

Compound 1B (0.6 g, 2.18 mmol), dimethylphosphine oxide (364.76 mg, 3.27 mmol), Xantphos (126.19 mg, 218.10 μmol), Pd(OAc)$_2$ (48.96 mg, 218.10 μmol), and K$_3$PO$_4$ (694.41 mg, 3.27 mmol) were dissolved in 10 mL of DMF and 2 mL of H$_2$O, and the reaction was carried out at 120° C. under the protection of nitrogen gas for 24 hours. After the reaction was completed, the reaction solution was concentrated and purified by column chromatography to obtain compound 1C.

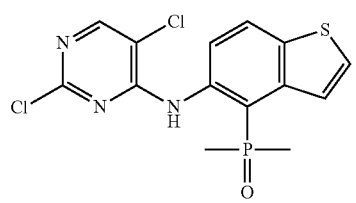

Compound 1D

Compound 1C (0.3 g, 1.33 mmol) was dissolved in 5 mL of EtOH, and 2,4,5-trichloropyrimidine (488.59 mg, 2.66 mmol, 303.47 μL) and DIEA (688.54 mg, 5.33 mmol, 927.95 μL) were added thereto. The reaction solution was refluxed under the protection of nitrogen gas for 24 hours. After the reaction was completed, the reaction solution was concentrated and purified by column chromatography to obtain compound 1D.

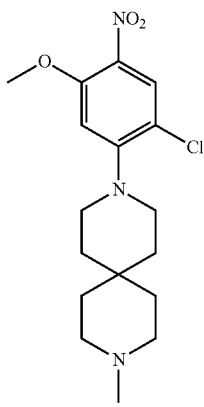

Compound 1E

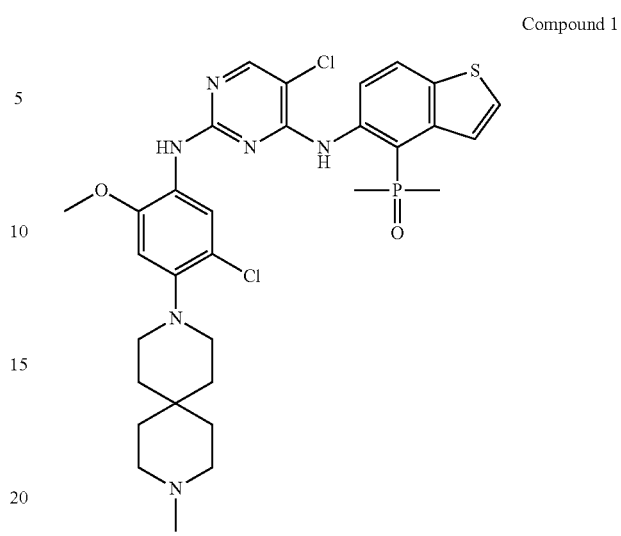

Compound 1

The compounds of 1-chloro-2-fluoro-4-methoxy-5-nitrobenzene and 3-methyl-3,9-diazaspiro[5.5]undecane were dissolved in 30 mL of DMF, and then K$_2$CO$_3$ (5.04 g, 36.48 mmol) was added. The reaction was carried out at 60° C. under the protection of nitrogen for 8 hours. After the reaction was completed, the reaction solution was filtered, and the filtrate was concentrated and purified by column chromatography to obtain compound 1E. $^1$H NMR (400 MHz, CDCl$_3$) δ=8.05 (s, 1H), 6.57 (s, 1H), 3.96 (s, 3H), 3.19-3.11 (m, 4H), 2.42 (m, 4H), 2.31 (s, 3H), 1.71-1.67 (m, 4H), 1.65-1.61 (m, 4H).

Compound 1D (100 mg, 268.67 μmol) and compound 1F (87.01 mg, 268.67 μmol) were dissolved in 4 mL of tert-butanol, and added with methylsulphonicacid (103.28 mg, 1.07 mmol, 76.50 μL). The reaction was carried out at 90° C. for 12 hours. After the reaction was completed, the reaction solution was concentrated, adjusted to pH value of about 9 with saturated NaHCO$_3$, and extracted three times with DCM. The organic phases were collected, dried and concentrated to give a crude product. The crude product was purified by preparative HPLC to obtain compound 1 (40.16 mg, 63.98 μmol). $^1$H NMR (400 MHz, MeOD) δ=8.54 (br s, 1H), 8.17 (d, J=9.0 Hz, 1H), 8.09 (s, 1H), 8.02 (d, J=5.6 Hz, 1H), 7.91-7.80 (m, 3H), 6.74 (s, 1H), 3.88 (s, 3H), 3.30-3.16 (m, 4H), 2.96-2.88 (m, 4H), 2.84 (s, 3H), 1.99 (s, 3H)), 1.95 (s, 3H), 1.83 (br s, 3H), 1.73 (br s, 4H).

Example 2

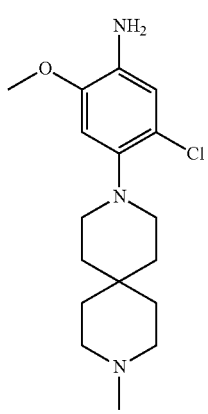

Compound 1F

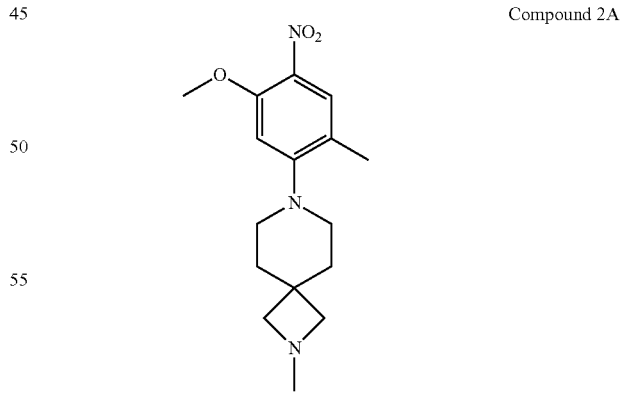

Compound 2A

Compound 1E (3.1 g, 8.76 mmol) was dissolved in 30 mL of EtOH, and iron powder (2.94 g, 52.57 mmol) and an aqueous solution of ammonium chloride (4.69 g of ammonium chloride dissolved in 10 mL of water) were added. Under the protection of nitrogen gas, the reaction was carried out at 90° C. for 2 hours. After the reaction was completed, the reaction solution was filtered and the filtrate was concentrated to obtain compound 1F. $^1$H NMR (400 MHz, DMSO-d$_6$) δ=6.71 (s, 1H), 6.66 (s, 1H), 4.73 (br s, 2H), 3.77 (s, 3H), 3.25 (m, 2H), 3.06 (m, 2H), 2.81 (m, 4H), 2.74 (s, 3H), 1.89 (m, 2H), 1.74 (m, 2H), 1.60 (m, 2H), 1.49 (m, 2H).

Except for separate replacement of the compounds of 1-chloro-2-fluoro-4-methoxy-5-nitrobenzene and 3-methyl-3,9-diazaspiro[5.5]undecane with the compounds of 1-fluoro-5-methoxy-2-methyl-4-nitrobenzene and 2-methyl-2,7-diazaspiro[3.5]nonane, compound 2A was prepared according to the method for preparing compound 1E.

Compound 2B

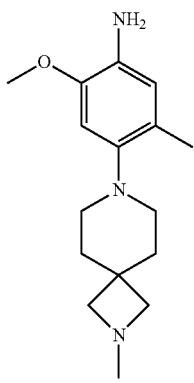

Except for replacing compound 1E with compound 2A, compound 2B was prepared according to the method for preparing compound 1F. $^1$H NMR (400 MHz, CDCl$_3$) δ=6.57 (s, 1H), 6.53 (s, 1H), 4.64 (s, 1H), 3.86-3.82 (m, 1H), 3.91-3.79 (m, 1H), 3.37 (s, 4H), 2.78-2.69 (m, 4H), 2.58-2.49 (m, 3H), 2.19 (d, J=15.8 Hz, 3H), 1.97-1.89 (m, 4H).

Compound 2

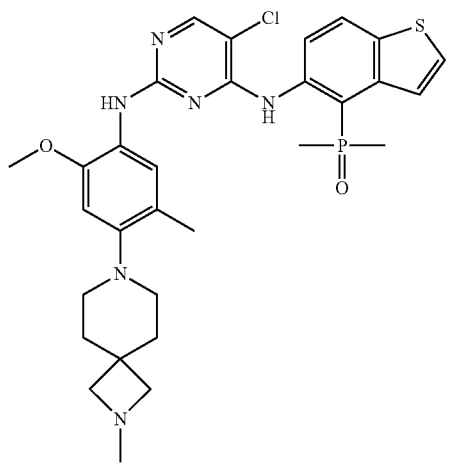

Except for replacing compound 1F with compound 2B, compound 2 was prepared according to the method for preparing compound 1. $^1$H NMR (400 MHz, CD$_3$OD) δ=8.54 (br s, 1H), 8.17 (d, J=9.0 Hz, 1H), 8.09 (s, 1H), 8.02 (d, J=5.6 Hz, 1H), 7.91-7.80 (m, 3H), 6.74 (s, 1H), 3.88 (s, 3H), 3.30-3.16 (m, 4H), 2.96-2.88 (m, 4H), 2.84 (s, 3H), 1.99 (s, 3H), 1.95 (s, 3H), 1.83 (brs, 3H), 1.73 (br s, 4H).

Example 3

Compound 3A

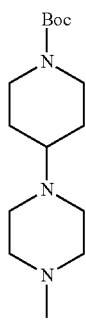

The compounds of tert-butyl 4-oxopiperidine-1-carboxylate (20 g, 100.38 mmol) and 1-methylpiperazine (12.06 g, 120.45 mmol, 13.36 mL) were dissolved in 200 mL of ethanol, and added with AcOH (6.03 g, 100.38 mmol, 5.74 mL) and NaBH(OAc)$_3$ (42.55 g, 200.76 mmol). The reaction was performed at 20° C. for 12 hours. After the reaction was completed, the reaction was quenched by adding methanol (10 mL) and water (10 mL) and then extracted with ethyl acetate (500 mL). The organic phase was collected, dried and concentrated to give compound 3A.

Compound 3B

Compound 3A (16 g, 56.46 mmol) was dissolved in HCl/MeOH (50 mL, 4M) and reacted at 0° C. for 12 hours. After the reaction was completed, the reaction solution was concentrated to give compound 3B.

Compound 3C

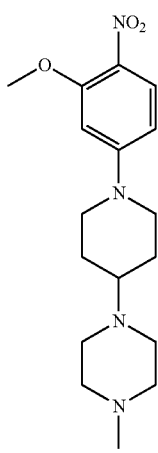

Except for separate replacement of the compounds of 1-chloro-2-fluoro-4-methoxy-5-nitrobenzene and 3-methyl-3,9-diazaspiro[5.5]undecane with the compounds of 4-fluoro-2-methoxy-1-nitrobenzene and 1-methyl-4-(4-piperidinyl)piperazine, compound 3C was prepared according to the method for preparing compound 1E. $^1$H NMR (400 MHz, CDCl$_3$) δ=8.02-7.88 (m, 1H), 6.40 (dd, J=2.5, 9.5 Hz, 1H), 6.29 (d, J=2.5 Hz, 1H), 3.99-3.84 (m, 5H), 3.26-2.86 (m, 4H), 2.65-2.41 (m, 8H), 2.29 (s, 3H), 2.00-1.92 (m, 2H), 1.59 (dq, J=4.0, 12.0 Hz, 2H).

Compound 3D

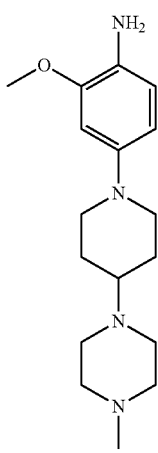

Except for replacing compound 1E with compound 3C, compound 3D was prepared according to the method for preparing compound 1F. $^1$H NMR (400 MHz, CDCl$_3$) δ=6.56 (d, J=8.3 Hz, 1H), 6.45 (d, J=2.4 Hz, 1H), 6.34 (dd, J=2.4, 8.6 Hz, 1H), 3.76 (s, 3H), 3.45 (br d, J=12.2 Hz, 3H), 2.75-2.47 (m, 7H), 2.46-2.36 (m, 3H), 2.31-2.20 (m, 5H), 1.85 (br d, J=12.5 Hz, 2H), 1.64 (dq, J=3.8, 12.0 Hz, 2H).

Compound 3

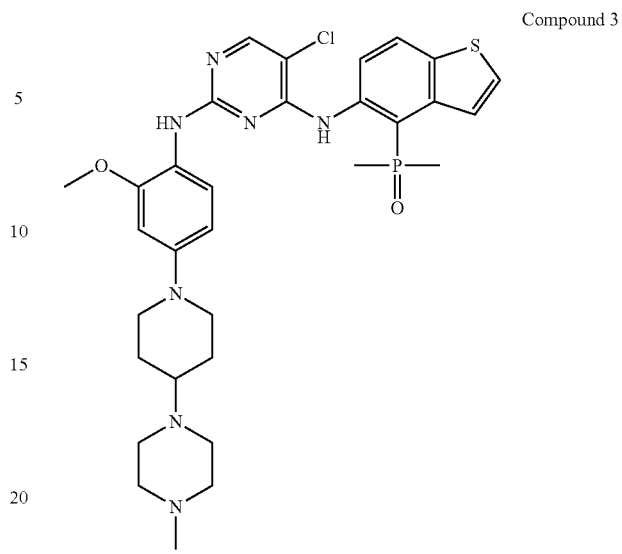

Except for replacing compound 1F with compound 3D, compound 3 was prepared according to the method for preparing compound 1. $^1$H NMR (400 MHz, CD$_3$OD) δ=8.14 (d, J=8.8 Hz, 1H), 8.04-7.87 (m, 4H), 7.36 (br d, J=8.6 Hz, 1H), 6.59 (d, J=2.2 Hz, 1H), 5.98 (br d, J=8.1 Hz, 1H), 3.83 (s, 3H), 3.64-3.57 (m, 3H), 2.96-2.56 (m, 10H), 2.47 (s, 4H), 2.02 (br d, J=12.5 Hz, 2H), 1.95 (s, 3H), 1.91 (s, 3H), 1.71-1.60 (m, 2H).

Example 4

Compound 4A

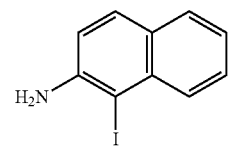

Under the protection of nitrogen gas, naphthalene-2-amine (4 g, 27.94 mmol) was dissolved in a mixed solution of 120 mL DCM and 40 mL MeOH, and added with benzyltrimethylammonium dichloroiodide (9.72 g, 27.94 mmol). The reaction solution was reacted at 20° C. for 0.5 hours. After the reaction was completed, the reaction solution was washed with sodium bicarbonate solution, and the organic phase was collected and concentrated to obtain a crude product. The crude product was purified by column chromatography to give compound 4A. $^1$H NMR (400 MHz, CDCl$_3$) δ=8.00 (d, J=8.4 Hz, 1H), 7.66 (dd, J=8.3, 17.6 Hz, 2H), 7.54 (ddd, J=1.2, 7.2, 8.4 Hz, 1H), 7.37-7.29 (m, 1H), 6.99 (d, J=8.8 Hz, 1H), 4.47 (br s, 2H).

Compound 4B

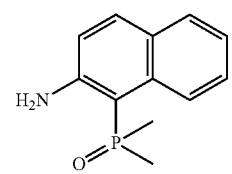

Except for replacing compound 1B with compound 4A, compound 4B was prepared according to the method for preparing compound 1C. $^1$H NMR (400 MHz, CDCl$_3$) δ=7.66 (d, J=8.8 Hz, 2H), 7.51-7.45 (m, 1H), 7.45-7.37 (m, 1H), 7.25-7.17 (m, 1H), 6.76 (dd, J=3.6, 8.8 Hz, 1H), 6.51 (br s, 2H), 2.05 (s, 3H), 2.01 (s, 2H); LC-MS (ESI): m/z: 220.1 [M+1].

Compound 4C

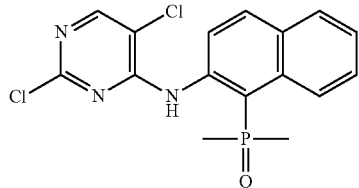

Except for replacing compound 1C with compound 4B, compound 4C was prepared according to the method for preparing compound 1D. $^1$H NMR (400 MHz, CDCl$_3$) δ=13.05 (s, 1H), 8.62 (dd, J=4.0, 9.2 Hz, 1H), 8.24 (s, 1H), 8.04 (d, J=9.6 Hz, 1H), 7.89 (d, J=8.0 Hz, 1H), 7.71 (d, J=8.4 Hz, 1H), 7.56 (dd, J=7.2, 7.2 Hz, 1H), 7.48 (dd, J=7.2, 7.2 Hz, 1H), 2.18 (s, 3H), 2.14 (s, 3H).

Compound 4

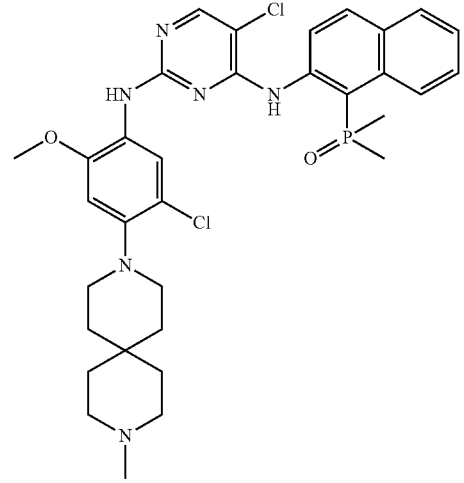

Except for replacing compound 1D with compound 4C, compound 4 was prepared according to the method for preparing compound 1. $^1$H NMR (400 MHz, MeOD) δ=8.45 (s, 1H), 8.24-8.17 (m, 2H), 8.11 (s, 1H), 8.06 (d, J=9.2 Hz, 1H), 7.98 (s, 1H), 7.91 (d, J=8.0 Hz, 1H), 7.63 (ddd, J=1.2, 7.2, 7.2 Hz, 1H), 7.53 (dd, J=7.2, 7.2 Hz, 1H), 6.75 (s, 1H), 3.89 (s, 3H), 3.32-3.12 (m, 4H), 2.98-2.90 (m, 4H), 2.88 (s, 3H), 2.14 (s, 3H), 2.10 (s, 3H), 2.05-1.49 (m, 8H); LC-MS (ESI): m/z: 653.0 [M+1].

Example 5

Compound 5

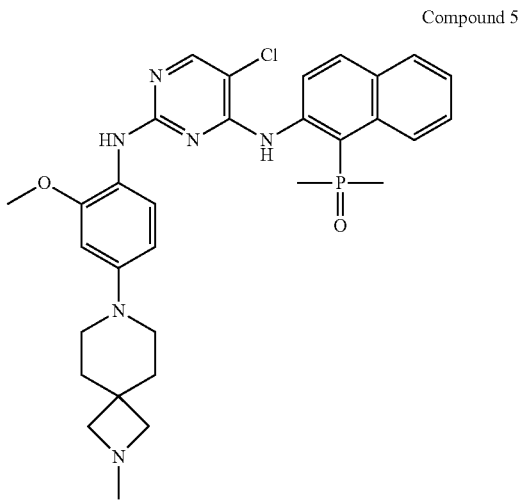 [SMILES: COc1cc(N2CCC3(CC2)CN(C)C3)ccc1Nc1ncc(Cl)c(Nc2ccc3ccccc3c2P(C)(C)=O)n1]

Except for respectively replacing compounds 1D and 1F with compounds 4C and 2B, compound 5 was prepared according to the method for preparing compound 1. $^1$H NMR (400 MHz, CD$_3$OD) δ=8.56 (br s, 1H), 8.30-8.21 (m, 2H), 8.06 (s, 1H), 8.02 (d, J=9.2 Hz, 1H), 7.96 (d, J=8.0 Hz, 1H), 7.67-7.61 (m, 1H), 7.61-7.53 (m, 2H), 6.62 (d, J=2.0 Hz, 1H), 6.11 (d, J=8.8 Hz, 1H), 3.87 (s, 4H), 3.84 (s, 3H), 3.09-2.97 (m, 4H), 2.88 (s, 3H), 2.10 (s, 3H), 2.07 (s, 3H), 2.04-1.94 (m, 4H); LCMS (ESI): m/z: 591.1 [M+1].

Example 6

Compound 6

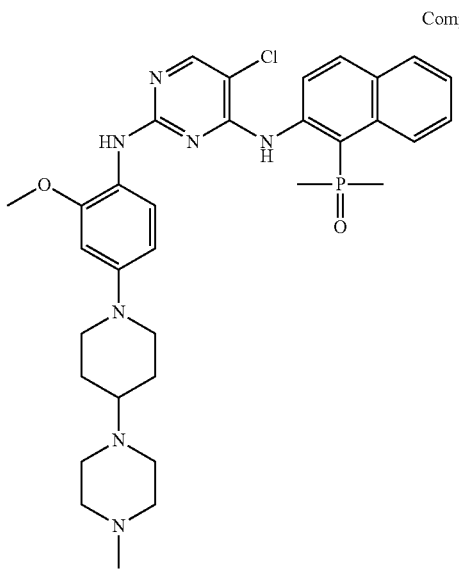

Except for respectively replacing compounds 1D and 1F with compounds 4C and 3D, compound 6 was prepared according to the method for preparing compound 1. $^1$H NMR (400 MHz, CD$_3$OD) δ=8.54 (br s, 1H), 8.30-8.22 (m, 2H), 8.06 (s, 1H), 8.02 (d, J=9.2 Hz, 1H), 7.97 (d, J=8.0 Hz, 1H), 7.67-7.62 (m, 1H), 7.60-7.49 (m, 2H), 6.63 (d, J=2.4

Hz, 1H), 6.13 (d, J=8.0 Hz, 1H), 3.85 (s, 3H), 3.63 (d, J=12.4 Hz, 2H), 2.79 (br s, 6H), 2.71-2.61 (m, 3H), 2.61-2.38 (m, 5H), 2.11 (s, 3H), 2.07 (s, 3H), 2.02 (br d, J=12.8 Hz, 2H), 1.72-1.61 (m, 2H); LCMS (ESI): m/z: 634.1 [M+1].

Example 7

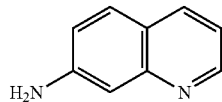

Compound 7A

7-Nitroquinoline (7 g, 40.19 mmol) was dissolved in 120 mL of methanol, and added with Pd/C (10%, 1 g) under nitrogen atmosphere. After purged with hydrogen 3 times, the reaction solution was stirred at 20° C. under hydrogen atmosphere for 12 hours. After the reaction was completed, the reaction mixture was filtered and the filtrate was concentrated to give compound 7A. $^1$H NMR (400 MHz, CDCl$_3$) δ=8.75 (dd, J=1.8, 4.3 Hz, 1H), 7.98 (dd, J=0.8, 8.0 Hz, 1H), 7.61 (d, J=8.8 Hz, 1H), 7.22 (d, J=2.3 Hz, 1H), 7.13 (dd, J=4.4, 8.2 Hz, 1H), 6.98 (dd, J=2.3, 8.5 Hz, 1H), 3.98 (br s, 2H).

Compound 7B

Compound 7A (2.5 g, 17.34 mmol) was dissolved in 75 mL of AcOH, and ICl (3.10 g, 19.07 mmol, 973.85 μL) was dissolved in 25 mL of acetic acid, which was added dropwise to the reaction solution. The reaction was stirred at 20° C. for 1 hour. After the reaction was completed, the reaction solution was subjected to rotary evaporation to remove acetic acid, and the residue was extracted with ethyl acetate and diluted, and then washed successively with water and saturated brine. The organic phase was collected, dried and concentrated to give a crude product. The crude product was purified by column chromatography to give compound 7B. $^1$H NMR (400 MHz, CDCl$_3$) δ=8.88 (dd, J=1.5, 4.3 Hz, 1H), 7.95 (dd, J=1.5, 8.0 Hz, 1H), 7.58 (d, J=8.5 Hz, 1H), 7.21 (dd, J=4.3, 8.0 Hz, 1H), 7.04 (d, J=8.5 Hz, 1H), 5.10-4.63 (m, 2H).

Compound 7C

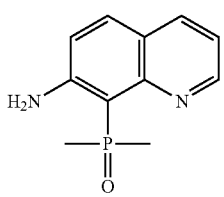

Except for replacing compound 1B with compound 7B, compound 7C was prepared according to the method for preparing compound 1C. $^1$H NMR (400 MHz, CDCl$_3$) δ=8.63 (dd, J=1.8, 4.3 Hz, 1H), 7.88 (td, J=1.5, 7.9 Hz, 1H), 7.61 (d, J=9.0 Hz, 1H), 7.10 (dd, J=4.4, 8.1 Hz, 1H), 6.80 (dd, J=3.9, 8.8 Hz, 1H), 6.73-6.23 (m, 1H), 2.07 (s, 3H), 2.03 (s, 3H).

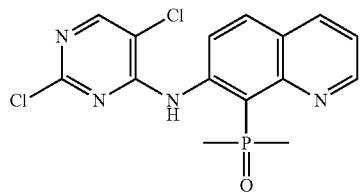

Compound 7D

Except for replacing compound 1C with compound 7C, compound 7D was prepared according to the method for preparing compound 1D. $^1$H NMR (400 MHz, CDCl$_3$) δ=13.31 (s, 1H), 8.93 (dd, J=3.9, 9.2 Hz, 1H), 8.82 (dd, J=1.8, 4.3 Hz, 1H), 8.27 (s, 1H), 8.14 (d, J=8.3 Hz, 1H), 8.01 (d, J=9.3 Hz, 1H), 7.38 (dd, J=4.3, 8.3 Hz, 1H), 2.19 (s, 3H), 2.15 (s, 3H).

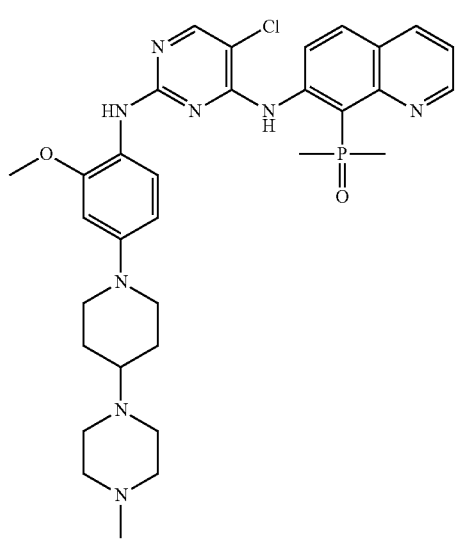

Compound 7

Except for replacing compound 3D with compound 7D, compound 7 was prepared according to the method for preparing compound 1. $^1$H NMR (400 MHz, CD$_3$OD) δ=8.92-8.79 (m, 2H), 8.50 (br s, 1H), 8.23 (br d, J=8.3 Hz, 1H), 8.07 (s, 1H), 7.90 (d, J=9.3 Hz, 1H), 7.69 (d, J=8.6 Hz, 1H), 7.43 (dd, J=4.3, 8.2 Hz, 1H), 6.69 (d, J=2.4 Hz, 1H), 6.53 (dd, J=2.4, 8.8 Hz, 1H), 3.85 (s, 3H), 3.74 (br d, J=12.2 Hz, 2H), 2.99-2.65 (m, 10H), 2.62-2.56 (m, 1H), 2.55 (s, 3H), 2.16 (s, 3H), 2.12 (s, 3H), 2.04 (br d, J=12.5 Hz, 2H), 1.76-1.65 (m, 2H).

Example 8

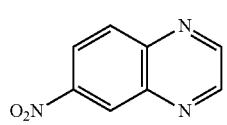

Compound 8A

4-Nitrobenzene-1,2-diamine (10 g, 65.30 mmol) was dissolved in 100 mL of ethanol and added with glyoxal (4.55 g, 78.36 mmol, 4.10 mL), with stirring at 80° C. for 15 hours. After the reaction was completed, the mixture was filtered and the filter cake was dried to give compound 10A. $^1$H NMR (400 MHz, DMSO-d$_6$) δ=9.18 (s, 2H), 8.93 (d, J=2.4 Hz, 1H), 8.58 (dd, J=2.4, 9.2 Hz, 1H), 8.36 (d, J=9.2 Hz, 1H); LC-MS (ESI): m/z: 176.1 [M+1].

Compound 8B

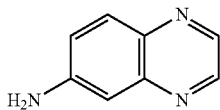

Except for replacing compound 1E with compound 8A, compound 8B was prepared according to the method for preparing compound 1F. $^1$H NMR (400 MHz, DMSO-d$_6$) δ=8.60 (d, J=1.6 Hz, 1H), 8.45 (d, J=1.6 Hz, 1H), 7.73 (d, J=9.2 Hz, 1H), 7.24 (dd, J=2.4, 9.2 Hz, 1H), 6.92 (d, J=2.4 Hz, 1H), 6.08 (s, 2H). LC-MS (ESI): m/z: 146.2 [M+1].

Compound 8C

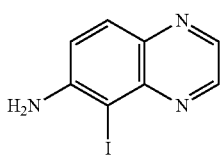

Except for replacing compound 7A with compound 8B, compound 8C was prepared according to the method for preparing compound 7B. $^1$H NMR (400 MHz, DMSO-d$_6$) δ=8.76 (d, J=1.6 Hz, 1H), 8.56 (d, J=1.6 Hz, 1H), 7.80 (d, J=9.2 Hz, 1H), 7.45 (d, J=9.2 Hz, 1H), 6.38 (br s, 2H). LC-MS (ESI): m/z: 271.9 [M+1].

Compound 8D

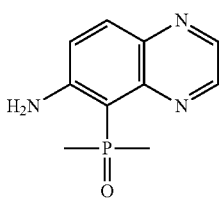

Except for replacing compound 1B with compound 8C, compound 8D was prepared according to the method for preparing compound 1C. $^1$H NMR (400 MHz, DMSO-d$_6$) δ=8.61 (d, J=1.6 Hz, 1H), 8.49 (d, J=1.6 Hz, 1H), 7.82 (d, J=9.2 Hz, 1H), 7.22 (d, J=9.2 Hz, 1H), 6.38 (br s, 2H), 1.89 (s, 3H), 1.85 (s, 3H). LC-MS (ESI): m/z: 222.1 [M+1].

Compound 8E

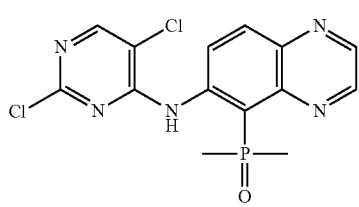

Except for replacing compound 1C with compound 8D, compound 8E was prepared according to the method for preparing compound 1D. $^1$H NMR (400 MHz, CDCl$_3$) δ=13.20 (s, 1H), 9.12 (dd, J=4.0, 9.6 Hz, 1H), 8.75 (s, 1H), 8.68 (s, 1H), 8.23 (s, 1H), 8.21 (d, J=9.6 Hz, 1H), 2.08 (s, 3H), 2.05 (s, 3H); LC-MS (ESI): m/z: 367.9 [M+1].

Compound 8

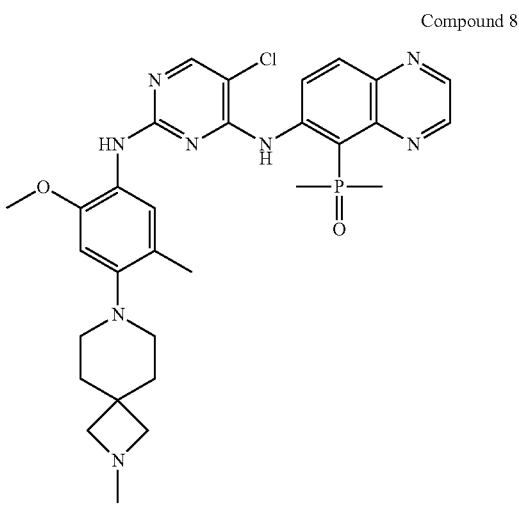 [SMILES: COc1cc(N2CCC3(CC2)CN(C)C3)c(C)cc1Nc1ncc(Cl)c(Nc2ccc3nccnc3c2P(C)(C)=O)n1]

Except for respectively replacing compounds 1D and 1F with compounds 8E and 2B, compound 8 was prepared according to the method for preparing compound 1. $^1$H NMR (400 MHz, DMSO-d$_6$) δ=12.90 (s, 1H), 9.09-8.96 (m, 1H), 8.87 (dd, J=2.0, 7.6 Hz, 2H), 8.31-8.24 (m, 2H), 8.20 (s, 1H), 7.93 (d, J=9.2 Hz, 1H), 7.37 (s, 1H), 6.74 (s, 1H), 3.78 (s, 3H), 3.10 (s, 4H), 2.77 (t, J=5.2 Hz, 4H), 2.33 (s, 3H), 2.12 (s, 3H), 2.05 (s, 3H), 2.02 (s, 3H), 1.84 (t, J=5.2 Hz, 4H); LC-MS (ESI): m/z: 607.1 [M+1].

Example 9

Compound 9

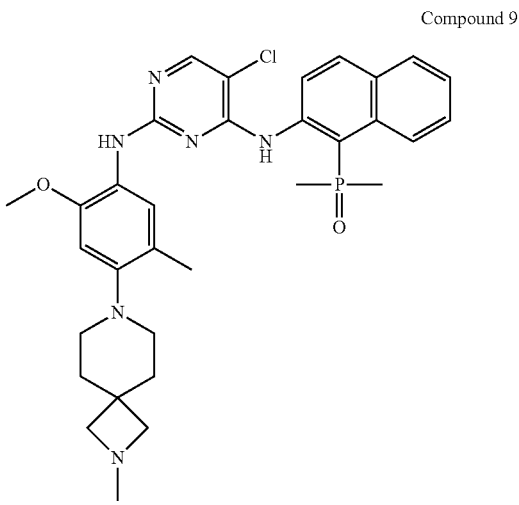 [SMILES: COc1cc(N2CCC3(CC2)CN(C)C3)c(C)cc1Nc1ncc(Cl)c(Nc2ccc3ccccc3c2P(C)(C)=O)n1]

Except for respectively replacing compounds 1D and 1F with compounds 4C and 2B, compound 9 was prepared according to the method for preparing compound 1. $^1$H NMR (400 MHz, CD$_3$OD) δ=8.57 (s, 1H), 8.27 (d, J=8.8 Hz, 1H), 8.24-8.19 (m, 1H), 8.08 (s, 1H), 8.00 (d, J=9.1 Hz, 1H), 7.93 (d, J=7.7 Hz, 1H), 7.68-7.53 (m, 3H), 6.65 (s, 1H), 3.84 (s, 3H), 3.58-3.50 (m, 4H), 2.79-2.71 (m, 4H), 2.66 (s, 3H), 2.12 (s, 3H), 2.09 (s, 3H), 1.98-1.90 (m, 4H), 1.79 (s, 3H).

Example 10

Compound 10

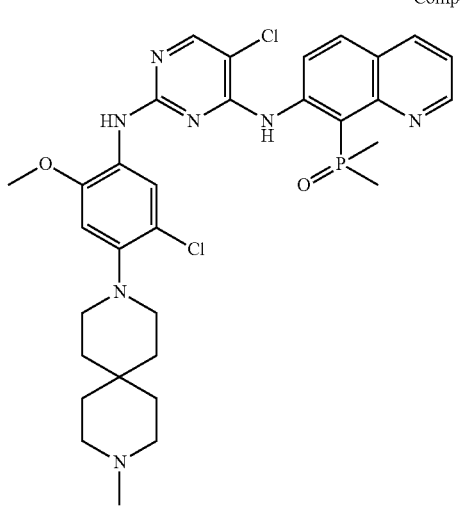

Except for replacing compound 1D with compound 7D, compound 10 was prepared according to the method for preparing compound 1. $^1$H NMR (400 MHz, CD$_3$OD) δ=8.83 (dd, J=1.7, 4.4 Hz, 1H), 8.71 (dd, J=3.7, 9.0 Hz, 1H), 8.49 (br s, 1H), 8.20 (br d, J=8.1 Hz, 1H), 8.11 (s, 1H), 8.06 (s, 1H), 8.00 (d, J=9.3 Hz, 1H), 7.43 (dd, J=4.3, 8.2 Hz, 1H), 6.78 (s, 1H), 3.89 (s, 3H), 3.24 (br s, 4H), 3.04-2.92 (m, 4H), 2.86 (s, 3H), 2.16 (s, 3H), 2.12 (s, 3H), 1.93-1.59 (m, 8H).

Example 11

Compound 11A

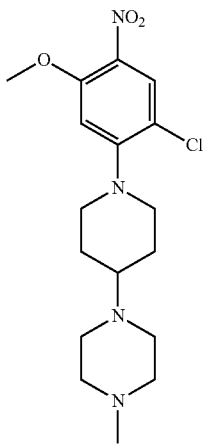

Except for respectively replacing the compounds of 1-chloro-2-fluoro-4-methoxy-5-nitrobenzene and 3-methyl-3,9-diazaspiro[5.5]undecane with the compounds of 1-chloro-2-fluoro-4-methoxy-5-nitrobenzene and 1-methyl-4-(piperidin-4-yl)piperazine, compound 11A was prepared according to the method for preparing compound 1E. $^1$H NMR (400 MHz, CD$_3$OD) δ=6.79 (s, 1H), 6.68 (s, 1H), 3.84 (s, 3H), 3.24-2.76 (m, 8H), 2.72 (br s, 1H), 2.71-2.65 (m, 2H), 2.02 (br d, J=10.8 Hz, 2H), 1.89-1.71 (m, 2H).

Compound 11B:

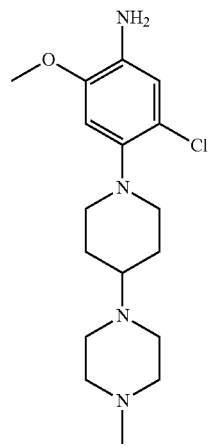 [SMILES: COc1cc(N2CCC(N3CCN(C)CC3)CC2)c(Cl)cc1N]

Except for replacing compound 1E with compound 11A, compound 11B was prepared according to the method for preparing compound 1F. $^1$H NMR (400 MHz, CDCl$_3$) δ=8.04 (s, 1H), 6.56 (s, 1H), 4.02-3.91 (m, 3H), 3.65 (br d, J=12.1 Hz, 2H), 2.81-2.73 (m, 2H), 2.66 (br s, 4H), 2.56-2.37 (m, 5H), 2.31 (s, 3H), 1.98 (br d, J=12.2 Hz, 2H), 1.84-1.71 (m, 2H).

Compound 11

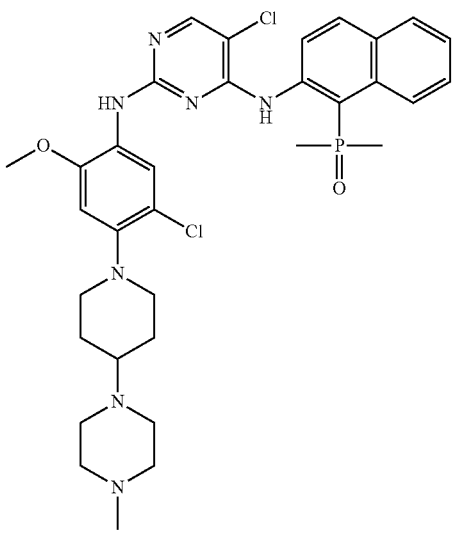

Except for separately replacing compounds 1D and 1F with compounds 4C and 11B, compound 11 was prepared according to the method for preparing compound 1. $^1$H NMR (400 MHz, CD$_3$OD) δ=8.23 (br d, J=8.7 Hz, 2H), 8.16-8.10 (m, 1H), 8.02 (br d, J=8.1 Hz, 1H), 7.76-7.55 (m, 3H), 6.85 (s, 1H), 4.01 (br s, 2H), 3.92 (s, 5H), 3.73 (br s, 3H), 3.69-3.56 (m, 2H), 3.50 (br d, J=10.1 Hz, 2H), 3.08 (s, 3H), 2.86 (br t, J=11.5 Hz, 2H), 2.36 (br d, J=11.5 Hz, 2H), 2.17 (s, 3H), 2.14 (s, 3H), 2.11-2.02 (m, 2H).

Example 12

Compound 12

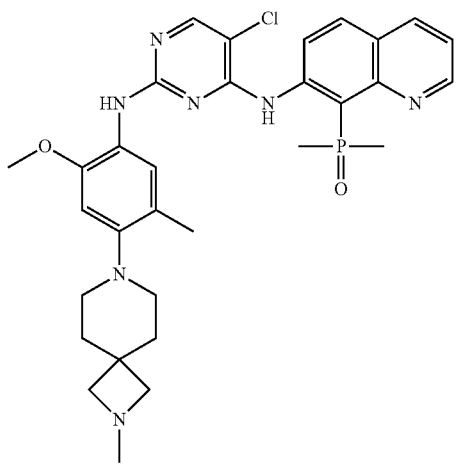

Except for respectively replacing compounds 1D and 1F with compounds 2B and 7D, compound 12 was prepared according to the method for preparing compound 1. $^1$H NMR (400 MHz, CD$_3$OD) δ=8.84 (br d, J=2.7 Hz, 1H), 8.79 (br dd, J=3.7, 9.0 Hz, 1H), 8.50 (br s, 1H), 8.22 (br d, J=8.1 Hz, 1H), 8.08 (s, 1H), 7.90 (br d, J=9.0 Hz, 1H), 7.74 (s, 1H), 7.44 (dd, J=4.3, 8.2 Hz, 1H), 6.71 (s, 1H), 4.01 (br s, 4H), 3.84 (s, 3H), 2.95 (s, 3H), 2.82 (br s, 4H), 2.16 (s, 3H), 2.13 (s, 3H), 2.08 (s, 3H), 2.03 (br s, 4H).

Example 13

Compound 13A

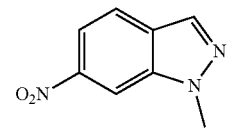

6-Nitro-1H-indazole (25 g, 153.25 mmol) was dissolved in 200 mL of DMF, NaH (6.74 g, 168.57 mmol, 60% purity) was added in portions at 0° C., and then MeI (23.93 g, 168.57 mmol, 10.49 mL) was added in portions at 0° C. The reaction was performed at 25° C. for 1 hour. After the reaction was completed, the reaction solution was poured into 500 mL of water and extracted with EtOAc. The organic phase was collected and washed successively with 20 mL of water and 20 mL of saturated brine. The organic phase was collected, dried and concentrated to give a crude product. The crude product was purified by column chromatography to give compound 13A. $^1$H NMR (400 MHz, DMSO-d$_6$) δ=8.71 (d, J=0.7 Hz, 1H), 8.29 (d, J=0.7 Hz, 1H), 8.03-7.97 (m, 1H), 7.96-7.92 (m, 1H), 4.19 (s, 3H).

Compound 13B

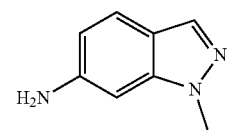

Except for replacing compound 1E with compound 13A, compound 13B was prepared according to the method for preparing compound 1F. $^1$H NMR (400 MHz, DMSO-d$_6$) δ=7.68 (s, 1H), 7.36 (d, J=8.6 Hz, 1H), 6.50 (dd, J=2.0, 8.6 Hz, 1H), 6.45 (s, 1H), 5.32 (s, 2H), 3.81 (s, 3H).

Compound 13C

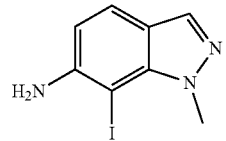

Except for replacing compound 7A with compound 13B, compound 13C was prepared according to the method for preparing compound 7B. $^1$H NMR (400 MHz, CDCl$_3$) δ=7.76 (s, 1H), 7.40 (d, J=8.5 Hz, 1H), 6.61 (d, J=8.3 Hz, 1H), 4.38 (s, 3H).

Compound 13D

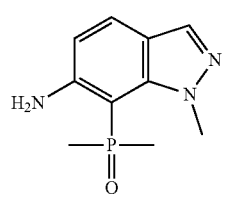

Except for replacing compound 1B with compound 13C, compound 13D was prepared according to the method for preparing compound 1C. $^1$H NMR (400 MHz, DMSO-d$_6$) δ=7.81 (d, J=1.7 Hz, 1H), 7.50 (dd, J=1.1, 8.7 Hz, 1H), 6.55 (dd, J=3.2, 8.8 Hz, 1H), 6.50 (s, 2H), 4.05 (s, 3H), 1.93 (s, 3H), 1.89 (s, 3H).

Compound 13E

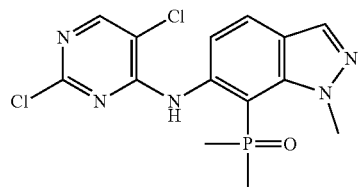

Except for replacing compound 1C with compound 13D, compound 13E was prepared according to the method for preparing compound 1D. $^1$H NMR (400 MHz, DMSO-d$_6$) δ=10.38 (s, 1H), 8.43 (s, 1H), 8.22 (s, 1H), 8.00 (br d, J=8.6 Hz, 1H), 7.24 (dd, J=2.8, 8.4 Hz, 1H), 4.41 (s, 3H), 1.88 (s, 3H), 1.84 (s, 3H).

Compound 13

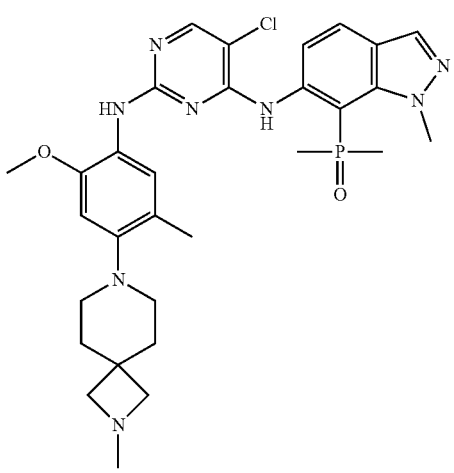

Except for replacing compound 1D with compound 13E and replacing compound 1F with compound 2B, compound 13 was prepared according to the method for preparing compound 1. ¹H NMR (400 MHz, DMSO-d$_6$) δ=9.56 (br s, 1H), 8.33 (s, 1H), 8.19 (d, J=1.5 Hz, 1H), 8.11 (s, 1H), 7.96 (dd, J=1.1, 8.4 Hz, 1H), 7.55 (s, 1H), 7.25 (s, 1H), 7.18 (dd, J=2.9, 8.6 Hz, 1H), 6.53 (s, 1H), 4.37 (s, 3H), 3.72 (s, 3H), 3.21 (s, 4H), 2.57 (br s, 4H), 2.39 (s, 3H), 1.79 (s, 3H), 1.76 (s, 7H).

Example 14

Compound 14A

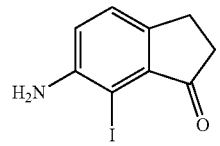

2,3-Dihydro-1H-indene-1-one (10 g, 75.67 mmol, 9.09 mL) was dissolved in 100 mL of concentrated sulfuric acid, and KNO$_3$ (8.03 g, 79.45 mmol) was added thereto at 0° C. The reaction was carried out at 0-5° C. for 1.5 hours. After the reaction was completed, the reaction solution was poured into 300 mL of water. After filtration, the filter cake was dissolved in EtOAc, dried and then concentrated to give a crude product. The crude product was purified by column chromatography to give compound 14A. ¹H NMR (400 MHz, DMSO-d$_6$) δ=8.60 (d, J=2.0 Hz, 1H), 8.48 (dd, J=2.3, 8.5 Hz, 1H), 7.69 (d, J=8.3 Hz, 1H), 3.34-3.27 (m, 2H), 2.90-2.83 (m, 2H).

Compound 14B

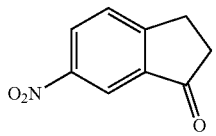

Except for replacing compound 1E with compound 14A, compound 14B was prepared according to the method for preparing compound 1F. ¹H NMR (400 MHz, DMSO-d$_6$) δ=7.29-7.25 (m, 1H), 7.02 (s, 1H), 6.98 (br d, J=8.3 Hz, 1H), 3.81 (br s, 2H), 3.09-3.00 (m, 2H), 2.74-2.66 (m, 2H); LCMS (ESI) m/z: 147.9 [M+1].

Compound 14C

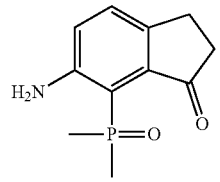

Except for replacing compound 7A with compound 14B, compound 14C was prepared according to the method for preparing compound 7B. ¹H NMR (400 MHz, CDCl$_3$) δ=7.26 (d, J=8.3 Hz, 1H), 7.09 (d, J=8.1 Hz, 1H), 5.49 (s, 2H), 2.86-2.81 (m, 2H), 2.65-2.60 (m, 2H); LCMS (ESI) m/z: 273.9 [M+1].

Compound 14D

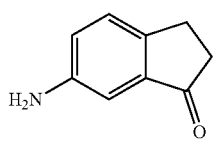

Except for replacing compound 1B with compound 14C, compound 14D was prepared according to the method for preparing compound 1C. LCMS (ESI) m/z: 223.9 [M+1].

Compound 14E

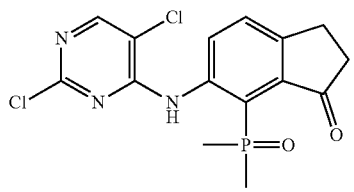

Except for replacing compound 1C with compound 14D, compound 14E was prepared according to the method for preparing compound 1D. ¹H NMR (400 MHz, DMSO-d$_6$) δ=13.09 (s, 1H), 8.84 (dd, J=3.5, 8.8 Hz, 1H), 8.24 (s, 1H), 7.71 (d, J=8.3 Hz, 1H), 3.21-3.16 (m, 2H), 2.80-2.75 (m, 2H), 2.08 (s, 3H), 2.04 (s, 3H); LC-MS (ESI) m/z: 369.9 [M+1].

Compound 14

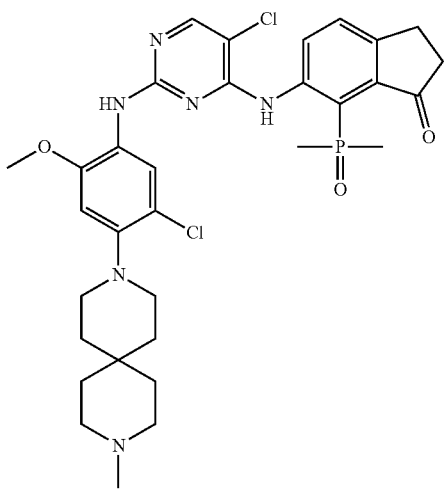

Except for replacing compound 1D with compound 14E, compound 14 was prepared according to the method for preparing compound 1. ¹H NMR (400 MHz, DMSO-d₆) δ=12.60 (s, 1H), 8.61 (br d, J=6.6 Hz, 1H), 8.30 (br s, 1H), 8.15 (s, 1H), 8.07 (s, 1H), 7.75 (s, 1H), 7.63 (br d, J=8.6 Hz, 1H), 6.87 (s, 1H), 3.84 (s, 3H), 3.08-3.01 (m, 2H), 2.93 (m, 4H), 2.74-2.67 (m, 2H), 2.60 (m, 4H), 2.36 (s, 3H), 1.93 (s, 3H), 1.90 (s, 3H), 1.60 (m, 8H); LCMS (ESI) m/z: 657.0 [M+1].

Example 15

Compound 15A

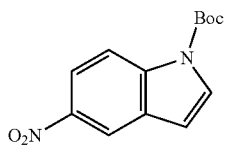

DMAP (376 mg, 3.08 mmol) was added to a solution of 5-nitro-1H-indole (10 g, 61.6 mmol) and Boc₂O (14.1 g, 64.7 mmol, 14.9 mL) in tetrahydrofuran (100 mL) at room temperature, and stirred for 1 hour. After the reaction was completed, the reaction solution was concentrated and slurried with petroleum ether to give compound 15A. ¹H NMR (400 MHz, CDCl₃) δ ppm 8.52 (d, J=1.88 Hz, 1H), 8.17-8.35 (m, 2H), 7.76 (d, J=3.76 Hz, 1H), 7.28 (s, 1H), 6.74 (d, J=3.64 Hz, 1H), 1.72 (s, 9H), 1.59 (s, 7H).

Compound 15B

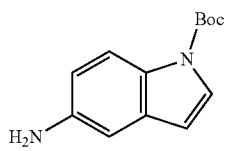

Except for replacing compound 15A with the compound of 7-nitroquinoline, compound 15B was prepared according to the preparation method of compound 7A. ¹H NMR (400 MHz, CDCl₃) δ ppm 1.58 (s, 13H), 3.41 (s, 1H), 3.52 (br s, 2H), 6.32 (d, J=3.67 Hz, 1H), 6.64 (dd, J=8.68, 2.20 Hz, 1H), 6.77 (d, J=2.20 Hz, 1H), 7.19 (s, 1H), 7.36-7.51 (m, 1H), 7.74-7.93 (m, 1H).

Compound 15C

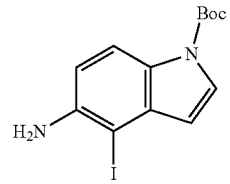

Except for replacing compound 15B with compound 1A, compound 15C was prepared according to the preparation method of compound 1B. ¹H NMR (400 MHz, CDCl₃) δ 1.58 (s, 9H), 6.34 (d, J=3.67 Hz, 1H), 6.69 (d, J=8.68 Hz, 1H), 7.19 (s, 1H), 7.43-7.56 (m, 1H), 7.83 (br d, J=8.44 Hz, 1H).

Compound 15D

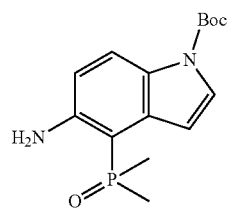

Except for replacing compound 1B with compound 15C, compound 15D was prepared according to the preparation method of compound 1C. ¹H NMR (400 MHz, m) 6 ppm 1.57 (s, 9H), 2.88 (s, 3H), 3.01 (s, 3H), 6.47-6.56 (m, 1H), 6.59 (d, J=3.91 Hz, 1H), 6.75 (dd, J=9.05, 4.16 Hz, 4H).

Compound 15E

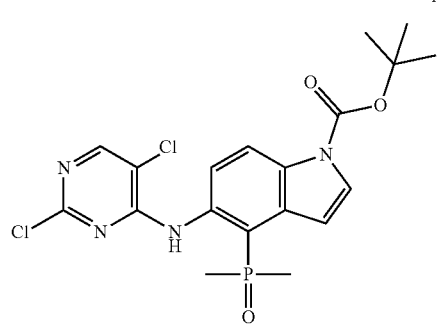

Except for replacing compound 1C with compound 15D, compound 15E was prepared according to the preparation method of compound 1D.

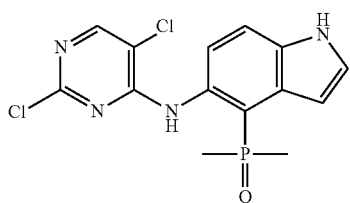

Compound 15F

Compound 15E (1.5 g, 3.29 mmol) was dissolved in 20 mL of DCM, and TFA (3.76 g, 32.9 mmol, 2.44 mL) was added thereto. The reaction was carried out at room temperature for 1 hour. After the reaction was completed, the organic phase was concentrated and purified by preparative HPLC to give compound 15F. $^1$H NMR (400 MHz, CDCl$_3$) δ ppm 11.88 (s, 1H), 8.45 (d, J=8.8 Hz, 1H), 7.65 (d, J=8.8 Hz, 1H), 7.28 (s, 1H), 6.41 (s, 1H), 2.07 (s, 3H), 2.03 (s, 3H).

Compound 15G

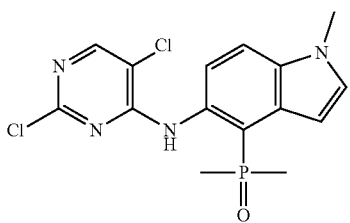

Sodium hydrogen (59.9 mg, 1.49 mmol, 60% purity) and methyl iodide (211 mg, 1.49 mmol, 92.9 μL) were added to a solution of compound 15F (0.53 g, 1.49 mmol) in DMF (10 ml), and the solution was cooled down to the temperature of 0° C. and reacted for 1 hour. After the reaction was completed, it was quenched by adding water, extracted with ethyl acetate, and the organic phase was washed with saturation solution, dried over anhydrous sodium sulfate, concentrated, and purified by preparative thin-layer chromatography to give compound 15G $^1$H NMR (400 MHz, CDCl$_3$) δ ppm 8.52-8.49 (m, 1H), 8.21 (s, 1H), 7.61-7.59 (m, 1H), 7.20 (s, 1H), 6.31 (s, 1H), 3.87 (s, 3H), 2.03 (s, 3H), 1.99 (s, 3H).

Compound 15

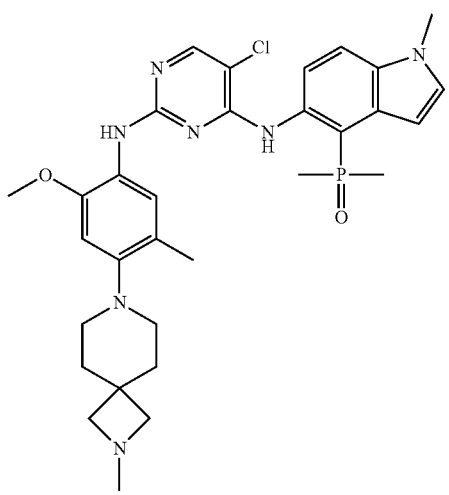

Except for replacing compound 1D with compound 15G and replacing compound 1F with compound 2B, compound 15 was prepared according to the preparation method of compound 1. $^1$H NMR (400 MHz, CDCl$_3$) δ ppm 11.31 (s, 1H), 8.59 (s, 1H), 8.41 (dd, J=9.16, 3.76 Hz, 1H), 7.51 (d, J=9.29 Hz, 1H), 7.37 (s, 1H), 7.28 (s, 1H), 6.34 (d, J=3.01 Hz, 1H), 3.86 (m, 8H), 3.72 (s, 3H), 2.76 (m, 7H), 2.11 (s, 3H), 2.03-1.98 (m, 9H).

Example 16

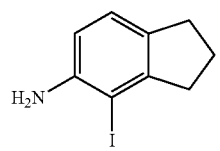

Compound 16A

Except for replacing compound 1A with the compound of 2,3-dihydro-1H-inden-5-amine, compound 16A was prepared according to the method for preparing compound 1B. $^1$H NMR (400 MHz, CDCl$_3$) δ=7.26 (d, J=8.0 Hz, 1H), 7.01 (d, J=8.0 Hz, 1H), 2.96-2.96 (m, 4H), 2.76-2.73 (m, 2H).

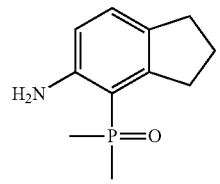

Compound 16B

Except for replacing compound 1B with compound 16A, compound 16B was prepared according to the method for preparing compound 1C. Except for replacing compound 1B with compound 16A, compound 16B was prepared according to the method for preparing compound 1C. $^1$H NMR (400 MHz, CDCl$_3$) δ=7.11 (d, J=8.0 Hz, 1H), 6.47 (d, J=8.0 Hz, 1H), 2.84-2.76 (m, 4H), 2.08-2.06 (m, 2H), 1.84 (s, 3H), 1.81 (s, 3H).

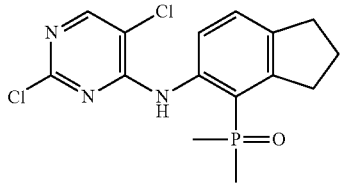

Compound 16C

Except for replacing compound 1C with compound 16B, compound 16C was prepared according to the method for preparing compound 1D. $^1$H NMR (400 MHz, CDCl$_3$) δ=12.18 (s, 1H), 8.41 (dd, J=3.9, 8.4 Hz, 1H), 8.19 (s, 1H), 7.47 (d, J=7.8 Hz, 1H), 2.93 (t, J=7.4 Hz, 4H), 2.15 (quuin, J=7.3 Hz, 2H), 1.93 (s, 3H), 1.89 (s, 3H).

Compound 16

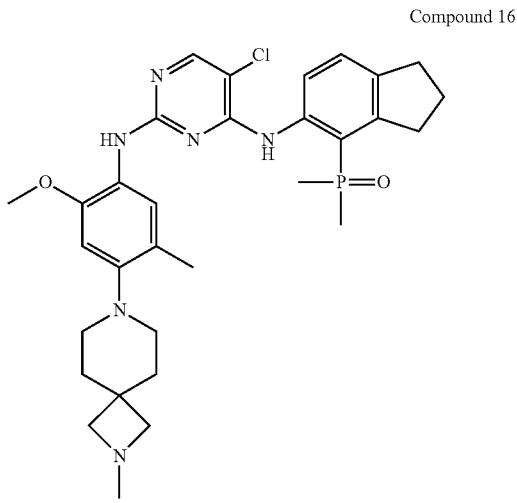 [SMILES: COc1cc(N2CCC3(CC2)CN(C)C3)c(C)cc1Nc1ncc(Cl)c(Nc2ccc3c(c2P(C)(C)=O)CCC3)n1]

Except for replacing compound 1D with compound 16C and replacing compound 1F with compound 2B, compound 16 was prepared according to the method for preparing compound 1. $^1$H NMR (400 MHz, DMSO-$d_6$) δ=11.50 (s, 1H), 8.33 (br s, 1H), 8.09 (br dd, J=3.2, 8.1 Hz, 1H), 8.06 (s, 1H), 7.86 (s, 1H), 7.47 (s, 1H), 7.26 (d, J=8.3 Hz, 1H), 6.68 (s, 1H), 3.77 (s, 3H), 3.45 (br s, 3H), 2.97 (br t, J=7.1 Hz, 2H), 2.80 (br t, J=7.3 Hz, 2H), 2.73 (br s, 4H), 2.56-2.52 (m, 4H), 2.07 (s, 3H), 2.05-1.97 (m, 2H), 1.87 (br s, 4H), 1.80 (s, 3H), 1.76 (s, 3H).

Example 17

Compound 17A

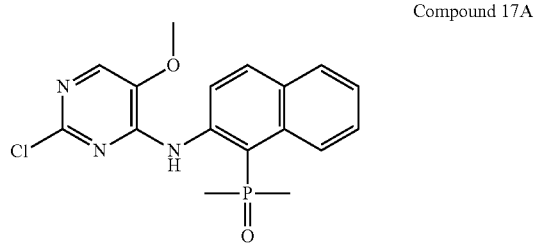 [SMILES: COc1cnc(Cl)nc1Nc1ccc2ccccc2c1P(C)(C)=O]

Except for replacing the compound 2,4,5-trichloropyrimidine with the compound 2,4-dichloro-5-methoxypyrimidine and replacing compound 1C with compound 4B, compound 17 was prepared according to the method for preparing compound 1D. $^1$H NMR (400 MHz, CDCl$_3$) δ ppm 12.78 (s, 1H), 8.65-9.42 (m, 1H), 8.02 (d, J=9.29 Hz, 1H), 7.68 (d, J=8.56 Hz, 1H), 7.49-7.57 (m, 1H), 7.40-7.46 (m, 1H), 7.31-7.39 (m, 1H), 7.36 (s, 1H), 2.50 (s, 3H), 2.09 (s, 3H), 2.06 (s, 3H).

Compound 17B

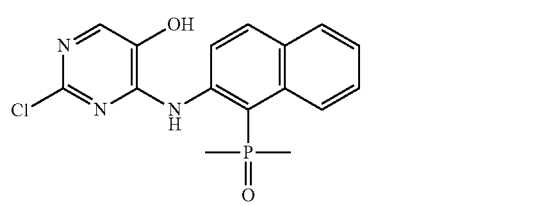

Compound 17A (0.94 g, 2.60 mmol) was dissolved in 25 mL of DCE, and added with BBr$_3$ (6.51 g, 25.9 mmol, 2.50 mL). After purged with nitrogen gas 3 to 5 times, the mixture was stirred at room temperature of about 25° C. for 2 hours, and stirred at 80° C. for 1 hour. The reaction solution was cooled down to 0° C. and adjusted to the pH of 7 to 8 by adding saturated NaHCO$_3$ solution. After filtration, the filtrate was extracted with DCM, and the organic phase was dried and concentrated to give compound 17B. $^1$H NMR (400 MHz, DMSO-$d_6$) δ ppm 2.05 (s, 3H), 2.08 (s, 3H), 6.54 (s, 1H), 7.47-7.53 (m, 1H), 7.60 (ddd, J=8.50, 6.91, 1.47 Hz, 1H), 7.78 (s, 1H), 7.92-8.04 (m, 2H), 8.13 (d, J=9.54 Hz, 1H), 8.64 (dd, J=9.41, 3.55 Hz, 1H), 12.73 (br s, 1H). LCMS (ESI): m/z: 348.0 [M+1].

Compound 17C

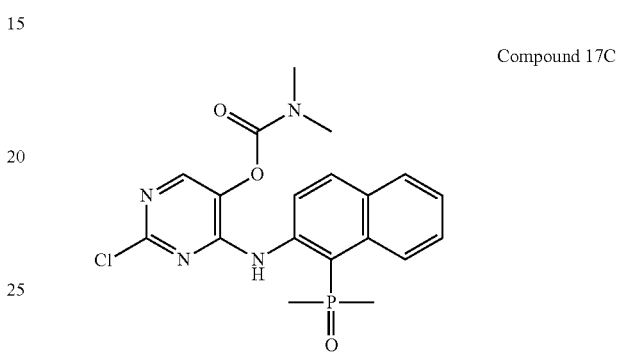

Compound 17B (0.2 g, 575 μmol) and N,N-dimethylcarbamoyl chloride (92.7 mg, 862 μmol, 79.3 μL) were dissolved in 4 mL of DMF, added with K$_2$CO$_3$ (158 mg, 1.15 mmol), and stirred at 25° C. for 2 hours. After the reaction was completed, the reaction solution was diluted with EtOAc and washed twice with saturated brine, and the organic phase was dried and concentrated to give compound 17C. $^1$H NMR (400 MHz, CDCl$_3$) δ ppm 2.13 (d, J=13.05 Hz, 6H), 3.07 (s, 3H), 3.28 (s, 3H), 7.46 (t, J=7.03 Hz, 1H), 7.51-7.57 (m, 1H), 7.69 (d, J=8.78 Hz, 1H), 7.88 (d, J=8.03 Hz, 1H), 8.04 (d, J=9.29 Hz, 1H), 8.15 (s, 1H), 8.80 (dd, J=9.16, 3.89 Hz, 1H), 12.87 (s, 1H). LC-MS (ESI): m/z: 419.0 [M+1].

Compound 17

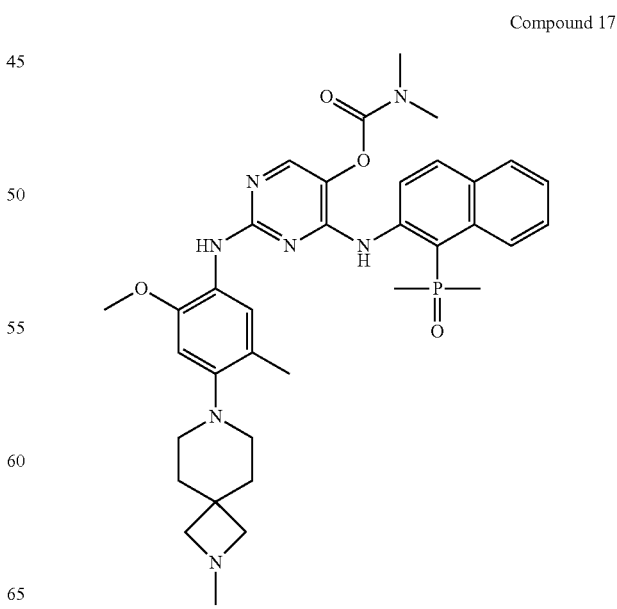

Except for replacing compound 1D with compound 7C and replacing compound 1F with compound 2B, compound 17 was prepared according to the method for preparing compound 1. ¹H NMR (400 MHz, DMSO-d₆) δ ppm 1.85 (br s, 4H), 2.03 (s, 3H), 2.07 (br d, J=10.03 Hz, 6H), 2.40 (s, 3H), 2.75 (br s, 4H), 2.92 (s, 3H), 3.12-3.18 (m, 4H), 3.22 (s, 4H), 3.80 (s, 3H), 6.71 (s, 1H), 7.43-7.51 (m, 1H), 7.52-7.66 (m, 2H), 7.80 (s, 1H), 7.86-8.03 (m, 4H), 8.33 (s, 1H), 8.71 (br d, J=5.87 Hz, 1H), 12.52 (s, 1H). LCMS (ESI): m/z: 658.1 [M+1].

Example 18

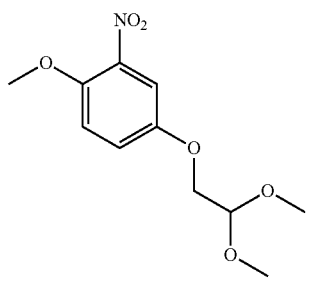

Compound 18A

The compounds of 4-methoxy-3-nitrophenol (1.25 g, 7.39 mmol) and 2-bromo-1,1-dimethoxyethane (1.60 g, 8.13 mmol) were dissolved in DMF (15 mL), and added with K₂CO₃ (1.12 g, 8.13 mmol), and the mixture was stirred at 100° C. for 4 hours. The reaction was quenched by adding 10 mL of water, and extracted three times with 100 mL of ethyl acetate. The organic phases were combined, washed twice with saturated brine, dried and concentrated to give a crude product. (400 MHz, CDCl₃) δ ppm 1.28-1.25 (m, 6H), 3.78-3.65 (m, 4H), 3.92 (s, 3H), 4.02-4.00 (m, 2H), 4.85 (m, 1H), 7.28-7.15 (m, 1H), 7.03 (d, J=9.2 Hz, 1H), 7.46 (s, 1H).

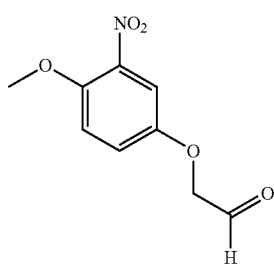

Compound 18B

Compound 18A (1.95 g, 6.88 mmol) was dissolved in THF (30 mL), and a hydrochloric acid solution (0.5 M, 223.80 mL) was added, followed by stirring at 70° C. for 12 hours. The reaction was quenched by adding 10 mL of water, and extracted three times with 100 mL of ethyl acetate. The organic phases were combined, washed twice with saturated brine, dried and concentrated to give compound 18B. (400 MHz, CDCl₃) δ ppm: 3.95 (s, 3H), 4.65 (s, 2H), 7.09 (m, 1H), 7.25 (d, J=9.2 Hz, 1H), 7.46 (s, 1H), 9.86 (s, 1H).

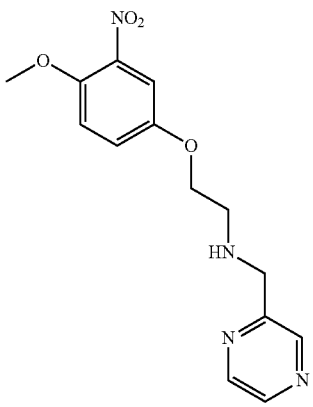

Compound 18C

At 25° C., compound 18B (200 mg, 947 μmol) was dissolved in 10 mL of a DCE mixed solution, followed by adding successively pyrazin-2-ylmethylamine (206 mg, 1.89 mmol), acetic acid (113 mg, 1.89 mmol, 108 μL) and sodium borohydride acetate (602 mg, 2.84 mmol), and stirring at room temperature for 12 hours. After the reaction was completed, a saturated NaHCO₃ aqueous solution was added to the reaction solution to adjust the pH to about 9, and extracted three times with DCM. The organic phase was dried over anhydrous Na₂SO₄, concentrated, and purified by thin-layer chromatography to give compound 18C. ¹H NMR (400 MHz, CDCl₃) δ ppm 8.64 (s, 1H), 8.38-8.40 (m, 3H), 7.24-7.42 (m, 1H), 6.93-7.21 (m, 2H), 4.03-4.30 (m, 4H), 3.91 (s, 3H), 3.01-3.18 (m, 2H).

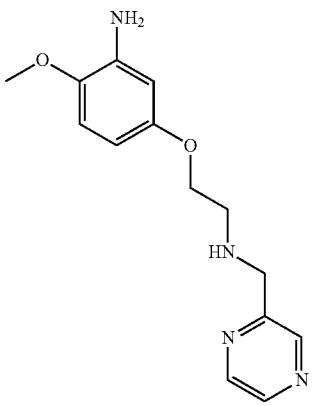

Compound 18D

Except for replacing compound 1E with compound 18C, compound 18D was prepared according to the method for preparing compound 1F. ¹H NMR (400 MHz, CDCl₃) δ ppm 8.67 (s, 1H), 8.54-8.57 (m, 1H), 8.49 (d, J=2.38 Hz, 1H), 6.70 (d, J=8.78 Hz, 1H), 6.37 (d, J=2.89 Hz, 1H), 6.27 (dd, J=8.78, 2.89 Hz, 1H), 4.03-4.10 (m, 4H), 3.82 (s, 3H), 3.06 (t, J=5.21 Hz, 2H).

Compound 18

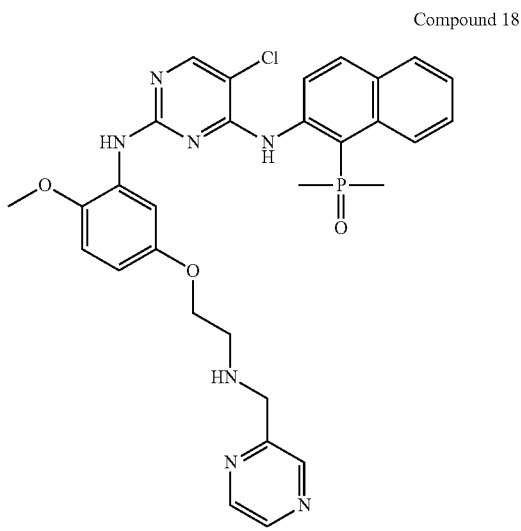

Except for replacing compound 1F with compound 18D and replacing compound 1D with compound 4C, compound 18 was prepared according to the method for preparing compound 1. $^1$H NMR (400 MHz, CD$_3$OD) δ ppm 2.05-2.19 (m, 7H), 2.79 (br s, 2H), 3.61-3.75 (m, 2H), 3.86 (s, 3H), 4.04 (s, 2H), 6.54 (dd, J=8.80, 2.81 Hz, 1H), 6.88 (d, J=8.93 Hz, 1H), 7.48-7.54 (m, 1H), 7.60 (br t, J=7.70 Hz, 1H), 7.82 (d, J=2.69 Hz, 1H), 7.93 (br d, J=7.95 Hz, 1H), 8.03 (d, J=9.05 Hz, 1H), 8.11-8.22 (m, 2H), 8.31 (dd, J=9.05, 3.91 Hz, 1H), 8.44-8.67 (m, 4H).

Example 19

Compound 19A

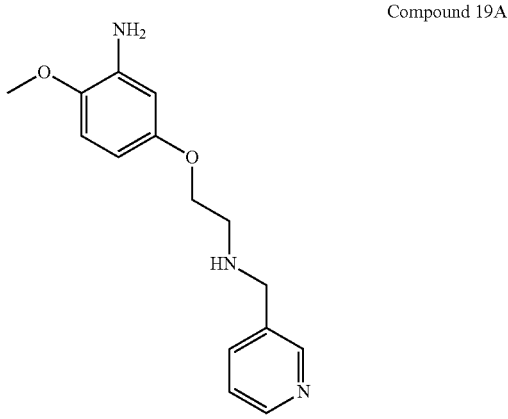 [SMILES: COc1ccc(OCCNCc2cccnc2)cc1N]

Except for replacing the compound pyrazin-2-ylmethylamine with the compound pyridin-3-ylmethylamine, compound 19A was prepared according to the method for preparing compound 18A.

Compound 19B

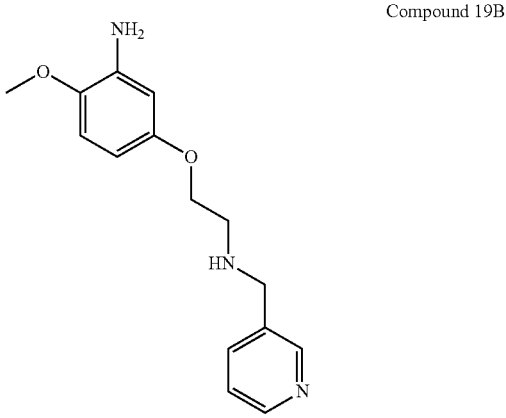 [SMILES: COc1ccc(OCCNCc2cccnc2)cc1N]

Except for replacing compound 1E with compound 19A, compound 19B was prepared according to the method for preparing compound 1F.

Compound 19

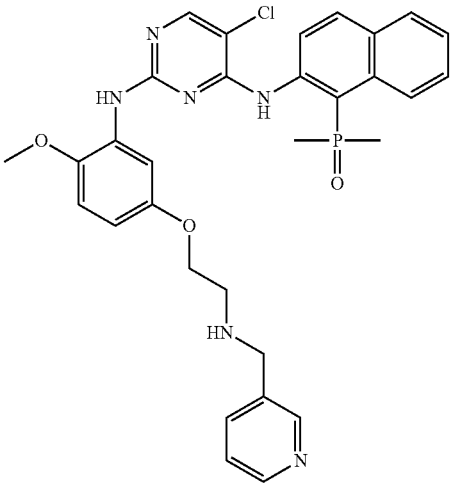

Except for replacing compound 1F with compound 19B and replacing compound 1D with compound 4C, compound 19 was prepared according to the method for preparing compound 1. $^1$H NMR (400 MHz, CD$_3$OD) δ=8.60-8.42 (m, 3H), 8.29 (dd, J=3.9, 9.0 Hz, 1H), 8.21 (d, J=8.2 Hz, 1H), 8.17 (s, 1H), 8.04 (d, J=9.0 Hz, 1H), 7.94 (d, J=8.1 Hz, 1H), 7.85-7.79 (m, 2H), 7.62 (ddd, J=1.5, 6.9, 8.5 Hz, 1H), 7.53 (t, J=7.5 Hz, 1H), 7.48-7.43 (m, 1H), 6.89 (d, J=8.8 Hz, 1H), 6.54 (dd, J=3.2, 8.8 Hz, 1H), 3.89-3.84 (m, 5H), 3.74-3.55 (m, 2H), 2.67 (br t, J=5.0 Hz, 2H), 2.19-2.06 (m, 7H).

Example 20

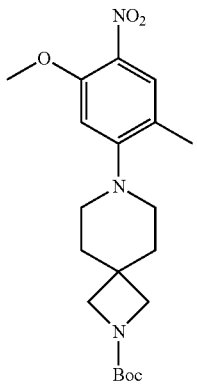

Compound 20A

Except for respectively replacing the compounds of 1-chloro-2-fluoro-4-methoxy-5-nitrobenzene and 3-methyl-3,9-diazaspiro[5.5]undecane with the compounds of 1-fluoro-5-methoxy-2-methyl-4-nitrobenzene and tert-butyl 2,7-diazaspiro[3.5]nonane-2-carboxylate, compound 20A was prepared according to the method for preparing compound 1E. $^1$H NMR (400 MHz, CDCl$_3$) δ ppm: 1.48 (s, 9H), 1.90-1.98 (m, 4H), 2.26 (s, 3H), 2.91-2.95 (m, 4H), 3.73 (s, 4H), 3.96 (s, 3H), 6.54 (s, 1H), 7.82-7.86 (m, 1H).

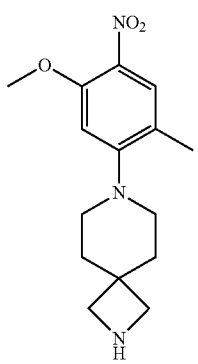

Compound 20B

Compound 20A (2.14 g, 5.47 mmol) was dissolved in DCM (15 mL), TFA (6.23 g, 54.67 mmol, 4.05 mL) was added thereto, and the mixture was stirred at 25° C. for 1 hour. The reaction solution was concentrated under reduced pressure to give compound 20B. $^1$H NMR (400 MHz, CD$_3$OD) δ ppm 2.05-2.09 (m, 4H), 2.28 (s, 3H), 2.98-3.02 (m, 4H), 3.33 (s, 4H), 3.94 (s, 3H), 6.74 (s, 1H), 7.78 (s, 1H).

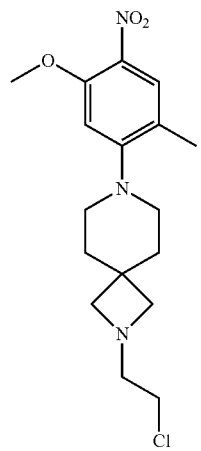

Compound 20C

Compound 20B and the compound 2-chloroacetaldehyde were dissolved in 5 mL of DCM, and added with acetic acid (43.19 microliters) and sodium borohydride acetate (218.2 mg, 1.03 mmol). The reaction was carried out at 20° C. for 2 hours. The reaction was quenched with water and extracted with ethyl acetate to give an organic phase. The organic phase was washed once with saturated brine, dried over anhydrous sodium sulfate, and concentrated to obtain a crude product. The crude product was purified by preparative thin-layer chromatography plate to give compound 20C. $^1$H NMR (400 MHz, CD3OD) δ ppm 7.77 (s, 1H), 6.72 (s, 1H), 3.93-3.95 (m, 3H), 3.60-3.64 (m, 2H), 3.41 (s, 4H), 3.04 (t, J=6.15 Hz, 2H), 2.95-2.99 (m, 4H), 2.26 (s, 3H), 2.03 (s, 2H), 1.97-2.00 (m, 4H).

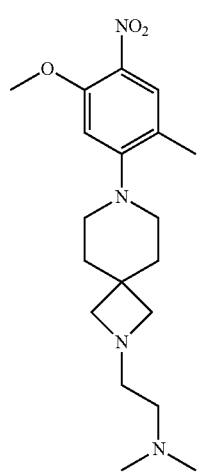

Compound 20D

Compound 20C was dissolved in 5 mL of EtOH and added with a solution of dimethylamine in ethanol (2 M, 10.8 mL). The mixture was heated to 90° C. and reacted for 12 hours. After the reaction was completed, the reaction solution was concentrated to give compound 20D.

Compound 20E

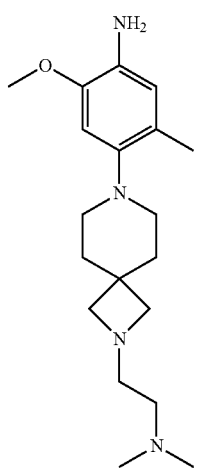

Except or replacing compound 1E with compound 20D, compound 20E was prepared according to the method for preparing compound 1F. ¹H NMR (400 MHz, CD₃OD) δ ppm 1.94-1.97 (m, 3H), 2.16 (s, 3H), 2.41-2.46 (m, 6H), 2.58-2.66 (m, 3H), 2.67-2.79 (m, 4H), 3.01 (t, J=6.53 Hz, 2H), 3.50-3.56 (m, 4H), 3.82 (s, 3H), 6.62 (d, J=2.76 Hz, 2H).

Compound 20

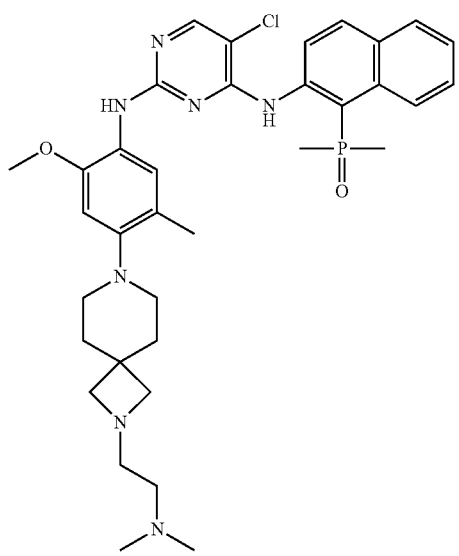

Except for replacing compound 1F with compound 20E and replacing compound 1D with compound 4C, compound 20 was prepared according to the method for preparing compound 1. ¹H NMR (400 MHz, DMSO-d₆) δ ppm=12.48 (br s, 1H), 8.38 (br d, J=5.9 Hz, 1H), 8.28 (br s, 2H), 8.14 (s, 1H), 8.05 (br d, J=8.6 Hz, 1H), 7.98-7.94 (m, 2H), 7.91 (br d, J=10.0 Hz, 2H), 7.59 (br t, J=7.3 Hz, 1H), 7.52-7.47 (m, 1H), 7.45 (s, 1H), 6.70 (s, 1H), 3.77-3.75 (m, 3H), 3.38 (s, 4H), 2.88 (br t, J=6.0 Hz, 2H), 2.72 (br s, 4H), 2.48-2.44 (m, 2H), 2.28 (s, 6H), 2.06 (s, 3H), 2.03 (s, 3H), 1.99 (s, 3H), 1.86 (br s, 4H).

Example 21

Compound 21A

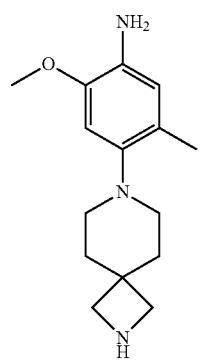

Except for replacing compound 20B with compound 1E, compound 21A was prepared according to the preparation method of compound 1F.

Compound 21B

Except for replacing compound 1F with compound 21A and replacing compound 1D with compound 4C, compound 21B was prepared according to the method for preparing compound 1. ¹H NMR (400 MHz, CDCl₃) δ=12.46 (s, 1H), 8.64 (dd, J=3.5, 9.3 Hz, 1H), 8.14 (s, 1H), 8.07 (s, 1H), 7.95 (d, J=9.3 Hz, 1H), 7.87 (br d, J=7.8 Hz, 1H), 7.74 (d, J=8.5 Hz, 1H), 7.56 (t, J=7.4 Hz, 1H), 7.50-7.44 (m, 1H), 7.41 (s, 1H), 3.87 (s, 3H), 3.71 (s, 3H), 2.77 (br s, 4H), 2.51 (br s, 4H), 2.19 (s, 3H), 2.16 (s, 3H), 2.01 (br s, 4H).

Compound 21

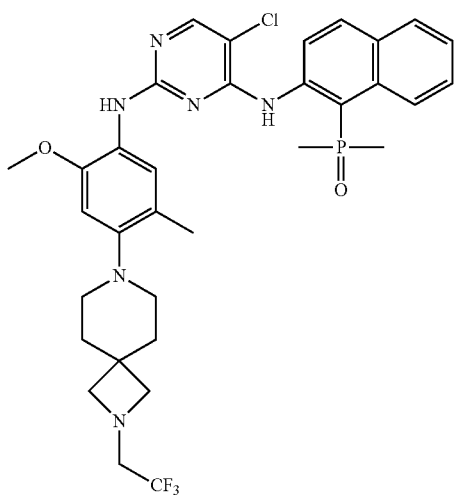

Compound 21B (0.1 g, 169 μmol) and 2,2,2-trifluoroethyl trifluoromethanesulfonate (392 mg, 1.69 mmol) were dissolved in 5 mL DMF, added with DIPEA (87.4 mg, 676 mol), and heated to 40° C. with stirring for 2 hours. After the reaction was completed, the reaction solution was concentrated, quenched by addition of saturated brine and extracted with EtOAc, and the organic phase was dried and concentrated. The crude product was purified by preparative HPLC to give compound 21. $^1$H NMR (400 MHz, CD$_3$OD) δ ppm 1.79 (s, 3H), 1.87-1.97 (m, 4H), 2.10 (s, 3H), 2.13 (s, 2H), 2.66-2.85 (m, 4H), 3.20 (q, J=9.78 Hz, 2H), 3.84 (s, 3H), 4.65 (br s, 5H), 4.78-4.85 (m, 2H), 6.66 (s, 1H), 7.54-7.67 (m, 3H), 7.94 (d, J=8.29 Hz, 1H), 8.01 (d, J=8.95 Hz, 1H), 8.08 (s, 1H), 8.22 (dd, J=9.17, 4.03 Hz, 1H), 8.27 (d, J=8.80 Hz, 1H). LC-MS (ESI): m/z: 673.0 [M+1].

Example 22

Compound 22A

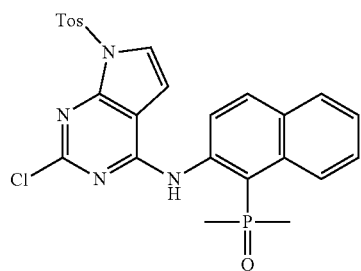

Compound 2,4-dichloro-7-tosyl-7H-pyrrolo[2,3-d]pyrimidine and compound 4B were dissolved in 25 mL of isobutanol, then added with methylsulfonic acid (842.54 mg, 8.77 mmol, 624.10 μL), and reacted at 110° C. for 12 hours. After the reaction was completed, the reaction solution was concentrated, and the crude product was purified by column chromatography to give compound 22A. $^1$H NMR (400 MHz, DMSO-d$_6$) δ=8.83 (br d, J=5.6 Hz, 1H), 8.20 (br d, J=9.0 Hz, 1H), 8.08 (br d, J=8.1 Hz, 1H), 8.03-7.95 (m, 3H), 7.77 (br d, J=3.7 Hz, 1H), 7.62 (br t, J=7.5 Hz, 1H), 7.55-7.47 (m, 3H), 6.82 (br d, J=2.9 Hz, 1H), 2.39 (s, 3H), 2.11 (br d, J=13.2 Hz, 6H).

Compound 22B

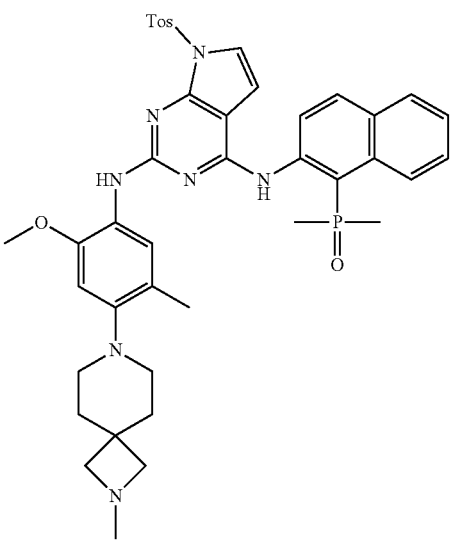

Compounds 22A (100 mg, 190.49 μmol) and 2B were dissolved in a mixed solution of 2 mL toluene and 0.4 mL tert-butanol, followed by adding Pd$_2$(dba)$_3$ (17.4 mg, 19.1 μmol), XPhos (18.2 mg, 38.1 μmol) and K$_2$CO$_3$ (52.6 mg, 380 μmol) successively and stirring at 100° C. for 12 hours. After the reaction was completed, the reaction solution was added with water, and extracted three times with DCM. The organic phase was dried over anhydrous Na$_2$SO$_4$, concentrated, and purified by thin-layer chromatography to give compound 22B.

Compound 22

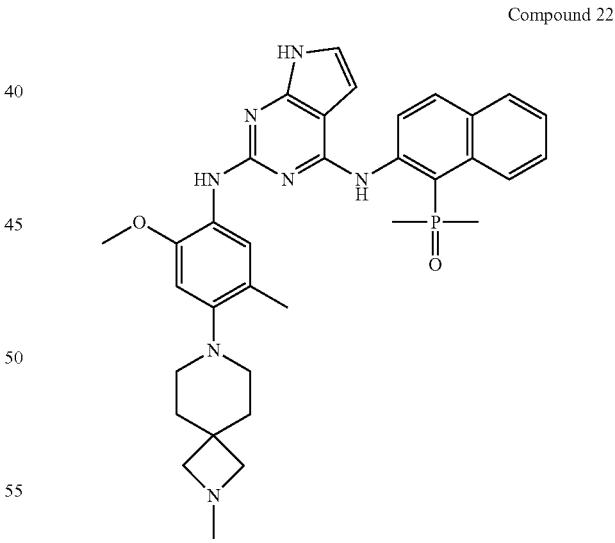

Compound 22B was dissolved in a mixed solution of 2 mL i-PrOH and 1 mL THF, and NaOH (13.0 mg, 327 μmol) was dissolved in 2 mL of water, added to the mixed solution and then reacted at 100° C. for 8 hours. After the reaction was completed, the reaction was quenched by adding water and extracted with EtOAc, and the organic phase was concentrated. The crude product was separated by preparative thin-layer chromatography to give compound 22. $^1$H NMR (400 MHz, CD$_3$OD) δ=8.86 (dd, J=4.1, 9.2 Hz, 1H), 8.16 (d, J=8.8 Hz, 1H), 8.03 (s, 1H), 8.01 (d, J=9.3 Hz, 1H), 7.91 (d, J=8.3 Hz, 1H), 7.73 (d, J=8.0 Hz, 1H), 7.62 (t, J=7.7 Hz, 1H), 7.52-7.46 (m, 1H), 7.25 (d, J=7.8 Hz, 1H), 6.94 (d, J=3.5 Hz, 1H), 6.71 (s, 1H), 6.55 (d, J=3.5 Hz, 1H), 3.89 (s, 3H), 3.67 (s, 4H), 2.84-2.78 (m, 4H), 2.73 (s, 3H), 2.18 (s, 3H), 2.15 (s, 3H), 2.05 (s, 3H), 2.01-1.96 (m, 4H).

Example 23

Compound 23A

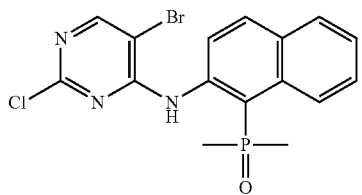

Compound 5-bromo-2,4-dichloro-pyrimidine (1.04 g, 4.56 mmol) and compound 4B (0.5 g, 2.28 mmol, 1 eq) were dissolved in ethanol (10 mL), and added with DIEA (1.18 g, 9.12 mmol, 1.59 mL). The reaction was heated to about 90° C. with stirring for 12 hours. After the reaction solution was concentrated, it was quenched with water and extracted three times with EtOAc, and the organic phase was concentrated to give compound 23A. $^1$H NMR (400 MHz, CDCl$_3$) δ ppm 8.48 (dd, J=9.16, 3.89 Hz, 1H), 8.38 (s, 1H), 8.05 (d, J=9.29 Hz, 1H), 7.91 (d, J=8.03 Hz, 1H), 7.73 (d, J=8.53 Hz, 1H), 7.54-7.61 (m, 1H), 7.47-7.53 (m, 1H), 2.16 (s, 3H), 2.19 (s, 3H).

Compound 23

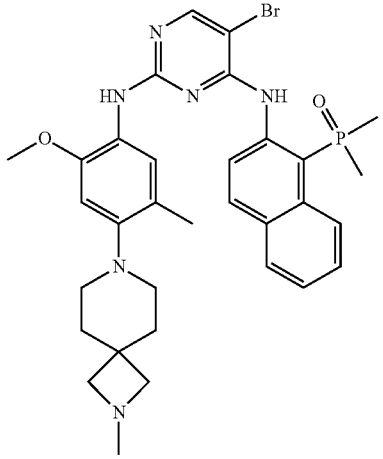

Except for replacing compound 1D with compound 23A and replacing compound 1F with compound 2B, compound 23 was prepared according to the method for preparing compound 1. $^1$H NMR (400 MHz, DMSO-d$_6$) δ ppm 1.83 (br s, 4H), 1.94 (s, 3H), 2.03 (d, J=13.20 Hz, 5H), 2.00-2.06 (m, 1H), 2.44 (br s, 3H), 2.70 (br s, 4H), 3.28 (br s, 4H), 3.77 (s, 3H), 6.68 (s, 1H), 7.42 (s, 1H), 7.47-7.53 (m, 1H), 7.54-7.62 (m, 1H), 7.87-7.97 (m, 3H), 8.06 (d, J=8.80 Hz, 1H), 8.18-8.24 (m, 2H), 8.37 (br s, 1H).

Example 24

Compound 24A

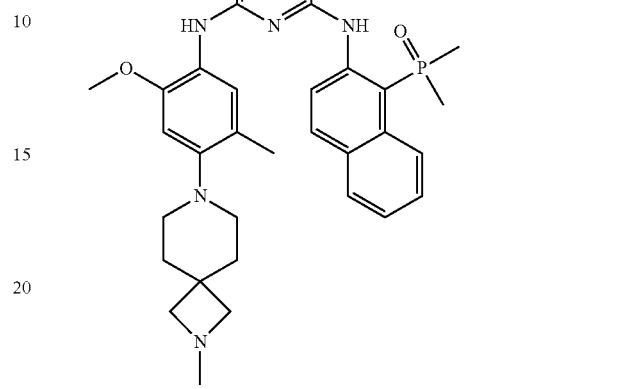

Compound 23 (0.1 g, 153 µmol) and tributyl(1-ethoxyvinyl)stannane (111 mg, 307 mol) were dissolved in 3 mL of toluene, and Pd(PPh$_3$)$_2$Cl$_2$ (10.8 mg, 15.4 µmol), CuBr (6.63 mg, 46.2 µmol, 1.41 µL) and PPh$_3$ (12.1 mg, 46.2 µmol) were added in portions successively. The mixture was stirred at 110° C. under protection of nitrogen gas for 12 hours. After the reaction was completed, the reaction solution was quenched by adding KF solution, and extracted three times with EtOAc. The organic phase was dried over anhydrous Na$_2$SO$_4$, concentrated, and purified by thin-layer chromatography to give compound 24A.

Compound 24

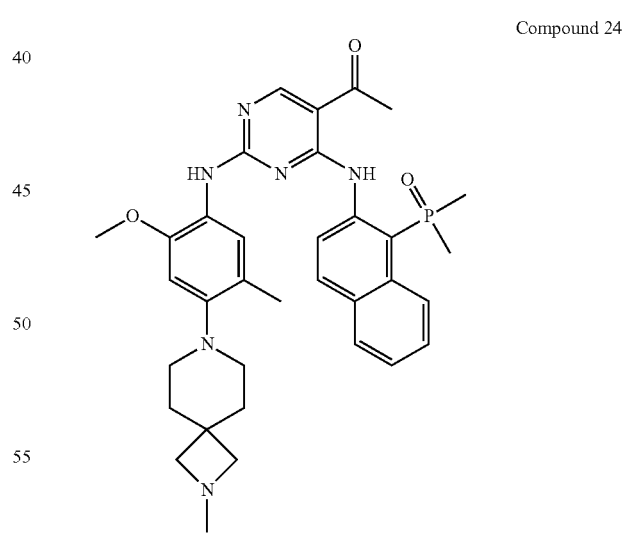

Compound 24A was dissolved in HCl/dioxane (4 M, 65.94 µL) and reacted at room temperature for half an hour. After the reaction was completed, the reaction solution was added with a saturated NaHCO$_3$ solution to adjust the pH to about 9. The mixture was extracted three times with EtOAc, and washed sequentially with water and saturated brine. The organic phase was concentrated. The crude product was purified by preparative HPLC to give compound 24. $^1$H NMR (400 MHz, DMSO-d$_6$) δ=11.17 (s, 1H), 9.36-9.28 (m, 1H), 8.85 (s, 1H), 8.28 (br d, J=13.3 Hz, 2H), 8.06 (br d, J=9.0 Hz, 1H), 7.96 (br s, 1H), 7.57 (br dd, J=3.3, 6.3 Hz, 3H), 7.25 (br s, 1H), 6.55 (br s, 1H), 3.74 (s, 3H), 3.31 (br s, 3H), 2.55 (m, 4H), 2.53-2.52 (m, 6H), 2.47 (br s, 4H), 1.81 (br s, 4H), 1.79-1.75 (m, 6H).

Example 25

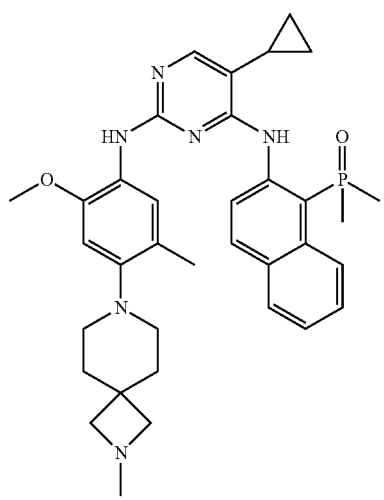

Compound 25

Compound 24 (0.1 g, 153 μmol) and cyclopropylboronic acid (52.9 mg, 615 μmol) were dissolved in a mixed solution of 5 mL toluene and 0.5 mL water, and added with Pd(OAc)$_2$ (3.46 mg, 15.4 μmol), K$_3$PO$_4$ (81.7 mg, 384 μmol), and P(Cy)$_3$ (8.63 mg, 30.8 μmol, 9.98 μL) successively. The reaction solution was heated to 110° C. and stirred for 12 hours. After the reaction was completed, the reaction solution was filtered and concentrated, and the crude product was purified by preparative HPLC to give compound 25. $^1$H NMR (400 MHz, DMSO-d$_6$) δ ppm 0.55-0.66 (m, 2H), 0.85-0.96 (m, 2H), 1.71-1.78 (m, 1H), 1.83 (br s, 4H), 1.96-2.01 (m, 3H), 2.03 (s, 3H), 2.07 (s, 3H), 2.45 (br s, 3H), 2.70 (br s, 5H), 3.30 (br d, J=7.09 Hz, 4H), 3.79 (s, 3H), 6.67 (s, 1H), 7.44-7.53 (m, 2H), 7.57 (br t, J=7.58 Hz, 1H), 7.71 (s, 1H), 7.85 (s, 1H), 7.91 (br d, J=8.07 Hz, 1H), 7.96 (d, J=9.17 Hz, 1H), 8.03 (d, J=8.56 Hz, 1H), 8.37 (br s, 1H), 8.56 (dd, J=9.17, 3.55 Hz, 1H), 12.25 (s, 1H). LCMS (ESI): m/z: 611.2 [M+1].

Example 26

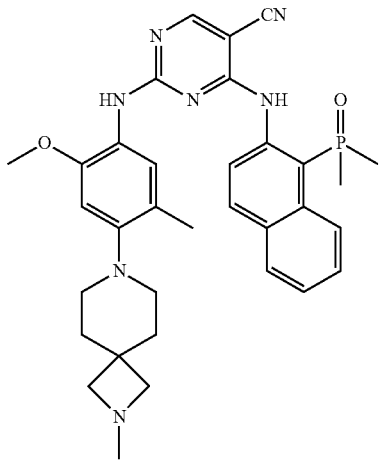

Compound 26

Compound 24 (0.1 g, 153 μmol) was dissolved in 5 mL of DMF, and zinc powder (5.03 mg, 76.9 μmol), Pd$_2$(dba)$_3$ (28.2 mg, 30.7 μmol), DPPF (17.1 mg, 30.8 μmol), and Zn(CN)$_2$ (36.1 mg, 307 μmol, 19.5 μL) were added successively. The reaction solution was heated to 120° C., and further stirred for 12 hours. After the reaction was completed, the reaction solution was filtered and concentrated, and the crude product was purified by preparative HPLC to give compound 26. $^1$H NMR (400 MHz, DMSO-d$_6$) δ ppm 1.83 (br s, 4H), 2.04 (br d, J=13.20 Hz, 8H), 1.91-2.12 (m, 1H), 2.40 (br s, 3H), 2.73 (br s, 4H), 3.21 (br s, 4H), 3.76 (s, 3H), 6.70 (s, 1H), 7.24 (s, 1H), 7.48-7.54 (m, 1H), 7.54-7.61 (m, 1H), 7.88 (br s, 2H), 8.10 (br d, J=8.31 Hz, 1H), 8.33 (br s, 2H), 8.46 (s, 1H), 8.78 (br s, 1H). LCMS (ESI): m/z: 596.2 [M+1].

Example 27

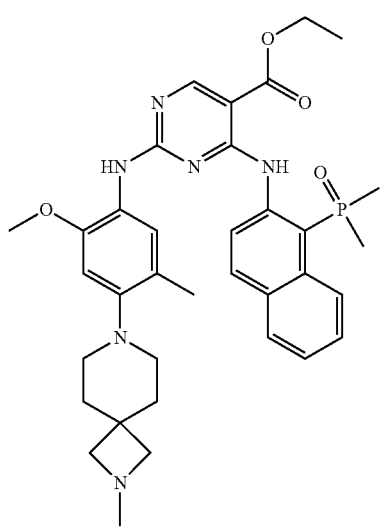

Compound 27A

Compound 24 (0.1 g, 153 μmol) was dissolved in 5 mL of EtOH, and Pd(dppf)Cl$_2$ (11.3 mg, 15.40 μmol) and Et$_3$N (46.7 mg, 461 μmol, 64.2 μL) were added successively. The reaction solution was reacted at 80° C. for 24 hours under carbon monoxide (50 psi) atmosphere. After the reaction was completed, the reaction solution was filtered and concentrated, and the crude product was purified by preparative TLC to give compound 27A.

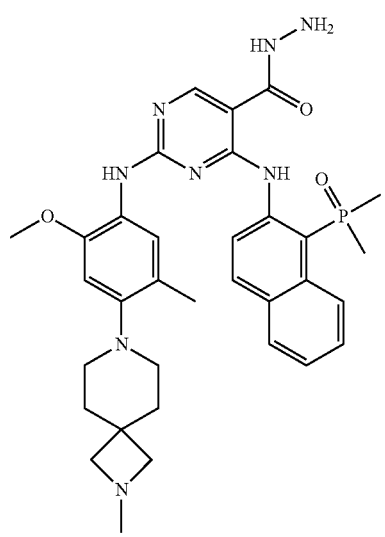

Compound 27B

Compound 27A (60 mg, 93.3 μmol) was dissolved in 2 mL of EtOH, and N$_2$H$_4$·H$_2$O (95.4 mg, 1.87 mmol, 92.6 μL) was added thereto. The reaction solution was warmed up to 100° C. and further stirred for 6 hours. After the reaction was completed, the reaction solution was filtered and concentrated, and compound 27B was obtained without further purification.

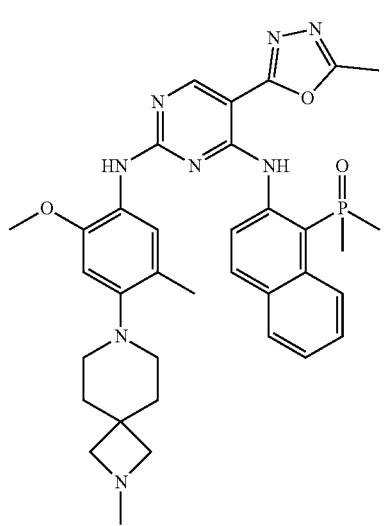

Compound 27

Compound 27B (30 mg, 47.7 μmol) and HOAc (210 mg, 3.50 mmol) were dissolved in 2 mL of triethyl orthoacetate. The reaction solution was warmed up to 120° C., and further stirred for 1 hour. After the reaction was completed, the reaction solution was filtered and concentrated, and the crude product was purified by preparative HPLC to give compound 27. $^1$H NMR (400 MHz, CD$_3$OD) δ=9.17 (br d, J=6.5 Hz, 1H), 8.71 (s, 1H), 8.55 (br s, 1H), 8.16 (br d, J=8.5 Hz, 1H), 8.02 (br d, J=7.3 Hz, 1H), 7.69-7.60 (m, 3H), 7.42 (br s, 1H), 6.58 (s, 1H), 4.64 (br s, 4H), 3.83 (br s, 3H), 2.85 (br s, 3H), 2.66 (br s, 6H), 1.97 (br d, J=13.1 Hz, 6H), 1.92 (br s, 4H), 1.30 (br s, 4H).

Example 28

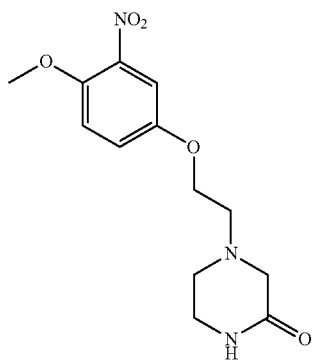

Compound 28A

Except for replacing the compound pyrazin-2-ylmethylamine with the compound piperazin-2-one, compound 28A was prepared according to the method for preparing compound 18A. $^1$H NMR (400 MHz, CDCl$_3$) δ ppm 7.44 (d, J=2.89 Hz, 1H), 7.23-7.34 (m, 1H), 7.16 (dd, J=9.16, 3.01 Hz, 1H), 4.13 (t, J=5.21 Hz, 2H), 3.95 (s, 3H), 3.37-3.49 (m, 2H), 3.33 (s, 2H), 2.92 (t, J=5.27 Hz, 2H), 2.84 (br t, J=5.27 Hz, 2H).

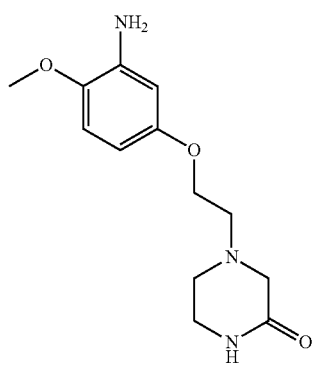

Compound 28B

Except for replacing compound 1E with compound 28A, compound 28B was prepared according to the method for preparing compound 1F. $^1$H NMR (400 MHz, CDCl$_3$) δ ppm 2.85 (dt, J=15.50, 5.36 Hz, 4H) 3.31 (s, 2H) 3.35-3.51 (m, 2H) 3.82 (s, 3H) 3.89-4.17 (m, 2H), 6.36 (d, J=2.89 Hz, 1H), 6.70 (d, J=8.66 Hz, 1H), 7.29 (s, 1H).

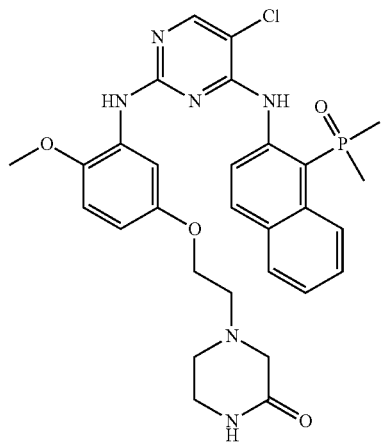

Compound 28

Except for replacing compound 1F with compound 28B and replacing compound 1D with compound 4C, compound 28 was prepared according to the method for preparing compound 1. $^1$H NMR (400 MHz, CD$_3$OD) δ ppm 2.18 (s, 3H), 2.21 (s, 3H), 3.45 (br s, 2H), 3.53-3.73 (m, 4H), 3.82 (br s, 2H), 3.88 (s, 3H), 3.97-4.24 (m, 2H), 6.99 (br d, J=8.44 Hz, 1H), 7.11 (d, J=8.98 Hz, 1H), 7.31 (br s, 1H), 7.65-7.78 (m, 2H), 8.08 (br d, J=8.19 Hz, 2H), 8.15-8.33 (m, 3H).

Example 29

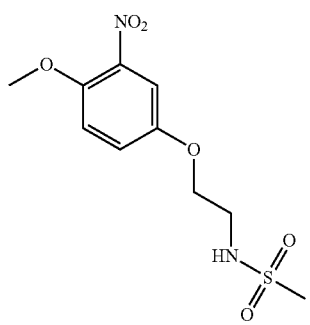

Comppound 29A

Except for replacing the compound pyrazin-2-ylmethylamine with the compound methane sulfonamide, compound 29A was prepared according to the method for preparing compound 18A.

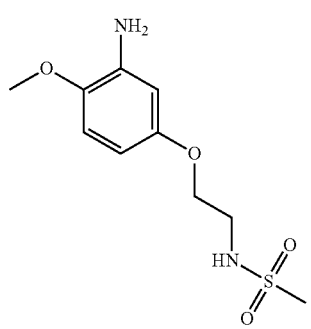

Comppound 29B

Except for replacing compound 1E with compound 29A, compound 29B was prepared according to the method for preparing compound 1F.

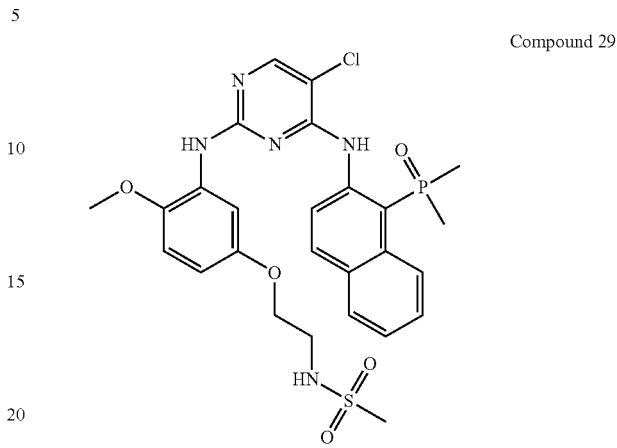

Compound 29

Except for replacing compound 1F with compound 29B and replacing compound 1D with compound 4C, compound 29 was prepared according to the method for preparing compound 1. $^1$H NMR (400 MHz, CD$_3$OD) δ ppm 2.18 (s, 3H), 2.21 (s, 3H), 3.45 (br s, 2H), 3.53-3.73 (m, 4H), 3.82 (br s, 2H), 3.88 (s, 3H), 3.97-4.24 (m, 2H), 6.99 (br d, J=8.44 Hz, 1H), 7.11 (d, J=8.98 Hz, 1H), 7.31 (br s, 1H), 7.65-7.78 (m, 2H), 8.08 (br d, J=8.19 Hz, 2H), 8.15-8.33 (m, 3H).

Example 30

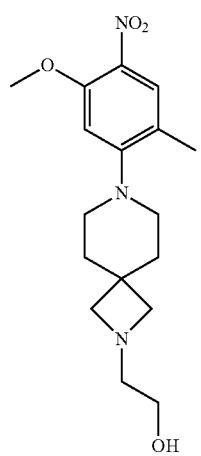

Compound 30A

Except for respectively replacing the compounds of 1-chloro-2-fluoro-4-methoxy-5-nitrobenzene and 3-methyl-3,9-diazaspiro[5.5]undecane with compound 20B and the compound 2-chloroethanol, compound 30A was prepared according to the method for preparing compound 1E.

Compound 30B

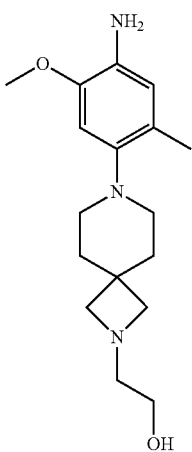

Except for replacing compound 1E with compound 30A, compound 30B was prepared according to the method for preparing compound 1F.

Compound 30

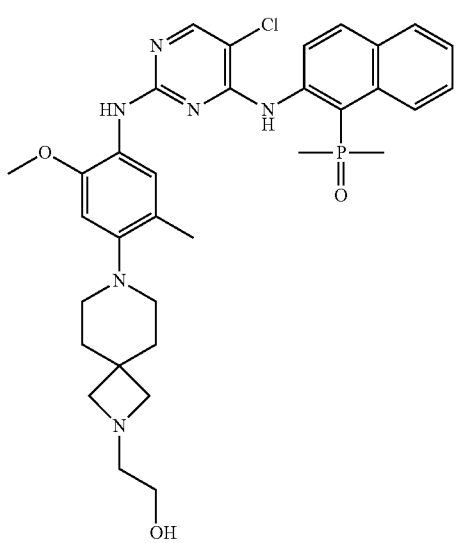

Except for replacing compound 1F with compound 30B and replacing compound 1D with compound 4C, compound 30 was prepared according to the method for preparing compound 1. $^1$H NMR (400 MHz, CD$_3$OD) δ ppm 1.78 (s, 3H), 1.95-2.06 (m, 4H), 2.09 (s, 3H), 2.13 (s, 3H), 2.71-2.83 (m, 4H), 3.24-3.31 (m, 1H), 3.71-3.81 (m, 1H), 3.85 (s, 3H), 3.88-3.96 (m, 4H), 4.58-4.86 (m, 7H), 6.67 (s, 1H), 7.53-7.59 (m, 1H), 7.61-7.68 (m, 2H), 7.94 (d, J=8.07 Hz, 1H), 8.02 (d, J=9.17 Hz, 1H), 8.09 (s, 1H), 8.21 (dd, J=9.05, 3.91 Hz, 1H), 8.30 (br d, J=8.93 Hz, 1H), 8.55 (s, 1H).

Example 31

Compound 31A

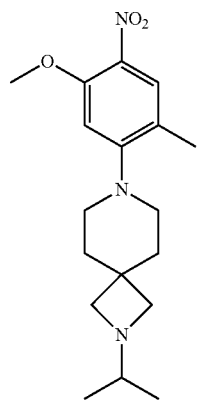

Compound 20B (200 mg, 686 μmol) and acetone (199 mg, 3.43 mmol, 252.34 μL) were dissolved in 4 mL of methanol, added with acetic acid (82.4 mg, 1.37 mmol, 78.52 μL), and stirred at 25° C. for one hour. The reaction solution was cooled, added with NaBH$_3$CN (86.2 mg, 1.37 mmol), and stirred at 0° C. for one hour. After the reaction was completed, the reaction solution was concentrated, added with a saturated solution of sodium bicarbonate, and extracted three times with DCM. The organic phase was dried over anhydrous Na$_2$SO$_4$ and concentrated to give compound 31A. $^1$H NMR (400 MHz, CDCl$_3$) δ ppm 1.15 (d, J=6.27 Hz, 6H), 1.99-2.03 (m, 5H), 2.25 (s, 4H), 2.91-2.97 (m, 1H), 2.91-2.97 (m, 1H), 2.91-2.97 (m, 1H), 2.91-2.97 (m, 3H), 3.44 (s, 3H), 3.96 (s, 3H), 6.55-6.56 (m, 1H), 7.83 (s, 1H). LCMS (ESI): m/z: 334.1 [M+1].

Compound 31B

Except for replacing compound 1E with compound 31A, compound 31B was prepared according to the method for preparing compound 1F. $^1$H NMR (400 MHz, CDCl$_3$) δ ppm 1.33 (d, J=6.60 Hz, 5H), 1.82 (br d, J=7.34 Hz, 4H), 2.07 (s, 3H), 2.25 (br s, 1H), 2.72 (br s, 4H), 3.28-3.53 (m, 4H), 3.74 (s, 3H), 4.00-4.14 (m, 2H), 6.42 (s, 1H), 7.96 (s, 1H). LC-MS (ESI): m/z: 304.1 [M+1]

Compound 31

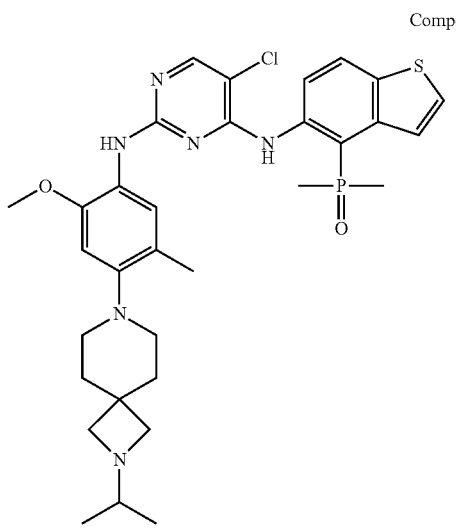

Except for replacing compound 1F with compound 32B, compound 31 was prepared according to the method for preparing compound 1. $^1$H NMR (400 MHz, MeOD) δ ppm 1.23 (d, J=6.60 Hz, 6H) 1.66 (s, 2H) 1.70 (s, 1H) 1.93 (s, 3H) 1.96 (s, 7H) 2.75 (br s, 4H) 4.58 (s, 8H) 6.64 (s, 1H) 7.48 (s, 1H) 7.87 (d, J=5.38 Hz, 2H) 8.07-8.17 (m, 3H) 8.55 (s, 1H). LC-MS (ESI): m/z: 639.1 [M+1].

Example 32

Compound 32A

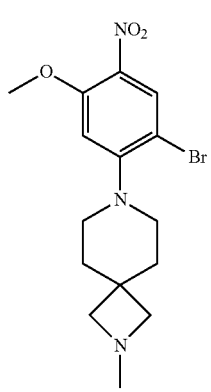

Except for respectively replacing the compounds of 1-chloro-2-fluoro-4-methoxy-5-nitrobenzene and 3-methyl-3,9-diazaspiro[5.5]undecane with the compounds of 1-bromo-2-fluoro-4-methoxy-5-nitrobenzene and 2-methyl-2,7-diazaspiro[3.5]nonane, compound 32A was prepared according to the method for preparing compound 1E. $^1$H NMR (400 MHz, CDCl$_3$) δ ppm 2.44 (s, 3H), 3.15-3.22 (m, 4H), 3.19 (s, 8H), 3.98 (s, 3H), 6.57 (s, 1H), 8.23 (s, 1H).

Compound 32B

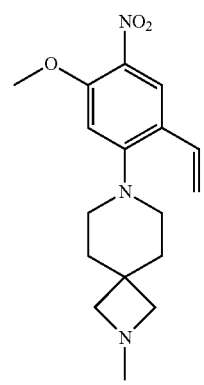

Except for replacing compound 23 with compound 32A and replacing the compound tributyl(1-ethoxyvinyl)stannane with the compound tributyl(vinyl)stannane, compound 32B was prepared according to the method for preparing compound 24A. $^1$H NMR (400 MHz, CDCl$_3$) δ ppm 1.27 (s, 2H), 1.80-2.01 (m, 4H), 2.39 (s, 3H), 2.91 (s, 2H), 2.96-3.03 (m, 4H), 3.51 (s, 1H), 3.93-4.04 (m, 3H), 5.27-5.35 (m, 1H), 5.71 (d, J=17.69 Hz, 1H), 6.51 (s, 1H), 6.72 (dd, J=17.63, 10.98 Hz, 1H), 8.04 (s, 1H), 8.12 (s, 1H).

Compound 32C

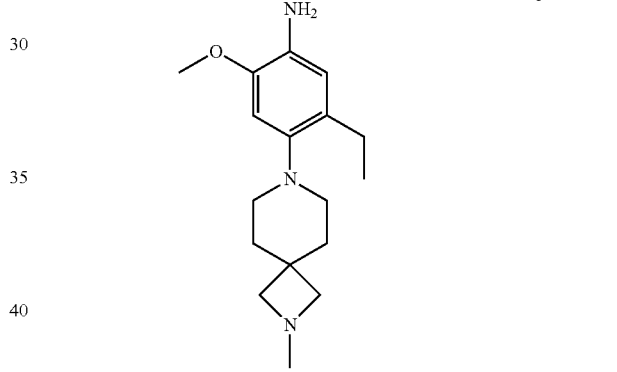

Except for replacing compound 49A with compound 32B, compound 32C was prepared according to the method for preparing compound 49B.

Compound 32

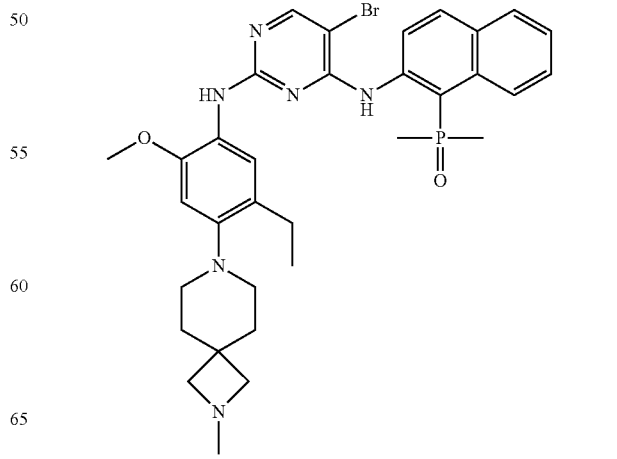

Except for replacing compound 1F with compound 32C and replacing compound 1D with compound 23A, compound 32 was prepared according to the method for preparing compound 1. ¹H NMR (400 MHz, CDCl₃) δ ppm 0.58-0.55 (m, 3H) 1.93-2.07 (m, 4H) 2.11-2.05 (s, 9H) 2.74-2.71 (m, 4H) 2.76 (s, 3H), 3.86 (d, J=2.89 Hz, 8H), 7.19 (d, J=3.14 Hz, 1H), 7.28 (s, 1H), 7.37 (s, 1H), 7.51 (d, J=9.29 Hz, 1H), 8.06 (s, 1H), 8.11 (s, 1H), 8.41 (dd, J=9.16, 3.76 Hz, 1H), 8.59 (s, 1H), 11.31 (s, 1H).

Example 33

Compound 33

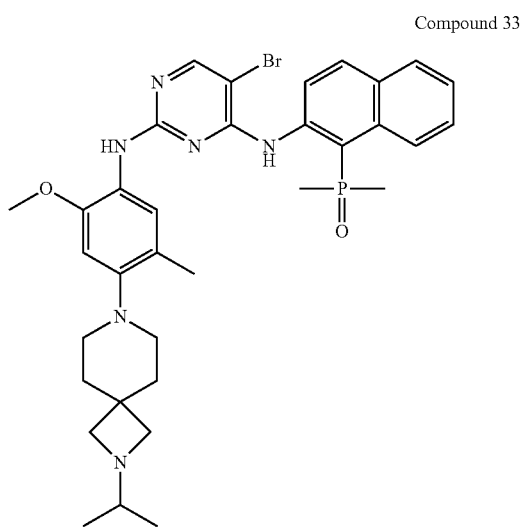 [SMILES: COc1cc(N2CCC3(CC2)CN(C(C)C)C3)c(C)cc1Nc1ncc(Br)c(Nc2ccc3ccccc3c2P(C)(C)=O)n1]

Except for replacing compound 1D with compound 23A and replacing compound 1F with compound 31B, compound 33 was prepared according to the method for preparing compound 1. ¹H NMR (400 MHz, CD₃OD) δ ppm 1.22 (d, J=6.36 Hz, 6H) 1.70 (s, 3H) 1.89-2.02 (m, 4H) 2.10 (d, J=13.45 Hz, 6H) 2.76 (br s, 4H) 3.85 (s, 3H) 4.64 (s, 4H) 6.65 (s, 1H) 7.55-7.60 (m, 2H) 7.61-7.69 (m, 1H) 7.96 (d, J=8.31 Hz, 1H) 8.02-8.10 (m, 2H) 8.19 (s, 1H) 8.38 (d, J=8.80 Hz, 1H) 8.56 (s, 1H). LCMS (ESI) m/z: 677.0 [M+1].

Example 34

Compound 34A

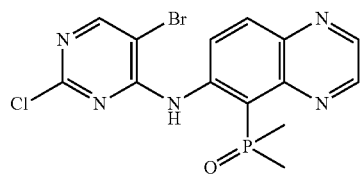

Except for replacing the compound 2,4,5-trichloropyrimidine with the compound 5-bromo-2,4-dichloropyrimidine, compound 34A was prepared according to the method for preparing compound 8E. ¹H NMR (400 MHz, CD₃OD) δ ppm 2.17 (s, 3H), 2.21 (s, 3H), 8.28 (d, J=9.54 Hz, 1H), 8.54 (s, 1H), 8.87 (d, J=2.01 Hz, 1H), 8.90 (d, J=2.01 Hz, 1H), 9.04 (dd, J=9.41, 4.14 Hz, 1H).

Compound 34B

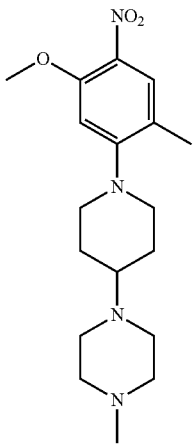

Except for respectively replacing the compounds of 1-chloro-2-fluoro-4-methoxy-5-nitrobenzene and 3-methyl-3,9-diazaspiro[5.5]undecane with the compounds of 2-fluoro-4-methoxy-5-nitrotoluene and 3B, compound 34B was prepared according to the method for preparing compound 1E. ¹H NMR (400 MHz, CDCl₃-d) δ=7.74 (s, 1H), 6.47 (s, 1H), 3.86 (s, 3H), 3.27 (br d, J=12.2 Hz, 2H), 2.71-2.52 (m, 10H), 2.44 (br s, 1H), 2.37-2.29 (m, 1H), 2.68-2.27 (m, 1H), 2.24 (s, 3H), 2.16 (s, 3H), 1.92 (br d, J=12.2 Hz, 2H), 1.73-1.59 (m, 2H).

Compound 34C

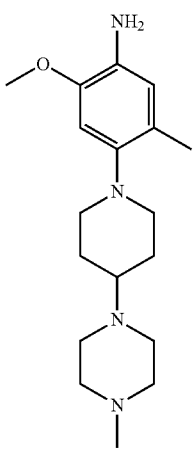

Except for replacing compound 1E with compound 34B, compound 34C was prepared according to the method for preparing compound 1F. ¹H NMR (400 MHz, CDCl₃-d) δ=6.57 (d, J=5.0 Hz, 2H), 3.87-3.80 (m, 3H), 3.08 (br d, J=12.0 Hz, 2H), 2.84-2.41 (m, 11H), 2.38-2.27 (m, 5H), 2.21-2.13 (m, 3H), 1.97-1.87 (m, 2H), 1.76-1.61 (m, 2H).

Compound 34

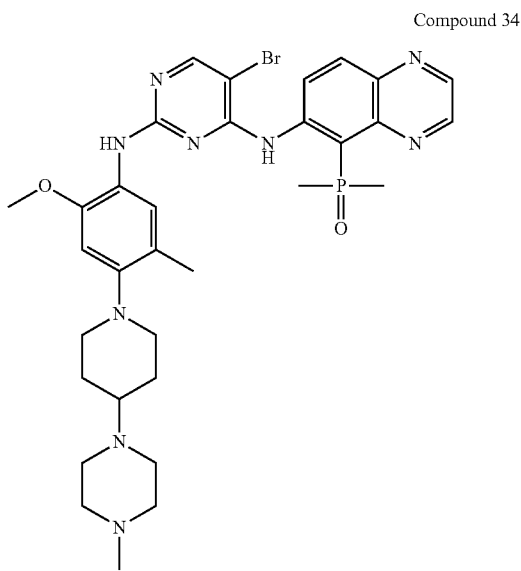

Except for replacing compound 1F with compound 34C and replacing compound 1D with compound 34A, compound 34 was prepared according to the method for preparing compound 1. $^1$H NMR (400 MHz, CD$_3$OD) δ ppm 1.64-1.82 (m, 2H), 2.09 (s, 3H), 2.14 (s, 3H), 2.18 (s, 3H), 2.43 (s, 3H), 2.50 (br t, J=11.43 Hz, 2H), 2.72 (br t, J=11.13 Hz, 6H), 2.82 (br s, 3H), 3.15-3.25 (m, 2H), 3.37 (s, 1H), 3.86 (s, 3H), 6.76 (s, 1H), 7.61 (s, 1H), 7.99 (d, J=9.41 Hz, 1H), 8.23 (s, 1H), 8.55 (br s, 1H), 8.83 (dd, J=17.12, 1.83 Hz, 2H), 8.97 (dd, J=9.48, 4.10 Hz, 1H).

Example 35

Compound 35

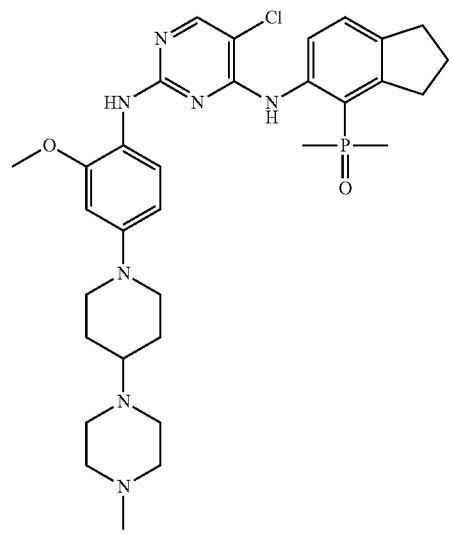

Except for replacing compound 1F with compound 3D and replacing compound 1D with compound 16C, compound 35 was prepared according to the method for preparing compound 1. $^1$H NMR (400 MHz, CD$_3$OD) δ ppm 1.71 (br dd, J=12.05, 3.26 Hz, 2H), 1.82 (s, 3H), 1.85 (s, 3H), 1.98-2.12 (m, 3H), 2.17 (quin, J=7.34 Hz, 2H), 2.61 (s, 3H), 2.72 (br t, J=11.54 Hz, 3H), 2.94-2.98 (m, 10H), 3.15 (br t, J=7.15 Hz, 3H), 3.68 (br d, J=12.55 Hz, 2H), 3.86 (s, 3H), 6.34 (dd, J=8.91, 2.13 Hz, 1H), 6.65 (d, J=2.26 Hz, 1H), 7.43 (d, J=8.03 Hz, 1H), 7.62 (d, J=8.78 Hz, 1H), 8.00 (s, 1H), 8.52 (br s, 1H).

Example 36

Compound 36

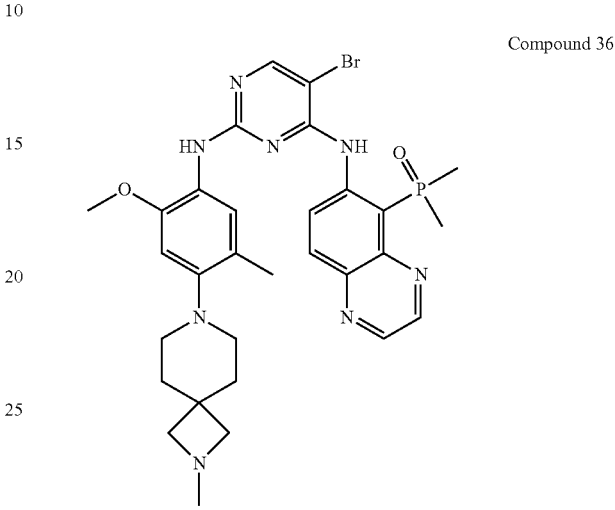

Except for replacing compound 1F with compound 2B and replacing compound 1D with compound 34A, compound 36 was prepared according to the method for preparing compound 1. $^1$H NMR (400 MHz, CD$_3$OD) δ ppm 2.00-2.05 (m, 4H), 2.08 (s, 3H), 2.14 (s, 3H), 2.17 (s, 3H), 2.85 (s, 7H), 2.80-2.84 (m, 2H), 3.85 (d, J=4.65 Hz, 5H), 3.80-3.88 (m, 1H), 3.85-3.87 (m, 1H), 6.73 (s, 1H), 7.62 (s, 1H), 7.98 (d, J=9.54 Hz, 1H), 8.22 (s, 1H), 8.57 (s, 1H), 8.83 (dd, J=18.95, 1.71 Hz, 2H), 8.95 (dd, J=9.48, 4.10 Hz, 1H).

Example 37

Compound 37

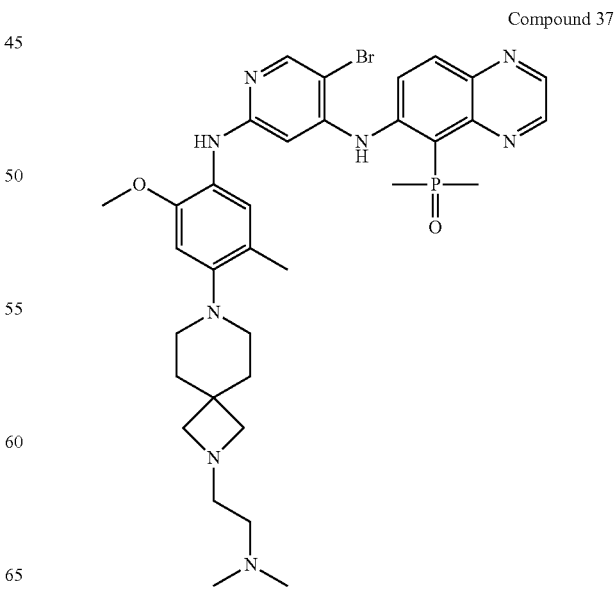

Except for replacing compound 1D with compound 34A and replacing compound 1F with compound 20C, compound 37 was prepared according to the method for preparing compound 1. $^1$H NMR (400 MHz, MeOD) δ ppm 1.99-2.03 (m, 4H), 2.06 (s, 3H), 2.12 (s, 3H), 2.16 (s, 3H), 2.54 (s, 6H), 2.77-2.80 (m, 2H), 2.82 (br d, J=6.53 Hz, 4H), 3.17 (t, J=6.02 Hz, 2H), 3.71 (s, 4H), 3.84 (s, 4H), 6.70 (s, 1H), 7.61 (s, 1H), 7.95 (br d, J=9.54 Hz, 1H), 8.19 (d, J=1.51 Hz, 1H), 8.54 (br s, 1H), 8.79 (d, J=1.26 Hz, 1H), 8.84 (s, 1H), 8.92 (br dd, J=9.16, 3.39 Hz, 1H).

Example 38

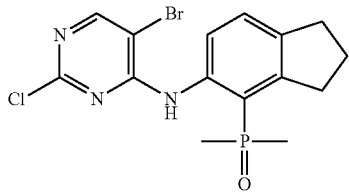

Compound 38A

Except for replacing the compound 2,4,5-trichloropyrimidine with the compound 5-bromo-2,4-dichloropyrimidine and replacing compound 1C with compound 16B, compound 38A was prepared according to the method for preparing compound 1D. $^1$H NMR (400 MHz, CD$_3$OD) δ ppm 1.89 (s, 2H), 1.89-1.89 (m, 1H), 1.92 (s, 3H), 2.12-2.20 (m, 2H), 2.95 (t, J=7.34 Hz, 2H), 3.08-3.16 (m, 2H), 7.49 (d, J=8.07 Hz, 1H), 7.96 (d, J=3.91 Hz, 1H), 8.37 (s, 1H).

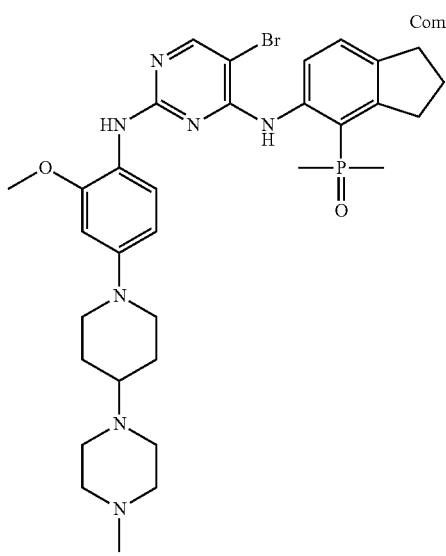

Compound 38

Except for replacing compound 1F with compound 3D and replacing compound 1D with compound 38A, compound 38 was prepared according to the method for preparing compound 1. $^1$H NMR (400 MHz, MeOD) δ ppm 1.66-1.76 (m, 2H), 1.82 (d, J=13.30 Hz, 6H), 2.04 (br d, J=11.80 Hz, 2H), 2.17 (quin, J=7.40 Hz, 2H), 2.63 (s, 4H), 2.70 (br t, J=11.80 Hz, 2H), 2.97 (br t, J=7.28 Hz, 12H), 3.17 (br t, J=7.28 Hz, 2H), 3.67 (br d, J=12.30 Hz, 2H), 3.85 (s, 3H), 6.29 (dd, J=8.78, 2.01 Hz, 1H), 6.63 (d, J=2.26 Hz, 1H), 7.44 (d, J=8.28 Hz, 1H), 7.57 (d, J=8.78 Hz, 1H), 8.09 (s, 1H), 8.52 (br s, 1H).

Example 39

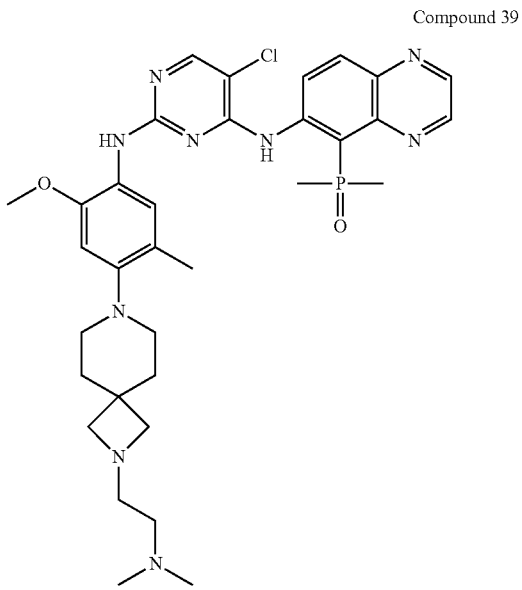 [SMILES: COc1cc(N2CCC3(CC2)CN(CCN(C)C)C3)c(C)cc1Nc1ncc(Cl)c(Nc2ccc3nccnc3c2P(C)(C)=O)n1]

Compound 39

Except for replacing compound 10E with compound 4C, compound 39 was prepared according to the method for preparing compound 20. $^1$H NMR (400 MHz, CD$_3$OD) δ=9.11 (dd, J=9.54, 4.27 Hz, 1H), 8.85 (s, 1H), 8.80 (s, 1H), 8.57 (s, 1H), 8.12 (s, 1H), 7.98 (d, J=9.54 Hz, 1H), 7.63 (s, 1H), 6.73 (s, 1H), 3.85 (s, 3H), 3.55 (s, 4H), 3.03 (t, J=6.53 Hz, 2H), 2.82-2.88 (m, 4H), 2.65 (t, J=6.65 Hz, 2H), 2.46 (s, 6H), 2.17 (s, 3H), 2.12-2.15 (m, 1H), 2.13 (d, J=3.51 Hz, 5H), 1.98-2.03 (m, 4H).

Example 40

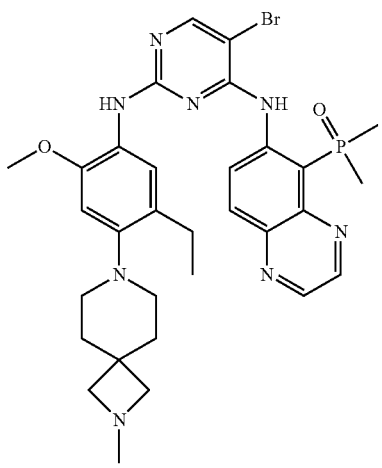

Compound 40

Except for replacing compound 1F with compound 32B and replacing compound 1D with compound 34A, compound 40 was prepared according to the method for preparing compound 1. $^1$H NMR (400 MHz, CD$_3$OD) δ ppm 0.86 (br t, J=7.34 Hz, 3H), 1.22-1.28 (m, 2H), 2.03 (s, 4H), 2.14 (s, 3H), 2.18 (s, 3H), 2.51 (q, J=7.46 Hz, 2H), 2.85 (br s, 4H), 2.89 (s, 3H), 3.86 (s, 3H), 3.90 (s, 4H), 6.79 (s, 1H), 7.67 (s, 1H), 8.00 (d, J=9.54 Hz, 1H), 8.26 (s, 1H), 8.56 (br s, 1H), 8.82 (d, J=1.83 Hz, 1H), 8.87 (d, J=1.83 Hz, 1H).

Example 41

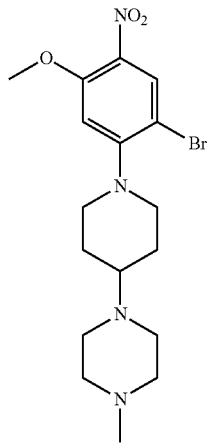

Compound 41A

Except for replacing the compound 1-chloro-2-fluoro-4-methoxy-5-nitrobenzene with the compound 1-bromo-2-fluoro-4-methoxy-5-nitrobenzene and replacing the compound 3-methyl-3,9-diazaspiro[5.5]undecane with the compound 1-methyl-4-(piperidin-4-yl)piperazine, compound 41A was prepared according to the method for preparing compound 1E. $^1$H NMR (400 MHz, CDCl$_3$) δ ppm 1.72-1.83 (m, 2H), 1.98 (br d, J=12.10 Hz, 4H), 2.29 (s, 3H), 2.64 (br d, J=4.28 Hz, 5H), 2.70-2.79 (m, 4H), 3.61 (br d, J=12.23 Hz, 2H), 3.94 (s, 3H), 6.54-6.60 (m, 1H), 8.18-8.21 (m, 1H).

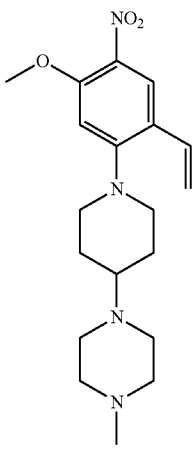

Compound 41B

Except for replacing compound 23 with compound 41A and replacing the compound tributyl(1-ethoxyvinyl)stannane with the compound tributyl(vinyl)stannane, compound 41B was prepared according to the method for preparing compound 24A. $^1$H NMR (400 MHz, CDCl$_3$) δ ppm 1.26-1.42 (m, 1H), 1.27-1.41 (m, 1H), 1.66 (s, 3H), 1.68-1.78 (m, 2H), 1.99 (br d, J=11.86 Hz, 2H), 2.31 (s, 2H), 2.39 (ddt, J=11.20, 7.57, 3.58, 3.58 Hz, 2H), 2.50 (br s, 2H), 2.66 (br s, 2H), 2.71-2.79 (m, 2H), 3.48 (br d, J=12.59 Hz, 2H), 3.96 (s, 3H), 5.26-5.32 (m, 1H), 5.69 (d, J=17.61 Hz, 1H), 6.51 (s, 1H), 6.71 (dd, J=17.67, 10.94 Hz, 1H), 8.10 (s, 1H).

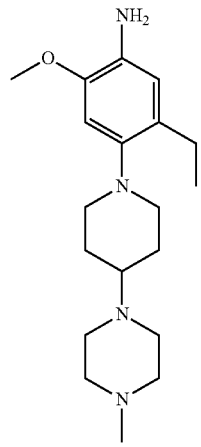

Compound 41C

Except for replacing compound 1E with compound 41B, compound 41C was prepared according to the method for preparing compound 1F.

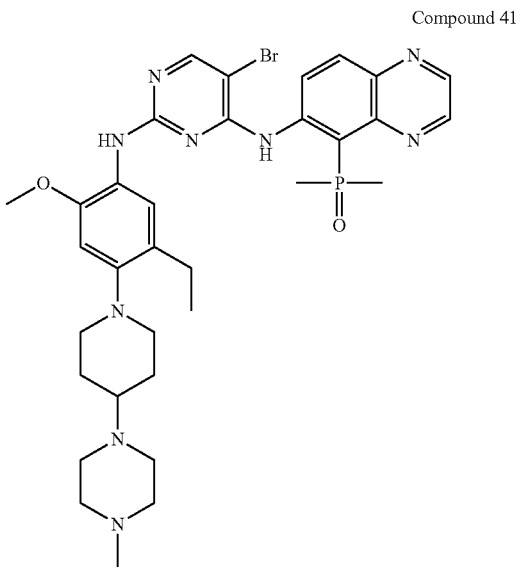 [SMILES: CCc1cc(Nc2ncc(Br)c(Nc3ccc4nccnc4c3P(C)(C)=O)n2)c(OC)cc1N1CCC(N2CCN(C)CC2)CC1]

Compound 41

Except for replacing compound 1F with compound 41C and replacing compound 1D with compound 34A, compound 41 was prepared according to the method for preparing compound 1. $^1$H NMR (400 MHz, CD$_3$OD) δ=8.90 (d, J=1.8 Hz, 1H), 8.87 (d, J=1.8 Hz, 1H), 8.82 (br s, 1H), 8.26 (s, 1H), 8.05 (br d, J=9.7 Hz, 1H), 7.48 (s, 1H), 6.91 (s, 1H), 3.87 (s, 3H), 3.38 (br s, 6H), 3.33 (d, J=1.7 Hz, 2H), 3.26 (br s, 4H), 3.12-3.02 (m, 1H), 2.95 (br t, J=11.7 Hz, 2H), 2.88 (s, 3H), 2.56 (q, J=7.5 Hz, 2H), 2.18 (s, 3H), 2.14 (s, 3H), 1.99-1.85 (m, 2H), 0.96 (br t, J=7.2 Hz, 3H).

Example 42

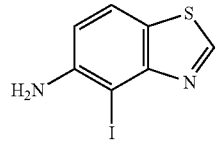

Compound 42A

Except for replacing compound 1A with the compound benzo[d]thiazole-5-amine, compound 42A was prepared according to the method for preparing compound 1B. $^1$H NMR (400 MHz, CDCl$_3$) δ ppm 4.37 (br s, 2H), 6.91 (d, J=8.56 Hz, 1H), 7.62-7.75 (m, 1H), 9.00 (s, 1H).

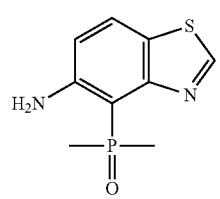

Compound 42B

Except for replacing compound 1B with compound 42A, compound 42B was prepared according to the method for preparing compound 1C.

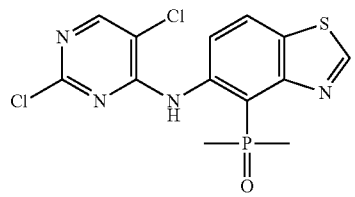

Compound 42C

Except for replacing compound 1C with compound 42B, compound 42C was prepared according to the method for preparing compound 1D. $^1$H NMR (400 MHz, DMSO-d$_6$) δ ppm 2.02 (s, 3H), 2.05 (s, 3H), 8.43 (d, J=9.16 Hz, 1H), 8.47 (s, 1H), 8.67 (dd, J=9.16, 3.26 Hz, 1H), 9.53-9.60 (m, 1H), 12.82 (s, 1H).

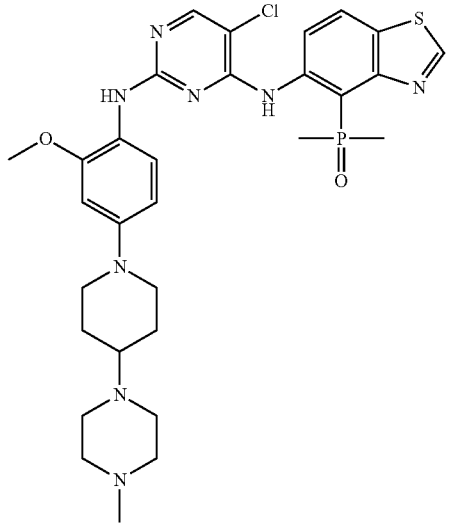

Compound 42

Except for replacing compound 1D with compound 42C and replacing compound 1F with compound 3D, compound 42 was prepared according to the method for preparing compound 1. $^1$H NMR (400 MHz, CD$_3$OD) δ ppm 1.61-1.73 (m, 2H), 2.00-2.06 (m, 1H), 2.04 (br d, J=14.43 Hz, 1H), 2.08 (s, 2H), 2.07-2.09 (m, 1H), 2.12 (s, 3H), 2.30 (s, 3H), 2.34-2.44 (m, 2H), 2.54 (br s, 4H), 2.67-2.77 (m, 4H), 3.73 (br d, J=12.47 Hz, 2H), 3.85 (s, 3H), 6.53 (dd, J=8.68, 2.32 Hz, 1H), 6.68 (d, J=2.32 Hz, 1H), 7.66 (d, J=8.68 Hz, 1H), 8.03 (s, 1H), 8.08 (d, J=9.17 Hz, 1H), 8.77 (dd, J=9.17, 3.55 Hz, 1H), 9.30 (s, 1H).

Example 43

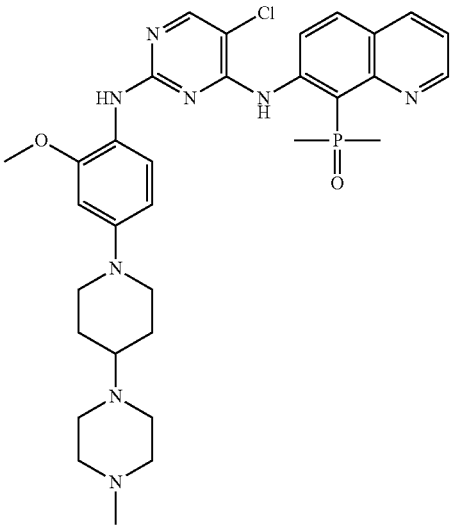

Compound 43

Except for replacing compound 1D with compound 7D and replacing compound 1F with compound 3D, compound 43 was prepared according to the method for preparing compound 1. $^1$H NMR (400 MHz, MeOD) δ ppm 1.67-1.79

(m, 2H), 2.06 (br d, J=12.10 Hz, 2H), 2.14 (s, 3H), 2.17 (s, 3H), 2.63 (s, 3H), 2.77 (br t, J=11.37 Hz, 2H), 2.95 (br s, 6H), 3.76 (br d, J=12.35 Hz, 2H), 3.86 (s, 3H), 4.60 (br s, 2H), 6.55 (dd, J=8.68, 2.45 Hz, 1H), 6.70 (d, J=2.32 Hz, 1H), 7.45 (dd, J=8.13, 4.34 Hz, 1H), 7.71 (d, J=8.68 Hz, 1H), 7.93 (d, J=9.29 Hz, 1H), 8.08 (s, 1H), 8.25 (br d, J=8.07 Hz, 1H), 8.45 (br s, 1H), 8.84 (dd, J=4.28, 1.59 Hz, 1H), 8.88 (dd, J=9.11, 3.73 Hz, 1H).

Example 44

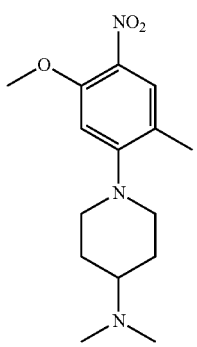

Compound 44A

Except for respectively replacing the compounds of 1-chloro-2-fluoro-4-methoxy-5-nitrobenzene and 3-methyl-3,9-diazaspiro[5.5]undecane with the compounds of 1-fluoro-5-methoxy-2-methyl-4-nitrobenzene and N,N-dimethylpiperidine-4-amine, compound 44A was prepared according to the method for preparing compound 1E. $^1$H NMR (400 MHz, CDCl$_3$) δ=7.83 (s, 1H), 6.55 (s, 1H), 3.94 (s, 3H), 3.34 (br d, J=12.5 Hz, 2H), 2.72 (dt, J=2.0, 11.9 Hz, 2H), 2.35 (s, 6H), 2.32-2.27 (m, 1H), 2.25 (s, 3H), 1.97 (br d, J=12.5 Hz, 2H), 1.70 (dq, J=3.8, 12.0 Hz, 2H).

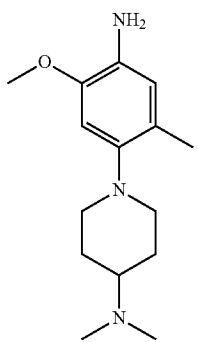

Compound 44B

Except for replacing compound 1E with compound 44A, compound 44B was prepared according to the method for preparing compound 1F. $^1$H NMR (400 MHz, CDCl$_3$) δ=6.58 (s, 1H), 6.57 (s, 1H), 3.82 (s, 3H), 3.56 (br s, 2H), 3.08 (brd, J=12.0 Hz, 2H), 2.61 (dt, J=1.6, 11.6 Hz, 2H), 2.34 (s, 6H), 2.30-2.20 (m, 1H), 2.18 (s, 3H), 1.93-1.85 (m, 2H), 1.73-1.64 (m, 2H).

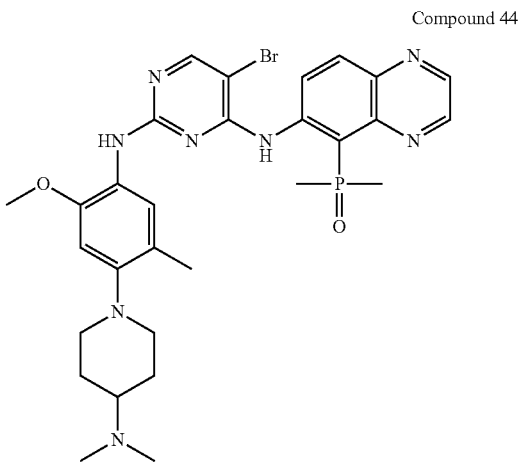 [SMILES: COc1cc(N2CCC(N(C)C)CC2)c(C)cc1Nc1ncc(Br)c(Nc2ccc3nccnc3c2P(C)(C)=O)n1]

Compound 44

Except for replacing compound 1F with compound 44B and replacing compound 1D with compound 34A, compound 44 was prepared according to the method for preparing compound 1. $^1$H NMR (400 MHz, CD$_3$OD) δ=8.93 (dd, J=4.3, 9.5 Hz, 1H), 8.83 (d, J=1.8 Hz, 1H), 8.79 (d, J=2.0 Hz, 1H), 8.19 (s, 1H), 7.95 (d, J=9.5 Hz, 1H), 7.60 (s, 1H), 6.72 (s, 1H), 3.84 (s, 3H), 3.16 (br d, J=11.8 Hz, 2H), 2.69 (br t, J=11.0 Hz, 2H), 2.53-2.47 (m, 1H), 2.45 (s, 6H), 2.16 (s, 3H), 2.12 (s, 3H), 2.07 (s, 3H), 2.04-1.99 (m, 2H), 1.71 (dq, J=3.8, 11.9 Hz, 2H).

Example 45

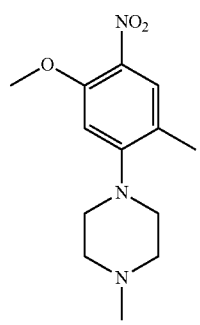

Compound 45A

Except for respectively replacing the compounds of 1-chloro-2-fluoro-4-methoxy-5-nitrobenzene and 3-methyl-3,9-diazaspiro[5.5]undecane with the compounds of 1-fluoro-5-methoxy-2-methyl-4-nitrobenzene and 1-methylpiperazine, compound 45A was prepared according to the method for preparing compound 1E.

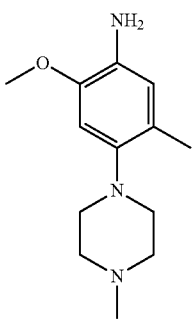

Compound 45B

Except for replacing compound 1E with compound 45A, compound 45B was prepared according to the method for preparing compound 1F.

Compound 45

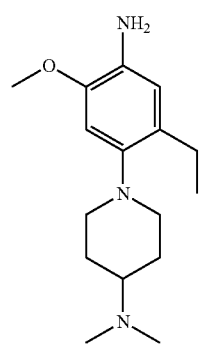

Except for replacing compound 1D with compound 34A and replacing compound 1F with compound 45B, compound 45 was prepared according to the method for preparing compound 1. ¹H NMR (400 MHz, CD₃OD) δ=8.97 (dd, J=4.3, 9.4 Hz, 1H), 8.86 (d, J=2.0 Hz, 1H), 8.82 (d, J=2.0 Hz, 1H), 8.55 (br s, 1H), 8.24 (s, 1H), 8.01 (d, J=9.3 Hz, 1H), 7.67 (s, 1H), 6.78 (s, 1H), 3.88 (s, 3H), 3.30-3.12 (m, 2H), 3.09-2.96 (m, 4H), 2.82 (br s, 3H), 2.51 (s, 3H), 2.18 (s, 3H), 2.15 (s, 3H), 2.10 (s, 3H).

Example 46

Compound 46A

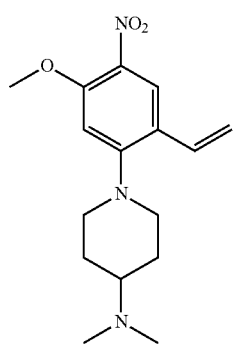

Except for respectively replacing the compounds of 1-chloro-2-fluoro-4-methoxy-5-nitrobenzene and 3-methyl-3,9-diazaspiro[5.5]undecane with the compounds of 1-fluoro-5-methoxy-4-nitro-2-vinylbenzene and N,N-dimethylpiperidine-4-amine 23A, compound 46A was prepared according to the method for preparing compound 1E. ¹H NMR (400 MHz, CDCl₃) δ=8.12 (s, 1H), 7.29 (s, 1H), 6.84-6.63 (m, 1H), 6.53 (s, 1H), 5.71 (dd, J=1.0, 17.6 Hz, 1H), 5.30 (dd, J=1.0, 11.0 Hz, 1H), 4.00-3.96 (m, 3H), 3.51 (s, 5H), 3.00 (br d, J=6.6 Hz, 1H), 2.82-2.72 (m, 2H), 2.55 (s, 1H), 2.39 (s, 6H), 2.00 (br d, J=12.5 Hz, 2H), 1.79-1.67 (m, 2H).

Compound 46B

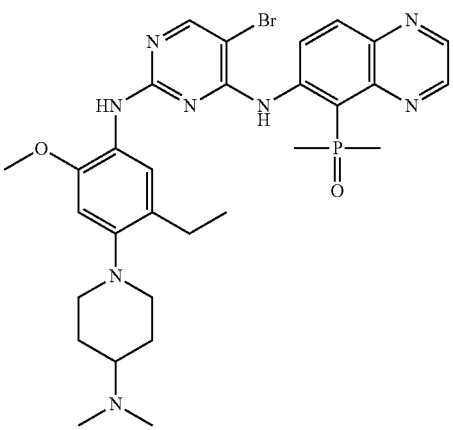

Except for replacing compound 1E with compound 46A, compound 46B was prepared according to the method for preparing compound 1F.

Compound 46

Except for replacing compound 1D with compound 34A and replacing compound 1F with compound 46B, compound 46 was prepared according to the method for preparing compound 1. ¹H NMR (400 MHz, CD₃OD) δ=8.84 (s, 2H), 8.80 (br s, 1H), 8.57 (s, 1H), 8.22 (s, 1H), 7.96 (d, J=9.5 Hz, 1H), 7.69 (s, 1H), 6.79 (s, 1H), 3.85 (s, 3H), 3.22-3.08 (m, 3H), 2.87-2.78 (m, 8H), 2.50 (q, J=7.3 Hz, 2H), 2.16 (s, 4H), 2.12 (s, 4H), 2.09-1.82 (m, 2H), 0.85 (br t, J=7.3 Hz, 3H).

Example 47

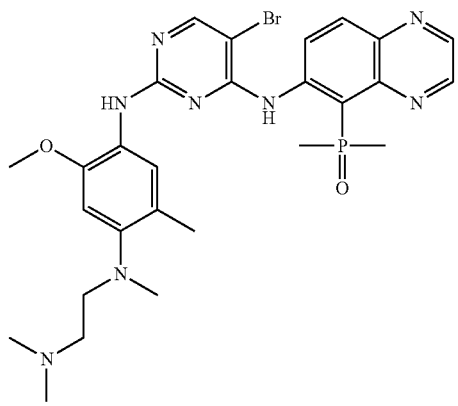

Compound 47

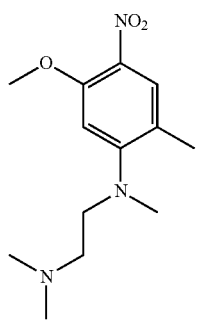

Compound 47A

Except for respectively replacing the compounds of 1-chloro-2-fluoro-4-methoxy-5-nitrobenzene and 3-methyl-3,9-diazaspiro[5.5]undecane with the compounds of 1-fluoro-5-methoxy-2-methyl-4-nitrobenzene and N1,N1,N2-trimethylethane-1,2-diamine, compound 47A was prepared according to the method for preparing compound 1E. $^1$H NMR (400 MHz, CDCl$_3$) δ=7.80 (s, 1H), 6.55 (s, 1H), 3.93 (s, 3H), 3.23-3.16 (m, 2H), 2.87 (s, 3H), 2.53-2.47 (m, 2H), 2.24 (s, 9H).

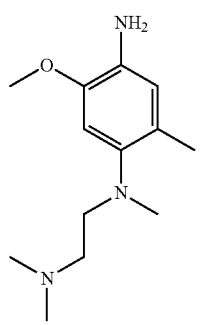

Compound 47B

Except for replacing compound 1E with compound 47A, compound 47B was prepared according to the method for preparing compound 1F. $^1$H NMR (400 MHz, CD$_3$OD-d$_4$) δ=6.70 (s, 1H), 6.60 (s, 1H), 5.00-4.78 (m, 1H), 4.91 (s, 3H), 3.81 (s, 3H), 3.02-2.95 (m, 2H), 2.60 (s, 3H), 2.46-2.40 (m, 2H), 2.24 (s, 5H), 2.26-2.22 (m, 1H), 2.15 (s, 3H).

Except for replacing compound 1D with compound 34A and replacing compound 1F with compound 47B, compound 47 was prepared according to the method for preparing compound 1. $^1$H NMR (400 MHz, CD$_3$OD) δ=8.98 (dd, J=4.2, 9.5 Hz, 1H), 8.85 (d, J=2.0 Hz, 1H), 8.80 (d, J=1.8 Hz, 1H), 8.53 (br s, 1H), 8.25 (s, 1H), 8.04 (d, J=9.4 Hz, 1H), 7.71 (s, 1H), 6.86 (s, 1H), 3.88 (s, 3H), 3.26 (t, J=6.6 Hz, 2H), 3.08-2.99 (m, 2H), 2.69 (s, 9H), 2.17 (s, 3H), 2.12 (d, J=7.6 Hz, 6H).

Example 48

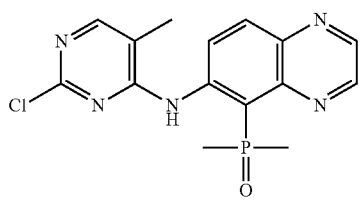

Compound 48A

Compound 34A (100 mg, 242 μmol), 2,4,6-trimethyl-1,3,5,2,4,6-trioxatricyclohexane were dissolved in water and 1,4-dioxane, and then added with Pd(dppf)Cl$_2$ (8.87 mg, 12.1 μmol) and K$_2$CO$_3$ (66.9 mg, 484 μmol). The reaction solution was warmed up to the temperature of 110° C., and stirred for 1 hour under nitrogen atmosphere. After the reaction was completed, the reaction mixture was concentrated, added with ethyl acetate, washed three times with saturated brine, dried over anhydrous sodium sulfate, and filtered. The filtrate was evaporated to dryness and purified by preparative thin-layer chromatography to give compound 48A.

Compound 48

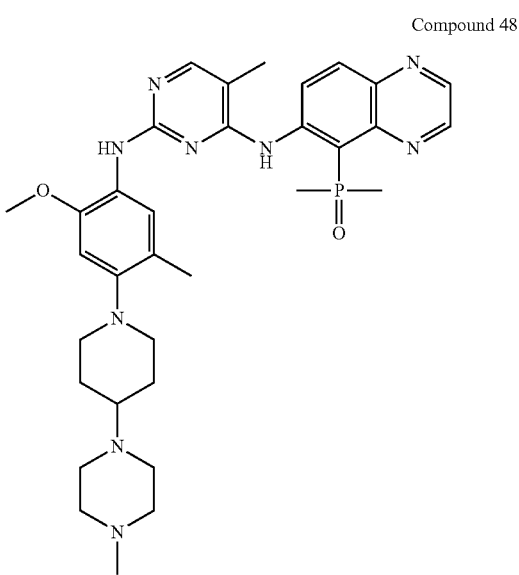

Except for replacing compound 1D with compound 34A and replacing compound 1F with compound 34C, compound 48 was prepared according to the method for preparing compound 1. $^1$H NMR (400 MHz, CD$_3$OD) δ ppm 9.03 (br s, 1H), 8.95 (s, 2H), 8.18 (d, J=9.41 Hz, 1H), 7.90 (s, 1H), 7.59 (s, 1H), 7.37 (s, 1H), 3.98-4.00 (m, 1H), 3.99 (s, 2H), 3.97 (s, 1H), 3.82 (br d, J=10.51 Hz, 5H), 3.70 (br d, J=10.27 Hz, 3H), 3.27-3.37 (m, 5H), 3.09 (s, 3H), 2.48-2.65 (m, 4H), 2.36 (d, J=12.59 Hz, 6H), 2.20 (d, J=14.55 Hz, 7H).

Example 49

Compound 49A

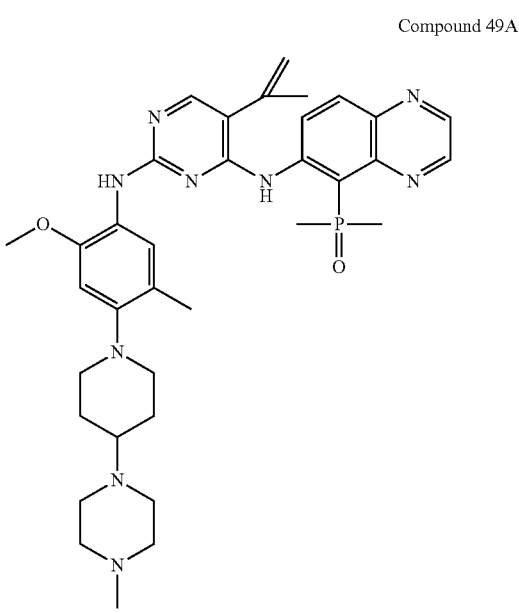 [SMILES: C=C(C)c1cnc(Nc2cc(C)c(N3CCC(N4CCN(C)CC4)CC3)cc2OC)nc1Nc1ccc2nccnc2c1P(C)(C)=O]

Compound 34 (150 mg, 215 μmol, 1 eq) and 2-isopropenyl-4,4,5,5-tetramethyl-1,3,2-dioxaborolane (72.5 mg, 431 μmol) were added to a mixed solvent of ethylene glycol dimethyl ether and water, then added with Pd(PPh$_3$)$_4$(24.9 mg, 21.60 μmol) and Na$_2$CO$_3$ (45.7 mg, 431 μmol), and stirred at 90° C. for 6 hours under protection of nitrogen gas. After the reaction was completed, the reaction solution was added with DCM, and washed three times with water. The organic phase was dried and concentrated to give a crude product. The crude product was separated by preparative thin-layer chromatography to give compound 49A.

Compound 49B

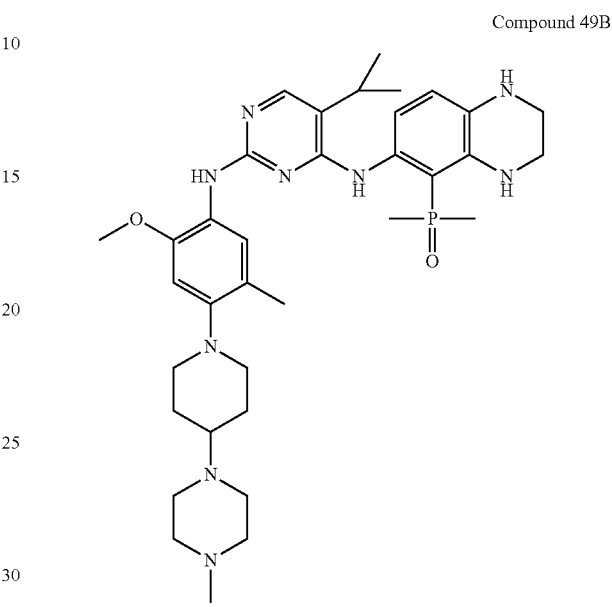

Compound 49A (90 mg, 113.71 μmol) was dissolved in MeOH (10 mL), and added with wet palladium-carbon (20 mg, 113.71 μmol, 10% purity, water content 50%). The reaction system was purged with a hydrogen balloon, and stirred at 20-30° C. for 18 hours under atmospheric pressure. After the reaction was completed, the reaction system was filtered, and the filtrate was concentrated to give compound 49B.

Compound 49

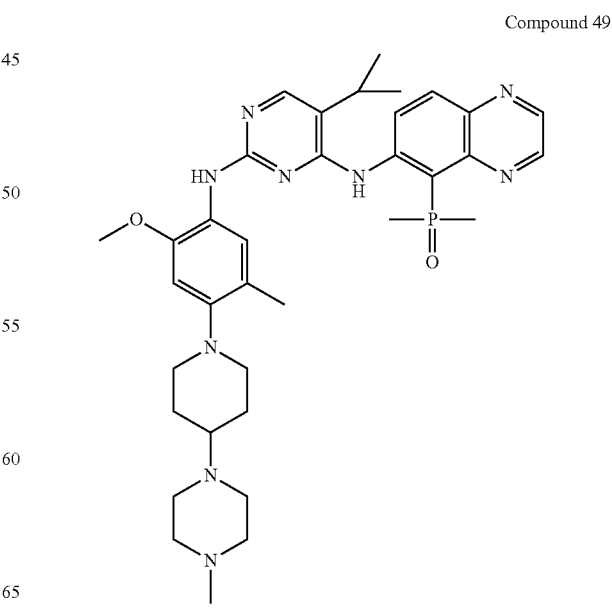

MnO₂ (39.4 mg, 453 μmol, 10 eq) was added to a toluene solution of compound 49B (30 mg, 45.33 μmol, 1 eq), and the mixture was stirred at 30° C. for 12 hours. After the reaction was completed, the mixture was diluted by adding DCM, and filtered. The filtrate was concentrated to give a crude product. The crude product was separated by thin-layer chromatography to give compound 49. ¹H NMR (400 MHz, CD₃OD) δ=9.14 (dd, J=4.2, 9.5 Hz, 1H), 8.83 (d, J=2.0 Hz, 1H), 8.77 (d, J=2.0 Hz, 1H), 8.07 (s, 1H), 7.99 (d, J=9.8 Hz, 1H), 7.71 (s, 1H), 6.77 (s, 1H), 3.87 (s, 3H), 3.19 (br d, J=13.2 Hz, 2H), 2.84-2.48 (m, 10H), 2.47-2.38 (m, 1H), 2.35 (s, 3H), 2.17 (s, 3H), 2.14 (s, 3H), 2.09 (s, 3H), 2.03 (br d, J=12.0 Hz, 2H), 1.79-1.66 (m, 2H), 1.34 (d, J=6.8 Hz, 6H).

Example 50

Compound 50

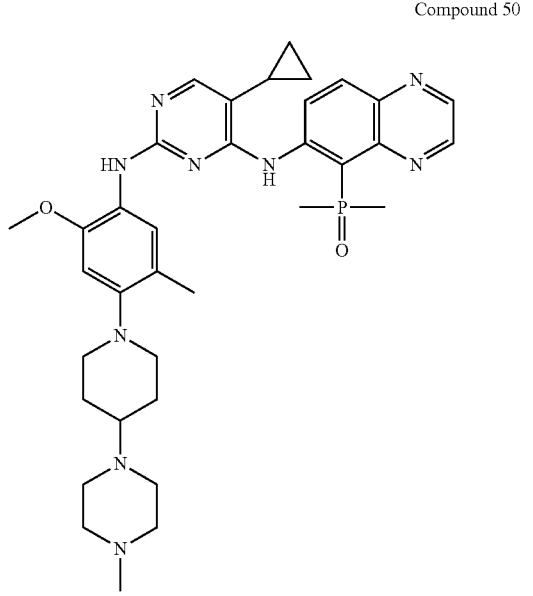 [SMILES: COc1cc(N2CCC(N3CCN(C)CC3)CC2)c(C)cc1Nc1ncc(C2CC2)c(Nc2ccc3nccnc3c2P(C)(C)=O)n1]

Compound 34 (0.1 g, 143 μmol, 1 eq) and cyclopropylboronic acid (49.4 mg, 575.87 mol, 4 eq) were added to a mixed solvent of toluene and water, and added with Pd(OAc)₂ (3.23 mg, 14.4 μmol, 0.1 eq), tricyclohexylphosphine (8.07 mg, 28.7 μmol, 0.2 eq) and K₂CO₃ (76.4 mg, 359.9 μmol, 2.5 eq). The mixture was stirred at 90° C. for 6 hours under protection of nitrogen gas. After the reaction was completed, the reaction system was diluted by adding DCM and washed once with water, and the organic phase was dried and concentrated to give a crude product. The crude product was separated by acidic preparative high-performance liquid chromatography to give compound 50. ¹H NMR (400 MHz, CD₃OD) δ=9.19 (dd, J=4.2, 9.5 Hz, 1H), 8.82 (d, J=1.7 Hz, 1H), 8.75 (d, J=2.0 Hz, 1H), 8.52 (br s, 1H), 7.96 (d, J=9.5 Hz, 1H), 7.88 (s, 1H), 7.70 (s, 1H), 6.73 (s, 1H), 3.85 (s, 3H), 3.18 (br d, J=11.7 Hz, 2H), 3.02 (br s, 8H), 2.71 (br t, J=11.7 Hz, 3H), 2.67 (s, 3H), 2.18-2.09 (m, 9H), 2.04 (br d, J=11.0 Hz, 3H), 1.83-1.71 (m, 3H), 1.08-1.01 (m, 2H), 0.66-0.60 (m, 2H).

Example 51

Compound 51A

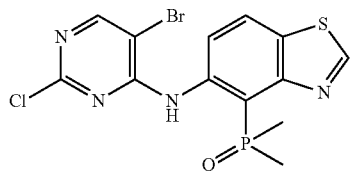

Except for replacing the compound 2,4,5-trichloropyrimidine with the compound 5-bromo-2,4-dichloropyrimidine and replacing compound 1C with compound 42B, compound 51A was prepared according to the method for preparing compound 1D.

Compound 51

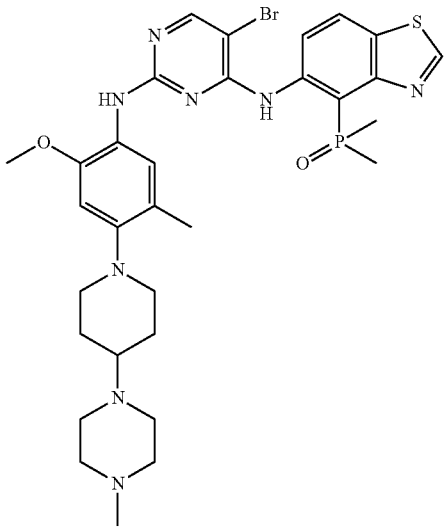

Except for replacing compound 1D with compound 51A and replacing compound 1F with compound 34C, compound 51 was prepared according to the method for preparing compound 1. ¹H NMR (400 MHz, CD₃OD) δ ppm 9.31 (s, 1H), 8.55 (dd, J=9.17, 3.42 Hz, 1H), 8.15 (s, 1H), 8.07 (d, J=9.17 Hz, 1H), 7.67 (s, 1H), 6.72 (s, 1H), 3.84 (s, 3H), 3.31 (dt, J=3.21, 1.64 Hz, 2H), 2.63-2.98 (m, 10H), 2.52-2.59 (m, 1H), 2.48 (s, 3H), 2.12 (s, 3H), 2.09 (s, 3H), 2.04 (s, 3H), 2.01 (br s, 2H), 1.64-1.76 (m, 2H).

Example 52

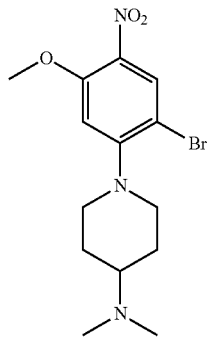
Compound 52A

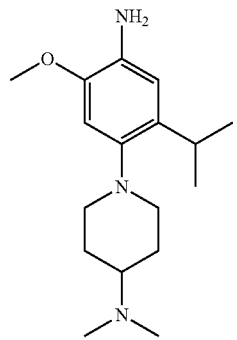
Compound 52C

Except for respectively replacing the compounds of 1-chloro-2-fluoro-4-methoxy-5-nitrobenzene and 3-methyl-3,9-diazaspiro[5.5]undecane with the compounds of 1-bromo-2-fluoro-4-methoxy-5-nitrobenzene and N,N-dimethylpiperidine-4-amine, compound 52A was prepared according to the method for preparing compound 1E.

Except for replacing compound 49A with compound 52B, compound 52C was prepared according to the method for preparing compound 49B.

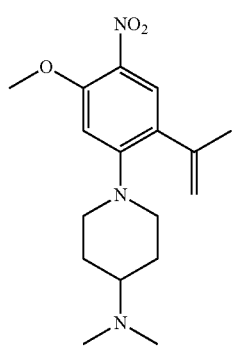
Compound 52B

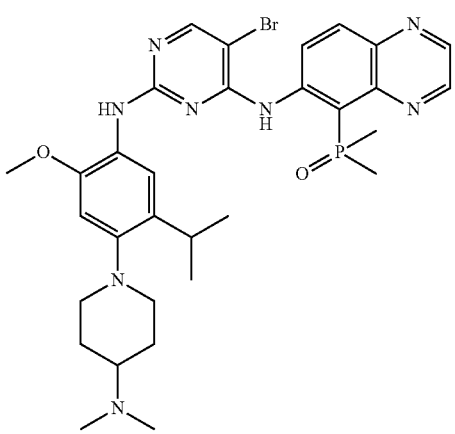
Compound 52

Compound 52A (0.1 g, 279 μmol, 1 eq), 2-isopropenyl-4,4,5,5-tetramethyl-1,3,2-dioxaborolane (234 mg, 1.40 mmol, 5 eq) were dissolved in a mixed solvent of DME and $H_2O$, and added with Pd(PPh$_3$)$_4$ (32.2 mg, 27.9 μmol, 0.1 eq) and Na$_2$CO$_3$ (59.1 mg, 558 μmol, 2 eq). The reaction system was purged 3 times with nitrogen gas and stirred at 110° C. for 12 hours under nitrogen atmosphere. The reaction solution was diluted with DCM, washed three times with water, and separated. The organic phase was dried over anhydrous sodium sulfate, and then filtered. The filtrate was evaporated to dryness to give compound 52B.

Except for replacing compound 1D with compound 34A and replacing compound 1F with compound 52C, compound 52 was prepared according to the method for preparing compound 1. $^1$H NMR (400 MHz, CD$_3$OD) δ ppm 0.96 (d, J=6.85 Hz, 6H), 1.74-1.86 (m, 2H), 2.10 (br d, J=12.47 Hz, 2H), 2.14 (s, 3H) 2.17 (s, 3H), 2.64 (s, 6H), 2.85 (br t, J=11.19 Hz, 3H), 3.13 (br d, J=11.86 Hz, 3H), 3.85 (s, 3H), 6.86 (s, 1H), 7.58 (s, 1H), 7.96 (d, J=9.29 Hz, 1H), 8.26 (s, 1H), 8.80 (d, J=1.83 Hz, 1H), 8.85 (d, J=1.83 Hz, 1H).

Example 53

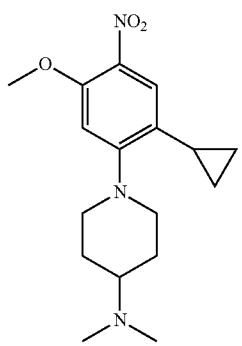

Compound 53A

Except for replacing the compound 2-isopropenyl-4,4,5,5-tetramethyl-1,3,2-dioxaborolane with the compound cyclopropylboronic acid, compound 53A was prepared according to the method for preparing compound 52B.

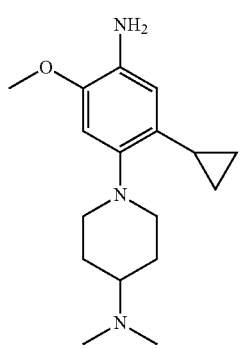

Compound 53B

Except for replacing compound 1E with compound 53A, compound 53B was prepared according to the method for preparing compound 1F.

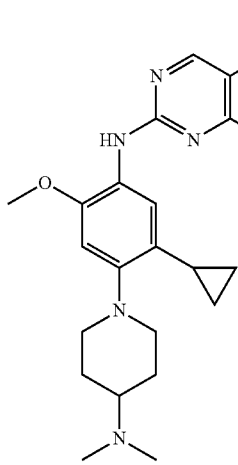

Compound 53

Except for replacing compound 1D with compound 34A and replacing compound 1F with compound 53B, compound 53 was prepared according to the method for preparing compound 1. $^1$H NMR (400 MHz, CD$_3$OD) δ ppm 0.28 (br d, J=3.91 Hz, 2H), 0.59 (br d, J=7.83 Hz, 2H), 1.81-1.97 (m, 2H), 2.16 (d, J=14.43 Hz, 9H), 2.78 (s, 6H), 2.80-2.88 (m, 2H), 3.05 (br t, J=11.86 Hz, 1H), 3.47 (br d, J=12.23 Hz, 2H), 3.86 (s, 3H), 6.77 (s, 1H), 7.17 (s, 1H), 7.95 (d, J=9.54 Hz, 1H), 8.24 (s, 1H), 8.56 (s, 1H), 8.80 (d, J=1.83 Hz, 1H), 8.86 (d, J=1.83 Hz, 1H).

Example 54

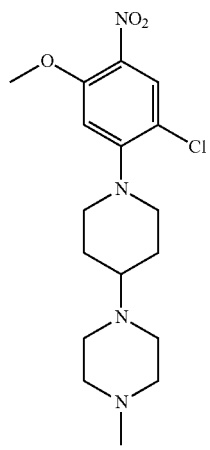

Compound 54A

Except for respectively replacing the compounds of 1-chloro-2-fluoro-4-methoxy-5-nitrobenzene and 3-methyl-3,9-diazaspiro[5.5]undecane with the compounds of 1-chloro-2-fluoro-4-methoxy-5-nitrobenzene and 1-methyl-4-(piperidin-4-yl)piperazine, compound 54A was prepared according to the method for preparing compound 1E. $^1$H NMR (400 MHz, CD$_3$OD) δ=6.79 (s, 1H), 6.68 (s, 1H), 3.84 (s, 3H), 3.24-2.76 (m, 8H), 2.72 (br s, 1H), 2.71-2.65 (m, 2H), 2.02 (br d, J=10.8 Hz, 2H), 1.89-1.71 (m, 2H).

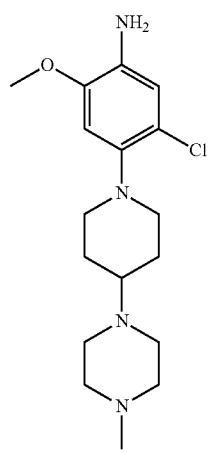

Compound 54B

Except for replacing compound 1E with compound 54A, compound 54B was prepared according to the method for preparing compound 1F. $^1$H NMR (400 MHz, CDCl$_3$) δ=8.04 (s, 1H), 6.56 (s, 1H), 4.02-3.91 (m, 3H), 3.65 (br d, J=12.1 Hz, 2H), 2.81-2.73 (m, 2H), 2.66 (br s, 4H), 2.56-2.37 (m, 5H), 2.31 (s, 3H), 1.98 (br d, J=12.2 Hz, 2H), 1.84-1.71 (m, 2H).

Compound 54

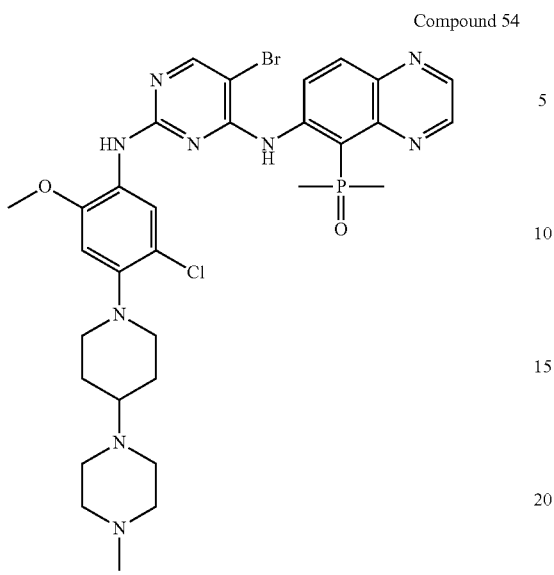

Except for replacing compound 1D with compound 34A and replacing compound 1F with compound 11B, compound 54 was prepared according to the method for preparing compound 1. $^1$H NMR (400 MHz, CD$_3$OD) δ=8.88 (dd, J=4.2, 9.4 Hz, 1H), 8.85 (d, J=1.7 Hz, 1H), 8.81 (d, J=1.7 Hz, 1H), 8.27 (s, 1H), 8.15 (d, J=9.4 Hz, 1H), 7.97 (s, 1H), 6.78 (s, 1H), 3.90 (s, 3H), 3.39 (br d, J=11.1 Hz, 2H), 2.95-2.56 (m, 10H), 2.48 (br t, J=11.6 Hz, 1H), 2.41 (s, 3H), 2.15 (d, J=14.4 Hz, 6H), 2.01 (br d, J=11.6 Hz, 2H), 1.82-1.67 (m, 2H).

Example 55

Compound 55A

Except for replacing compound 52A with the compound 1-bromo-2-fluoro-4-methoxy-5-nitrobenzene, compound 55A was prepared according to the method for preparing compound 52B. $^1$H NMR (400 MHz, CDCl$_3$) δ=7.95 (d, J=7.9 Hz, 1H), 6.78 (d, J=12.3 Hz, 1H), 5.36-5.26 (m, 2H), 3.97 (s, 3H), 2.14 (s, 3H).

Compound 55B

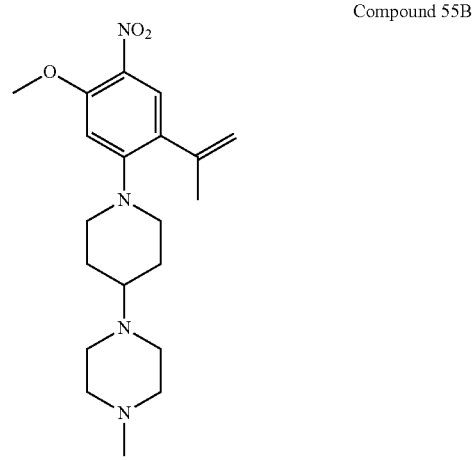 [SMILES: C=C(C)c1cc([N+](=O)[O-])c(OC)cc1N1CCC(N2CCN(C)CC2)CC1]

Except for respectively replacing the compounds of 1-chloro-2-fluoro-4-methoxy-5-nitrobenzene and 3-methyl-3,9-diazaspiro[5.5]undecane with compounds 55A and 1-methyl-4-(piperidin-4-yl)piperazine, compound 55B was prepared according to the method for preparing compound 1E

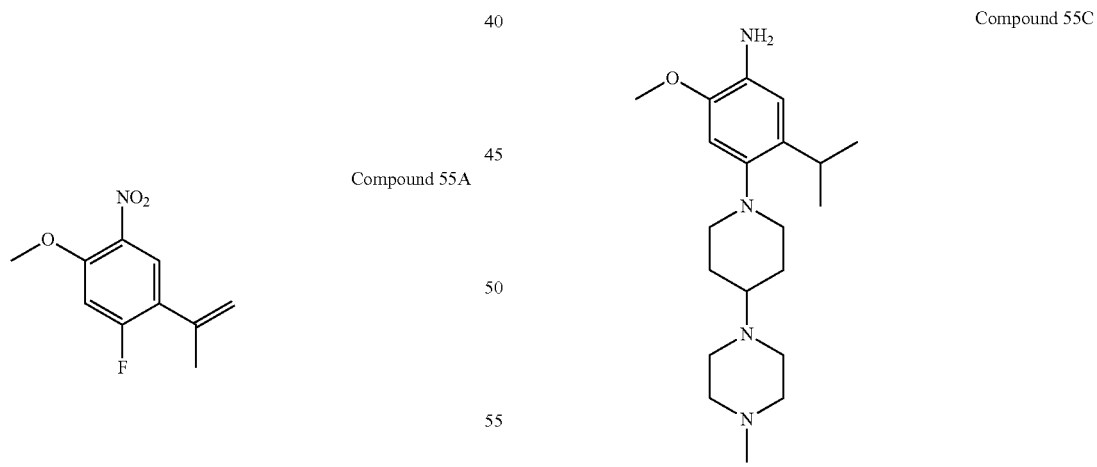

Compound 55C

Except for replacing compound 49A with compound 55B, compound 55C was prepared according to the method for preparing compound 49B.

Compound 55

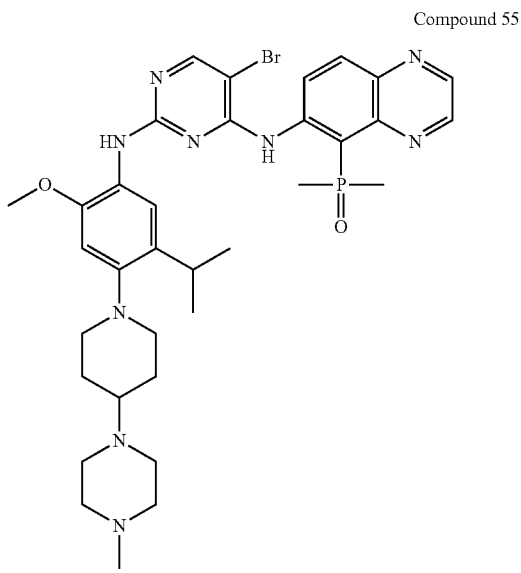

Compound 56B

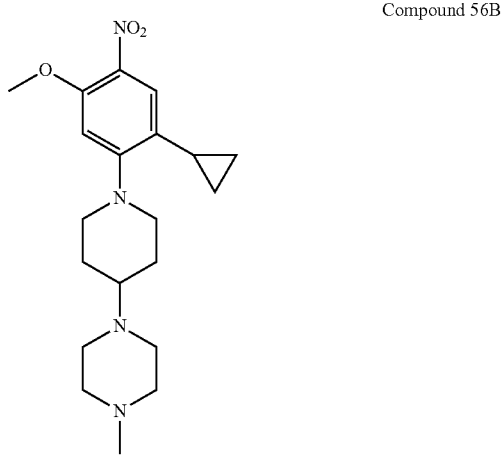

Except for replacing compound 1D with compound 34A and replacing compound 1F with compound 55C, compound 55 was prepared according to the method for preparing compound 1. $^1$H NMR (400 MHz, CD$_3$OD) δ=8.83 (d, J=1.8 Hz, 2H), 8.79 (d, J=1.8 Hz, 1H), 8.24 (s, 1H), 7.94 (br d, J=9.8 Hz, 1H), 7.53 (s, 1H), 6.84 (s, 1H), 3.83 (s, 3H), 3.45-3.37 (m, 2H), 3.08 (br d, J=10.9 Hz, 2H), 2.91-2.47 (m, 1H), 2.79 (br t, J=11.1 Hz, 8H), 2.41 (br s, 1H), 2.33 (s, 3H), 2.14 (d, J=14.4 Hz, 6H), 2.03 (br d, J=11.0 Hz, 2H), 1.77-1.64 (m, 2H), 1.30 (s, 2H), 0.95 (br d, J=6.8 Hz, 6H).

Except for respectively replacing the compound of 1-chloro-2-fluoro-4-methoxy-5-nitrobenzene and 3-methyl-3,9-diazaspiro[5.5]undecane with compounds 56A and 1-methyl-4-(piperidin-4-yl)piperazine, compound 56B was prepared according to the method for preparing compound 1E. $^1$H NMR (400 MHz, CDCl$_3$) δ=7.51 (s, 1H), 6.57-6.48 (m, 1H), 3.94 (s, 3H), 3.63 (br d, J=12.0 Hz, 2H), 2.83-2.45 (m, 11H), 2.43-2.36 (m, 1H), 2.31 (s, 3H), 2.06-1.93 (m, 4H), 1.79-1.67 (m, 2H), 1.34-1.21 (m, 1H), 1.07-0.94 (m, 2H), 0.78-0.69 (m, 2H).

Example 56

Compound 56A

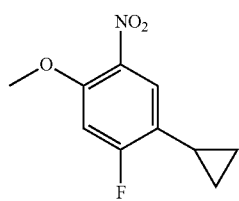

Compound 56C

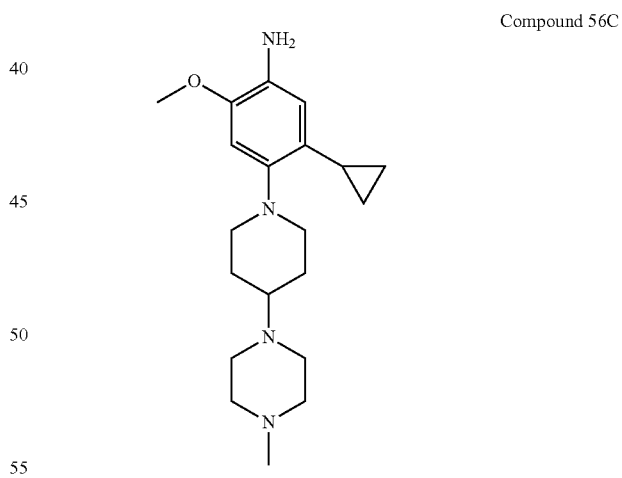

Except for replacing compound 52A with the compound 1-bromo-2-fluoro-4-methoxy-5-nitrobenzene, compound 56A was prepared according to the method for preparing compound 53A. $^1$H NMR (400 MHz, CDCl$_3$) δ=7.57 (d, J=7.8 Hz, 1H), 6.76 (d, J=11.4 Hz, 1H), 3.94 (s, 3H), 2.08-1.92 (m, 1H), 1.09-0.94 (m, 2H), 0.81-0.65 (m, 2H).

Except for replacing compound 1E with compound 56B, compound 56C was prepared according to the method for preparing compound 1F. $^1$H NMR (400 MHz, CDCl$_3$) δ=6.62-6.51 (m, 1H), 6.13 (s, 1H), 3.84-3.80 (m, 3H), 3.33-3.21 (m, 2H), 2.81-2.40 (m, 12H), 2.32 (s, 3H), 1.93 (br d, J=11.5 Hz, 2H), 1.78-1.68 (m, 2H), 1.31-1.17 (m, 1H), 0.92-0.84 (m, 2H), 0.67-0.53 (m, 2H).

Compound 56

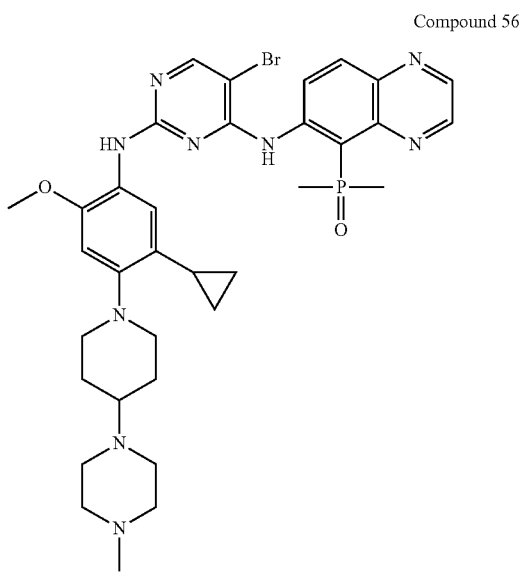 [SMILES: COc1cc(N2CCC(N3CCN(C)CC3)CC2)c(C2CC2)cc1Nc1ncc(Br)c(Nc2ccc3nccnc3c2P(C)(C)=O)n1]

Except for replacing compound 1D with compound 34A and replacing compound 1F with compound 56C, compound 56 was prepared according to the method for preparing compound 1. $^1$H NMR (400 MHz, CD$_3$OD) δ=8.85-8.79 (m, 2H), 8.77 (d, J=1.8 Hz, 1H), 8.20 (s, 1H), 7.98-7.86 (m, 1H), 7.11 (s, 1H), 6.73 (s, 1H), 3.82 (s, 3H), 3.38 (br d, J=11.7 Hz, 2H), 2.87-2.49 (m, 10H), 2.42 (br t, J=11.6 Hz, 1H), 2.33 (s, 3H), 2.13 (d, J=14.4 Hz, 6H), 2.02 (br d, J=10.9 Hz, 2H), 1.79-1.64 (m, 2H), 1.42-1.07 (m, 2H), 0.89-0.86 (m, 2H), 0.56 (br d, J=7.8 Hz, 2H), 0.25 (br d, J=3.8 Hz, 2H).

Example 57

Compound 57A

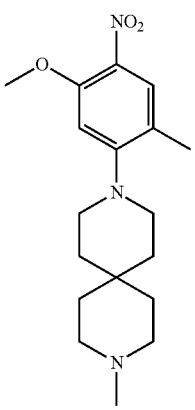

Except for replacing the compound 1-chloro-2-fluoro-4-methoxy-5-nitrobenzene with the compound 1-fluoro-5-methoxy-2-methyl-4-nitrobenzene, compound 57A was prepared according to the method for preparing compound 1E $^1$H NMR (400 MHz, CDCl$_3$) δ=7.75 (s, 1H), 6.48 (s, 1H), 3.87 (s, 3H), 2.93-2.85 (m, 4H), 2.33 (br s, 4H), 2.23 (s, 3H), 2.16 (s, 3H), 1.61-1.53 (m, 8H).

Compound 57B

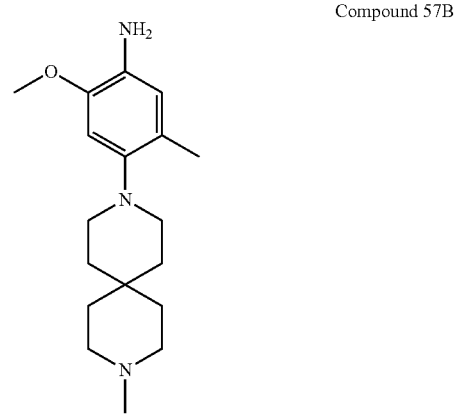

Except for replacing compound 1E with compound 57A, compound 57B was prepared according to the method for preparing compound 1F. $^1$H NMR (400 MHz, CDCl$_3$) δ=6.62 (s, 1H), 6.58 (s, 1H), 3.85 (s, 3H), 3.61-3.50 (m, 2H), 2.82-2.75 (m, 4H), 2.41 (br s, 4H), 2.32 (s, 3H), 2.19 (s, 3H), 1.65-1.60 (m, 8H).

Compound 57

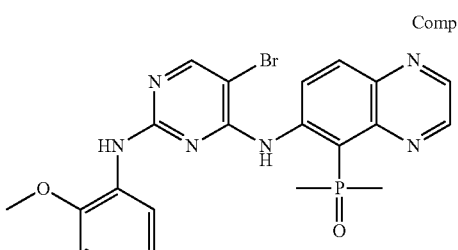

Except for replacing compound 1D with compound 34A and replacing compound 1F with compound 57B, compound 57 was prepared according to the method for preparing compound 1. $^1$H NMR (400 MHz, CD$_3$OD) δ=8.89 (dd, J=4.2, 9.5 Hz, 1H), 8.81 (d, J=1.7 Hz, 1H), 8.77 (d, J=2.0 Hz, 1H), 8.58 (s, 1H), 8.16 (s, 1H), 7.91 (d, J=9.5 Hz, 1H), 7.58 (s, 1H), 6.73 (s, 1H), 3.83 (s, 3H), 3.16 (br s, 4H), 2.89-2.82 (m, 4H), 2.81 (s, 3H), 2.12 (d, J=14.2 Hz, 6H), 2.04 (s, 3H), 1.84 (br s, 4H), 1.73 (br s, 4H).

Example 58

Compound 58A

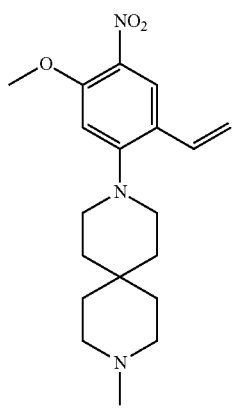

Except for replacing the compound 1-chloro-2-fluoro-4-methoxy-5-nitrobenzene with the compound 1-fluoro-5-methoxy-4-nitro-2-vinyl benzene, compound 58A was prepared according to the method for preparing compound 1E. $^1$H NMR (400 MHz, CDCl$_3$) δ=8.03 (s, 1H), 6.64 (dd, J=11.0, 17.9 Hz, 1H), 6.45 (s, 1H), 5.61 (dd, J=1.1, 17.7 Hz, 1H), 5.19 (dd, J=1.1, 10.9 Hz, 1H), 3.89 (s, 3H), 3.02-2.93 (m, 4H), 2.36-2.28 (m, 4H), 2.23 (s, 3H), 1.56 (td, J=5.5, 15.1 Hz, 8H).

Compound 58B

Except for replacing compound 49A with compound 58A, compound 58B was prepared according to the method for preparing compound 49B.

Compound 58

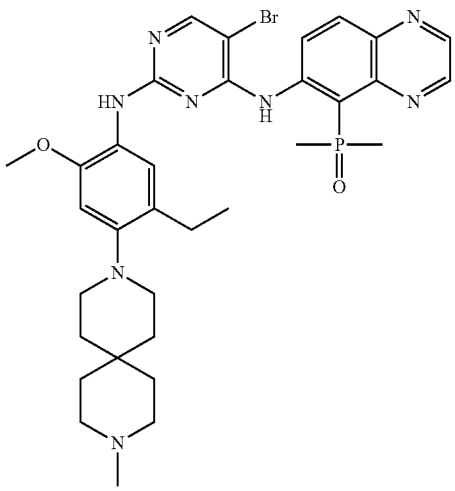

Except for replacing compound 1D with compound 34A and replacing compound 1F with compound 58B, compound 58 was prepared according to the method for preparing compound 1. $^1$H NMR (400 MHz, CD$_3$OD) δ=8.88-8.82 (m, 2H), 8.80 (d, J=1.7 Hz, 1H), 8.57 (s, 1H), 8.21 (s, 1H), 7.96 (d, J=9.5 Hz, 1H), 7.64 (s, 1H), 6.83 (s, 1H), 3.85 (s, 3H), 3.13 (br s, 4H), 2.92-2.83 (m, 4H), 2.79 (s, 3H), 2.49 (q, J=7.6 Hz, 2H), 2.14 (d, J=14.4 Hz, 6H), 1.85 (br s, 4H), 1.74 (br s, 4H), 0.84 (br t, J=7.5 Hz, 3H).

Example 59

Compound 59

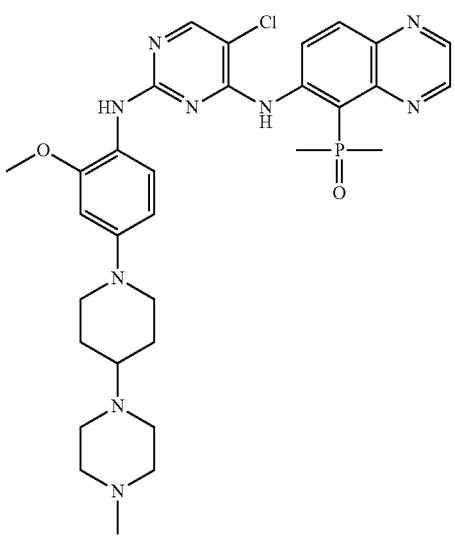

Except for respectively replacing compounds 1D and 1F with compounds 8E and 3D, compound 59 was prepared according to the preparation method of compound 1. $^1$H NMR (400 MHz, CD$_3$OD) δ=9.08 (d, J=4.2, 9.5 Hz, 1H), 8.79 (d, J=1.8 Hz, 1H), 8.75 (d, J=1.8 Hz, 1H), 8.53 (s, 1H), 8.04 (s, 1H), 7.92 (d, J=9.5 Hz, 1H), 7.57 (d, J=8.7 Hz, 1H), 6.63 (d, J=2.3 Hz, 1H), 6.46 (d, J=2.3, 8.7 Hz, 1H), 3.82 (s, 3H), 3.74-3.66 (m, 6H), 3.70 (d, J=12.2 Hz, 2H), 2.69 (t, J=11.6 Hz, 3H), 2.55 (s, 1H), 2.52 (s, 3H), 2.12 (s, 3H), 2.09 (s, 3H), 2.00 (d, J=12.2 Hz, 2H), 1.67 (q, J=3.7, 12.0 Hz, 2H).

Example 60

Compound 60

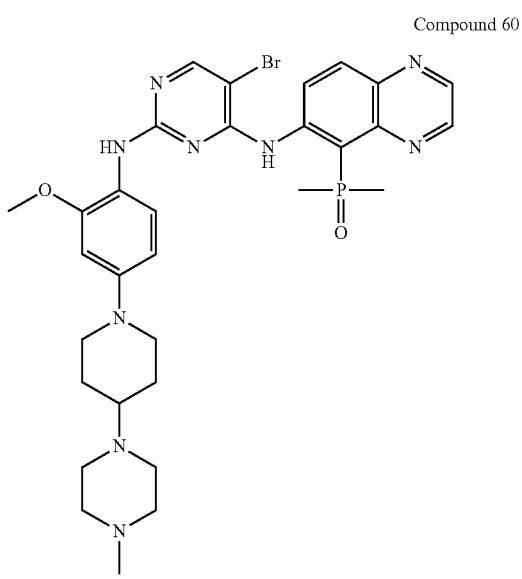 [SMILES: COc1cc(N2CCC(N3CCN(C)CC3)CC2)ccc1Nc1ncc(Br)c(Nc2ccc3nccnc3c2P(C)(C)=O)n1]

Except for respectively replacing compounds 1D and 1F with compounds 34A and 3D, compound 60 was prepared according to the preparation method of compound 1. $^1$H NMR (400 MHz, CD$_3$OD) δ=8.98 (dd, J=4.2, 9.5 Hz, 1H), 8.82 (d, J=2.0 Hz, 1H), 8.78 (d, J=2.0 Hz, 1H), 8.52 (s, 1H), 8.18 (s, 1H), 7.98 (d, J=9.5 Hz, 1H), 7.59 (d, J=8.7 Hz, 1H), 6.67 (d, J=2.4 Hz, 1H), 6.50 (dd, J=2.4, 8.7 Hz, 1H), 3.84 (s, 3H), 3.73 (br d, J=12.7 Hz, 2H), 2.97-2.61 (m, 10H), 2.60-2.52 (m, 1H), 2.49 (s, 3H), 2.14 (s, 3H), 2.11 (s, 3H), 2.03 (br d, J=12.3 Hz, 2H), 1.78-1.63 (m, 2H).

Example 61

Compound 61

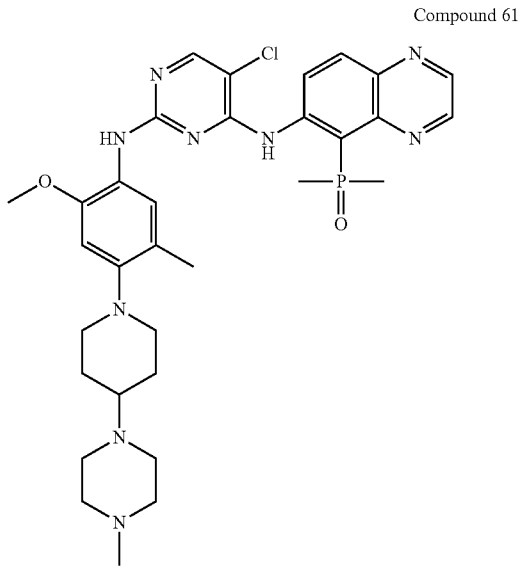 [SMILES: COc1cc(N2CCC(N3CCN(C)CC3)CC2)c(C)cc1Nc1ncc(Cl)c(Nc2ccc3nccnc3c2P(C)(C)=O)n1]

Except for respectively replacing compounds 1D and 1F with compounds 8E and 34C, compound 61 was prepared according to the preparation method of compound 1. $^1$H NMR (400 MHz, CD$_3$OD) δ=9.05 (dd, J=4.2, 9.5 Hz, 1H), 8.80 (d, J=1.7 Hz, 1H), 8.75 (d, J=1.8 Hz, 1H), 8.53 (s, 1H), 8.06 (s, 1H), 7.92 (d, J=9.5 Hz, 1H), 7.59 (s, 1H), 6.69 (s, 1H), 3.81 (s, 3H), 3.14 (br d, J=11.7 Hz, 2H), 3.01-2.54 (m, 11H), 2.52 (s, 3H), 2.13 (s, 2H), 2.16-2.12 (m, 1H), 2.10 (s, 3H), 2.08 (s, 3H), 2.00 (br d, J=11.7 Hz, 2H), 1.79-1.65 (m, 2H).

Example 62

Compound 62

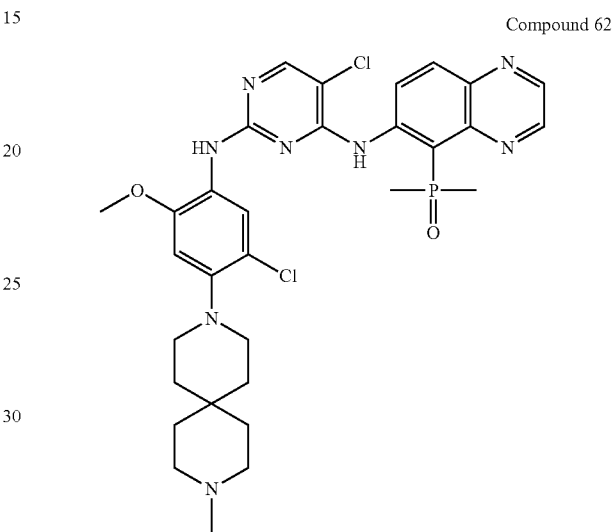

Except for replacing compound 1D with compound 8E, compound 62 was prepared according to the method for preparing compound 1. $^1$H NMR (400 MHz, DMSO-d$_6$) δ=12.92 (s, 1H), 9.08-8.94 (m, 1H), 8.87 (dd, J=2.0, 9.2 Hz, 2H), 8.35 (s, 1H), 8.29-8.21 (m, 2H), 8.04 (d, J=9.6 Hz, 1H), 7.72 (s, 1H), 6.90 (s, 1H), 3.84 (s, 3H), 3.00-2.92 (m, 4H), 2.56-2.53 (m, 4H), 2.32 (s, 3H), 2.06 (s, 3H), 2.02 (s, 3H), 1.65-1.54 (m, 8H); LC-MS (ESI): m/z: 655.0 [M+1].

Comparative Example 1

Comparative compound 1A

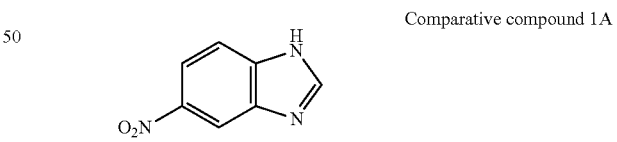

4-Nitrobenzene-1,2-diamine (10 g, 65.30 mmol) was dissolved in HCOOH (9.03 g, 187.92 mmol, 7.40 mL), and added with hydrochloric acid solution (5 M, 100.00 mL). The mixture was stirred at 110° C. for 15 hours. After the reaction was completed, the reaction solution was adjusted to neutrality with 2M sodium hydroxide solution, and a large amount of solids were precipitated. After filtration, the filter cake was dried to give a crude product. The crude product was recrystallized from water to give comparative compound 1A. $^1$H NMR (400 MHz, CD$_3$OD-d$_6$) δ=8.55 (d, J=1.6 Hz, 1H), 8.44 (s, 1H), 8.22-8.19 (m, 1H), 7.74 (d, J=8.8 Hz, 1H).

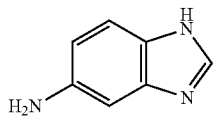

Comparative compound 1B

Except for replacing compound 1E with comparative compound 1A, comparative compound 1B was prepared according to the method for preparing compound 1F. ¹H NMR (400 MHz, CD₃OD-d₆) δ=7.93 (s, 1H), 7.37 (d, J=8.8 Hz, 1H), 6.93 (s, 1H), 6.78-6.75 (m, 1H).

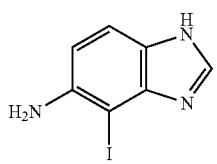

Comparative compound 1C

Comparative compound 1B (7.8 g, 58.58 mmol) was dissolved in 100 mL of AcOH, and added with iodine (14.87 g, 58.58 mmol) and sodium acetate (9.61 g, 117.16 mmol), and the reaction was stirred at 25° C. for 2 hours. After the reaction was completed, acetic acid was removed by concentration under reduced pressure, and the reaction mixture was adjusted to the pH of about 9 with 1M sodium hydroxide solution. The mixture was extracted with dichloromethane and washed successively with water and saturated brine, and the organic phase was collected and dried. After concentration, a crude product was obtained. The crude product was subjected to column chromatography to give comparative compound 1C. ¹H NMR (400 MHz, CD₃OD-d₆) δ=8.00 (s, 1H), 7.34 (m, J=8.8 Hz, 1H), 6.84 (d, J=8.8 Hz, 1H).

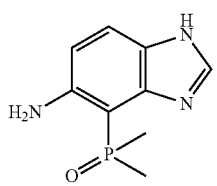

Comparative compound 1D

Except for replacing compound 1B with comparative compound 1C and replacing compound 1F with compound 31B, comparative compound 1D was prepared according to the method for preparing compound 1C. ¹H NMR (400 MHz, CD₃OD-d₆) δ=7.88 (s, 1H), 7.44 (d, J=5.2 Hz, 1H), 6.61-6.58 (m, 1H), 2.03 (s, 1H), 1.99 (s, 1H).

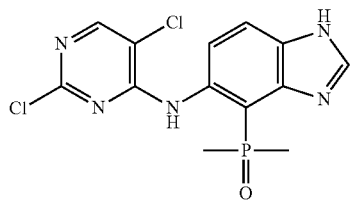

Comparative compound 1E

Except for replacing compound 1C with comparative compound 1D, comparative compound 1E was prepared according to the method for preparing compound 1D. ¹H NMR (400 MHz, DMSO-d₆) δ=12.84 (s, 1H), 12.33 (s, 1H), 8.43-8.36 (m, 3H), 7.82 (d, J=9.6 Hz, 1H), 2.03 (s, 3H), 1.99 (s, 3H).

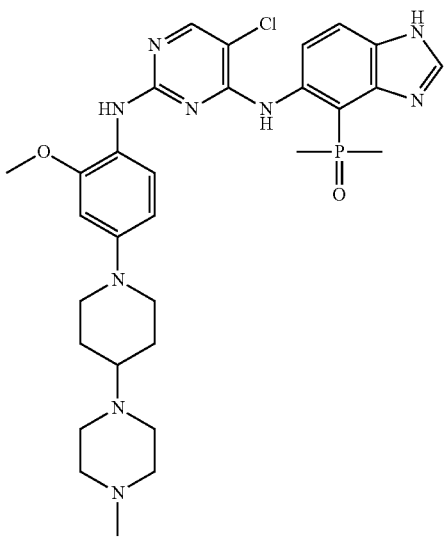

Comparative compound 1

Except for respectively replacing compounds 1D and 1F with comparative compound 1E and compound 3D, comparative compound 1 was prepared according to the method for preparing compound 1. ¹H NMR (400 MHz, CD₃OD-d₄) d=8.50 (s, 1H), 8.36-8.08 (m, 2H), 8.00 (s, 1H), 7.82-7.68 (m, 1H), 7.59 (br s, 1H), 6.63 (d, J=1.8 Hz, 1H), 6.24 (br s, 1H), 3.84 (s, 3H), 3.66 (br d, J=11.9 Hz, 2H), 3.13-2.78 (m, 8H), 2.76-2.56 (m, 6H), 2.01 (br d, J=14.1 Hz, 8H), 1.80-1.59 (m, 2H).

Experimental Example 1: Enzyme Activity Experiment (1)

Experimental Procedure

1. Compound Preparation 1) 10 μL of the compounds to be tested and reference compounds diluted to 10 mM were taken into an Echo LDV plate, which were diluted according to the compound profile with Echo.

2. Reaction Steps 1) 1×enzyme reaction buffer was prepared: 1× enzyme buffer, 5 mM MgCl₂, 1 mM DTT (dithiothreitol), water.

2) A mixed solution of 10 nM enzyme (final concentration of 5 nM) and 2 μM substrate (final concentration of 1 μM) and a solution containing the substrate alone were prepared with the diluted enzyme reaction buffer.

3) 5 μL of the substrate was added into A1-H1, J24-P24 (the number of the well position), and 5 μL of the mixture of the enzyme and substrate was added into the remaining wells.

4) Centrifugation was performed at 1000 rpm at 23° C. for 30 s.

5) Incubation was performed at 23° C. for 15 min.

6) 5 μL of 40 μM ATP (EGFR (Δ19del/T790M/C797S), a final ATP concentration of 20 μM) prepared with 1× enzyme buffer solution was added.

7) Centrifugation was performed at 1000 rpm at 23° C. for 30 s.

8) Incubation was performed at 23° C. for 60 min.

9) 10 μL of 250 nM TK Antibody-Crypate (a final concentration of 125 nM) and 1×D2 (a final concentration ½ time) prepared with Detection buffer were added.

10) Centrifugation was performed at 1000 rpm at 23° C. for 30 s.

11) Incubation was performed at 23° C. for 60 min.

12) The data was read with Envision, and the ratio was calculated to obtain the $IC_{50}$ of the compound for inhibiting the enzyme activity.

Experimental results: $IC_{50}$ of the compounds of the present application for inhibiting the EGFR (Δ19del/T790M/C797S) enzyme activity were shown in Table 1.

Conclusion: it can be seen from Table 1 that the preferred compounds of the present application have strong inhibitory effects on the EGFR (Δ19del/T790M/C797S) enzyme activity.

Experimental Example 2: Enzyme Activity Experiment (2)

1. Gradient Dilution of the Compound:

40 μL of the test compound solution (which has been diluted to 0.1 mM) and the reference compounds (at 0.1 mM & 0.03 mM) were respectively taken and added into an Echo 384-well PP plate. The dilution and transfer of the compounds were completed by Echo by Labcyte Inc., with a three-fold concentration gradient, a total of 11 dose points, and 100 nL of the compounds per well. The maximum concentration of the test compounds in the kinase reaction solutions was 1000 nM. The maximum concentration of the reference compound (Crizotinib & AP26113) in the kinase reaction solution was 1000 nM. The maximum concentration of the reference compound (AZD9291) in the kinase reaction solution was 300 nM.

2. Enzymatic Reaction (1) In a 384-well test plate, except for wells A1-H1 and 124-P24, 5 μL of 2×EGFR WT and peptide TK mixed solution (0.1 nM EGFR WT, 2 uM TK) or 5 μL of 2×EGFR C797S T790M L858R and peptide TK mixed solution (0.4 nM EGFR C797S/T790M/L858R, 2 μM TK) were added into each well; 5 μL of kinase reaction buffer solution was added to wells A1-H1 and 124-P24 as a 100% inhibition control. The plate was centrifuged at a speed of 1000 rpm for 60 seconds. The test plate was incubated at 23° C. for 15 minutes.

(2) The test plate was added with 5 μL of 2×ATP solution (EGFR WT: ATP is at 50 M; EGFR (C797S/T790M/L858R): ATP is at 20 μM) into each well, and centrifuged at a speed of 1000 rpm for 60 seconds.

(3) The test plate was film sealed and incubated at 23° C. for 90 minutes.

(4) The test plate was added with 2× detection solution (4 nM TK antibody and 125 nM XL665), 10 μL per well, and centrifuged at a speed of 1000 rpm for 60 seconds, and film sealed, which was incubated at 23° C. for 60 minutes.

(5) The plate was read on the Multi-Mark Detector Envision.

Data analysis: The data analysis was performed as 205 formula using XLfit software, to give the $IC_{50}$ of the compounds.

Experimental results: The $IC_{50}$ of the compounds of the present application for inhibiting EGFR (WT) and EGFR (C797S/T790M/L858R) enzyme activity were shown in Table 1.

Conclusion: It can be seen from Table 1 that the compounds of the present application have better selectivity for the enzyme activity of EGFR (WT), and better inhibition to the enzyme activity of EGFR (C797S/T790M/L858R).

TABLE 1

| compounds of the Examples | EGFR (WT) $IC_{50}$ (nM) | EGFR (Δ19del/ T790M/C797S) $IC_{50}$ (nM) | EGFR (L858R/ T790M/C797S) $IC_{50}$ (nM) |
| --- | --- | --- | --- |
| 1 | — | 2.64 | — |
| 2 | — | 0.613 | — |
| 5 | — | 1.63 | — |
| 6 | — | 2.54 | — |
| 8 | — | 0.792 | — |
| 9 | — | 0.485 | — |
| 13 | — | 5.79 | — |
| 16 | — | 0.491 | — |
| 17 | — | 856 | — |
| 18 | — | 25.3 | — |
| 19 | — | 12.9 | — |
| 20 | — | <0.0508 | — |
| 21 | — | 30.6 | — |
| 23 | — | 0.0517 | — |
| 25 | — | 1.79 | — |
| 26 | — | 0.679 | — |
| 28 | — | 185 | — |
| 29 | — | 67.6 | — |
| 34 | 7.92 | 0.218 | 0.16 |
| 41 | 5.12 | 0.212 | 0.26 |
| 44 | 11 | 0.281 | 0.21 |

Experimental Example 3: Cell Antiproliferation Experiment (1)

Experimental Method:

1) Cell Culture and Passage (1) A431 medium: 88% DMEM+10% fetal bovine serum+1% L-glutamine+1% double-antibody (2) A431 cells were isolated and passaged every 3-4 days, wherein the number of the cells for 3-day passage was 5e6 cells per T75 culture flask, and the number of the cells for 4-day passage was 3e6 cells per T75 culture flask.

2) Day 1: Preparation of Cell Plate (1) Phosphate buffer, trypsin, and a culture medium were placed in a water bath at 37° C. to preheat.

(2) The original medium was removed from the cell culture flask and washed once with 6 mL of PBS.

(3) 5 mL of phosphate buffer was pipetted into the culture flask to rinse the cells (passage 17), and then the liquid was discarded.

(4) The cell culture flask was added with 3.5 mL of trypsin, and shaken gently, trypsin was removed after fully contact with the cells, and then the culture flask was placed in an incubator containing 5% $CO_2$ at 37° C. for about 1 minute;

(5) The cells were resuspended in 10 mL cell culture medium, and about 0.6 mL of cell suspension was take out for counting (ViCell XR);

(6) The cell suspension was diluted with the medium to the cell density of 5e4 cells per ml, which was required for plating (cell concentration: 2500 cells per well);

(7) 100 μL of phosphate buffer solution was added to each well around the cell plate, while 50 μL of the cell suspension was added to other wells, and the plate was incubated overnight in an incubator containing 5% $CO_2$ at 37° C.

3) Day 2: Dosing (1) 9 μL of the compound (concentration: 1 mM) was added into a shallow well plate for Echo.

(2) The shallow well plate was centrifuged at 1000 rpm for 10 s and the cell plate was removed from the incubator.

(3) According to the layout of the microplate, the compounds was diluted with a three-fold concentration gradient using Echo, each compound was diluted to 10 concentration gradients and 250 nL of the diluted compounds was respectively added to the cell plate, and then the cell plate was returned to the incubator and further incubated for 3 days.

4) Day 5: Adding CTG and Reading the Plate (1) After incubation for 72 h, 25 µL of CellTiter Glo was added to each well of the cell plate, followed by shaking the plate for 10 min in the dark.

(2) The plate was read on Envision.

Data analysis: By computer fitting, the corresponding concentration of the compound at 50% inhibition rate was read as the $IC_{50}$ of the compound for inhibiting cell activity.

Experimental Results:

The $IC_{50}$ of compounds of the present application for inhibiting activity of A431 cells were shown in Table 2.

Conclusion:

It can be seen from Table 2 that the compounds of the present application have good selectivity for A431 cells.

Experimental Example 4: Anti-Proliferation Experiment on Cells (2)

Experimental Method:

For Ba/F3 (EGFR Δ19del/T790M/C797S) suspension cells

The compounds to be tested were diluted with a three-fold concentration gradient using Echo, and 10 dose concentrations from 10 µM to 0.508 nM were obtained. The compounds ware transferred to a 384-well plate, with 125 nL of compound per well. The cell density was adjusted, and 2000 Ba/F$_3$ (EGFR Δ19del/T790M/C797S) cells were seeded in each well in a volume of 50 µL, incubated in a CO$_2$ incubator at 37° C. for 3 days. After 3 days, 25 µL of detection reagent was added. The plate was incubated at room temperature for 10 minutes and then read with Envision.

Data Analysis:

The reading was converted into the inhibition rate (%) by the following formula: (Max−Sample)/(Max−Min)*100% ((maximum concentration−sample reading)/(maximum concentration−minimum concentration)*100%). $IC_{50}$ data was obtained by parametric curve fitting (Model 205 in Activity Base, IDBS).

Experimental Results:

The $IC_{50}$ values of the compounds of the present application for inhibiting activity of Ba/F$_3$ (EGFR Δ19del/T790M/C797S) cells were shown in Table 2.

Conclusion:

It can be seen from Table 2 that the compounds of the present application have a good inhibitory effect on Ba/F$_3$ cells with three mutations (EGFR Δ19del/T790M/C797S). Comparative Example 1 has almost no inhibitory effect on Ba/F$_3$ cells with three mutations (EGFR Δ19del/T790M/C797S).

Experimental Example 5: Cell Phosphorylation Inhibition Experiment

Experimental Method:

The test compounds and reference compounds were diluted with 100% DMSO to 10 mM or 1 mM, and then a gradient dilution was performed by using Echo, 150 nL per well, with a three-fold concentration gradient and a ten-point dose response curve. The final concentration of the compounds was 100 µM or 10 µM. The suspension cells was centrifuged at 1000 rp for 5 minutes, suspend in Hanks' balanced salt solution, and added to a 384-well plate containing the compounds at 10 L/120K/well (the cell density of 1.2×10$^7$), followed by centrifugation at 1200 rpm for 30 s and incubation at 37° C. for 30 min. 5 µL of EGF (which has been diluted with 0.1% BSA Hanks' balanced salt solution) was added to each well, in which the final concentration of EGF was 1 µM. The plate was centrifuged at 1200 rpm for 30 s and incubated at 37° C. for 20 min. 5 µL of 4× lysis buffer containing blocking solution was added to each well, and then the plate was centrifuged at 1200 rpm for 30 s, and incubated at 37° C. for 30 min. 5 µL of 0.25×Eu and D2 mixture was added to each well, and the plate was centrifuged at 1200 rpm for 30 s, sealed with light-shielding film, and incubated at room temperature (22-26° C.) for 4 h-24 h. The fluorescence signals were read at 665 nm/620 nm by a microplate reader.

Experimental results: $IC_{50}$ values of the compounds of the present application for inhibiting phosphorylation activity of pEGFR Ba/F$_3$ (EGFR Δ19del/T790M/C797S) cells were shown in Table 2.

Conclusion:

Since self-phosphorylation of EGFR, namely dimerization, can activate its kinase pathway located inside the cell, and many tumors have high or abnormal expression of EGFR, it plays a very important role in the progress of malignant tumors. Inhibition of the activity of pEGFR Ba/F$_3$ (Δ19del/T790M/C797S) cells can show most intuitively the inhibitory effect of a compound on phosphorylation of Ba/F$_3$ (Δ19del/T790M/C797S) triple-mutant cell model, so as to specifically screen the compounds in vitro. As can be seen from Table 2, the compounds of the present application have excellent inhibitory effect on the phosphorylation activity of Ba/F$_3$ (Δ19del/T790M/C797S) cells, while comparative Example 1 has almost no inhibitory effect on the phosphorylation of Ba/F$_3$ (Δ19del/T790M/C797S) cells.

TABLE 2

| Test compounds | anti-proliferation effect on cells A431 EGFR WT $IC_{50}$ (nM) | anti-proliferation effect on cells Ba/F$_3$(Δ19del/T790M/C797S) $IC_{50}$ (nM) | Effect on cellular EGFR phosphorylation Ba/F$_3$(Δ19del/T790M/C797S) $IC_{50}$ (nM) |
|---|---|---|---|
| 2 | 811 | 178 | 68 |
| 3 | 3239 | 638 | 187 |
| 4 | 3751 | 556 | 278 |
| 5 | 890 | 313 | 96 |
| 6 | 997 | 361 | 187 |
| 7 | — | — | 533 |
| 8 | — | 275 | 133 |
| 9 | 282 | 149 | 149 |
| 10 | — | 6026 | — |
| 11 | — | 180 | — |
| 12 | 1256 | 239 | 203 |
| 13 | >10000 | 3620 | 1725 |
| 14 | — | 351 | — |
| 15 | — | 583 | — |
| 16 | — | 211 | — |
| 17 | — | 4753 | — |
| 18 | — | 1646 | — |
| 19 | — | 1220 | — |
| 20 | — | 214 | — |
| 21 | — | 1959 | — |
| 22 | — | 249 | — |
| 23 | — | 103 | 34 |
| 24 | — | 4085 | — |
| 25 | — | 642 | — |
| 26 | — | 764 | — |

TABLE 2-continued

| Test compounds | anti-proliferation effect on cells A431 EGFR WT IC$_{50}$ (nM) | anti-proliferation effect on cells Ba/F$_3$(Δ19del/ T790M/C797S) IC$_{50}$ (nM) | Effect on cellular EGFR phosphorylation Ba/F$_3$(Δ19del/ T790M/C797S) IC$_{50}$ (nM) |
|---|---|---|---|
| 27 | — | 2713 | — |
| 28 | — | 2657 | — |
| 29 | — | 1594 | — |
| 30 | — | 290 | — |
| 31 | — | 242 | — |
| 32 | — | 79 | 57 |
| 33 | — | 162 | — |
| 34 | 154 | 22 | 19 |
| 35 | — | 533 | — |
| 36 | 168 | 45 | 25 |
| 37 | 357 | 56 | 94 |
| 38 | — | 371 | — |
| 39 | — | 187 | 195 |
| 40 | 561 | 31 | 24 |
| 41 | 245 | 9 | 25 |
| 42 | — | 442 | — |
| 43 | — | 496 | — |
| 44 | — | — | 9 |
| 45 | — | 87 | 27 |
| 48 | — | 152 | — |
| 51 | — | 36 | — |
| 54 | — | 39 | — |
| 57 | — | 26.8 | — |
| 58 | — | 18.6 | — |
| 59 | 534 | 54.3 | 534 |
| 60 | 271 | 47.6 | 271 |
| 61 | 58 | 32.2 | 58 |
| Comparative example 1 | — | >5000 | 1014.0 |

Experimental Example 6: Study on In Vivo Efficacy (1)

Experimental method:

In vivo efficacy experiment was performed on xenograft (CDX) BALB/c nude mice derived from implanted subcutaneously Ba/F3 (Δ19del/T790M/C797S). BALB/c nude mice, female, 6-8 weeks old, 18-20 g of body weight, were housed in SPF-grade environment, and each cage was individually ventilated (5 mice per cage). All cages, bedding and water were sterilized before use. All animals have free access to standard certified commercial and laboratory diets. A total of 48 mice purchased from Beijing Weitonglihua company were used for the study. Each mouse was implanted with cells at the right flank, for tumor growth. The experiment was started when the average tumor volume reached approximately 80-120 mm$^3$. The test compounds were administered orally daily, wherein compound Birgatinib (15 mg/kg), compound 34 (5 mg/kg, 15 mg/kg, 45 mg/kg, respectively) and compound 41 (5 mg/kg, 15 mg/kg, 45 mg/kg, respectively) was administered for 13 consecutive days. The data were shown in Table 3. Tumor volume was measured twice a week with a two-dimensional caliper, measured in mm$^3$ and calculated by the following formula: V=0.5a×b$^2$, wherein a and b are the long and short diameters of the tumor, respectively. Antitumor efficacy was determined by dividing the average increase of the tumor volume of the animals treated with the compound by the average increase of the tumor volume of the untreated animals. TGI (the tumor inhibition value) was used to evaluate the tumor growth inhibition effect of the test drugs in vivo, wherein the TGI of the compound Birgatinib (15 mg/kg) group was 8.6%, the TGI of the compound 34 (45 mg/kg administered separately) group was 101%, and the TGI of the compound 41 (45 mg/kg administered separately) group was 109%.

On Day 14 after administration to the groups for the efficacy experiment, the plasma was collected from the mice by submandibular blood collection before last administration and 2 hours after last administration, and the plasma samples were collected from the mice at 1 h, 4 h, 8 h and 24 h after administration. About 100 ul of blood was collected each time, placed in an anticoagulation tube, and centrifuged at 8000 rpm for 7 min, to collect plasma, which was stored at −80° C. The lung and tumor tissues of the mice were collected at 2 h after administration and stored at −80° C., wherein the tumors were divided into two parts (wherein the tumor for PD analysis did not exceed 100 mg) for detection and data analysis.

Experimental results: see Tables 3 and 4.

TABLE 3

| Test compounds | dosage | Tumor volume (mm$^3$) | | | | | | |
|---|---|---|---|---|---|---|---|---|
| | | Day 0 | Day 2 | Day 5 | Day 8 | Day 10 | Day 12 | Day 13 |
| Blank control | N/A | 85 | 143 | 315 | 582 | 765 | 929 | 1048 |
| Birgatinib | 15 mg/kg/day | 84 | 124 | 292 | 477 | 646 | 880 | 965 |
| Compound 34 | 5 mg/kg/day | 84 | 108 | 212 | 395 | 505 | 748 | 881 |
| | 15 mg/kg/day | 84 | 76 | 107 | 126 | 176 | 292 | 326 |
| | 45 mg/kg/day | 84 | 56 | 32 | 35 | 42 | 73 | 68 |
| Compound 41 | 5 mg/kg/day | 84 | 103 | 203 | 348 | 485 | 707 | 814 |
| | 15 mg/kg/day | 84 | 68 | 69 | 82 | 115 | 146 | 211 |
| | 45 mg/kg/day | 84 | 47 | 24 | 7 | 4 | 0 | 0 |

TABLE 4

| compounds | Test | | |
|---|---|---|---|
| Test Items | Brigatinib | Compound 34 | Compound 41 |
| Dosage (mg/kg/day) | 15.0 | 15.0 | 15.0 |
| T$_{1/2}$ (h) | 5.57 | 10.0 | 20.5 |
| AUC$_{0-last}$ (nM·h) | 32808 | 57037 | 121718 |
| Plasma (nM), 2 h | 5177 | 3553 | 6990 |
| Tumor (nmol/kg), 2 h | 5807 | 16667 | 18567 |
| Lung (nmol/kg), 2 h | 10217 | 32533 | 29567 |

Conclusion:

The compounds of the present application showed strong antitumor effect in xenograft (CDX) BALB/c nude mouse drug-resistance model derived from implanted subcutaneously with Ba/F$_3$ (Δ19del/T790M/C797S). The half-life and the amount of exposure in plasma and tissues for the compounds of the present application were significantly improved, indicating that the compounds of the present application have good pharmacokinetic effect in mice.

Experimental Example 7: In Vivo Pharmacodynamics Study (2)

Experimental Method:

1. Cell culture: lung cancer PC-9 cells were monolayer cultured in vitro, culture conditions: RPMI-1640 (cell culture medium) plus 10% fetal bovine serum, 100 U/mL penicillin and 100 μg/mL streptomycin, culture in a 5% CO$_2$ incubator at 37° C. The cells were conventionally digested with trypsin-EDTA twice a week for passage. When the cell saturation was 80%-90%, and the number reached the requirements, the cells were collected and counted. The density was $5\times10^6$ cells.

2. Cell inoculation: 0.2 mL (containing $5\times10^6$ cells) of PC-9 cell suspension (PBS: Matrigel=1:1) was subcutaneously inoculated into the right back of each mouse, with a total of 64 mice. On Day 7 after inoculation, when the average tumor volume measured reached 169 mm³, the animals were randomly hierarchically grouped based on tumor volume and animal weight, and started to administrate each group. PBS was a phosphate buffer solution, and Matrigel was a matrix.

3. Administration: dosage: Days 0-9: 50 mg/kg; Days 10-21: 25 mg/kg; oral administration; administration frequency: once a day×3 weeks.

Tumor Measurement and Experimental Indicators

Tumor diameter was measured twice a week with a vernier caliper. The formula for calculating tumor volume was: $V=0.5a\times b^2$, wherein a and b represented the long and short diameters of the tumor, respectively.

The antitumor effect of the compound was evaluated by TGI (%).

The relative tumor volume (RTV) was calculated according to the results of tumor measurement. The calculation formula was $RTV=V_t/V_0$, wherein $V_0$ was the tumor volume measured during group administration (i.e., D0), and $V_t$ was the tumor volume of the corresponding mice measured at a certain time. The data on the same day were taken for TRTV and CRTV.

TGI (%) reflected tumor growth inhibition rate. TGI (%)=[(1−(average tumor volume at the end of administration in a treatment group−average tumor volume at the start of administration in the treatment group))/(average tumor volume at the end of treatment in a solvent control group−average tumor volume at the start of treatment in the solvent control group)]×100%.

After the end of the experiments, the tumor weight would be measured and the TGI (%) was calculated.

Experimental results: see Table 5. The TGI of compound 34 on day 23 was 100%.

Conclusion:

In a subcutaneously transplanted tumor PC-9 (Δ19del) model in mouse, the compounds of the present application have a significant inhibitory effect on tumor growth and tumor-shrinking effect, showing good antitumor effects.

What is claimed is:

1. A compound of formula (I) or a pharmaceutically acceptable salt thereof,

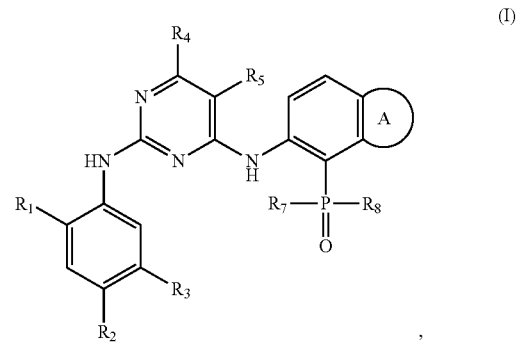

(I)

wherein, ring A is selected from phenyl, 5- to 6-membered heteroaryl, 5- to 7-membered heterocycloalkyl, $C_{5-7}$ cycloalkenyl and $C_{5-7}$ cycloalkyl, wherein said phenyl, 5- to 6-membered heteroaryl, 5- to 7-membered heterocycloalkyl, $C_{5-7}$ cycloalkenyl and $C_{5-7}$ cycloalkyl are optionally substituted with $R_6$;

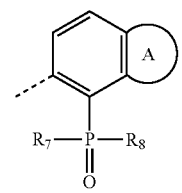

and the structural unit

TABLE 5

| Test compounds | dosage | Tumor volume (mm³) | | | | | | | |
|---|---|---|---|---|---|---|---|---|---|
| | | Day 0 | Day 2 | Day 6 | Day 9 | Day 13 | Day 16 | Day 20 | Day 23 |
| Blank control | / | 186 | 257 | 285 | 326 | 482 | 527 | 637 | 921 |
| Compound 34 | 50 mg/kg (days 0-9) 25 mg/kg (days 10-21) | 185 | 198 | 92 | 75 | 40 | 45 | 76 | 111 |
| Compound 41 | 50 mg/kg (days 0-9) 25 mg/kg (days 10-21) | 184 | 198 | 54 | 44 | 36 | 30 | 37 | 42 | is not selected from:

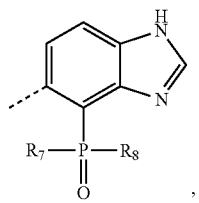

$R_1$ is selected from H, halogen, $C_{1-6}$ alkyl, $C_{1-6}$ heteroalkyl, $C_{2-6}$ alkenyloxy, and $C_{3-6}$ cycloalkyloxy, wherein the $C_{1-6}$ alkyl, $C_{1-6}$ heteroalkyl, $C_{2-6}$ alkenyloxy and $C_{3-6}$ cycloalkyloxy are optionally substituted with 1, 2 or 3 R groups;

$R_2$ is selected from H, halogen, CN, OH, $NO_2$, $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl, and 3- to 14-membered heterocyclic groups, wherein said $NH_2$, $C_{1-6}$ alkyl, $C_{2-6}$ alkenyl, $C_{2-6}$ alkynyl, $C_{3-14}$ cycloalkyl, $C_{3-6}$ cycloalkenyl, $C_{4-6}$ cycloalkynyl, phenyl and 3- to 14-membered heterocyclic group are optionally substituted with 1, 2 or 3 R groups;

$R_3$ is selected from H, halogen, $C_{1-6}$ alkoxy, $C_{2-6}$ alkenyloxy, $C_{3-6}$ cycloalkyloxy, —OC(=O)$NH_2$, —OC(=O)NHR, —OC(=O)NRR, —NRC(=O)OR, —NHC(=O)OR, —NHC(=O)OH, —O(CH$_2$)$_n$NR$_a$R$_b$, $C_{1-6}$ alkyl, $C_{3-6}$ cycloalkyl and 5- to 6-membered heterocyclic group containing 1, 2, or 3 N or O atoms, wherein said $C_{1-6}$ alkyl, $C_{3-6}$ cycloalkyl, and 5- to 6-membered heterocyclic group containing 1, 2 or 3 N or O atoms are optionally substituted with 1, 2 or 3 R groups;

n is selected from 0, 1, 2, 3 or 4;

$R_a$ and $R_b$ are each independently selected from H, $C_{1-5}$ alkyl and $C_{1-5}$ heteroalkyl, and said $C_{1-5}$ alkyl and $C_{1-5}$ heteroalkyl are optionally substituted with 1, 2 or 3 R groups;

or alternatively $R_a$ and $R_b$ are bonded together to form a 5- to 6-membered heterocyclic ring;

$R_4$ and $R_5$ are each independently selected from H, halogen, CN, $NH_2$, $C_{1-4}$ alkyl, $C_{1-4}$ heteroalkyl, $C_{3-6}$ cycloalkyl, phenyl, and 5- to 6-membered heterocyclic group, wherein said $NH_2$, $C_{1-4}$ alkyl, $C_{1-4}$ heteroalkyl, $C_{3-6}$ cycloalkyl, phenyl and 5- to 6-membered heterocyclic group are optionally substituted with 1, 2 or 3 R groups;

each $R_6$ is independently selected from H, halogen, CN, OH, $NH_2$, $C_{1-6}$ alkyl, $C_{1-6}$ heteroalkyl, =O and =S;

$R_7$ and $R_8$ are each independently selected from H or $C_{1-6}$ alkyl;

or alternatively $R_7$ and $R_8$ are bonded together to form a 5- to 6-membered heterocyclic ring, and the 5- to 6-membered heterocyclic ring is optionally substituted with 1, 2 or 3 R groups;

R is selected from halogen, CN, OH, $NH_2$, $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl, and 5- to 6-membered heteroaryl, wherein said $C_{1-6}$ alkyl, $C_{2-6}$ alkenyl, $C_{2-6}$ alkynyl, $C_{3-6}$ cycloalkyl, $C_{3-6}$ cycloalkenyl, $C_{4-6}$ cycloalkynyl, $C_{1-6}$ heteroalkyl, 3- to 6-membered heterocycloalkyl, phenyl, and 5- to 6-membered heteroaryl are optionally substituted with 1, 2 or 3 R' groups;

R' is selected from H, F, Cl, Br, I, CN, OH, $NH_2$, $CH_3$, $CH_3CH_2$, $CH_3CH_2CH_2$, $(CH_3)_2CH$, $CH_3O$, $CF_3$, $CHF_2$ and $CH_2F$;

"hetero" represents a heteroatom or a heteroatom group, and each "hetero" group in said 5- to 6-membered heterocyclic group, 5- to 6-membered heterocyclic ring, 5- to 7-membered heterocycloalkyl, 3- to 14-membered heterocyclic group, $C_{1-4}$ heteroalkyl, $C_{1-5}$ heteroalkyl, $C_{1-6}$ heteroalkyl, 3- to 6-membered heterocycloalkyl, and 5- to 6-membered heteroaryl is independently selected from —C(=O)N(R)—, —N(R)—, —C(=NR)—, —(R)C=N—, —S(=O)$_2$N(R)—, —S(=O)N(R)—, N, —NH—, —O—, —S—, —C(=O)O—, —C(=O)—, —C(=S)—, —S(=O)—, —S(=O)$_2$— and —N(R)C(=O)N(R)—;

in any one of the cases as described above, the number of the heteroatom or heteroatomic group is each independently selected from 1, 2, or 3.

2. The compound or the pharmaceutically acceptable salt thereof according to claim 1, wherein R is selected from F, Cl, Br, I, CN, OH, $NH_2$, $CH_3$, $CH_3CH_2$, $CH_3CH_2CH_2$, $(CH_3)_2CH$, $CH_3O$, $(CH_3)_2N$,

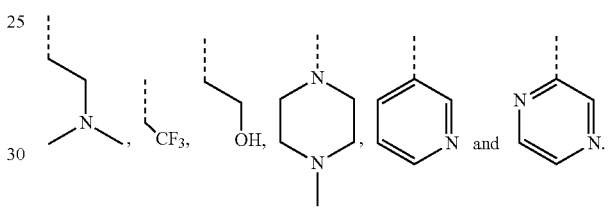

3. The compound or the pharmaceutically acceptable salt thereof according to claim 1, wherein $R_1$ is selected from H, halogen, $C_{1-3}$ alkyl, $C_{1-3}$ heteroalkyl, $C_{2-5}$ alkenyloxy, and $C_{4-6}$ cycloalkyloxy, wherein said $C_{1-3}$ alkyl, $C_{1-3}$ heteroalkyl, $C_{2-5}$ alkenyloxy and $C_{4-6}$ cycloalkyloxy are optionally substituted with 1, 2, or 3 R groups.

4. The compound or the pharmaceutically acceptable salt thereof according to claim 1, wherein $R_2$ is selected from H, halogen, CN, OH, $NO_2$, $NH_2$, $C_{3-12}$ cycloalkyl, and 3- to 12-membered heterocycloalkyl, wherein said $NH_2$, $C_{3-12}$ cycloalkyl and 3- to 12-membered heterocycloalkyl are optionally substituted with 1, 2 or 3 R groups.

5. The compound or the pharmaceutically acceptable salt thereof according to claim 1, wherein R6 is selected from H, F, Cl, Br, CN, OH, $NH_2$, $CH_3$, $CH_3CH_2$, $CH_3CH_2CH_2$, $(CH_3)_2CH$, $CH_3O$, =S and =O.

6. The compound or the pharmaceutically acceptable salt thereof according to claim 1, wherein ring A is selected from phenyl, thienyl, pyridyl, pyrazinyl, pyrazolyl, cyclopentanonyl, cyclopentenyl, thiazolyl, isothiazolyl, and pyrrolyl, wherein said phenyl, thienyl, pyridyl, pyrazinyl, pyrazolyl, cyclopentanonyl, cyclopentenyl, thiazolyl, isothiazolyl, and pyrrolyl are optionally substituted with $R_6$.

7. The compound or the pharmaceutically acceptable salt thereof according to claim 6, wherein the structural unit

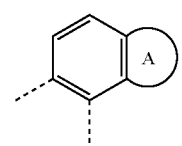

is selected from

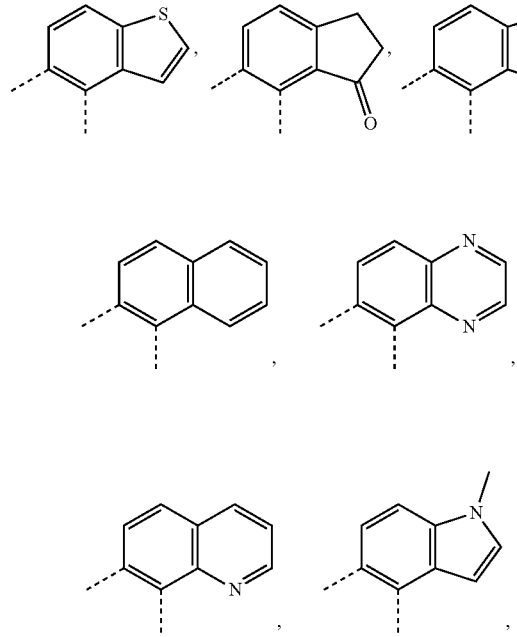

8. The compound or the pharmaceutically acceptable salt thereof according to claim 1, wherein Ra and Rb are each independently selected from H, CH$_3$, CH$_3$CH$_2$,

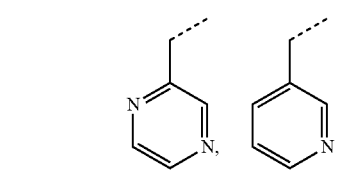

and —S(=O)$_2$CH$_3$, wherein said CH$_3$, CH$_3$CH$_2$,

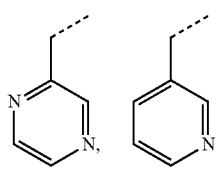

and —S(=O)$_2$CH$_3$ are optionally substituted with 1, 2 or 3 R groups.

9. The compound or the pharmaceutically acceptable salt thereof according to claim 1, wherein R3 is selected from H, F, Cl, Br, CH$_3$, CH$_3$CH$_2$, (CH$_3$)$_2$CH,

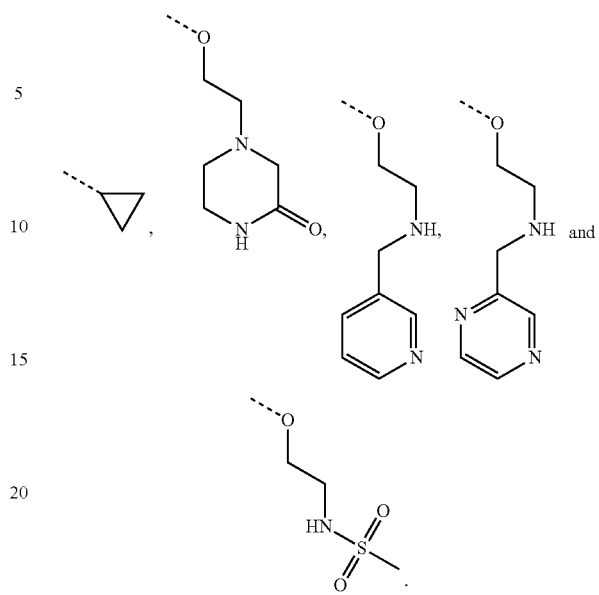

10. The compound or the pharmaceutically acceptable salt thereof according to claim 1, wherein R$_5$ is selected from H, F, Cl, Br, I, CN, CH$_3$, CH$_3$CH$_2$, CH$_3$CH$_2$CH$_2$, (CH$_3$)$_2$CH,

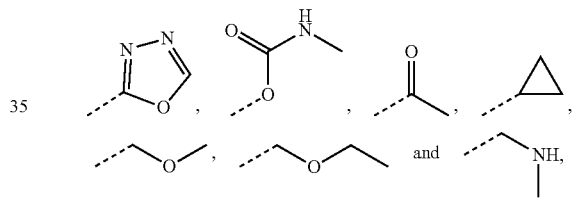

wherein said CH$_3$, CH$_3$CH$_2$, CH$_3$CH$_2$CH$_2$, (CH$_3$)$_2$CH,

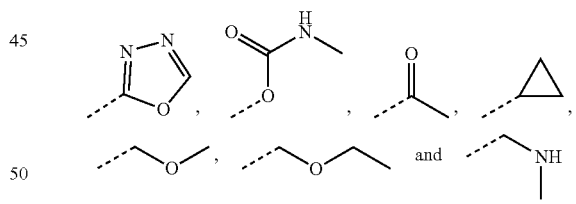

are optionally substituted with 1, 2 or 3 R groups.

11. The compound or the pharmaceutically acceptable salt thereof according to claim 1, wherein the structural unit

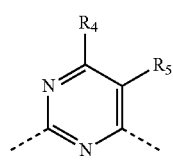

is selected from
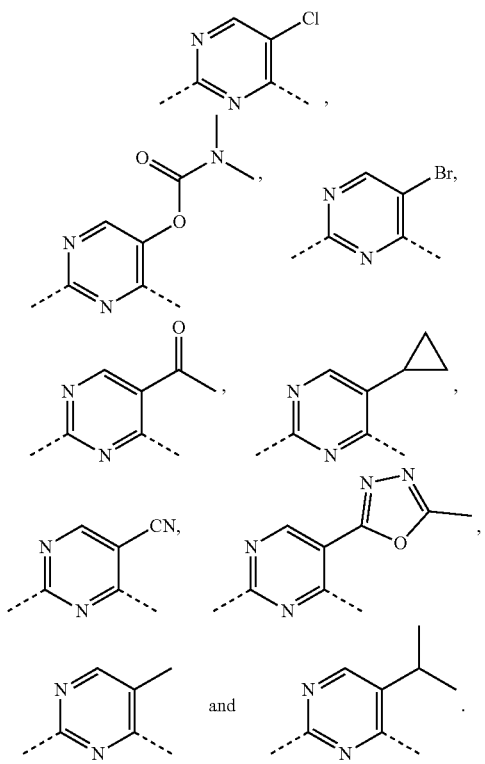
12. The compound or the pharmaceutically acceptable salt thereof according to claim 1, wherein $R_7$ and $R_8$ are each independently selected from H or $CH_3$.
13. The compound or the pharmaceutically acceptable salt thereof according to claim 1, which is selected from
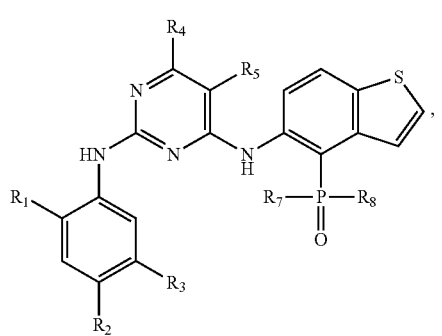
(II)
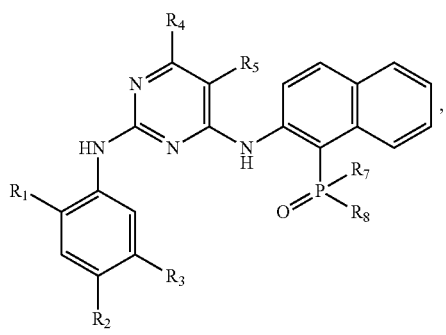
(III)
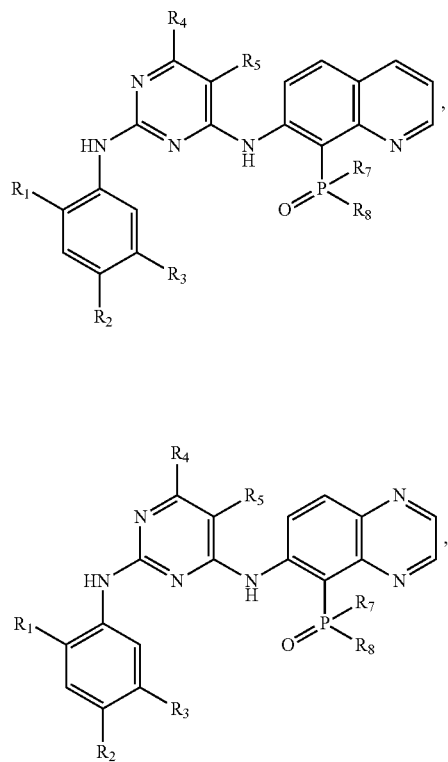
(IV)
(V)
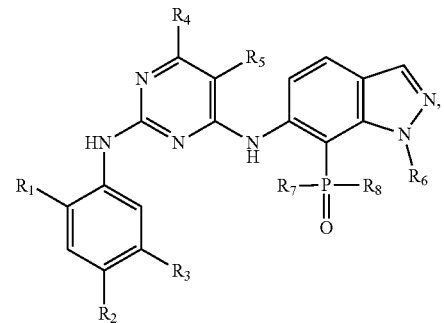
(VI)
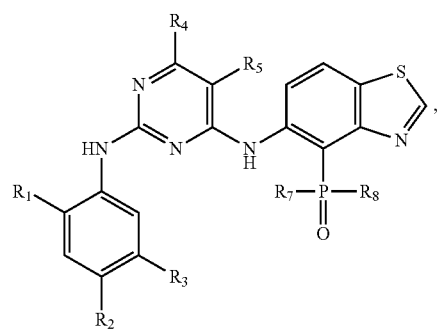
(VII)

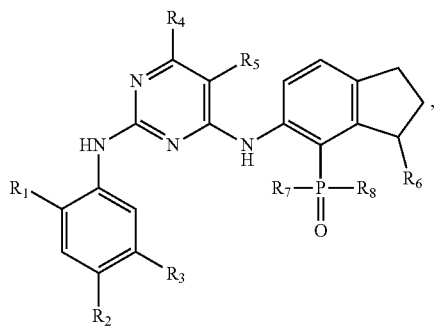
(VIII)
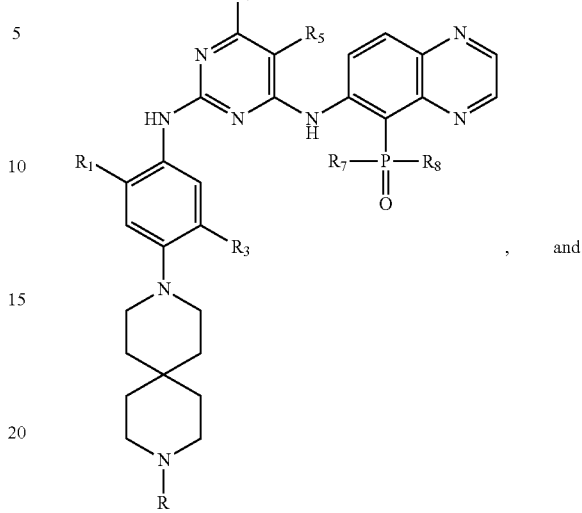
(V-2)
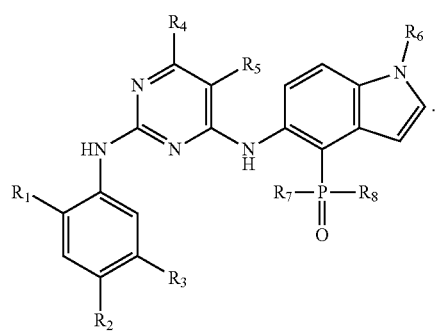
(IX)
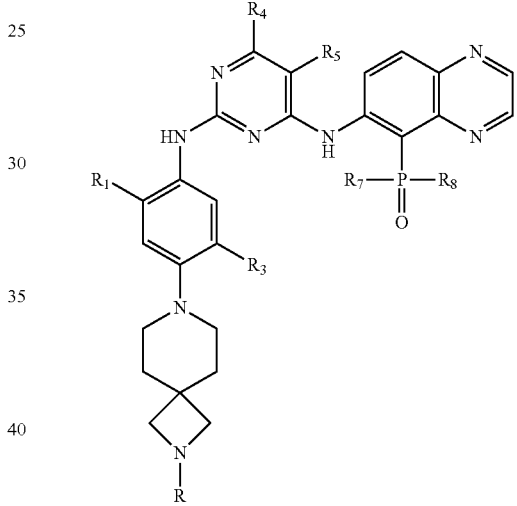
(V-3)
14. The compound or the pharmaceutically acceptable salt thereof according to claim 13, which is selected from
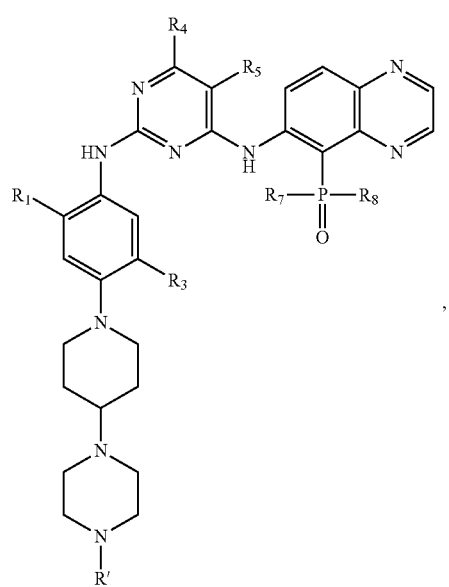
(V-1)
15. A compound or a pharmaceutical acceptable salt thereof, which is selected from
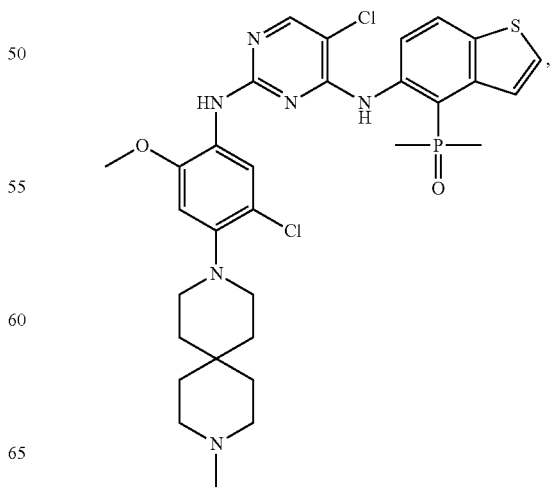

197
-continued
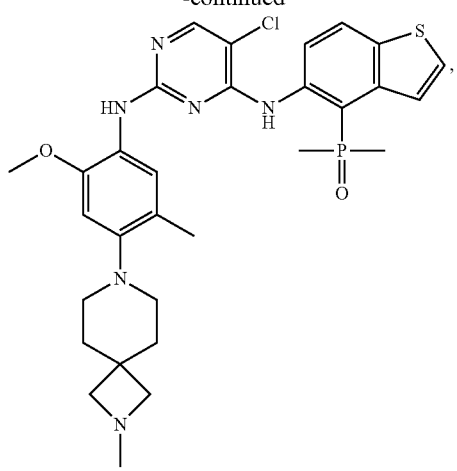
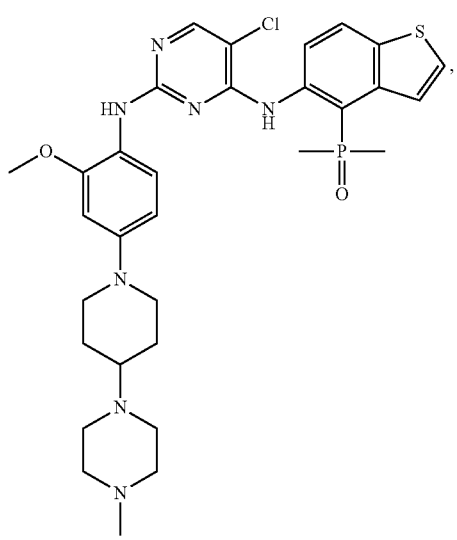
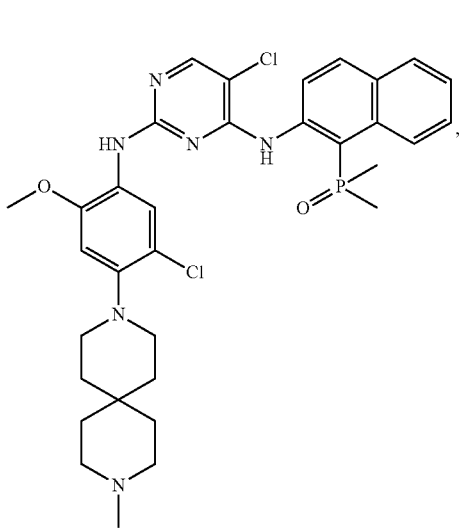 [SMILES: COc1cc(N2CCC3(CCN(C)CC3)CC2)c(Cl)cc1Nc1ncc(Cl)c(Nc2ccc3nccnc3c2P(C)(C)=O)n1]
198
-continued
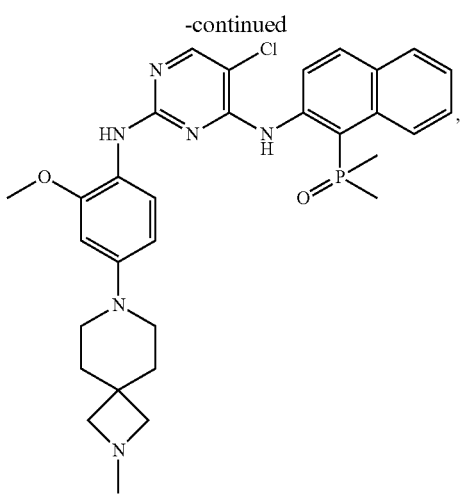
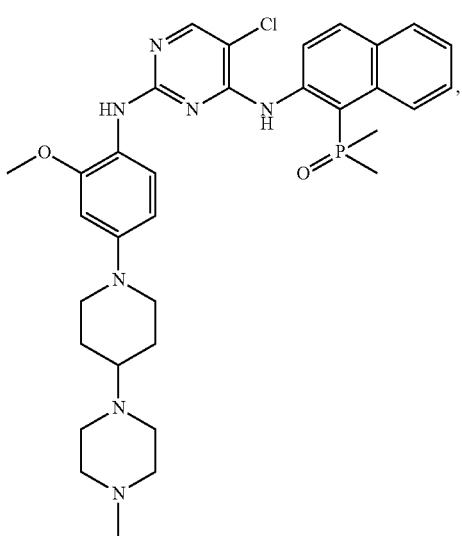
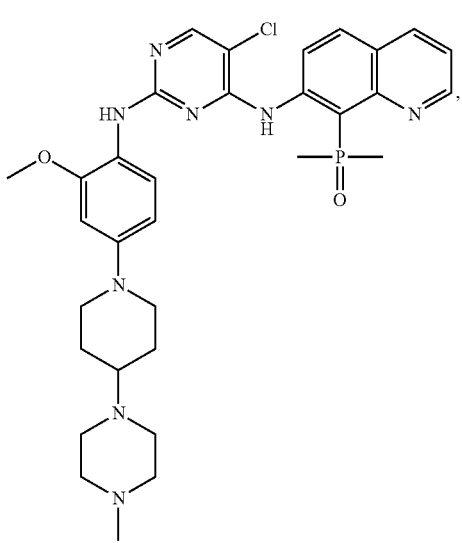

199
-continued
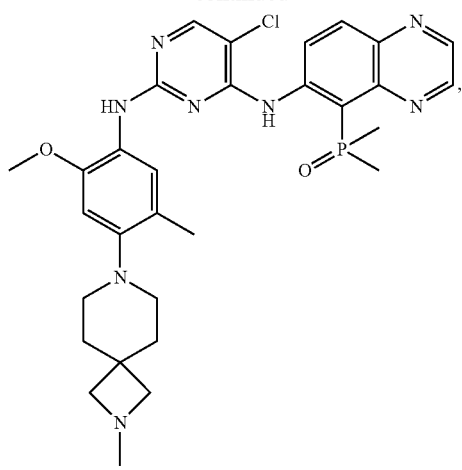
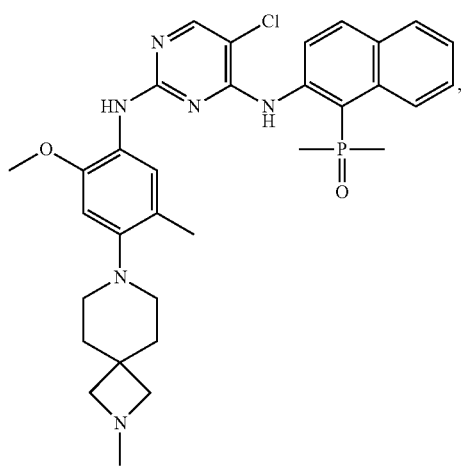
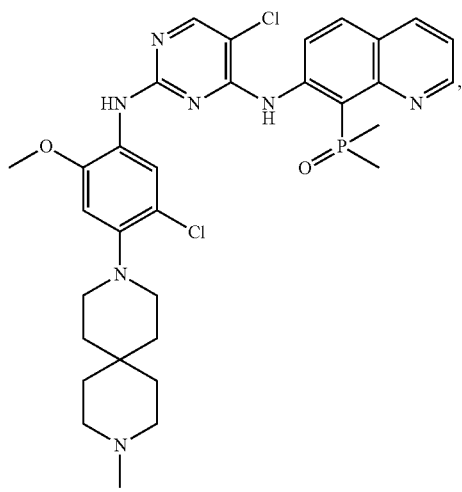
200
-continued
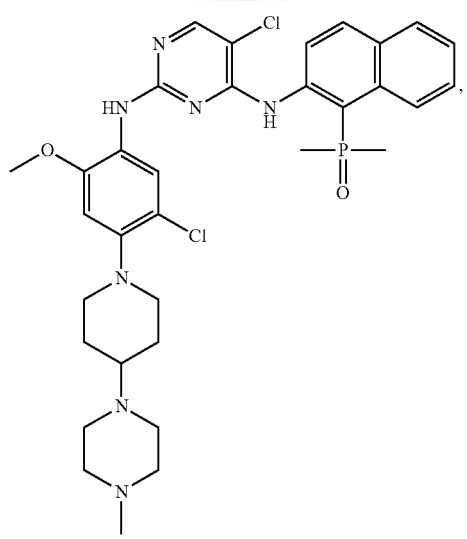
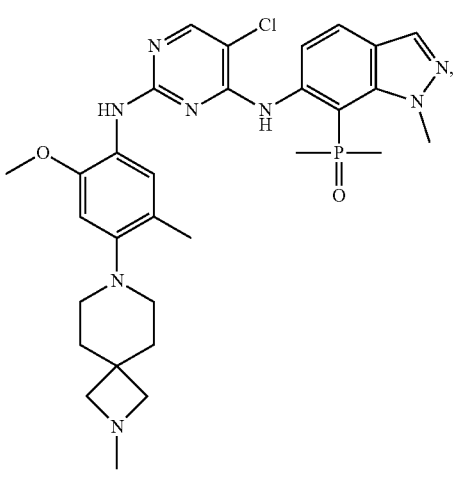

201 -continued
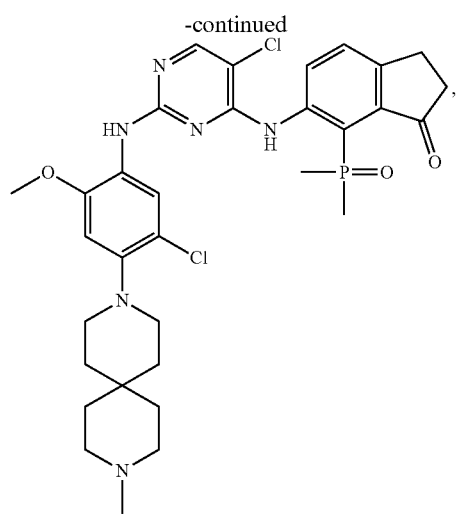
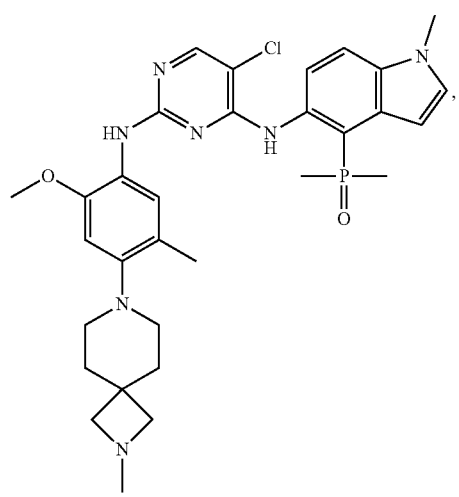
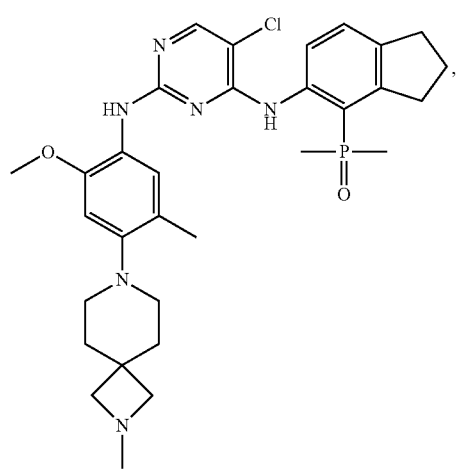
202 -continued
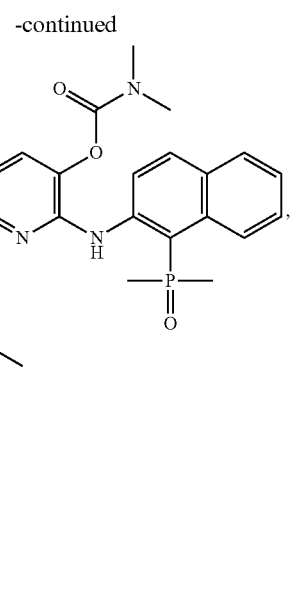
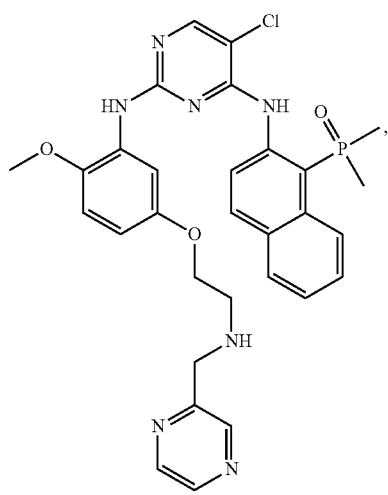
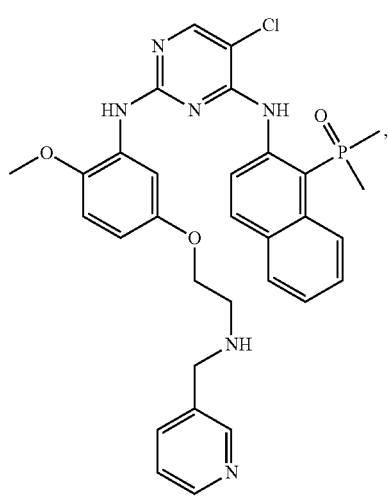

203
-continued
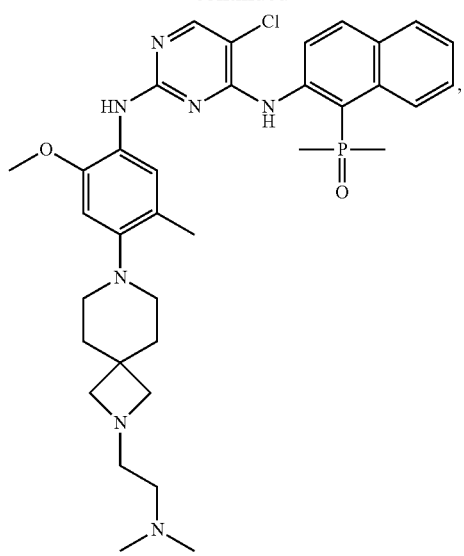
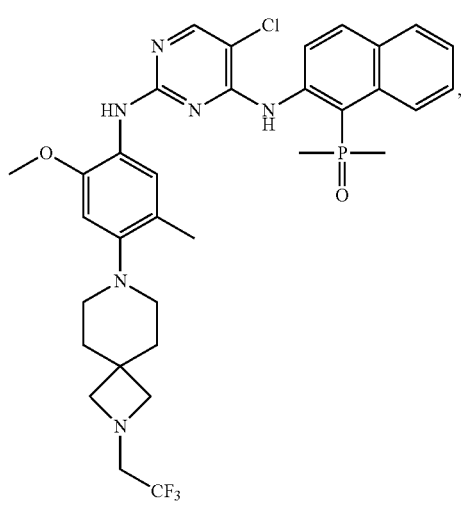
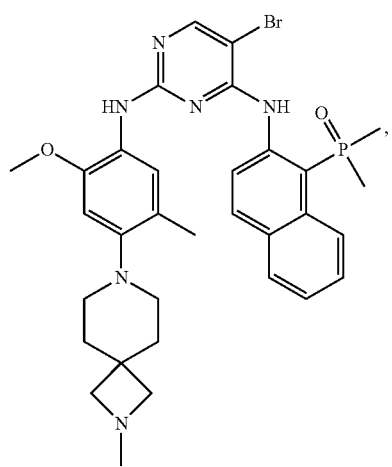
204
-continued
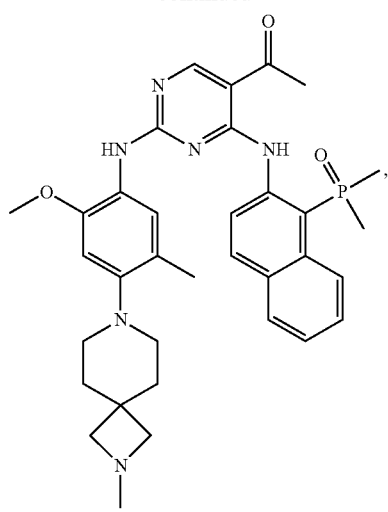
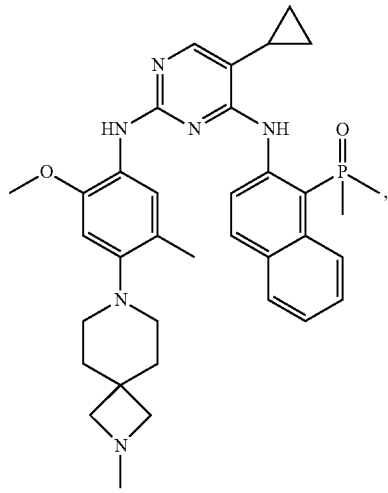
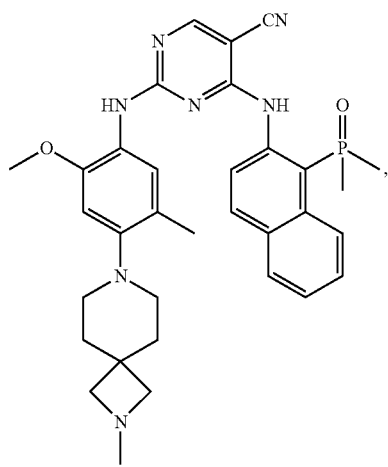

205
-continued
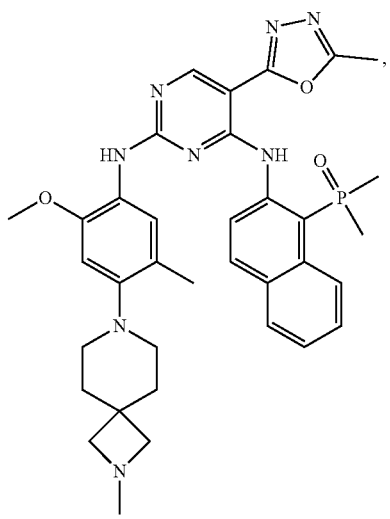
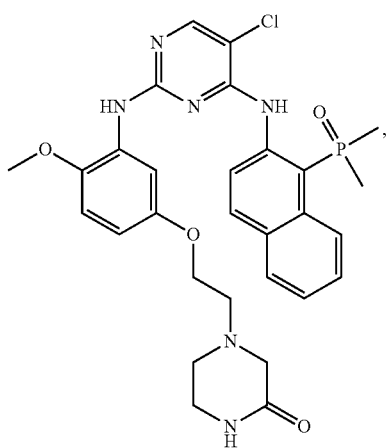
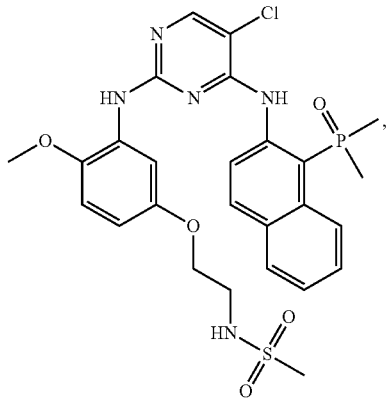
206
-continued
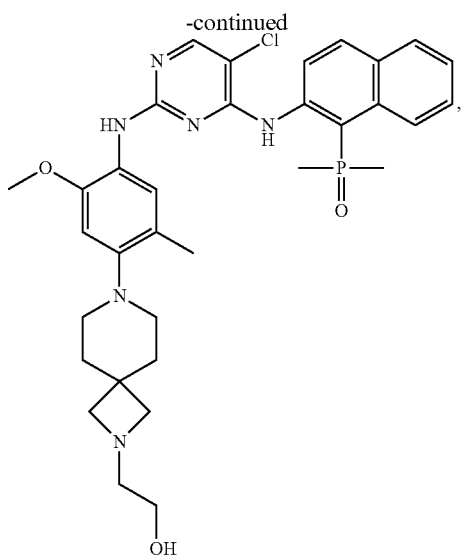
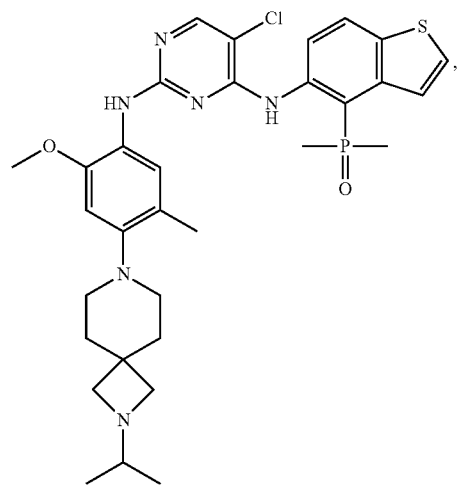
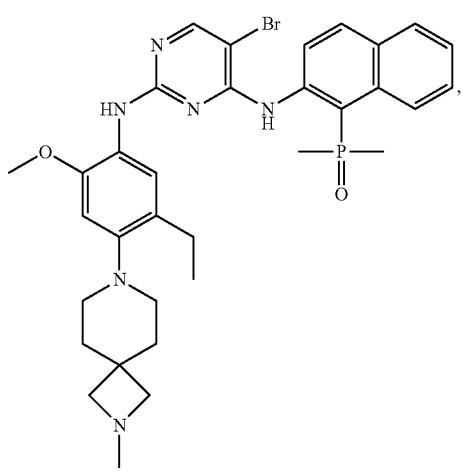

207
-continued
208
-continued
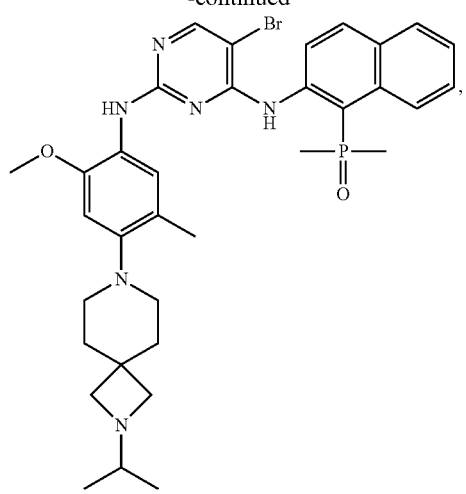
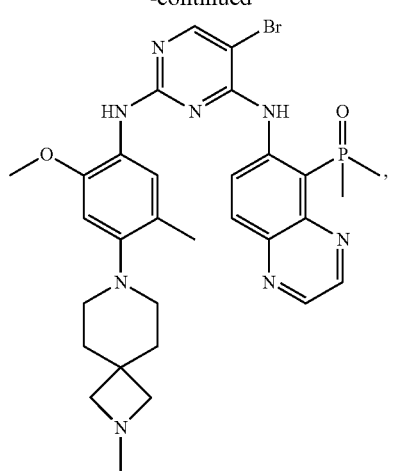
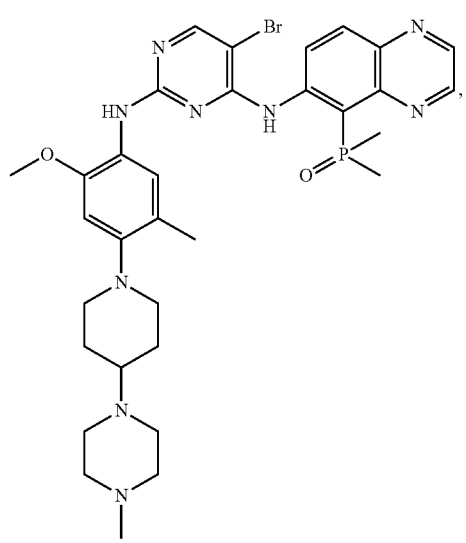
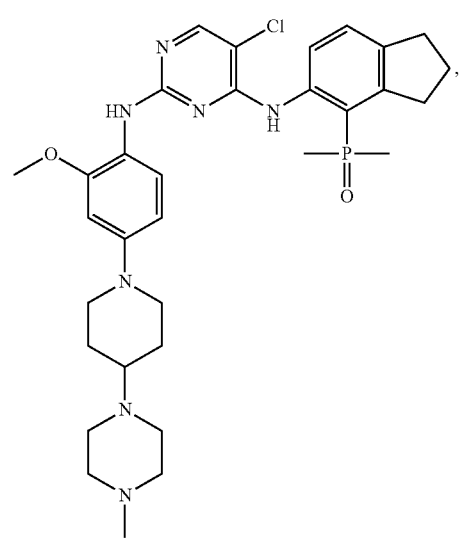
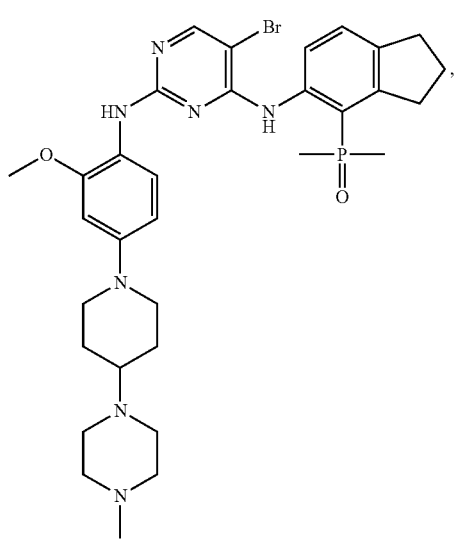

209
-continued
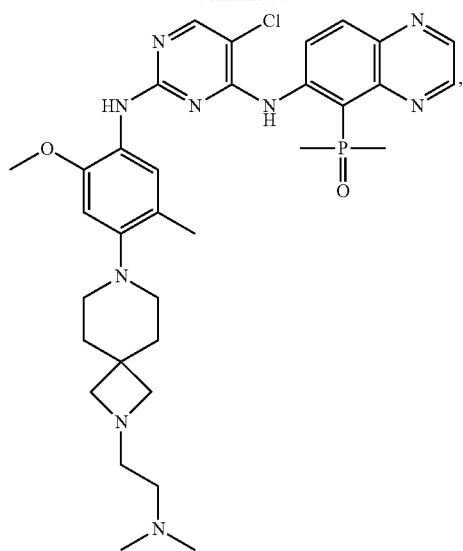
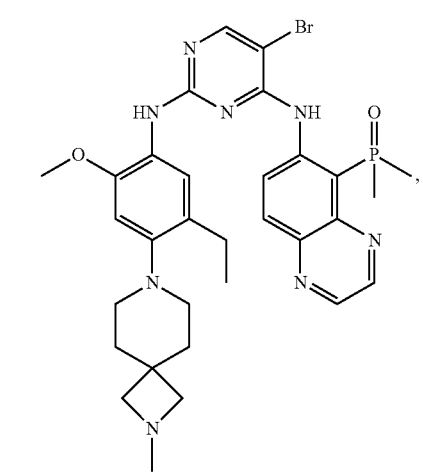
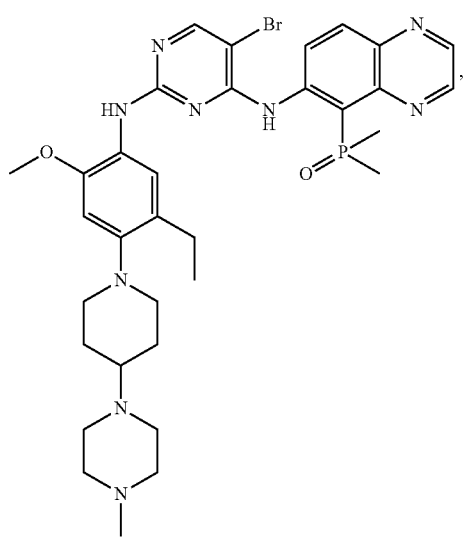
210
-continued
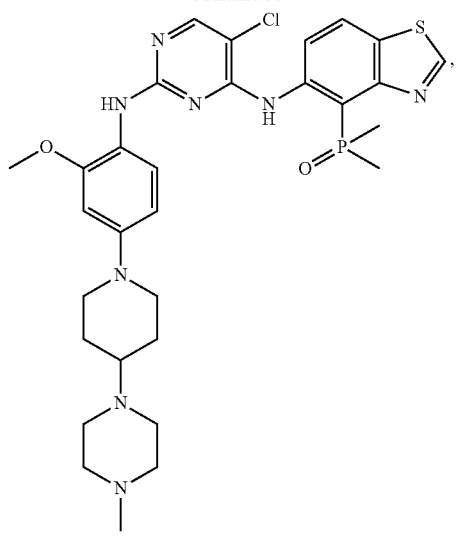
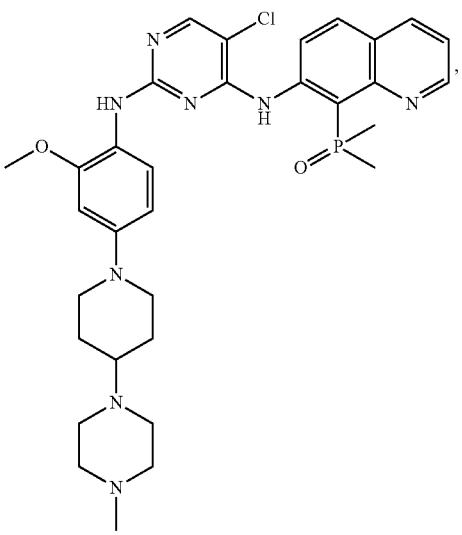
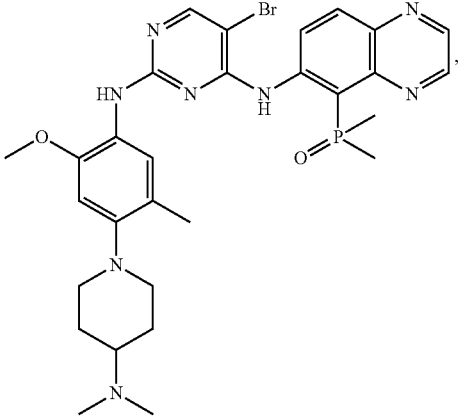

211
-continued
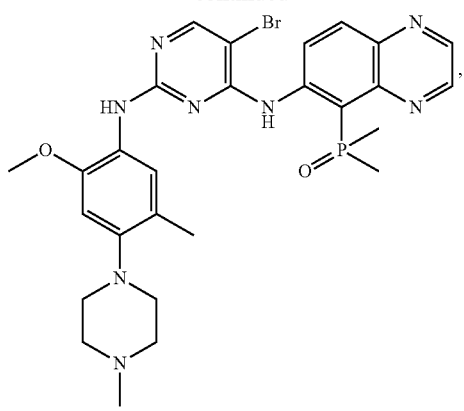
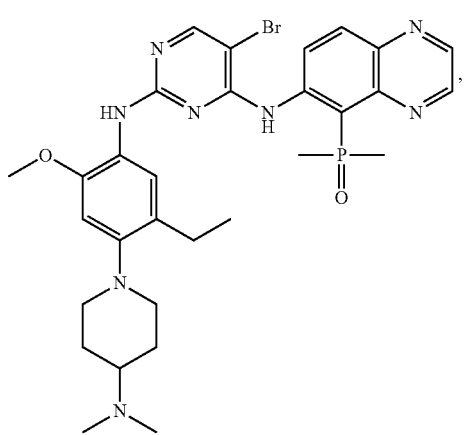
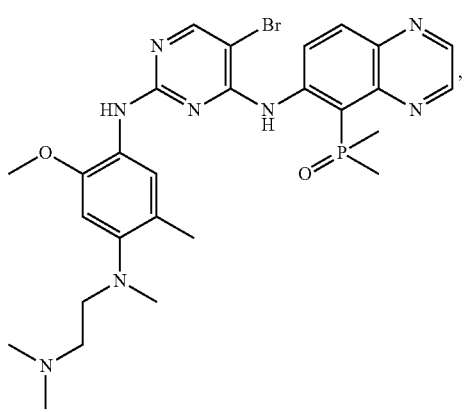
212
-continued
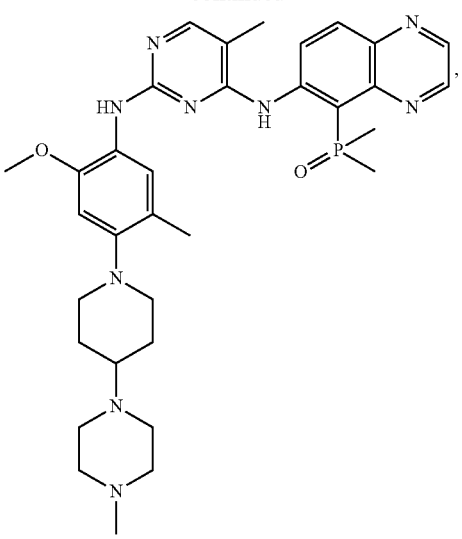
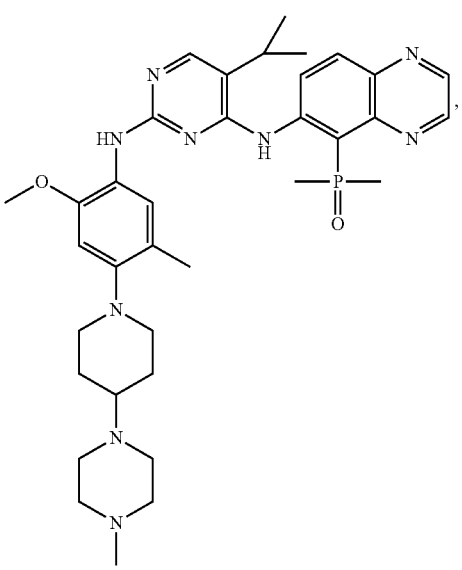
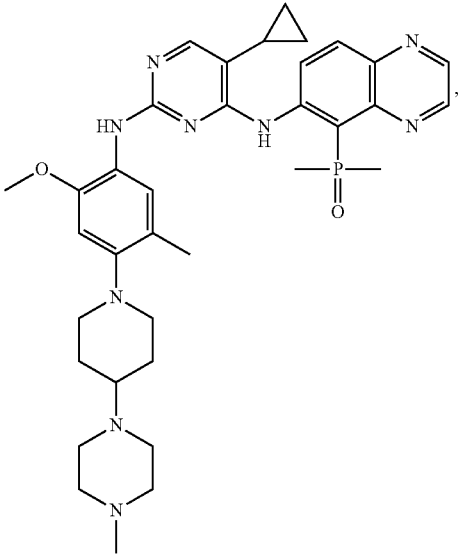

-continued
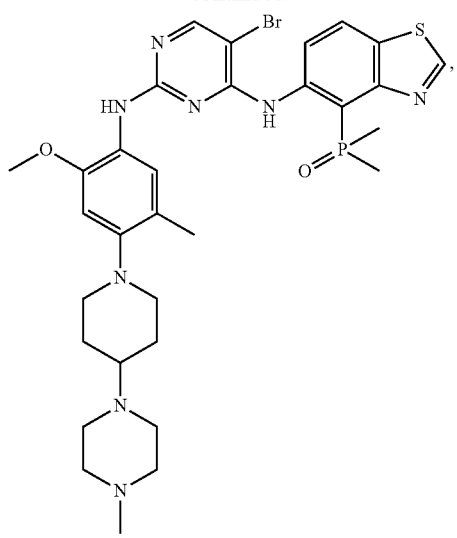
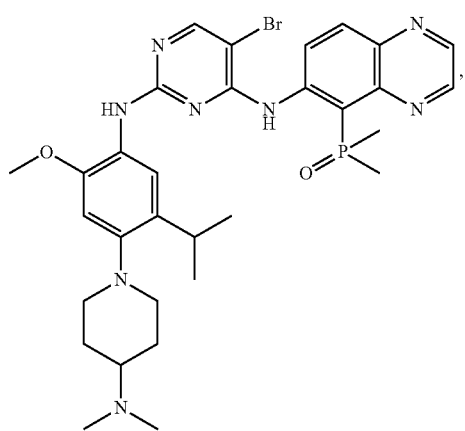
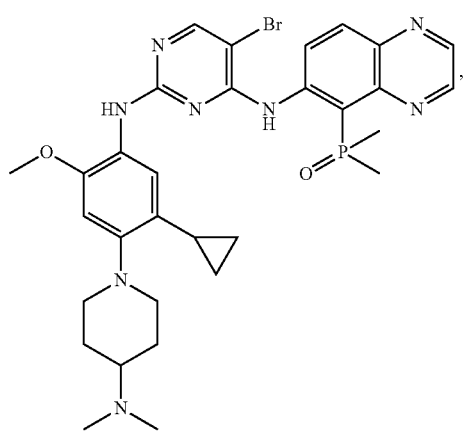
-continued
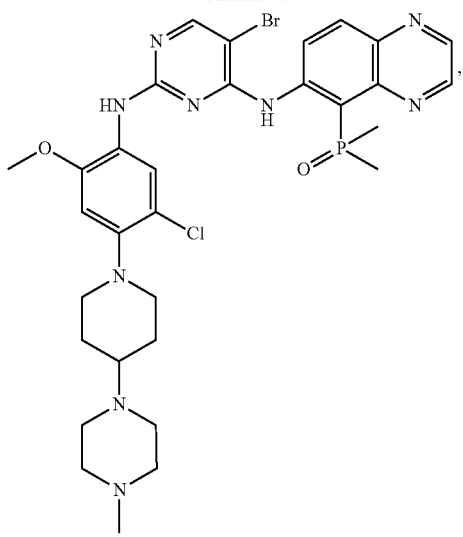
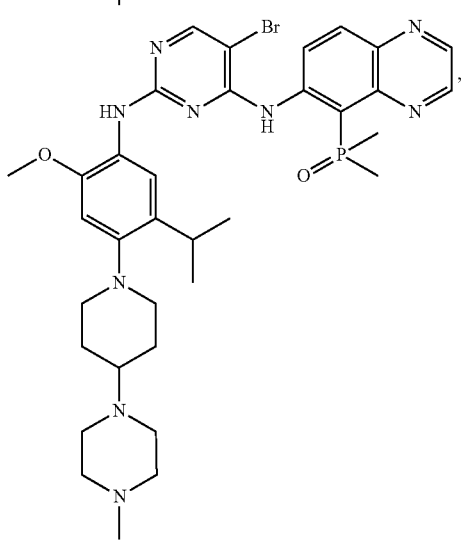
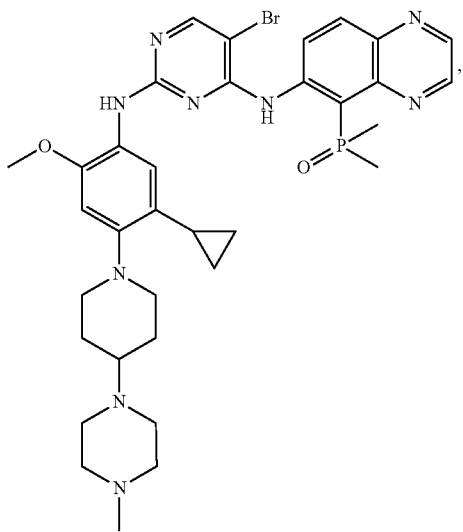

215
-continued
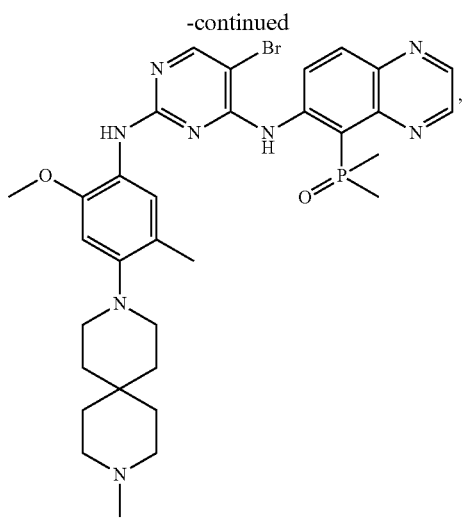
216
-continued
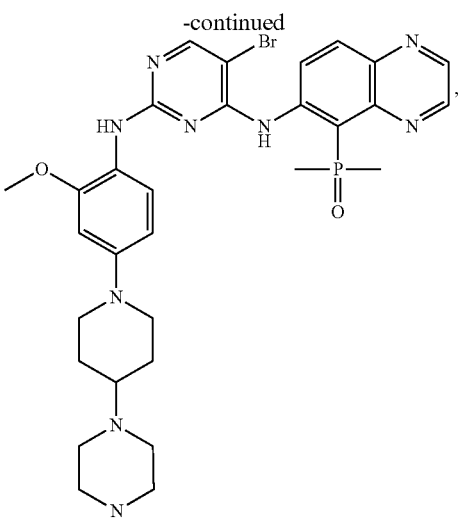
16. A pharmaceutical composition comprising a therapeutically effective amount of the compound or the pharmaceutically acceptable salt thereof according to claim 1, and a pharmaceutically acceptable carrier.
* * * * *